(12) United States Patent
Dejima et al.

(10) Patent No.: US 8,021,293 B2
(45) Date of Patent: Sep. 20, 2011

(54) MEDICAL TREATMENT ENDOSCOPE

(75) Inventors: Takumi Dejima, Tokyo (JP); Kiyotaka Matsuno, Sagamihara (JP); Shotaro Takemoto, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 1034 days.

(21) Appl. No.: 11/809,488

(22) Filed: Jun. 1, 2007

(65) Prior Publication Data

US 2008/0051631 A1 Feb. 28, 2008

Related U.S. Application Data

(63) Continuation-in-part of application No. 11/652,880, filed on Jan. 12, 2007, which is a continuation-in-part of application No. 11/435,183, filed on May 16, 2006, which is a continuation-in-part of application No. 11/331,963, filed on Jan. 13, 2006.

(51) Int. Cl.
*A61B 1/00* (2006.01)

(52) U.S. Cl. .................. 600/104; 600/106; 600/146

(58) Field of Classification Search .................. 600/104, 600/106, 107, 114, 121–125, 139–146; 606/205, 606/206, 208
See application file for complete search history.

(56) References Cited

U.S. PATENT DOCUMENTS

| | | | |
|---|---|---|---|
| 4,577,621 A * | 3/1986 | Patel ........................... | 600/114 |
| 5,318,013 A | 6/1994 | Wilk | |
| 5,395,367 A | 3/1995 | Wilk | |
| 5,448,989 A | 9/1995 | Heckele | |
| 5,683,349 A | 11/1997 | Makower et al. | |
| 5,916,147 A | 6/1999 | Boury | |
| 5,976,075 A * | 11/1999 | Beane et al. ................... | 600/146 |
| 6,013,024 A | 1/2000 | Mitsuda et al. | |
| 6,352,503 B1 | 3/2002 | Matsui et al. | |
| 6,780,151 B2 | 8/2004 | Grabover et al. | |
| 2002/0087048 A1 | 7/2002 | Brock et al. | |
| 2004/0117032 A1 | 6/2004 | Roth | |
| 2004/0138525 A1 | 7/2004 | Saadat et al. | |
| 2004/0138529 A1 | 7/2004 | Wiltshire et al. | |

(Continued)

FOREIGN PATENT DOCUMENTS

EP 1 872 709 A1 1/2008

(Continued)

OTHER PUBLICATIONS

U.S. Office Action dated Mar. 24, 2010, received in related U.S. Appl. No. 11/435,183.

(Continued)

*Primary Examiner* — Thomas J Sweet
*Assistant Examiner* — Ryan Henderson
(74) *Attorney, Agent, or Firm* — Scully, Scott, Murphy & Presser, P.C.

(57) ABSTRACT

The medical treatment endoscope according to the present invention includes a sheath having a flexibility; at least one arm member having a bending part that projects out from a front end of the sheath and performs bending actions; an open/close mechanism which directs the arm member from a direction along a central axis of the sheath to a direction deviated from the central axis of the sheath, and from a direction deviated from the central axis of the sheath to a direction along the central axis of the sheath; and a viewing device and an illuminating member that are disposed to the front end side of the sheath.

13 Claims, 104 Drawing Sheets

U.S. PATENT DOCUMENTS

| | | |
|---|---|---|
| 2004/0193212 A1 | 9/2004 | Taniguchi et al. |
| 2005/0065397 A1 | 3/2005 | Saadat et al. |
| 2005/0075538 A1 | 4/2005 | Banik et al. |
| 2005/0119522 A1 | 6/2005 | Okada |
| 2005/0222495 A1 | 10/2005 | Okada et al. |
| 2005/0228224 A1 | 10/2005 | Okada et al. |
| 2005/0234294 A1 | 10/2005 | Saadat et al. |
| 2005/0234296 A1 | 10/2005 | Saadat et al. |
| 2005/0250989 A1* | 11/2005 | Suzuki .......................... 600/106 |
| 2006/0111615 A1 | 5/2006 | Danitz et al. |
| 2007/0004967 A1 | 1/2007 | Ueno et al. |
| 2007/0156019 A1 | 7/2007 | Larkin et al. |
| 2007/0167679 A1 | 7/2007 | Miyamoto et al. |
| 2007/0167680 A1 | 7/2007 | Miyamoto et al. |
| 2007/0232856 A1 | 10/2007 | Ueno et al. |
| 2007/0299387 A1 | 12/2007 | Williams et al. |
| 2008/0051631 A1 | 2/2008 | Dejima et al. |

FOREIGN PATENT DOCUMENTS

| | | |
|---|---|---|
| EP | 1 967 123 A1 | 9/2008 |
| JP | 55-45436 | 3/1980 |
| JP | 56-104501 | 8/1981 |
| JP | 63-102401 | 7/1988 |
| JP | 5-49594 | 3/1993 |
| JP | 8-131441 | 5/1996 |
| JP | 10-258022 | 9/1998 |
| JP | 11-318815 A | 11/1999 |
| JP | 2004-180781 | 7/2004 |
| JP | 2004-290569 | 10/2004 |
| JP | 2005-287963 | 10/2005 |
| JP | 2005-296412 | 10/2005 |
| JP | 2006-516910 | 7/2006 |
| JP | 2007-151595 | 6/2007 |
| JP | 2007-175070 | 7/2007 |
| JP | 2007-275624 | 10/2007 |
| WO | WO 2004/064600 A2 | 8/2004 |
| WO | WO 2007/057880 A2 | 5/2007 |
| WO | WO 2007/074571 A1 | 7/2007 |
| WO | WO 2007/080974 A1 | 7/2007 |

OTHER PUBLICATIONS

U.S. Office Action dated Jul. 9, 2010.

U.S. Office Action dated Mar. 2, 2011 received in related U.S. Appl. No. 11/652,880.

U.S. Office Action dated Mar. 16, 2011 received in related U.S. Appl. No. 11/435,183.

* cited by examiner

VIEW ALONG DIRECTION A

VIEW ALONG DIRECTION B

VIEW ALONG DIRECTION C

VIEW ALONG DIRECTION D

MEDICAL TREATMENT ENDOSCOPE

CROSS REFERENCE TO RELATED APPLICATIONS

This is a Continuation In-part Application (CIP) based on U.S. patent application Ser. No. 11/652,880, titled "MEDICAL TREATMENT ENDOSCOPE", filed Jan. 12, 2007, which is a CIP based on U.S. patent application Ser. No. 11/435,183, titled "MEDICAL TREATMENT ENDOSCOPE", filed May 16, 2006, which is a CIP based on U.S. patent application Ser. No. 11/331,963, titled "MEDICAL TREATMENT ENDOSCOPE", filed Jan. 13, 2006.

BACKGROUND OF THE INVENTION

1. Field of the Invention

The present invention relates to an endoscope apparatus.

2. Background Art

Laparoscopic surgery is a conventionally known technique that has been employed when performing a medical procedure such as observation or treatment of the internal organs of the human body. Rather than making a large abdominal incision, laparoscopic surgery provides for the procedure to be carried out by making several openings in the abdominal wall, and inserting a laparoscope and surgical instruments such as forceps into these respective openings. This type of surgery offers the benefit of being less invasive on the patient, since only small openings are made in the abdominal wall.

As a method of even further reducing stress on the patient, it has been proposed in recent years to carry out medical procedures by inserting a flexible endoscope into the patient via a natural opening such as the mouth, nostrils or anus. An example of a medical treatment endoscope used in such procedures is disclosed in U.S. Patent Application Publication No. 2005/0065397.

In the medical treatment endoscope disclosed in this reference, arm members that have a bendable end are respectively inserted into a plurality of lumens disposed within a flexible inserted part that is inserted into the body via the mouth of the patient. By inserting respective instruments through these arm members, the procedure site of interest can be approached from different directions with the various instruments. Accordingly, a plurality of procedures can be carried out in continuum by means of a single endoscope inserted into the body.

SUMMARY OF THE INVENTION

The medical treatment endoscope according to a first aspect of the present invention includes a sheath having flexibility; at least one arm member having a bending part that projects out from a front end of the sheath and performs bending actions; an open/close mechanism which directs the arm member from a direction along a central axis of the sheath to a direction that deviates from the central axis of the sheath, and from a direction that deviates from the central axis of the sheath to a direction along the central axis of the sheath; and a viewing device and an illuminating member that are disposed at the front end side of the sheath.

The medical treatment endoscope according to a second aspect of the present invention includes a sheath having flexibility, in which a first lumen with an open end is formed; at least one arm member having a second lumen with an open-end extending in the axial direction into which a procedure device for performing a procedure in an organ is insertable, and a bending part for performing bending actions, a front end of the arm member projecting out from the open end of the first lumen; an open/close mechanism which directs the arm member projecting out from the first lumen from a direction along the central axis of the sheath to a direction that deviates from the central axis of the sheath, and from a direction that deviates from the central axis of the sheath to a direction along the central axis of the sheath; and a viewing device and an illuminating member that are disposed at a front end side of the sheath.

The medical treatment endoscope according a third aspect of the present invention includes a first sheath having flexibility and an open end; a second sheath that is provided with a first arm member that has a front end and a base end and is inserted so that the front end area projects out from the first sheath, and that has a bending part that is freely bendable through manipulation by an operator; a third sheath provided with a second arm member that has a front end and a base end and is inserted so that the front end region projects out from the first sheath, and that has a bendable part that is freely bendable through manipulation by the operator; a viewing device that is independently disposed at the front end of the first sheath from the second sheath and the third sheath, and is for viewing a target image; and an illuminating member that is independently disposed at the front end of the first sheath from the viewing device, the second sheath and the third sheath, and is for radiating illuminating light on the target image.

The medical treatment endoscope according to a third aspect of the present invention includes a sheath having a flexibility; an arm means that projects out from the end of the sheath and is for performing bending actions; an open/close means which directs the arm means from a direction along a central axis of the sheath to a direction deviated from the central axis of the sheath, and from a direction deviated from the central axis of the sheath to the direction of the central axis of the sheath; a viewing means for viewing an area further toward the front end than the sheath; and an advance/retract means for advancing or retracting the arm means with respect to the sheath.

BRIEF DESCRIPTION OF DRAWINGS

FIG. 114 is a view showing the overcoat tube enclosing the needle.

FIG. 115 illustrates a main body of the operation section pushed into the overcoat tube.

FIG. 116 illustrates the needle protruding into the inner wall of the body cavity.

FIG. 117 illustrates the protruding stabbing into the inner wall of the body cavity.

FIG. 118 illustrates a forwarded state of a slider.

FIG. 119 illustrates an anchor extruded from the needle.

DETAILED DESCRIPTION OF THE INVENTION

Embodiments according to the present invention will now be described in detail below. Structural elements that are equivalent in the following will be assigned the same numeric symbols and redundant explanations thereof will be omitted.

First Embodiment

Figure 1:
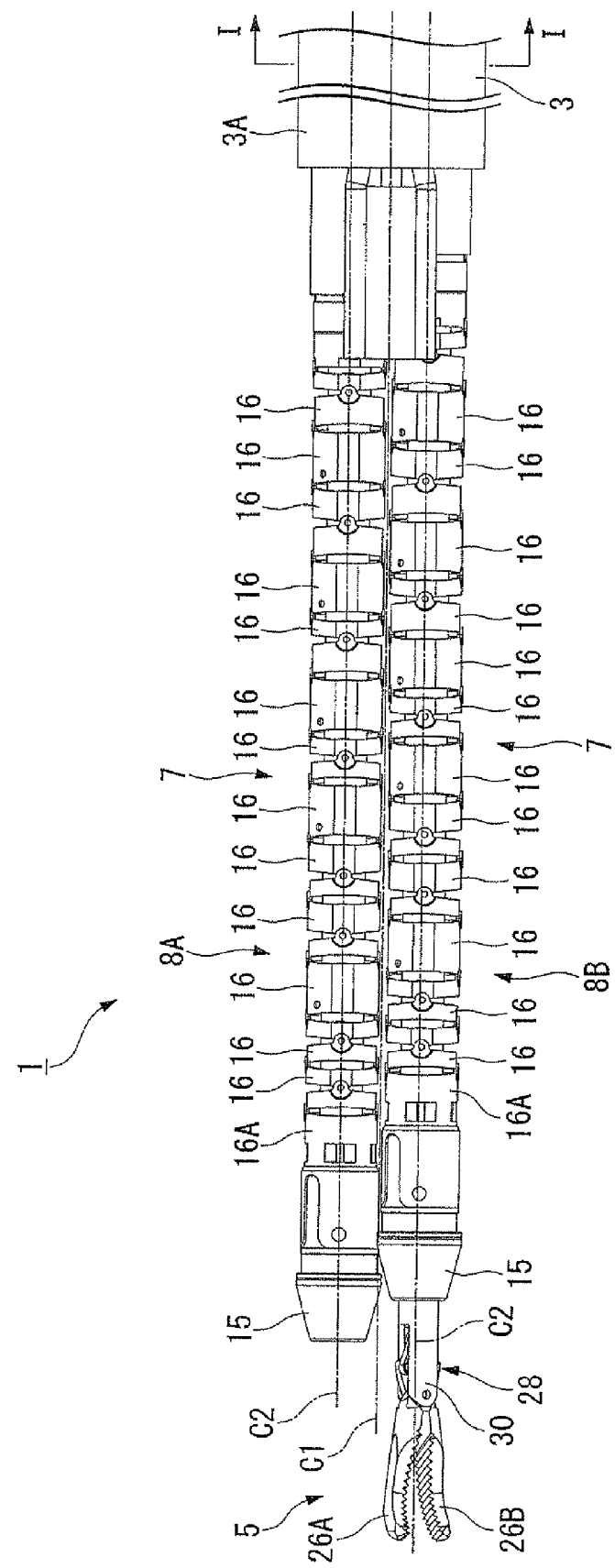
FIG. 1 shows the configuration of a tip end of the endoscope apparatus according to a first embodiment of the present invention.
Figures 2A, 2B:
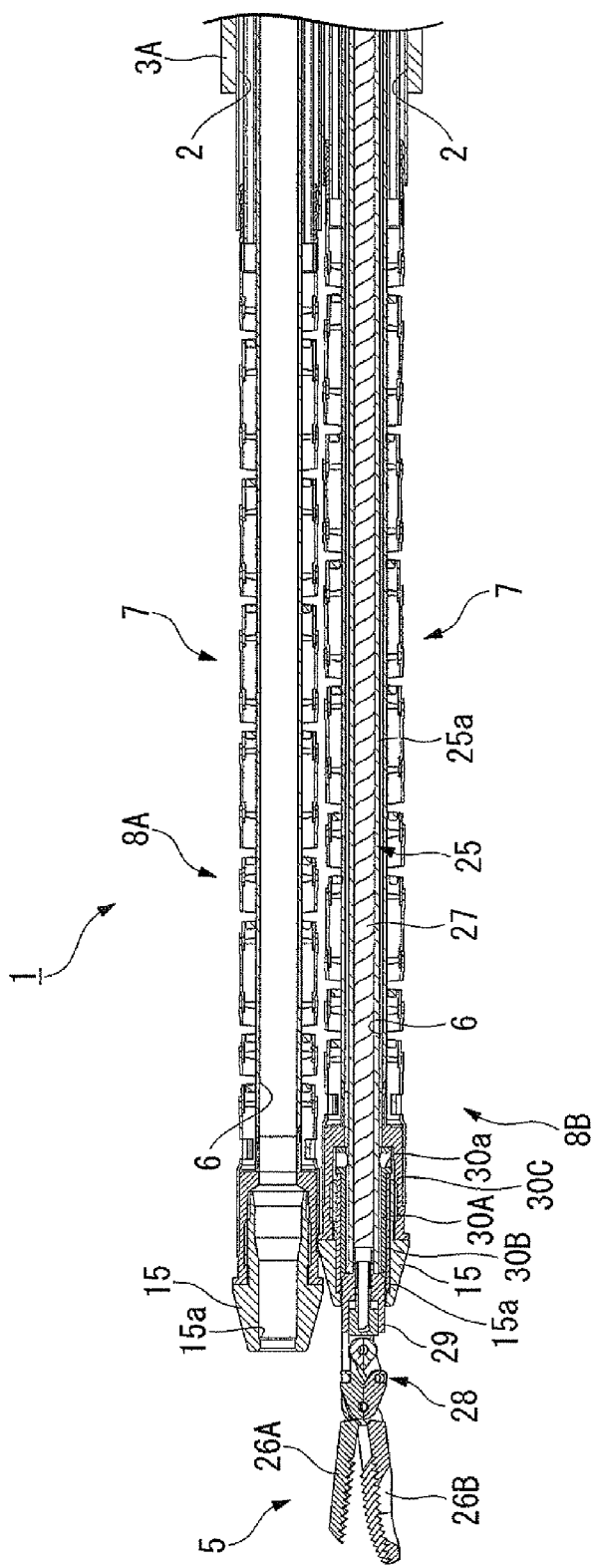
FIG. 2A shows the configuration of a tip end of the endoscope apparatus according to the first embodiment of the present invention.
FIG. 2B is a partially enlarged diagram of FIG. 2A.
Figure 3:
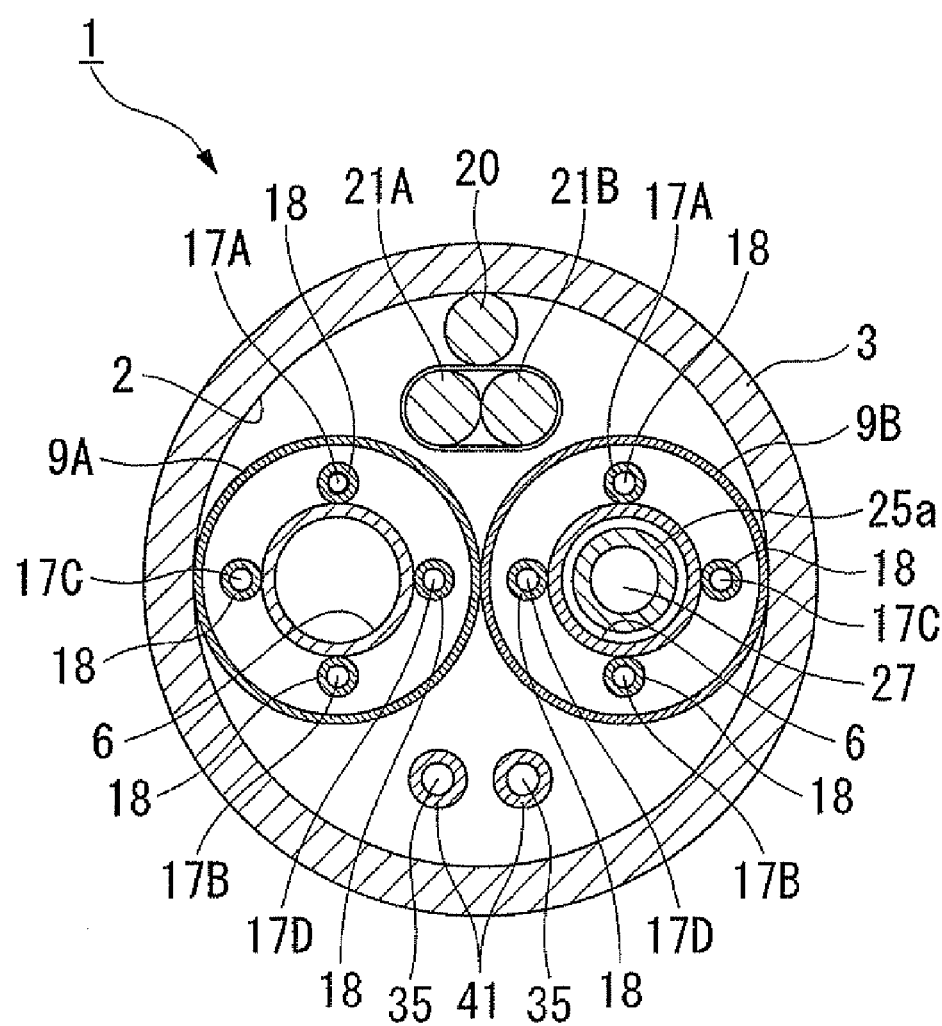
FIG. 3 is a cross-section viewed along line I-I of FIG. 1.
Figure 4:
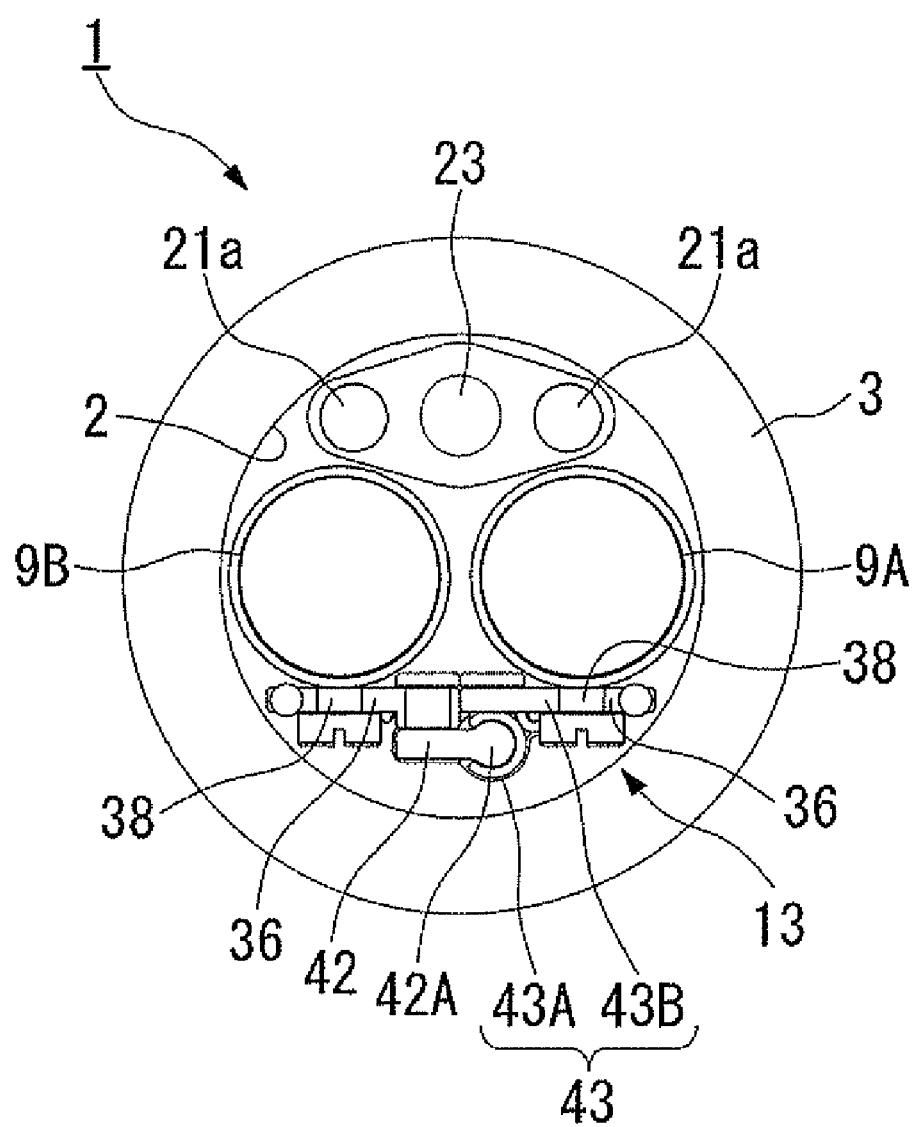
FIG. 4 is a view of the front end of the medical treatment endoscope according to the first embodiment.

As shown in FIGS. 1 through 3, the medical treatment endoscope 1 according to this embodiment is provided with a flexible first sheath (sheath) 3 in which an open-ended first lumen 2 is formed; a second sheath 9A having a first arm member 8A to which is disposed an open-ended instrument insertion channel (second lumen) 6 into which instruments such as gripping forceps 5 are inserted, and a bending part 7 that projects out from the first sheath 3 and carries out bending actions; and a third sheath 9B having a second arm member 8B to which the instrument insertion channel 6 and the bending part 7 are disposed. Moreover, as shown in FIGS. 4 through 8B, the medical treatment endoscope 1 according to this embodiment is further provided with an open/close mechanism 10 for changing the inclination of the first arm member 8A and the second arm member 8B that project out from the first sheath 3, from the central axis C1 of the first sheath 3 to a direction away from the central axis C1, and from this direction away from the central axis C1 toward the direction of the central axis C1 (separation release); a viewing device 12 that is disposed at the front end side of the first sheath 3; and an advance/retract mechanism 13 for advancing and retracting the first arm member 8A with respect to the first sheath 3.

The second sheath 9A has a front end and a base end, the front end region forming the first arm member 8A. The second sheath 9A is inserted into the first lumen 2 so as to project out from the first sheath 3, at a position in the first lumen 2 so as to appear on the right side of the viewing screen. The third sheath 9B has a front end and a base end, the front end region forming the second arm member 8B. The third sheath 9B is inserted into the first lumen 2 adjacent to the second sheath 9A, so as to project out from the first sheath 3.

As shown in FIGS. 1 and 2, rigid front end parts 15 are disposed at the front ends of the first arm member 8A and the second arm member 8B. A bumper 15a is provided at the front end part 15 for limiting movement in the forward direction when gripping forceps 5 or the like are inserted from the base end side of the instrument insertion channel 6.

As in the case of the typical flexible endoscope, the bending part 7 is designed such that a plurality of joint wheels 16 are mutually axially supported to enable rotation, and are connected along the direction of the central axis C2 of the first arm member 8A and the second arm member 8B. Furthermore, bending wires 17A, 17B, 17C, and 17D such as shown in FIG. 3, are connected to the joint wheel 16A disposed farthest from the front end. Bending wires 17A, 17B, 17C, and 17D are each inserted into and pass through the joint wheels 16 at positions so as to divide the circumferential periphery of the joint wheels 16 into quarters.

Figure 7A:
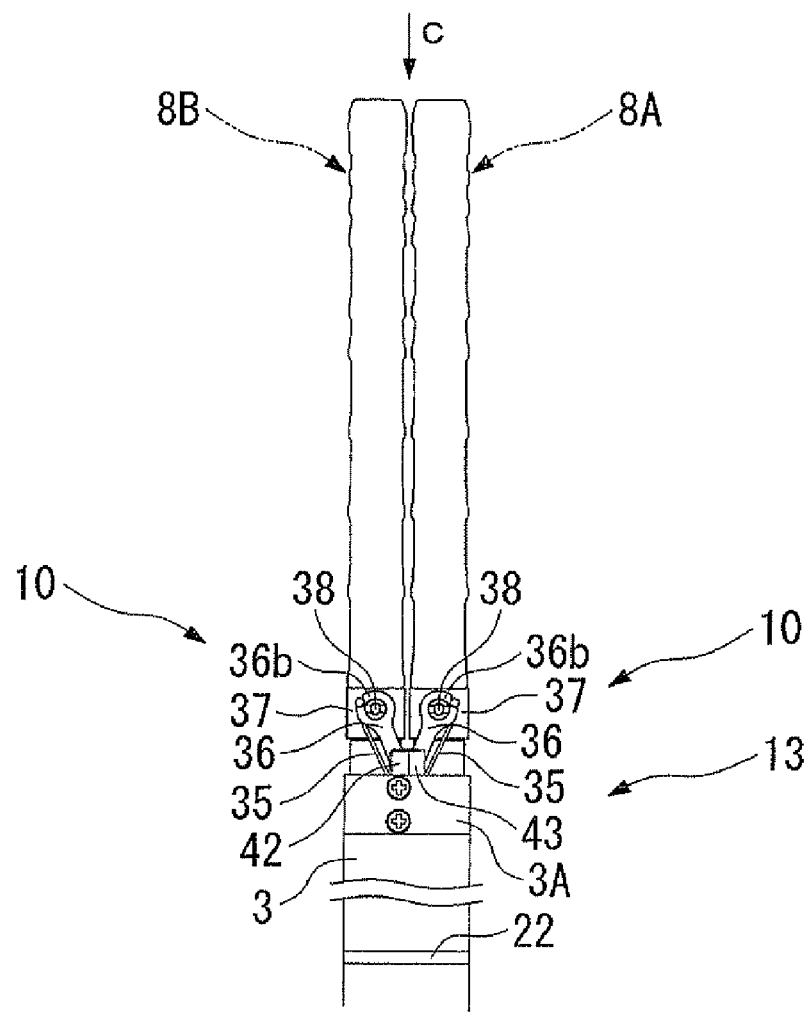
FIG. 7A is a plan view showing the starting state of the arm member of the medical treatment endoscope according to the first embodiment.
Figure 7B:
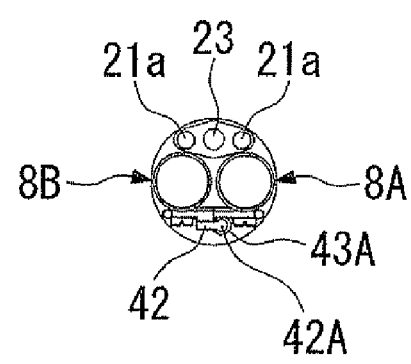
FIG. 7B is a view along direction C in FIG. 7A.

Bending wires 17A and 17B, and bending wires 17C and 17D are paired respectively, and positioned so as to be symmetrical about the center of bending part 7. Each bending wire 17A, 17B, 17C, and 17D is inserted into a bending wire coil 18 within the first sheath 3. A video cable 20, which is connected to a viewing device 12 which includes an image pick-up unit 11 and an objective lens (optical member for viewing) 23, and two light guides (illuminating members) 21A and 21B which emit illuminating light onto illuminating lenses (illuminating optical members) 21a, which are structural components of the illuminating members and are for lighting the object to be illuminated by forming the illuminating light bundles into a desired light bundle profile, are inserted into the first sheath 3 so as not to interfere with the second sheath 9A, the third sheath 9B and the various bending wires. A rigid sheath front end part 3A is disposed to the front end of the first sheath 3. An objective lens 23, and illuminating lenses 21a which are on either side of the objective lens so as to interpose the objective lens 23 therebetween, are disposed to the sheath front end part 3A. In other words, the illuminating members are disposed on either side of the viewing device. As shown in FIG. 7A, a plurality of markings 22, for understanding the length of the inserted portion when the endoscope is inserted into the patient, are provided at predetermined intervals along the surface of the first sheath 3 on the hand-held side thereof.

As shown in FIGS. 1, 2A, 2B, and 10, a gripping forceps 5 is provided with a forceps insertion part 25 that has a long narrow coil sheath 25a. A pair of forceps pieces 26A and 26B are disposed to the front end of the forceps insertion part 25. This pair of forceps pieces 26A and 26B is connected to a forceps manipulating wire 27, which is inserted into the coil sheath 25a to enable free advancing and retracting, via a forceps linking part 28 which converts the advancing/retracting operation of the forceps manipulating wire 27 into the opening/closing operation of the paired forceps pieces 26A and 26B. A forceps linking part 28 is disposed to a front end cover 29 which is attached to the coil sheath 25a.

As shown in FIGS. 2A and 2B, this gripping forceps 5 is fixed in place via a first connecting member 30A, a second connecting member 30B and a third connecting member 30C to the second arm member 8B to enable free rotation. The first connecting member 30A is tubular, with its inner peripheral surface fixed in place near the front end of the gripping forceps 5 by a screw, adhesive agent or the like. The second connecting member 30B is in the form of a short pipe, and is interposed between the bumper 15a of the front end part 15 and the first connecting member 30A. The third connecting member 30C is in the form of a short pipe, and is formed so that the base end projects inward in the radial direction. This third connecting member 30C engages with the front end part 15, and pushes the first connecting member 30A in the forward direction. As a result, the second connecting member 30B is pushed further forward than the first connecting member 30A, coming into contact with the bumper 15a of the front end part 15, thereby restricting movement of the gripping forceps 5 in the advancing or retracting direction. On the other hand, the gripping forceps 5 are attached in a freely rotating manner with respect to the instrument insertion channel 6. Note that the third connecting member 30C may also be attached to the front end part 15 by screwing, or by an adhesive agent or the like.

The gripping forceps 5 are provided with a forceps operating part (procedure operating part) 31. The forceps operating part 31 is provided with a forceps operating part main body 32 to which the coil sheath 25a is connected, and a forceps handle 33 to which a forceps manipulating wire 27 is connected and which is disposed in a freely retracting and advancing manner with respect to the forceps operating part main body 32.

The open/close mechanisms 10 are respectively provided corresponding to the number of the first arm members 8A and the second arm members 8B. Note that since the structure is almost entirely the same, the following explanation will be directed to the open/close mechanism 10 of the first arm member 8A.

As shown in FIGS. 4 through 8B, the open/close mechanism 10 is provided with a bending opening/closing wire (open/close operating member) 35, which is capable of advancing and retracting with respect to the first sheath 3; a linking part 36 to which the end of the bending opening/closing wire 35 is connected, which converts the advancing/retracting operation of the bending opening/closing wire 35 into the opening/closing operation of the first arm member 8A with respect to the first sheath 3; and a support 37 which is in the form of a short pipe that is axially supported to enable rotation about the linking part 36, or, alternatively, is connected to the linking part 36 in a manner so as to prevent rotation. This short pipe-shaped support 37 is fixed in place along the bending part 7 of the arm member 8A. Note that it is also acceptable to fix this short pipe-shaped support 37 further toward the base end than the bending part 7.

The linking part 36 is formed extending in the form of a long plate, and one end 36a is axially supported by a guide member 42 of the first sheath 3, explained below, to enable rotation. Note that in the case of the second arm member 8B, one end 36a of the linking part 36 is axially supported by a sliding member 43, explained below, that can advance and retract along the central axis C1.

The support 37 is supported by another end 36b of the linking part 36 via a support axis 38, to enable rotation thereof, or alternatively, is connected so that rotation is not possible. The other end 36b of the linking part 36 is formed in the shape of a disk centered about the position of attachment to the support axis 38, with bending opening/closing wires 35 supported by the periphery thereof. The bending opening/closing wires 35 are disposed inside the first sheath 3, inserted into respective bending opening/closing wire coils 41.

An advance/retract mechanism 13 is provided with a guide member 42 extending in the direction of the central axis C1 of the first sheath 3 and fixed in place to the first sheath 3, and a sliding member 43 that can be freely advanced and retracted with respect to the guide member 42. The guide member 42 is formed in the shape of a flat plate extending a predetermined length in one direction, and, with respect to the central axis C1 of the first sheath 3, is disposed at a position opposite where the light guides 21A and 21B and the video cable 20 are inserted (i.e., the area opposite where the light guides 21A and 21B and the video cable 20 are inserted, such that the second sheath 9A and the third sheath 9B are interposed therebetween). An engaging convexity 42A, approximately cylindrical in shape, is provided to one end in the width direction of the guide member 42 on the first arm member 8A side. The sliding member 43 is provided with a roughly C-shaped engaging concavity 43A that engages with the engaging convexity 42A to enable sliding, and a connector 43B that links the engaging concavity 43A and the first arm member 8A. The amount of movement of the sliding member 43 with respect to the guide member 42 is restricted to predetermined limits. Note that it is also acceptable to enable advancing and retracting of the second arm member 8B, rather than the first arm member 8A, using the same type of advance/retract mechanism.

Figure 9:
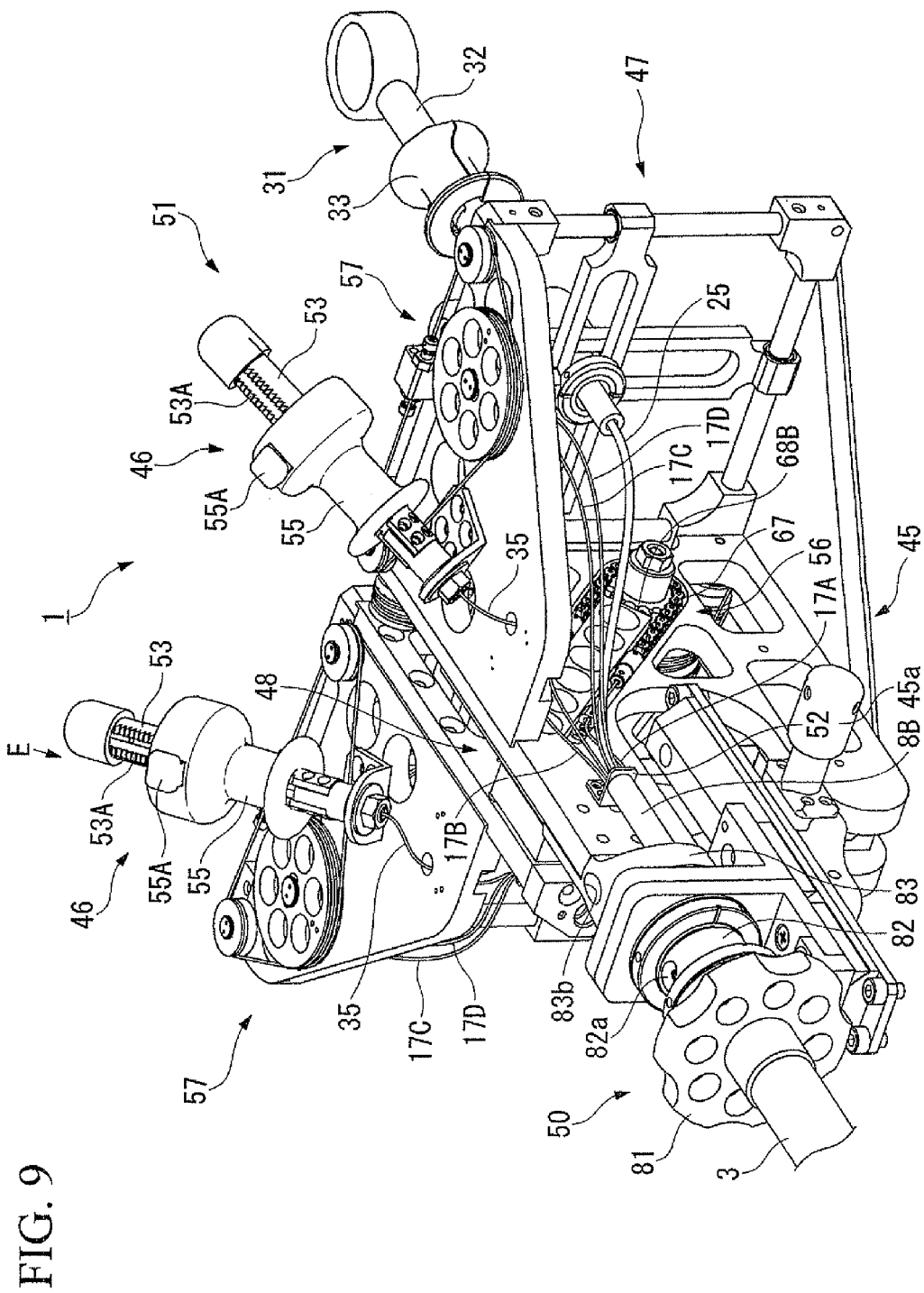
FIG. 9 is a perspective view showing the operating part of the medical treatment endoscope according to the first embodiment.
Figure 10:
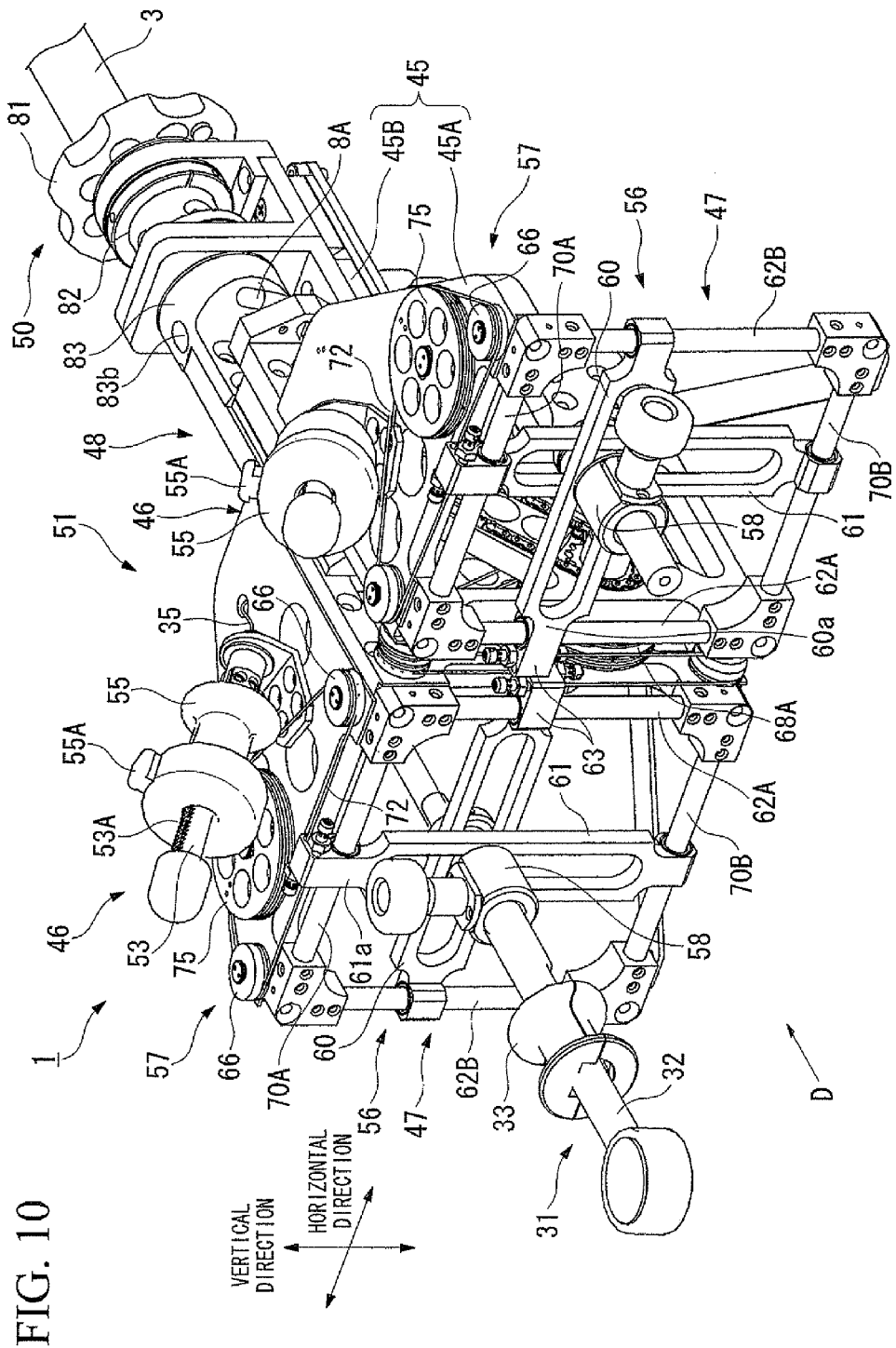
FIG. 10 is a view along direction E in FIG. 9.
Figure 11:
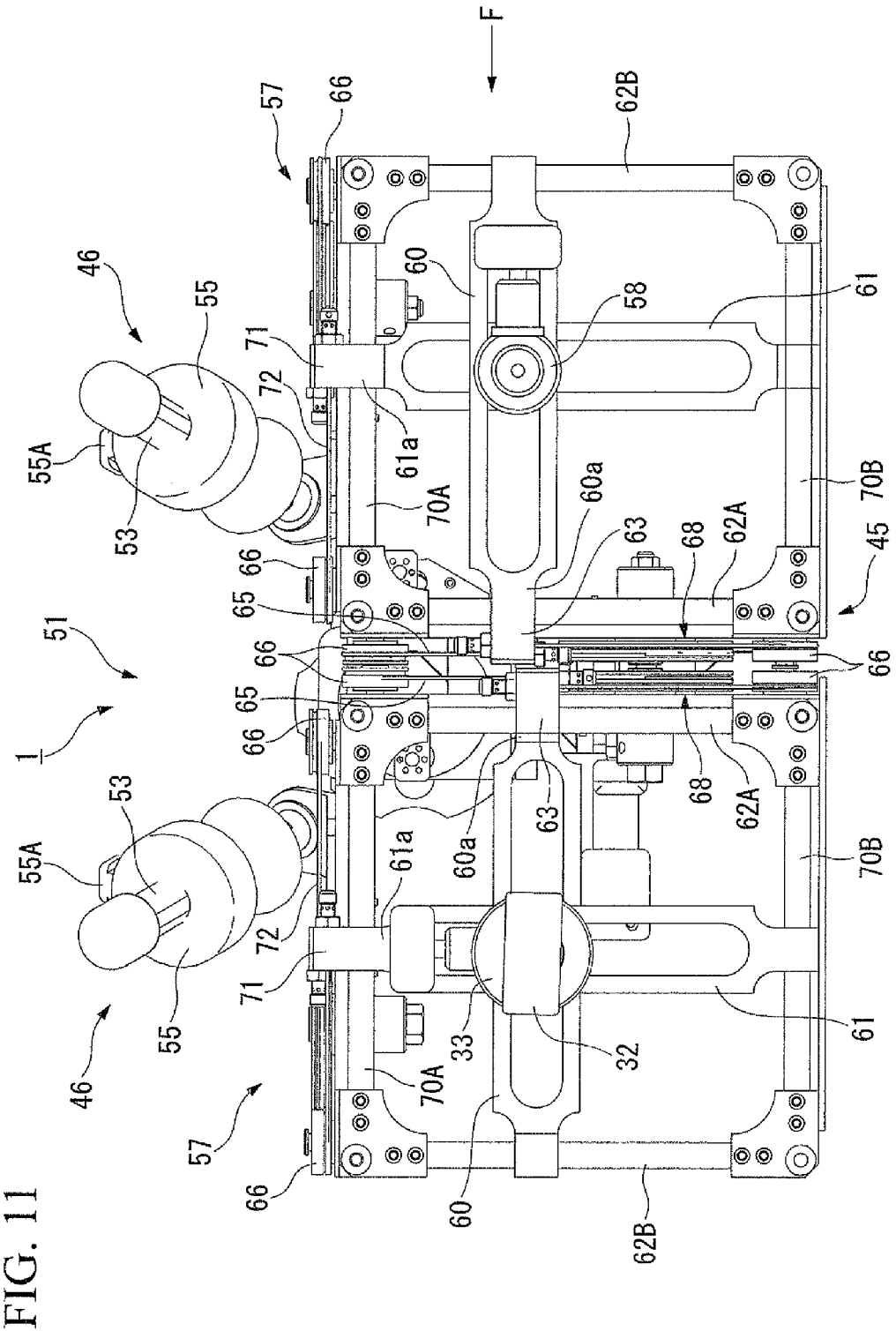
FIG. 11 is a view along direction E in FIG. 10.
Figure 12:
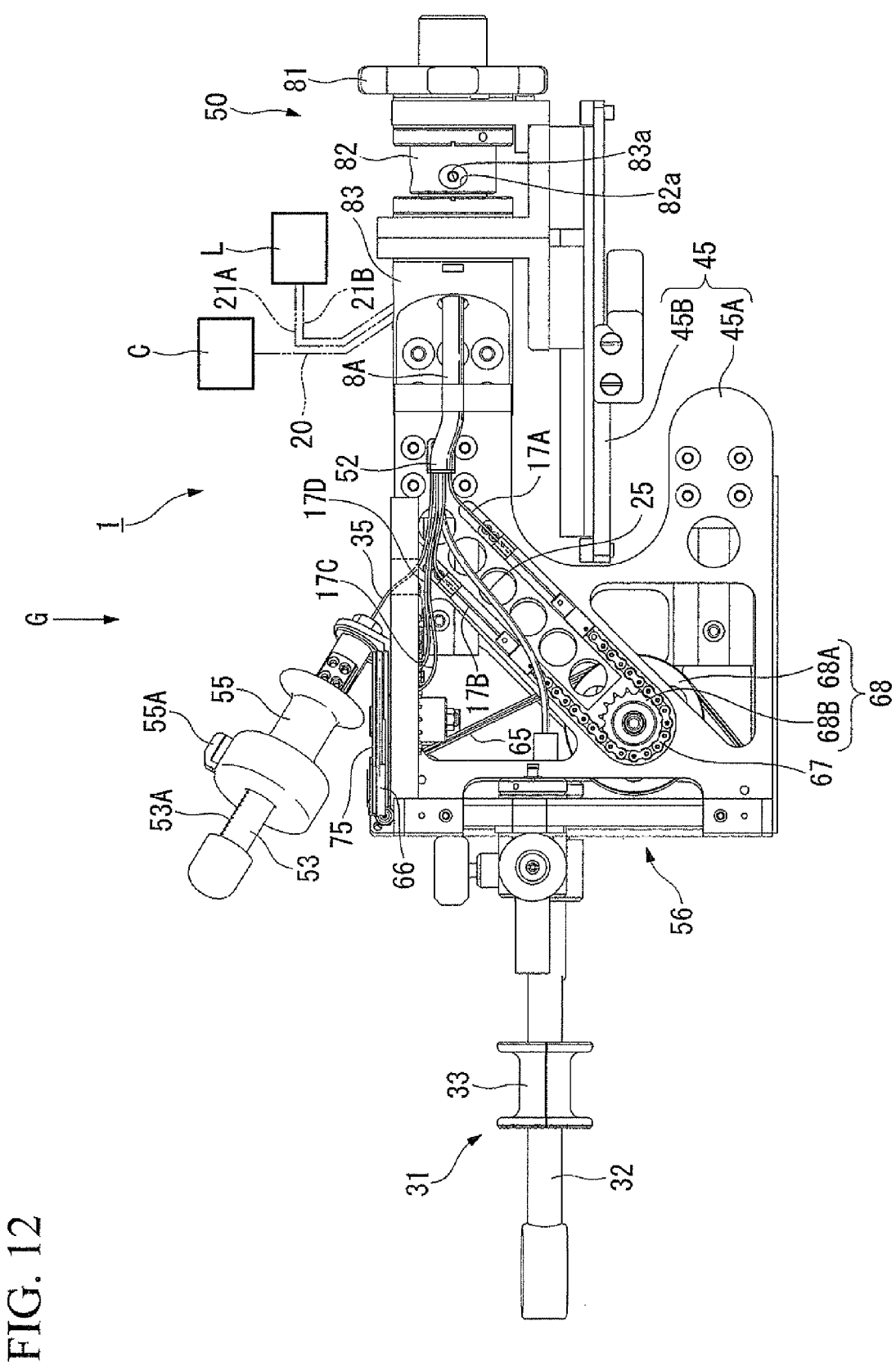
FIG. 12 is a view along direction F in FIG. 11.
Figure 13:
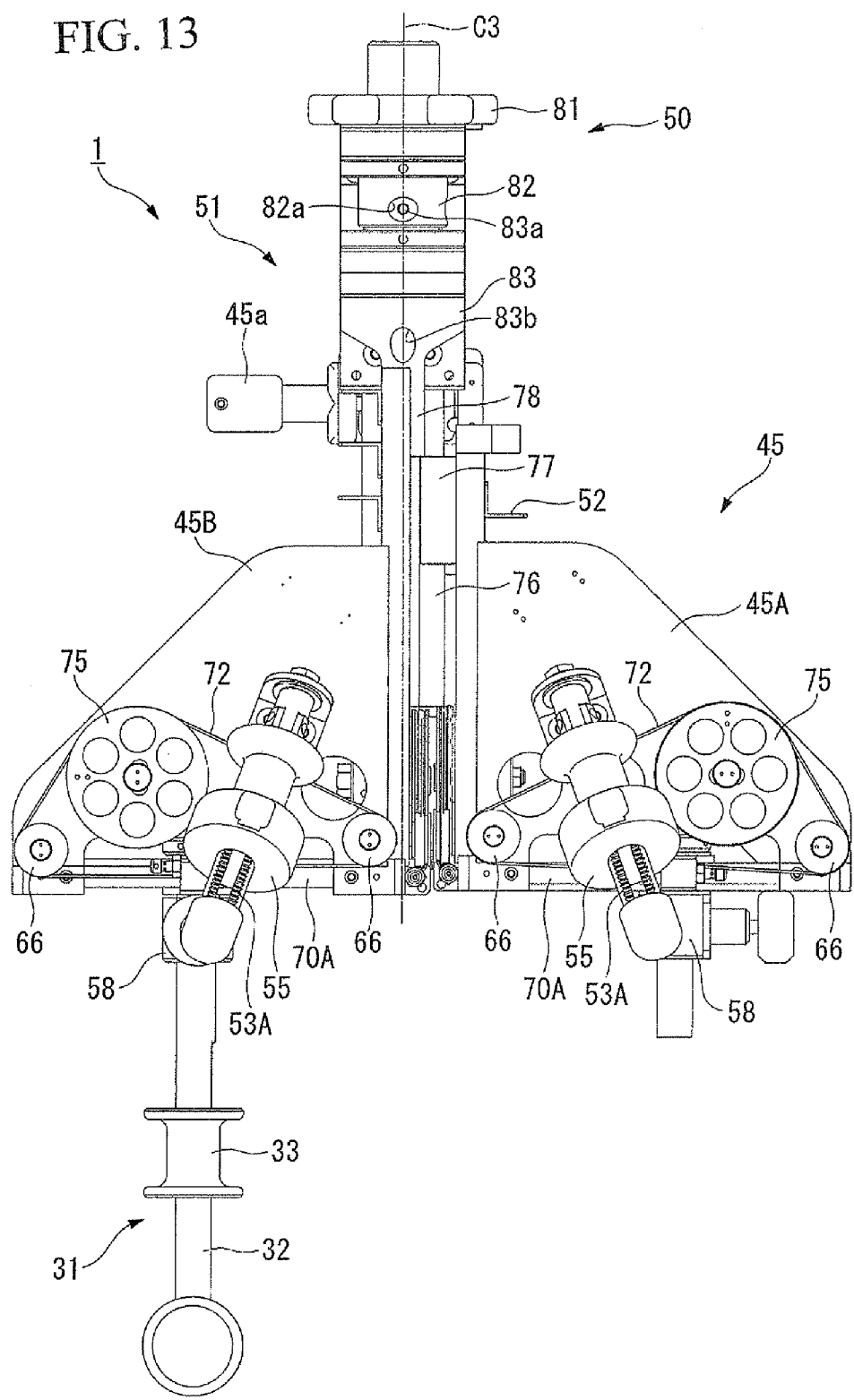
FIG. 13 is a view along direction G in FIG. 12.

As shown in FIGS. 9 though 12, the medical treatment endoscope 1 is provided with an operating part 51 having a frame 45; an open/close operating part 46 that is connected to the base end of the bending opening/closing wire 35 of the open/close mechanism 10, for carrying out advancing and retracting manipulation of the bending opening/closing wire 35; a bending operating part 47, to which the forceps operating part 31 of the gripping forceps 5 can be attached, for advancing and retracting manipulation of the bending wires 17A, 17B, 17C, and 17D that are connected to the respective bending parts 7 of the first arm member 8A and the second arm member 8B by movement of the forceps operating part 31; an advance/retract operating part 48 for advancing and retracting the sliding member 43 of the advance/retract mechanism 13 with respect to the guide member 42; and a rotation operating part 50 for connecting the base end of the first sheath 3 to the frame 45 in a manner to enable rotation.

The frame 45 is provided with a moving frame 45A where the open/close operating part 46 and the bending operating part 47 of the arm member 8A are disposed; and a fixed frame 45B where the open/close operating part 46 and the bending operating part 47 of the arm member 8B, and the rotation operating part 50 of the first sheath 3, are disposed. Arm clamps 52 for supporting the first arm member 8A and the second arm member 8B projecting from the base end of the first sheath 3 farther toward the hand-held side are respectively disposed along the central axis C3 to moving frame 45A and fixed frame 45B. In addition to the first arm member 8A and the second arm member 8B, the light guides 21A and 21B and the video cable 20 project out from the base end of the first sheath 3, and are connected respectively to a light source device L and a controller C. A fixing screw 45a for connecting and fixing in place a scope holder 86, explained below, is disposed to the bottom of the fixed frame 45B. Note that with respect to fixing with the scope holder 86, it is also acceptable to enable free sliding so that it is possible to adjust the position of the front end of the medical treatment endoscope 1 inside the body cavity by advancing and retracting the entire operating part.

The open/close operating part 46 is provided with an open/close operating part main body 53 and an open/close handle 55 to which the base end of the bending opening/closing wire 35 is connected and which can advance and retract with respect to the open/close operating part main body 53. The open/close operating part main body 53 is respectively fixed in place to the fixed frame 45B and the moving frame 45A. A rack 53A is formed at the open/close operating part main body 53 for restricting movement toward the front end side when the open/close handle 55 is pulled toward the hand-held side. The advance of the open/close handle 55 with respect to the open/close operating part main body 53 is restricted as a result of engagement of this rack 53A with a gear, not shown in the figures, that is provided inside the open/close handle 55. In this restricted state, the above-mentioned gear can be moved away and released from the rack 53A by pressing a release button 55A that is provided at the open/close handle 55. When a starting state for the open/close mechanism 10 is defined as the state in which the first arm member 8A and the second arm member 8B are closed at a position along the direction of the central axis C1 of the first sheath 3, then, in this starting state, the open/close handle 55 is set so as to be positioned toward the front end of the open/close operating part main body 53.

The bending operating part 47 is provided with a vertical bending operating part 56 for moving bending part 7 in the vertical direction, for example; a horizontal bending operating part 57 for moving the bending part 7 in a direction perpendicular to the aforementioned, i.e., moving the bending part 7 in the horizontal direction, for example; and an attachment part 58 for attaching the forceps operating part main body 32 of the forceps operating part 31 in a manner so as to enable its rotation. The attachment part 58 is connected to enable movement in the respective directions inside the each of the frames at the area of intersection between a first movement restricting member 60, which is in the form of a rectangular frame provided for causing relative displacement of the attachment part 58 in the horizontal direction only, and a second movement restricting member 61, which is in the form of a rectangular frame disposed perpendicular to the first movement restricting member 60 and provided for causing relative displacement of the attachment part 58 in the vertical direction only. Note that the bending operating parts 47 are disposed to each of the first arm member 8A and the second arm member 8B.

A vertical bending operating part 56 is provided with a pair of rod-shaped first bending guides 62A and 62B in which the longitudinal ends of the first movement restricting member 60 are engaged in a manner to enable sliding, in order to cause parallel displacement of the first movement restricting member 60 in the vertical direction; a first die part 63 that is connected to the end 60a of the first movement restricting member 60, and moves along the first bending guide 62A; a first belt member 65, in which both ends are connected to the first die part 63 so as to be in opposition to one another from the direction along the first bending guide 62A; two adjusting wheels 66 for adjusting the tension by winding the first belt member 65; a first chain belt 67 in which the bases of the bending wires 17A and 17B are connected at either end; and a first gear 68 having a small diameter part 68b in which the first chain belt 67 engages and a large diameter part 68a around which the first belt member 65 is wound.

The horizontal bending operating part 57 is provided with the same construction as the vertical bending operating part 56. In other words, the horizontal bending operating part 57 is equipped with a pair of rod-shaped second bending guides 70A and 70B in which the longitudinal ends of the second movement restricting member 61 are engaged in a manner to enable sliding, in order to cause parallel displacement of the second movement restricting member 61 in the horizontal direction; a second die part 71 that is connected to the end 61a of the second movement restricting member 61, and moves along the second bending guide 70A; a second belt member 72, in which both ends are connected with respect to the second die part 71 so as to be in opposition to one another from the direction along the second bending guide 70A; adjusting wheels 66 for adjusting the tension by winding the second belt member 72; a second chain belt, not shown in the figures, in which the bases of the bending wires 17C and 17D are connected at either end; and a second gear 75 in which the second chain belt engages and around which the second belt member 72 is wound.

The advance/retract operating part 48 is provided with a slide rail 76 for moving the moving frame 45A, to which the open/close operating part 46 and the bending operating part 47 connected to the aim member 8A are disposed, with respect to the fixed frame 45B; and a base 77 which is disposed to the moving frame 45A and engages in a sliding manner with the slide rail 76. An advance/retract restricting member 78 is disposed to the front end side of the slide rail 76. The amount of sliding of the moving frame 45A is restricted to a predetermined range as a result of the base 77 coming into contact with this advance/retract restricting member 78. This advance/retract restricting member 78 is positioned at a predetermined location so that the sliding member 43 of the advance/retract mechanism 13 does not come free from the guide member 42.

The rotation operating part 50 is disposed further toward the front end side of the frame 45 than the arm clamp 52, and is provided with a sheath connector 82, to which a rotation knob 81 is disposed and the base end of the first sheath 3 is connected; and a rotation support 83 for supporting the sheath connector 82 in a manner to enable rotation. A screw hole 83a is formed in the rotation support 83, and a through-hole 82a is formed in the sheath connector 82. The rotation of the sheath connector 82 with respect to the rotation support 83 is restricted as a result of the engagement of a stopping screw or the like at the position where the screw hole 83a and the through-hole 82a are overlapped. The amount of rotation is preferably on the order of 180 degrees to either side. Note that a through-hole 83b is disposed to the rotation support 83 for insertion of the light guides 21A and 21B and the video cable 20.

Next, the operation of the embodiment of the present invention will be explained.

Figure 5A:
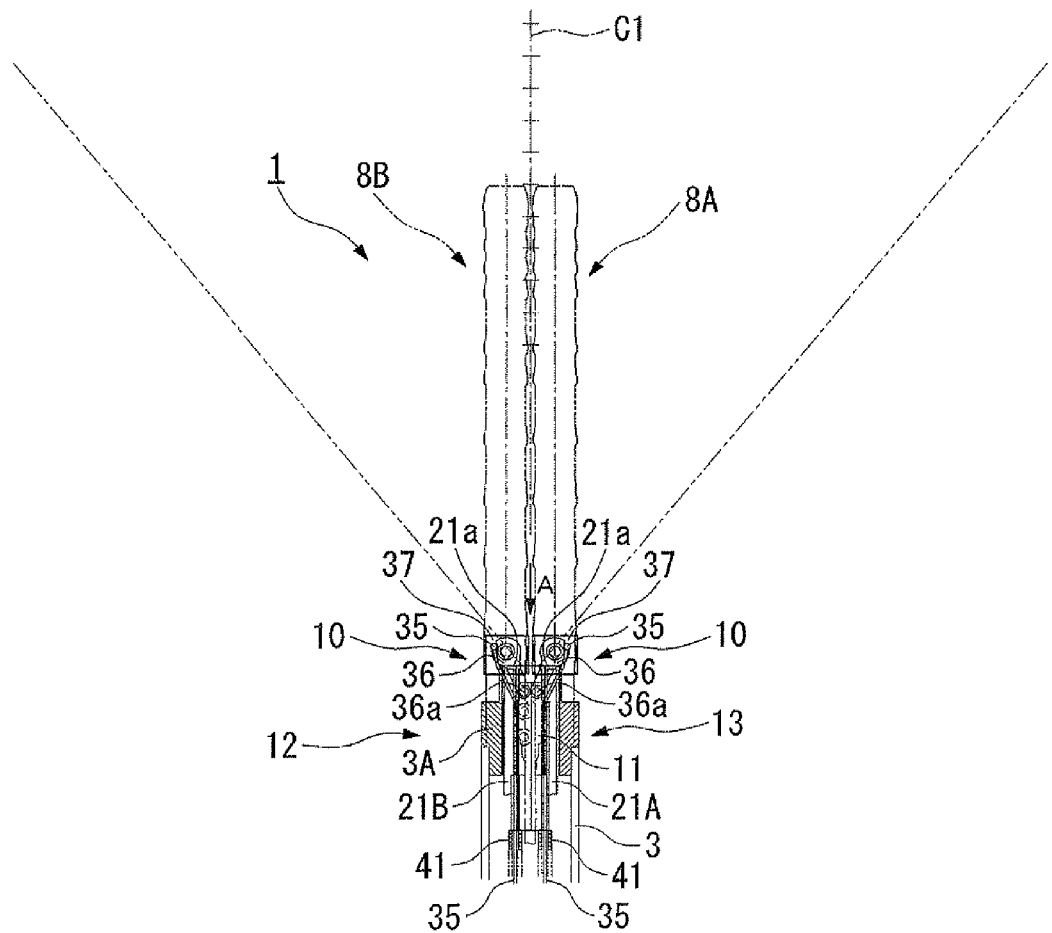
FIG. 5A is a perspective view showing the starting state of the arm member of the medical treatment endoscope according to the first embodiment.
Figure 5B:
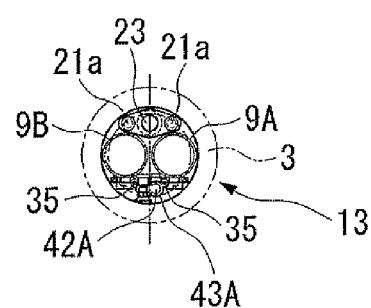
FIG. 5B is a view along direction A in FIG. 5A.
Figure 6A:
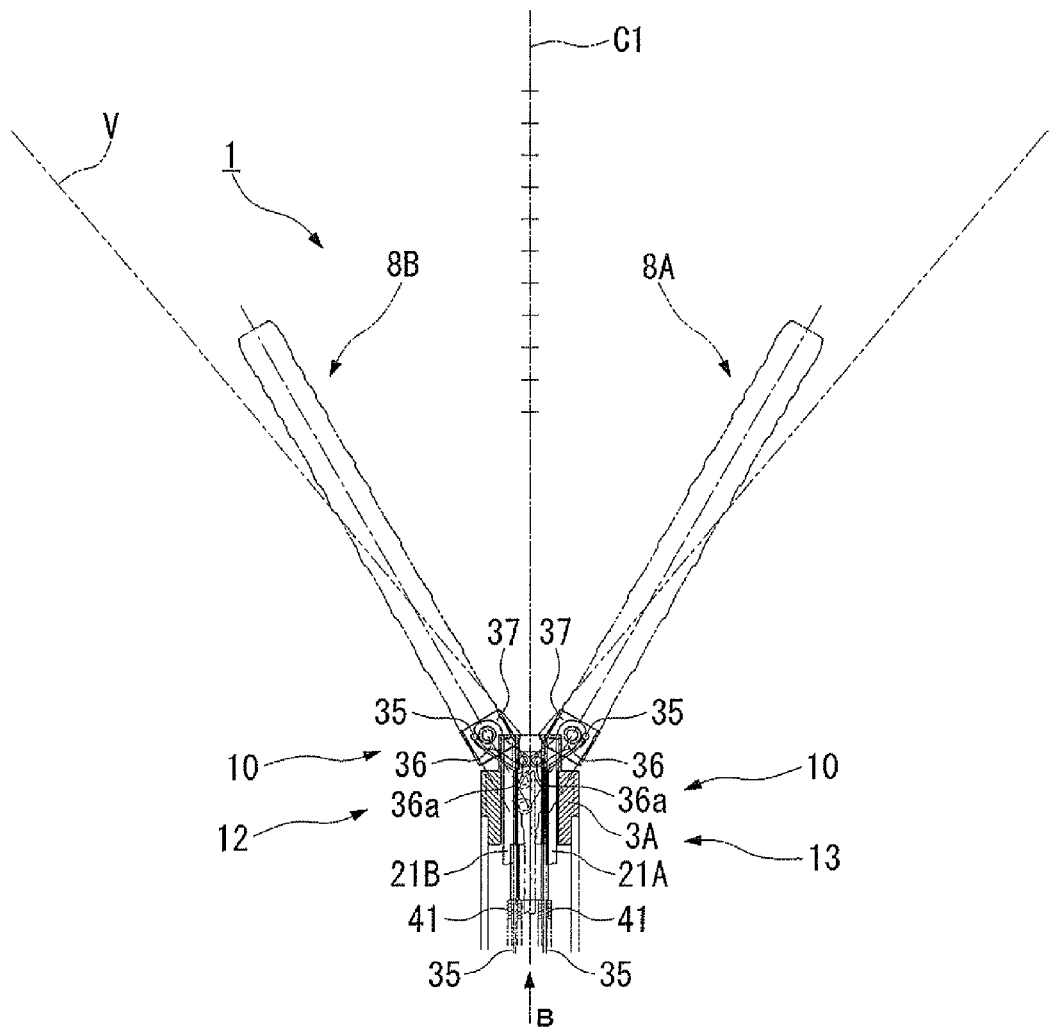
FIG. 6A is a perspective view of the front end showing the arm member of the medical treatment endoscope according to the first embodiment in the open state.
Figure 6B:
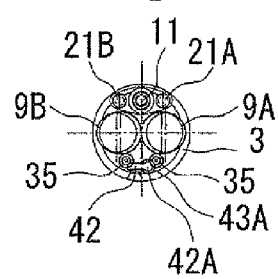
FIG. 6B is a view along direction B in FIG. 6A.
Figure 8A:
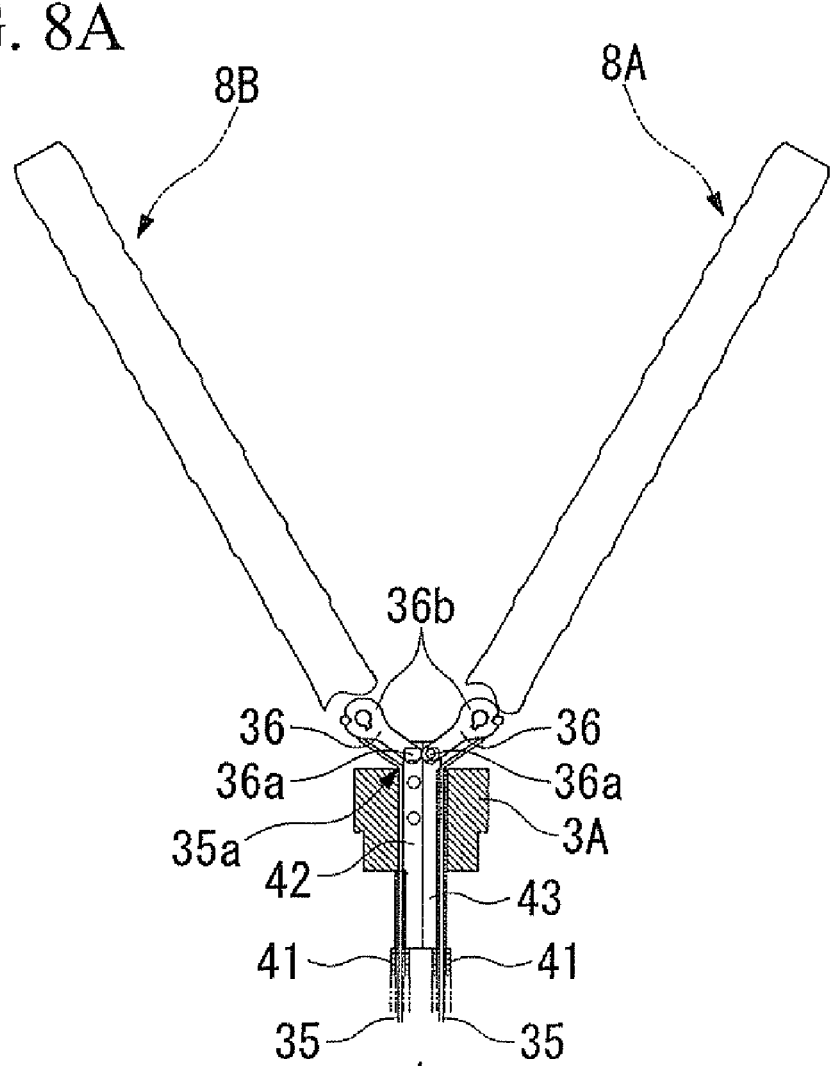
FIG. 8A is a plan view showing the open/close mechanism when the arm member of the medical treatment endoscope according to the first embodiment is in the open state.
Figure 8B:
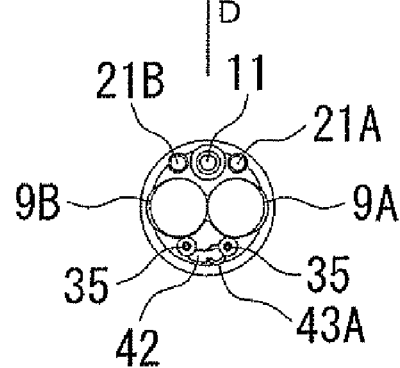
FIG. 8B is a view along direction D in FIG. 8A.

When opening the first arm member 8A and the second arm member 8B with respect to the first sheath 3 from the starting state shown in FIGS. 5A and 7A, the open/close handle 55 is slid with respect to the open/close operating part main body 53 a predetermined distance toward the hand-held side. The bending opening/closing wire 35 is thus retracted with respect to the first sheath 3 toward the hand-held side. Accompanying this, the other end 36b of the linking part 36 receives a rotational torque toward the base end side of the first sheath 3. The other end 36b side of the linking part 36 is rotated about the one end 36a by a predetermined angle in the direction away from the central axis C1 of the first sheath 3. As shown in FIGS. 6A and 8A, the support 37 rotates with respect to the first sheath 3, and opens. In this case, the position of the open/close handle 55 is fixed in place by the rack 53A of open/close operating part main body 53, and the position of the bending opening/closing wire 35 is thus fixed in place with respect to the first sheath 3.

When closing the first arm member 8A and the second arm member 8B with respect to the first sheath 3, the open/close handle 55 is advanced forward with respect to the open/close operating part main body 53, while pressing on the release button 55A of the open/close handle 55. At this time, the bending opening/closing wire 35 is advanced forward with respect to the front end side of the first sheath 3. Accompanying this, the rotational torque applied on the linking part 36 is released, and the other end 36b of the linking part 36 is rotated about the one end 36a of the linking part 36 in a direction toward the central axis C1 of the first sheath 3. As a result, the support 37 rotates with respect to the first sheath 3 and closes, i.e., resumes the starting state.

Figure 14:
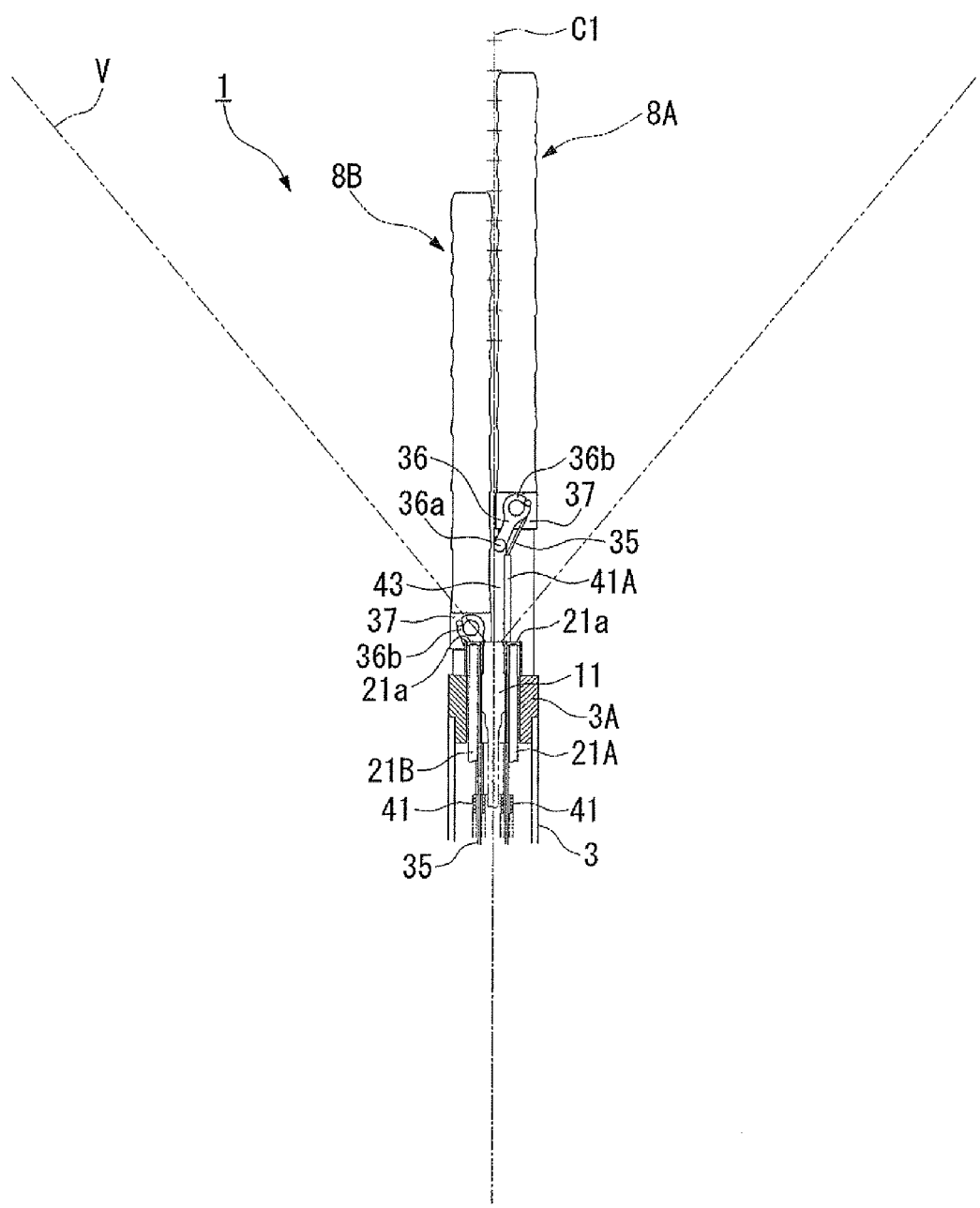
FIG. 14 is a view showing the state in which one of the arm members of the medical treatment endoscope according to the first embodiment has been moved forward with respect to the sheath.
Figure 15:
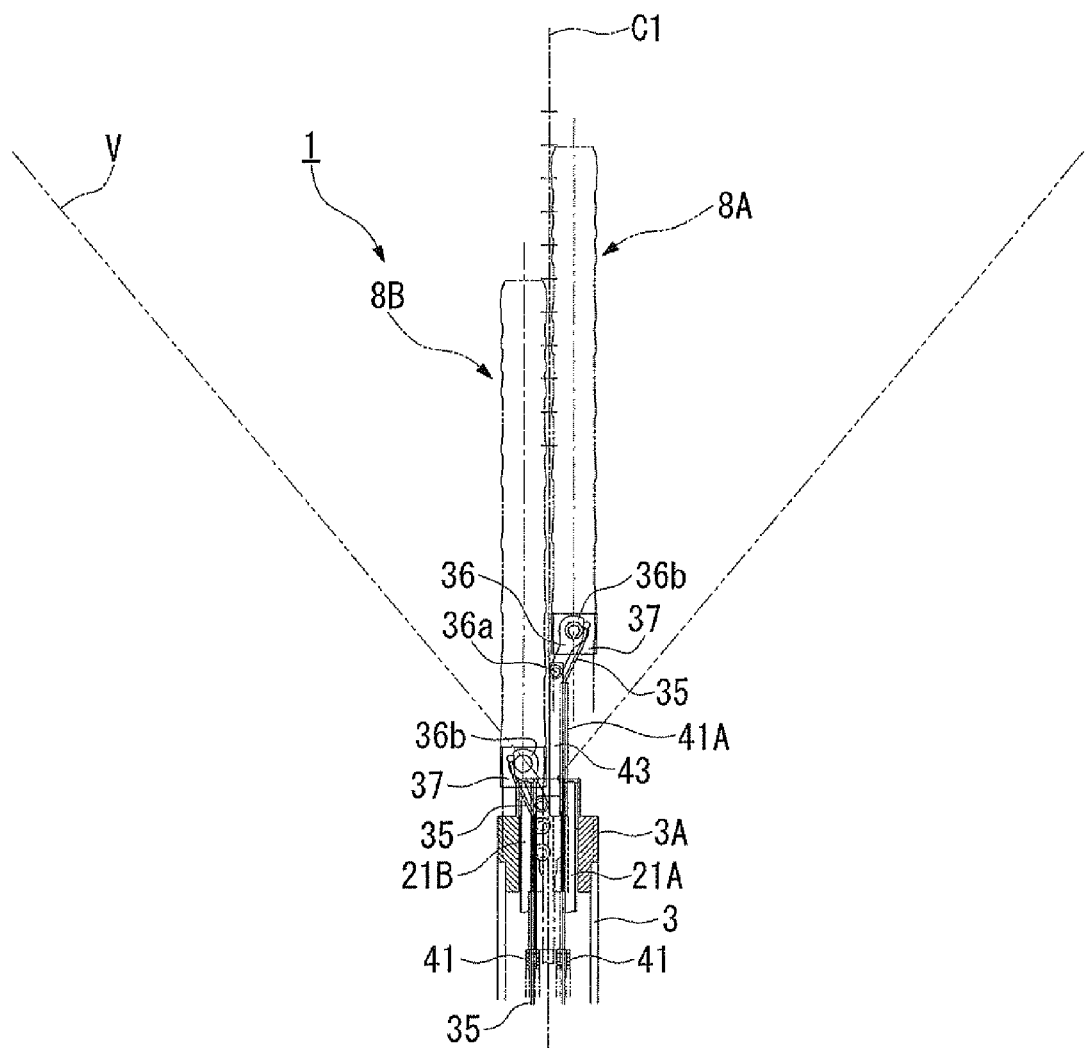
FIG. 15 is a partial perspective view of FIG. 14.
Figure 16:
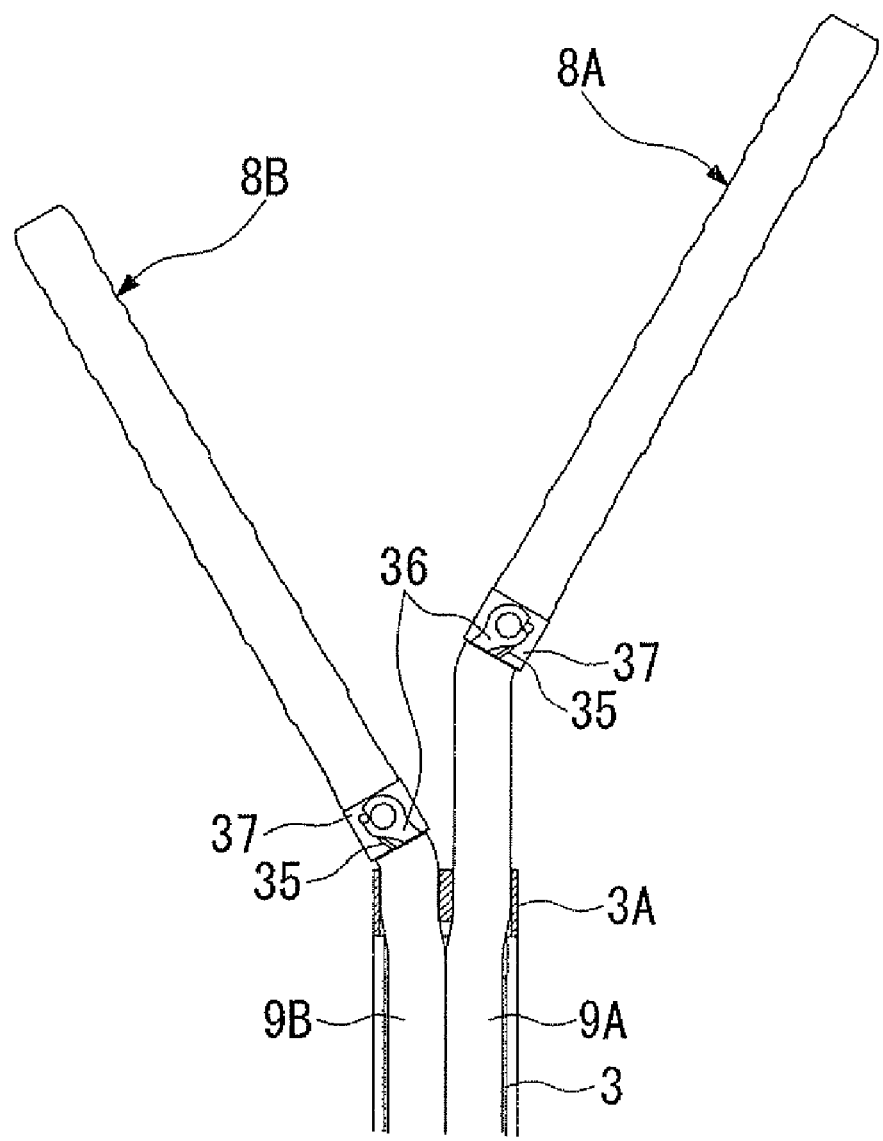
FIG. 16 is a view showing the state in which one of the arm members of the medical treatment endoscope according to the first embodiment has been moved forward with respect to the sheath, and further opened.
Figure 17:
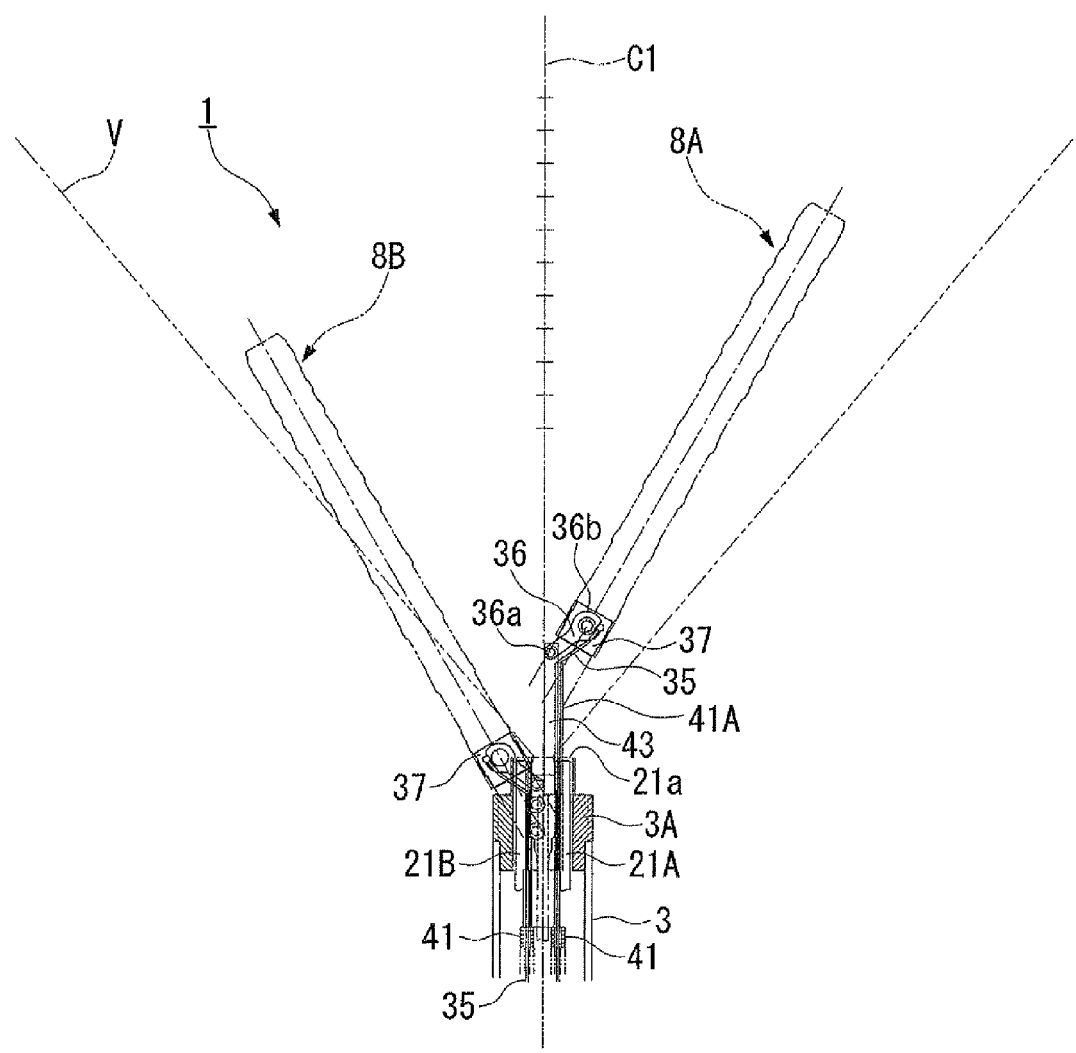
FIG. 17 is a partial perspective view of FIG. 16.

The moving frame 45A of the operating part 51 is advanced with respect to the fixed frame 45B, from the starting state shown in FIGS. 5A and 7A, when moving the first arm member 8A further toward the front end side of the first sheath 3. At this time, the base 77 advances along the slide rail 76, while the sliding member 43 of the open/close mechanism 10 moves forward with respect to the guide member 42. In this case, the entirety of the moving frame 45A moves, so that both the bending operating part 47 and the open/close operating part 46 move. Accordingly, there is no change in the open/close state and the bending state of the first arm member 8A. In this way, as shown in FIGS. 14 and 15, the first arm member 8A enters a state where it is advanced with respect to the first sheath 3.

In contrast, the moving frame 45A of the operating part 51 is retracted with respect to the fixed frame 45B when moving the first arm member 8A toward the hand-held side of the first sheath 3. At this time, the base 77 is retracted along the slide rail 76, while the sliding member 43 of the open/close mechanism 10 is retracted with respect to the guide member 42. As a result, the first arm member 8A is again disposed at the starting state position.

When bending the first arm member 8A and the second arm member 8B in the vertical direction, the vertical bending operating part 56 is manipulated. In other words, the forceps operating part 31 which is attached to the attachment part 58 is gripped and moved in the vertical direction. In this case, the attachment part 58 moves vertically within the limits of the second movement restricting member 61, while at the same time, the first movement restricting member 60 moves together with the attachment part 58 along the paired first bending guides 62A and 62B. Here, the first die part 63 also moves in the vertical direction, so that the first belt member 65 moves accompanying this, and the first gear 68 is rotated in either direction. At this time, the first chain belt 67 is rotated in either direction, and, accompanying this, one of the bending wires 17A and 17B is advanced with respect to the first sheath 3, while the other is retracted. In this way, the joint wheels 16 of the bending part 7 are inclined accompanying the movement of the bending wires 17A and 17B, and bend vertically.

In contrast, when bending the first arm member 8A and the second arm member 8B in the horizontal direction, the horizontal bending operating part 57 is manipulated. In other words, the forceps operating part 31 which is attached to the attachment part 58 is gripped and moved in the horizontal direction. In this case, the attachment part 58 moves horizontally within the limits of the first movement restricting member 60, while at the same time, the second movement restricting member 61 moves together with the attachment part 58 along the paired second bending guides 70A and 70B. Here, the second die part 71 also moves in the horizontal direction, so that the second belt member 72 moves accompanying this, and the second gear 75 is rotated in either direction. At this time, the second chain belt 73 is rotated in either direction, and, accompanying this, one of the bending wires 17C and 17D is advanced with respect to the first sheath 3, while the other is retracted. In this way, the joint wheels 16 of the bending part 7 are inclined accompanying the movement of the bending wires 17C and 17D, and bend horizontally.

When rotating the first sheath 3 with respect to the operating part 51, the rotation knob 81 of the rotation operating part 50 is gripped and rotated in the desired direction. As a result, the sheath connector 83 rotates relative to the rotation support 82, causing the first sheath 3 to rotate in the desired direction relative to operating part 51.

Figure 18:
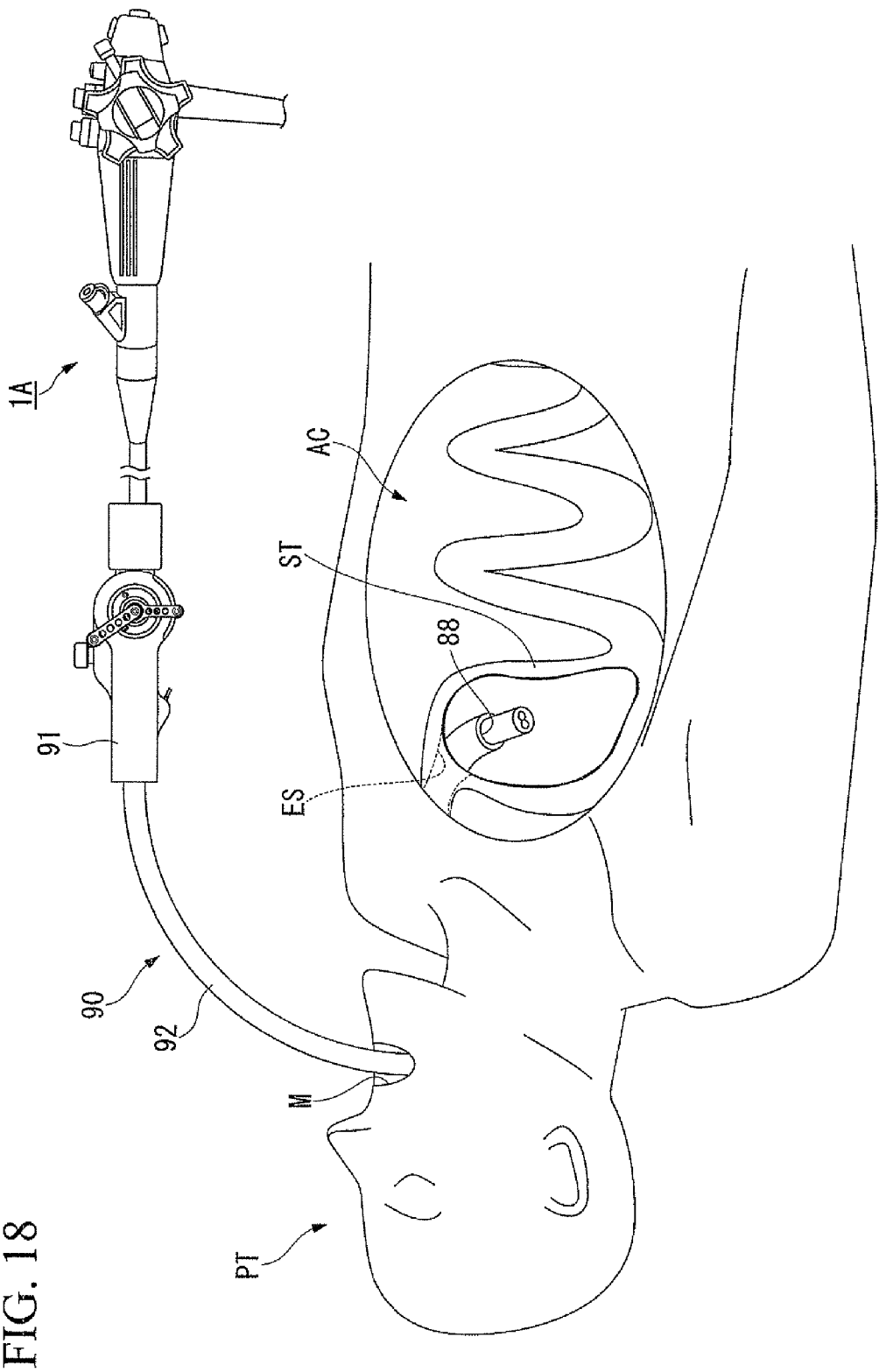
FIG. 18 is a view explaining the state in which the endoscope has been inserted into an over-tube, and then inserted into the stomach, in an operative procedure using the medical treatment endoscope according to the first embodiment.

Next, an explanation will be made with reference to FIGS. 18 through 20 of an operative procedure performed via a natural orifice using the medical treatment endoscope 1. Note that the following explanation concerns the technique of inserting the medical treatment endoscope 1 from the mouth M of a patient PT into the stomach ST, opening a hole in the wall of the stomach, and then carrying out a procedure by inserting the first sheath 3 of the medical procedure endoscope 1 into the abdominal cavity AC. In the case of the present embodiments, a predetermined procedure is performed by inserting a high frequency knife 85 into the first arm member 8A, and a gripping forceps 85 into the second arm member 8B.

The patient PT is placed on his/her back, and a typical endoscope 1A is introduced into the open-ended lumen 88 of an over-tube 90 from the base end 91 of the over-tube 90. This open-ended lumen 88 extends along the axial direction of the over-tube 90. The over-tube 90 is then inserted from the mouth M of the patient PT into the esophagus ES, and positioned in the stomach ST as shown in FIG. 18.

Next, the stomach ST is inflated by relaying air into it, after which an opening SO is formed in the stomach wall by excision. The insertion part 92 of the over-tube 90 and the endoscope 1A are introduced into the abdominal cavity AC via the opening SO. Next, the endoscope 1A is withdrawn from the over-tube 90, and the first sheath 3 of the medical treatment endoscope 1 is inserted in its place into the lumen 88 of the over-tube 90, so as to project out from the front end of the over-tube 90.

As an example here, the case will be explained where a high-frequency knife 85 is inserted into the second sheath 9A and the first arm member 8A. First, the high-frequency knife 85 is inserted into the instrument insertion channel 6, and the front end of the high-frequency knife 85 comes into contact with the bumper 15a that is provided at the front end part 15 of the first arm member 8A. The front end of the high-frequency knife 85 is urged toward the bumper 15a by pushing the high-frequency knife 85 further in from the base end side, so that the knife operating part, not shown, of the high-frequency knife attaches into the attachment part 58 of the operating part 51. In this way, advancing and retracting of the high-frequency knife 85 with respect to the first arm member 8A is restricted. Note that the high-frequency knife 85 is supported to enable free rotation with respect to the first arm member 8A and the operating part 51.

Figure 19:
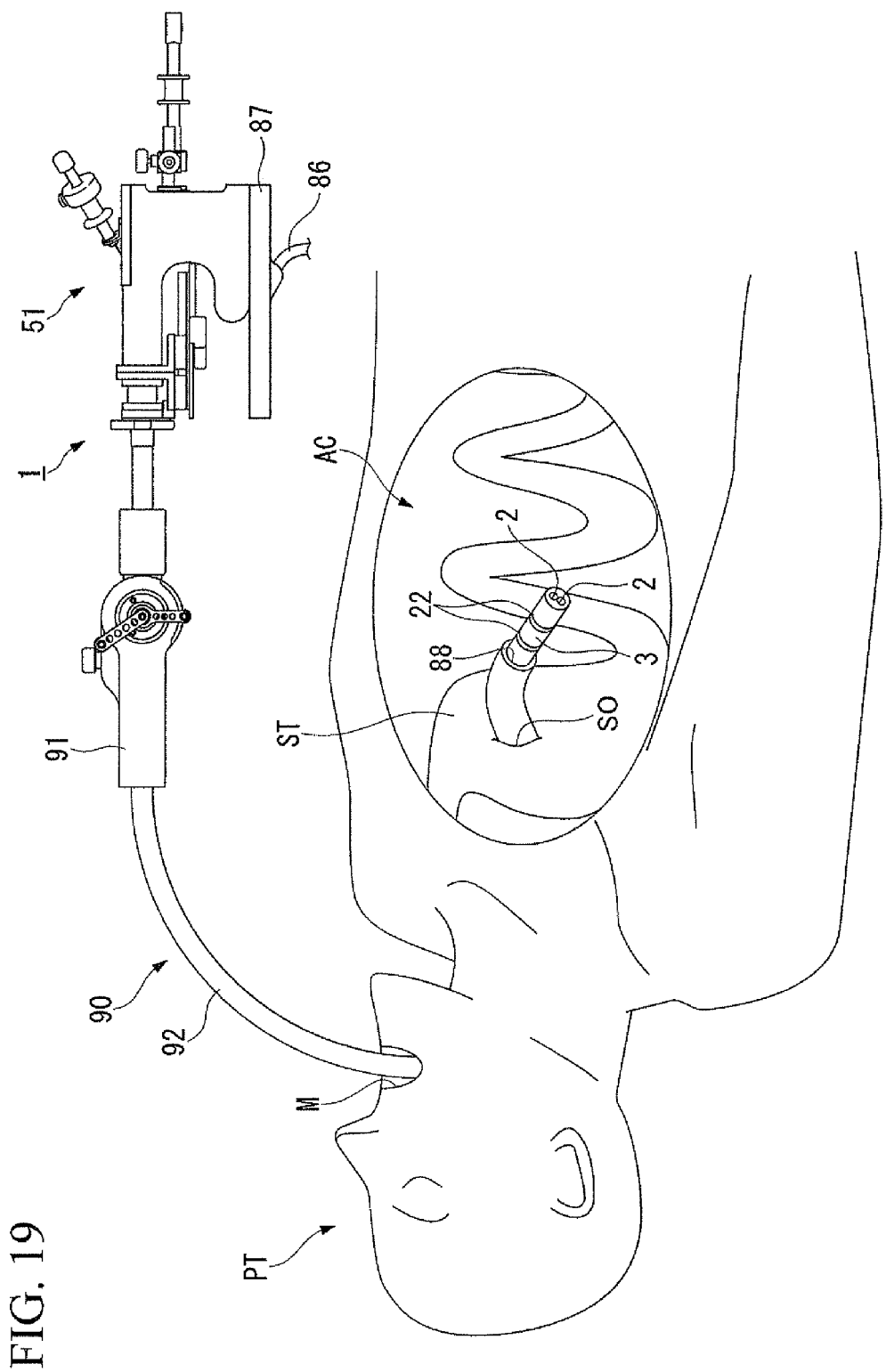
FIG. 19 is a view explaining the state in which the endoscope has been inserted into an over-tube, and then inserted from the stomach into the abdominal cavity, in an operative procedure using the medical treatment endoscope according to the first embodiment.

As shown in FIG. 19, the operating part 51 of the medical treatment endoscope 1 is mounted in a manner to enable sliding to a mount 87 that is disposed at a scope holder 86 which is attached to a bed not shown in the figures.

Figure 20:
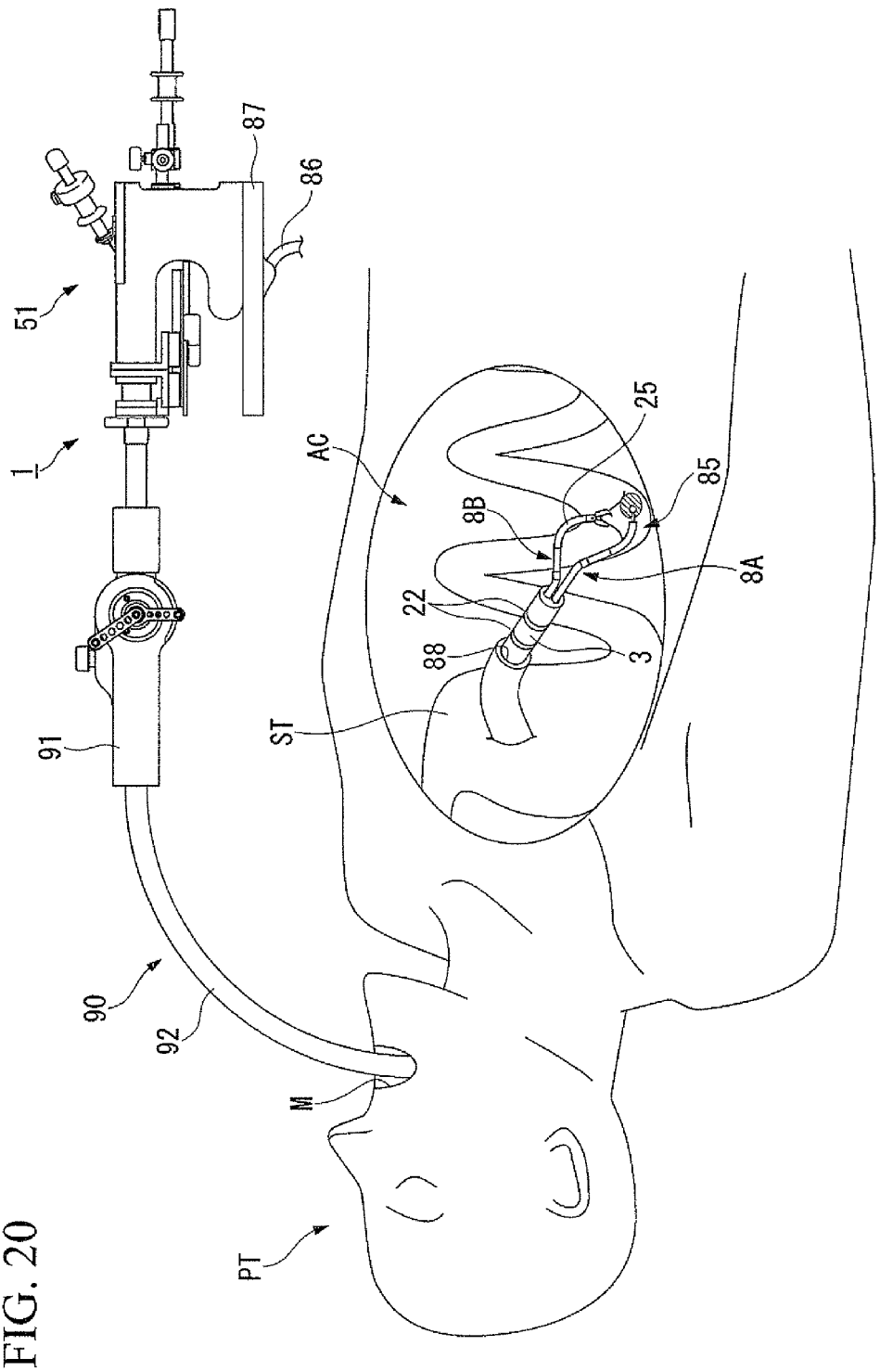
FIG. 20 is a view explaining the state in which the procedure is carried out inside the abdominal cavity, in an operative procedure using the medical treatment endoscope according to the first embodiment.

After positioning, the operations of opening/closing, bending, and advancing/retracting of the first arm member 8A and the second arm member 8B are carried out according to the desired procedures, to perform a predetermined procedure, as shown in FIG. 20. After the procedure is carried out, the medical treatment endoscope 1 is withdrawn back into the stomach ST from the opening SO in the stomach wall, and then removed from the mouth M of the patient PT.

For example, a case for gallbladder extraction will be explained.

A cervical part or bottom part of a gallbladder is grasped and retracted with a grasping forceps 5 inserted through the second arm member 8B to expose a Calot trigone.

The serous membrane of the cervical part of the gallbladder is excised a little at a time with a high frequency knife 85 inserted through the first arm member 8A. A retracting direction exerted by the grasping forceps 5 inserted through a second arm member 8B is adjusted in order to apply appropriate tensions to the excised part. Meanwhile, adipose tissue and fiber tissue including the serous membrane are peeled with the high frequency knife 85 from the cervical part of the gallbladder to the cystic duct.

After identifying the cystic duct, the periphery is totally peeled. Similarly, arteria cystica is identified and its periphery is totally peeled. Consequently, the treatment instruments used in the first arm member 8A are exchanged for a clip, which is not shown in the drawings, and the cystic duct in the vicinity of the cervical part of the gallbladder is clipped.

After replacing the treatment instruments at the first arm member 8A with the high frequency knife 85 or a pair of scissors which is not shown in the drawings, a half of the cystic duct is incised so as to observe bile outflow. Consequently, the treatment instruments used in the first arm member 8A are exchanged for an imaging tube, which is inserted into the cystic duct. After confirming the absence of a stone in the bile duct, the clip is re-applied to the first arm member 8A to double-clip the bile duct. The clip at the first arm member 8A is replaced by the high frequency knife 85 to incise the cystic duct.

A portion in the vicinity of the gallbladder and two portions in the vicinity of the nerve center are clipped by a similar method of incising the arteria cystica and the cystic duct. The arteria cystica is thus incised. The margin of the cystic duct is grasped and retracted by the grasping forceps 5 at the second arm member 8B, and the gallbladder is peeled from a gallbladder bed by operating the high frequency knife 85 attached to the first arm member 8A.

While grasping the gallbladder between the grasping forceps attached to the second arm member 8B, the medical treatment endoscope 1 is extracted from the overtube 90 to take out the liberated gallbladder. In the case of a somewhat a larger gallbladder, the bile in the gallbladder may be sucked into a smaller volume with a hollow needle which is not shown in the drawings. In addition, prior to taking out the gallbladder from the body, the medical treatment endoscope 1 may be extracted from the overtube 90, and an organ-container pouch, not shown in the drawings, grasped by the grasping forceps 5 attached to the second arm member 8B may be reinserted to contain the gallbladder.

In addition to the previously explained gallbladder extraction, the medical treatment endoscope according to the present invention can be used for various manipulations, e.g., appendectomy, gastroduodenal bypass, liver biopsy, biopsy of the pancreas, tubal interruption, and hysterectomy.

After the abdominal cavity having been treated is suitably irrigated, the medical treatment endoscope 1 is retracted into the stomach ST via the wall of the opening SO. After releasing the pressure applied to the abdominal cavity AC, the medical treatment endoscope 1 is taken out of the mouth M of the patient PT.

The opening SO formed on the wall of the stomach is sutured, and the overtube 90 and the medical treatment endoscope 1 are subsequently extracted from the patient; thus, the manipulation is completed.

According to the medical treatment endoscope 1, the open/close mechanism 10 can be used to move the central axis C1 of the first arm member 8A and the second arm member 8B, which are respectively inserted into the first lumen 2 of the first sheath 3, away from the central axis C1 of the first sheath 3, further bending the bending part 7 of the first arm member 8A and the second arm member 8B. As a result, even if an instrument device such as the gripping forceps 5 is inserted into the instrument insertion channel 6, the hand-held side of the first arm member 8A and the second arm member 8B bend with respect to the front end side of the first sheath 3. Thus, the inclination of the instrument device can be deviated from the line of vision V of the image pick-up unit 11 that is disposed to the sheath front end part 3A of the first sheath 3. Accordingly, it is possible to visually confirm the front end side of the first arm member 8A and the second arm member 8B with sufficient confirmation of the line of vision V of the image pick-up unit 11. As a result, the medical procedure can be carried out safely and assuredly.

In this case, the axial force generated by advancing and retracting the bending opening/closing wire 35 with respect to the first sheath 3 can be converted through the linking part 36 of the open/close mechanism 10 into the force for opening and closing the first arm member 8A and the second arm member 8B. As a result, the first arm member 8A and the second arm member 8B can be opened or closed with respect to the central axis C1 of the first sheath 3. In particular, when opening the first arm member 8A and the second arm member 8B, the bending opening/closing wire 35 is pulled toward the hand-held side. Accordingly, it is possible to adjust the transmission of force to the bending part 7, and to finely adjust the opening angle of the first sheath 3 with respect to the central axis C1. In addition, in the case where it has been designed that the first arm member 8A and the second arm member 8B will have a suitable angle of opening with respect to the central axis C1 by means of at once pulling the open/close handle 55 toward the hand-held side until it comes into contract with the open/close operating part main body 53, it is possible to simplify the open/close operation of the first arm member 8A and the second arm member 8B.

In addition, it is possible to operate the open/close mechanism 10 by operating the open/close operating part 46 of the operating part 51 to advance and retract the bending opening/closing wire 35 with respect to the first sheath 3. In addition, by performing operations with the forceps operating part 31 for the gripping forceps 5 in a state of attachment to the bending operating part 47, it is possible to carry out not only the opening/closing operation of the pair of forceps pieces 26A and 26B of the gripping forceps 5, but also carry out the bending operation of the bending part 7, thus facilitating the procedure.

Furthermore, by sliding the moving frame 45A with respect to the fixed frame 45B in the advance/retract operating part 48, it is possible to carry out the advance/retract operation of the first arm member 8A and the second arm member 8B with respect to the first sheath 3 by advancing or retracting the sliding member 43 with respect to the guide member 42. Accordingly, the treatment scope of the gripping forceps 5 with respect to the first sheath 3 can be expanded.

Furthermore, by rotating the rotation knob 81 of the rotation operating part 50, the first sheath 3 can be rotated along with the first arm member 8A and the second arm member 8B from the base end side of the first sheath 3, and the opening/closing direction of the first arm member 8A and the second arm member 8B with respect to the first sheath 3 can be changed. Note that when it is desired to rotate a single instrument, then rotation to the desired state can be achieved by rotating the forceps operating part 31 with respect to the attachment part 58.

Because it is possible to use the support 37 of the open/close mechanism to support the first arm member 8A and the second arm member 8B farther toward the base end side than the bending part 7, the entirety of the bending part 7 can be used in the bending action, regardless of whether performing the open/close operation or the bending operation. Thus, the degree of freedom of the arm can be improved. Conversely, when the support 37 is provided along the bending part 7, the degree of freedom of each of the arm members is decreased, however, a greater force can be delivered. In addition, by manipulating the bending part 7 of the first arm member 8A and the second arm member 8B, which has a larger diameter than the diameter of the instrument insertion channel 6, the instrument can be more easily bent, and the procedure performed, than in the case where inserting a single instrument having bending capabilities through the instrument insertion channel 6 and then bending the instrument.

In addition, since the bending part 7 is employed only for bending an instrument such as the gripping forceps 5 or the like, it is possible to achieve greater bending, and output a greater force, as compared to a design that requires bending of a plurality of objects such as instruments, video cables (image guides in optical endoscopes), light guides and the like, such as seen in conventional endoscopes.

Second Embodiment

A second embodiment will now be explained with reference to the figures.

The second embodiment differs from the first embodiment with respect to the point that both the first arm member 8A and the second arm member 8B of a medical treatment endoscope 100 according to this embodiment are designed to advance and retract with respect a sheath 101.

Figure 21:
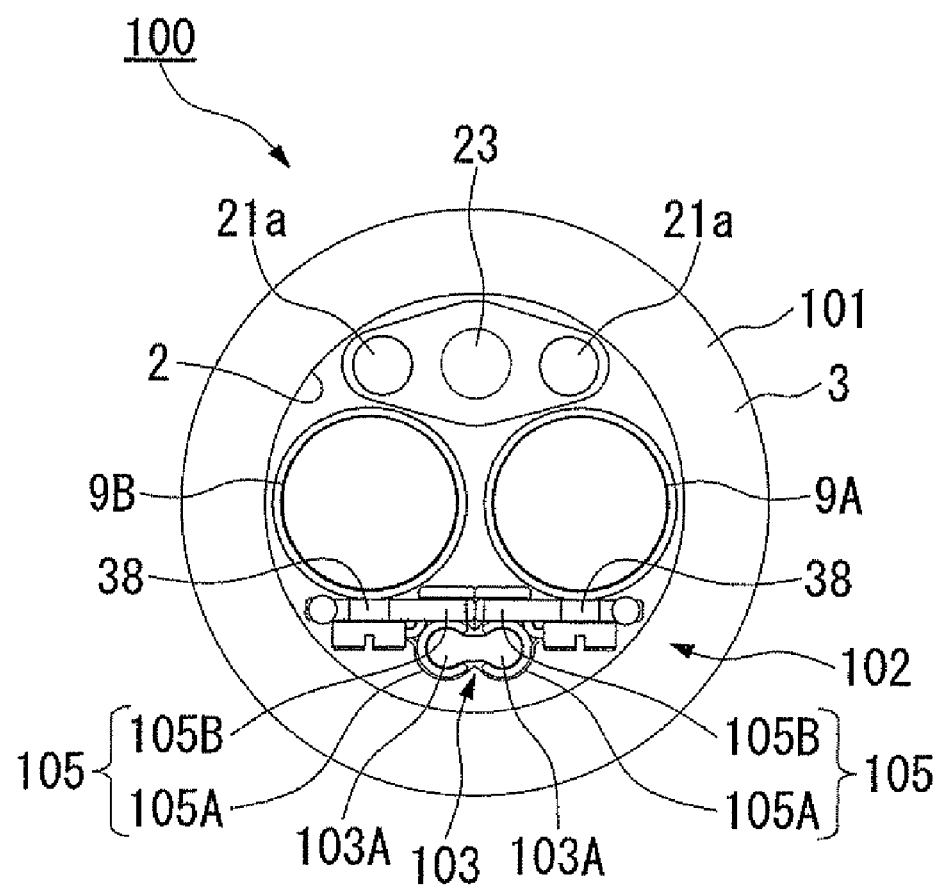
FIG. 21 is a view of the front end of the medical treatment endoscope according to the first embodiment.

Namely, as shown in FIG. 21, roughly cylindrical engaging convexities 103A are disposed at either end of a guide member 103 for an advance/retract mechanism 102, along the width direction of the guide member 103. The first arm member 8A and the second arm member 8B are connected to a sliding member 105 that has an engaging concavity 105A for engaging in a freely sliding manner with the engaging convexities 103A via a connector 105B.

As in the case of the moving frame 45A of the operating part 51 according to the first embodiment, this operating part is designed so that the open/close operating part 46 and the bending operating part 47 of not only the first arm member 8A, but also the second arm member 8B, are capable of movement with respect to the fixed frame.

Next, the effects of this embodiment will be explained. Note that the case when opening and closing the first arm member 8A and the second arm member 8B with respect to the sheath 101, the case when bending the first arm member 8A and the second arm member 8B, and the case when rotating the sheath 101, provide the same effects as those of the first embodiment.

The case when advancing or retracting the first arm member 8A and the second arm member 8B with respect to the sheath 101, as well, provides the same effects as in the case when advancing or retracting the first arm member 8A with respect to the fixed frame 45B in the first embodiment. In other words, when moving both the first arm member 8A and the second arm member 8B farther toward the front end side of the sheath 101, each of the moving frames of the operating part to which the first arm member 8A and the second arm member 8B are respectively connected is advanced with respect to the fixed frame. At this time, as in the first embodiment, the base at the operating part is advanced along the slide rail, while the sliding members 105 of the advance/retract mechanism 102 each advance with respect to the guide member 103. In this way, the first arm member 8A and the second arm member 8B are advanced with respect to the sheath 101.

On the other hand, when moving the first arm member 8A and the second arm member 8B toward the hand-held side of the sheath 101, the respective moving frames are retracted with respect to the fixed frame. At this time, the base is retracted along the slide rail, while the sliding members 105 are retracted with respect to the guide member 103. In this way, the first arm member 8A and the second arm member 8B are once again disposed at the starting state position.

The medical treatment endoscope 100 of this embodiment offers the same actions and effects as described in the first embodiment. In particular, since the first arm member 8A and the second arm member 8B are advanced and retracted with respect to the sheath 101, it is possible to ensure a wider line of vision V for the image pick-up unit 11. Furthermore, the approach angle for instruments such as gripping forceps and the like can be adjusted to a more suitable position. In addition, it is possible to increase the operating stroke for the gripping forceps, etc.

The technical scope of the present invention is not limited to the embodiments described above. Rather, various modifications may be added provided that they do not depart from the spirit of the invention.

For example, the arm members are not limited to two; rather, three or more arm members may be provided. It is also acceptable to design the front end of the second arm member so as to enable relative displacement of the gripping forceps in the advancing/retracting direction with respect to the second arm member. In addition, while an illuminating member for radiating illuminating light on the target object was formed using the light guides 21A and 21B and an illuminating lens 21a, it is also acceptable to provide an illuminating member by disposing a light emitting element, an LED for example, to the sheath front end part 3A.

Third Embodiment

An eighth embodiment will now be explained with reference to the figures. The medical treatment endoscope according to this embodiment represents a further improvement over the medical treatment endoscope according to the first embodiment.

Figure 22:
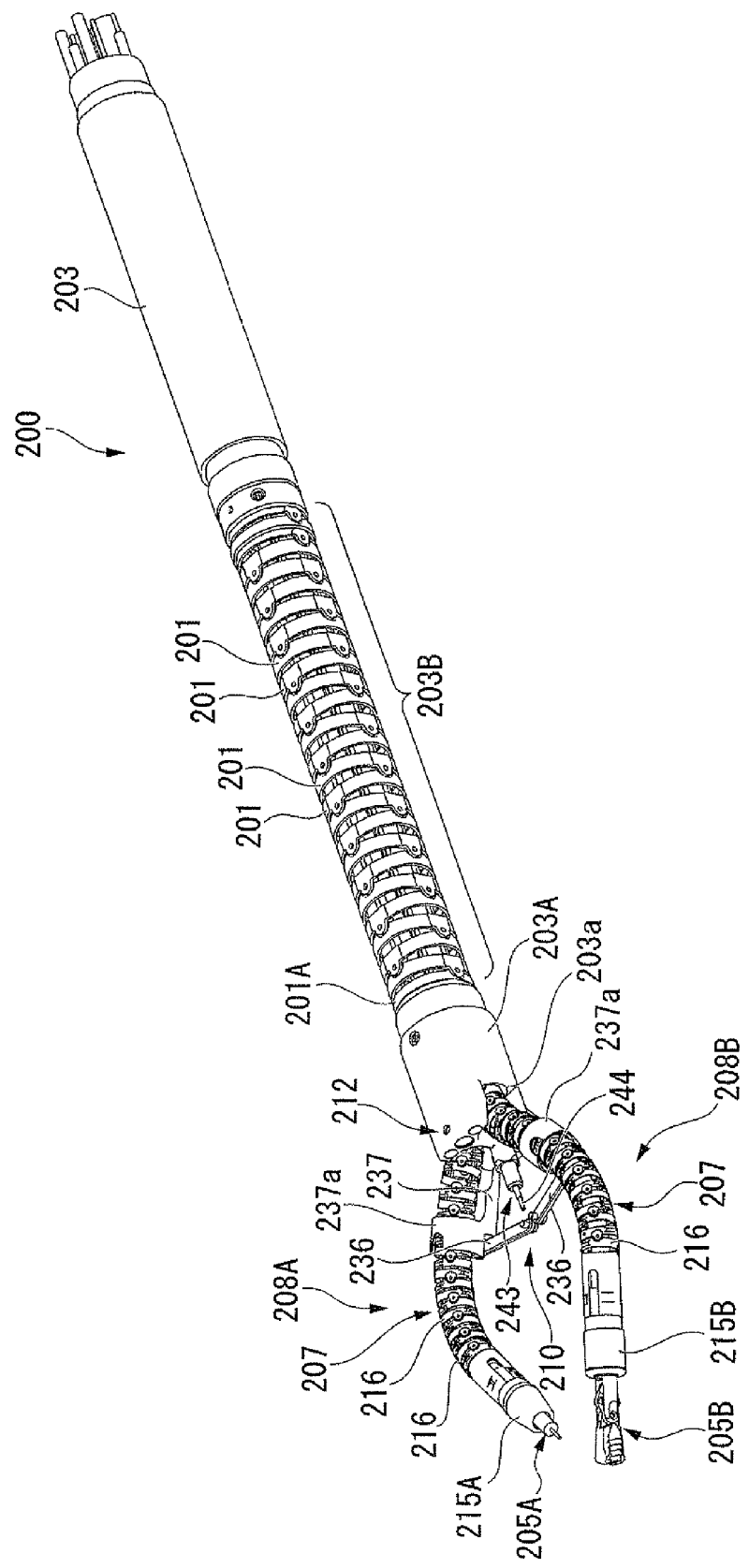
FIG. 22 is a view showing the structure of the medical treatment endoscope according to the third embodiment.

As shown in FIG. 22, and similar to the medical treatment endoscope 1 according to the first embodiment, a medical treatment endoscope 200 is provided with a first arm member 208A and a second arm member 208B that can be opened and closed. Instruments are provided at the front end parts of these first and second arm members 208A and 208B. FIGS. 22 through 25 are views showing the front end part of the endoscope in the case where the arm members 208A and 208B are spread open. FIGS. 26 through 29 are views showing the front end part of the endoscope in the case where the arm members 208A, 208B are closed. Note that in FIGS. 23 through 28, the bending parts 203B and 207 are shown with the joint wheels 201 and 216 that form these bending parts 203B and 207 covered by cover members.

Figure 30:
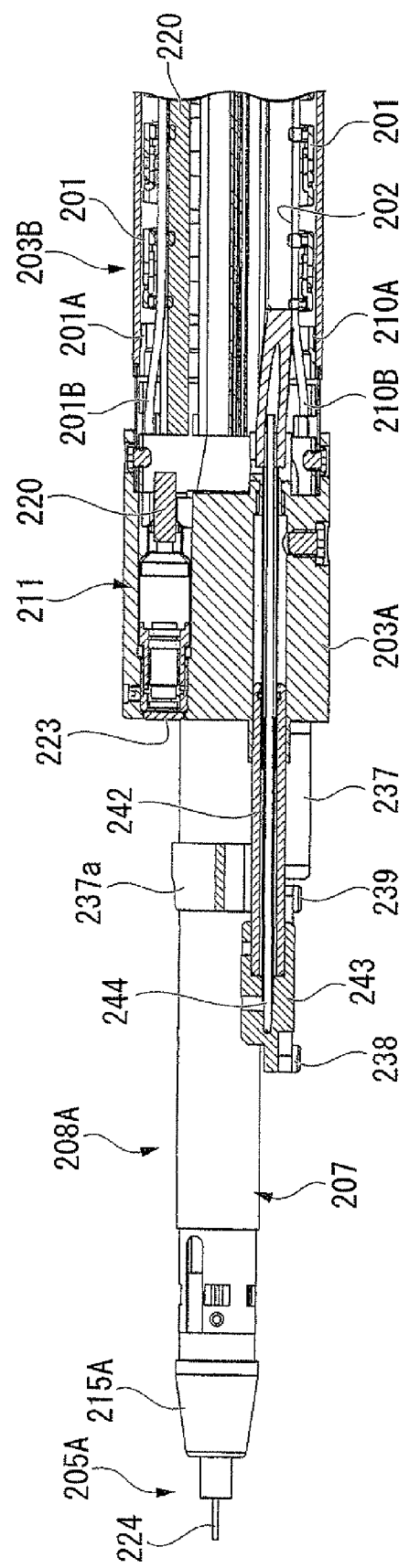
FIG. 30 is a cross-sectional view along line II-II in FIG. 26.
Figure 31:
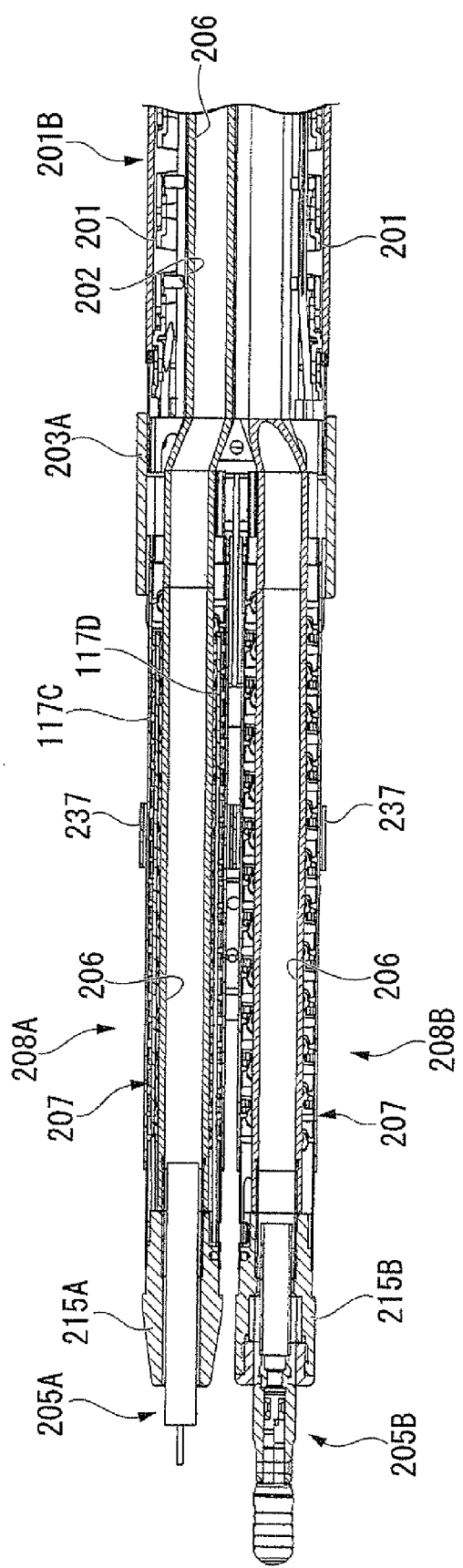
FIG. 31 is a cross-sectional view along line III-III in FIG. 27.
Figure 32:
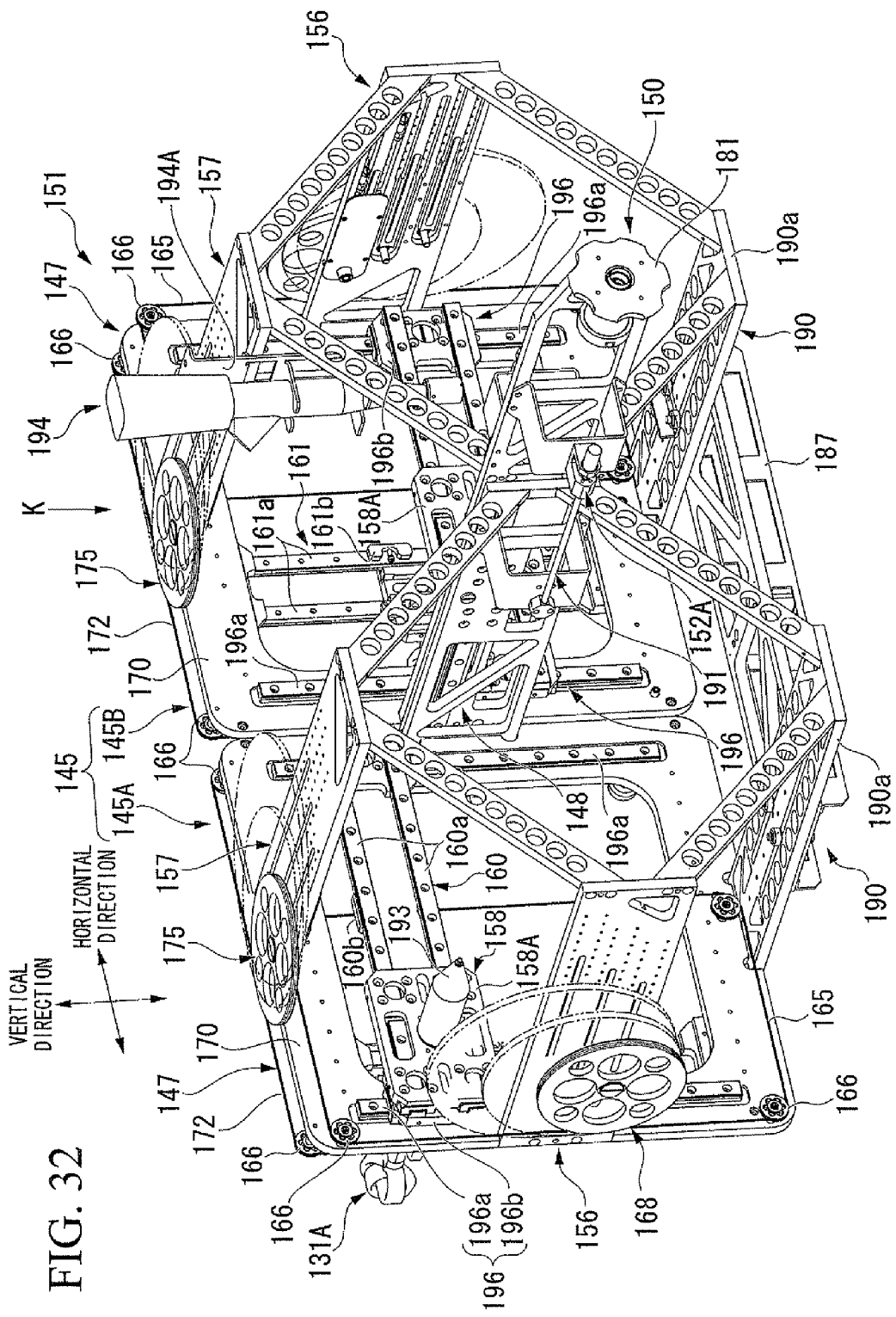
FIG. 32 is a perspective view showing the operating part of the medical treatment endoscope according to the first embodiment.
Figure 33:
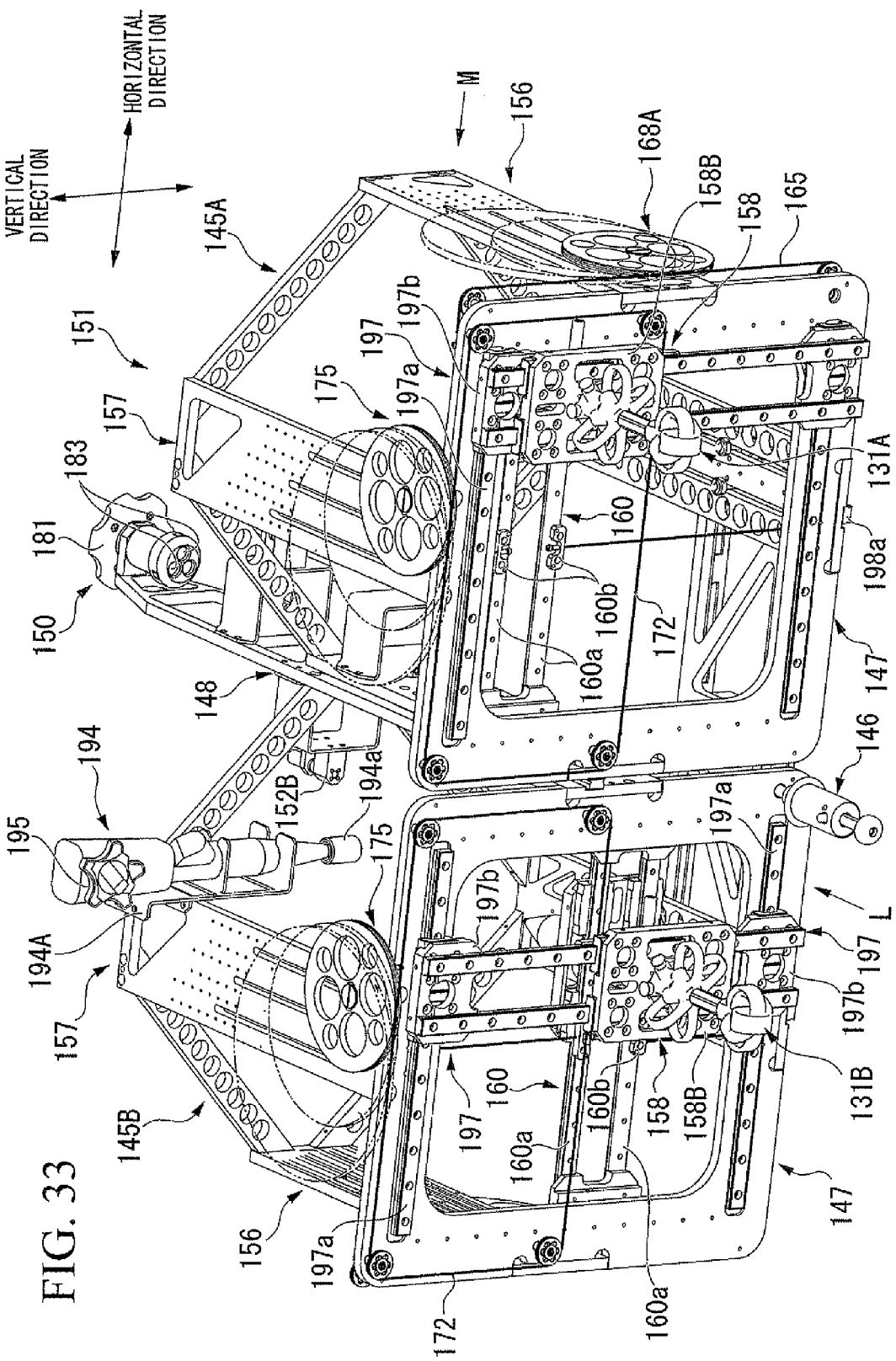
FIG. 33 is a perspective view showing the operating part of the medical treatment endoscope according to the first embodiment.

The medical treatment endoscope 200 according to this embodiment is provided with a first sheath 203 having flexibility, a sheath front end part 203A having rigidity which is provided at the front end of the first sheath 203, and a bending part 203B that is provided at a base end of the sheath front end part 203A. Openings are provided at front ends of the first sheath 203 and the bending part 203B. As shown in FIGS. 30 and 31, these openings form a first lumen 202 through which the first arm member 208A (a second sheath), the second arm member 208B (a third sheath), a video cable 220 and the like, are inserted. Furthermore, the sheath front end part 203A which is provided at the open end of the bending part 203B has an opening 203a through which the first arm member 208A and the second arm member 208B are respectively passed.

As in the case of the typical flexible endoscope, the bending part 203B is constructed such that a plurality of joint wheels 201 are continuous along the direction of the central axis of the first sheath 203 and are axially supported to enable mutual rotation, and four bending wires 201B are connected to the most distal joint wheel 201A and extend along the inside of the bending part 203B. These four bending wires 201B are each passed through the joint wheels 201 at positions so as to divide a circumferential periphery of the joint wheels 201 into quarters, and are passed through a bending wire coil that is provided inside the first sheath 203.

As shown in FIG. 31, the first arm member 208A and the second arm member 208B are provided at the sheath front end part 203A. An instrument insertion channel (a second lumen) 206, through which instruments such as gripping forceps 205B are inserted and which is open at the distal end, and a bending part 207, which projects out from the sheath front end part 203A and carries out bending operations, are disposed at each of these arm members 208A and 208B respectively. Openings 203a for enabling advance of the bending parts 207 in the lateral direction are provided on each side of the sheath front end part 203A where the first arm member 208A and the second arm member 208B are disposed. The bending part 207 is equipped with the same structure as the bending part 7 shown in FIG. 1. Namely, a plurality of joint wheels 216 are mutually axially supported to enable rotation, and are connected along the direction of the central axes of the first arm member 208A and the second arm member 208B. Furthermore, as in the case of the preceding bending part 7, bending wires 117A, 117B, 117C, and 117D extended along the inside of the bending part 207 are connected to the joint wheel 216 that is disposed farthest toward the front end. The bending wires 117A, 117B, 117C, and 117D are each inserted into and pass through the joint wheels 216 at positions so as to divide a circumferential periphery of the joint wheels 216 into quarters.

A tubular front end part 215A is attached to the front end of the bending part 207 of the first arm member 208A. The front end part 215A having an opening communicates with the instrument insertion channel 206. A high-frequency scalpel 205A projects out from the open end of the front end part 215A. And a gripping forceps 205B projects out from the open end of the front end part 215B that is attached to the second arm member 208B. The base ends of the high-frequency scalpel 205A and the gripping forceps 205B are connected to an instrument insertion part 125 which is inserted inside the instrument insertion channel 206. The high-frequency scalpel 205A is provided with a needle-shaped high-frequency knife 224 at its end that is capable of impressing high frequency power. The gripping forceps 205B has the same construction as the gripping forceps 5 according to the preceding first embodiment, and is provided with a pair of forceps pieces 226A and 226B capable of opening and closing operations via a forceps linking part 228.

In the case of this embodiment, the high frequency scalpel 205A and the gripping forceps 205B are not restricted from advancing and retracting at the front end parts 215A and 215B. Accordingly, the high frequency scalpel 205A and the gripping forceps 205B can be advanced and retracted with respect to the front end parts 215A and 215B by the advancing/retracting operation of the instrument insertion part 125 that is inserted into the instrument insertion channel 206. According to this mechanism, instruments such as the high-frequency scalpel 205A, gripping forceps 205B, etc. can be advanced or retracted with respect to an affected part regardless of the bending state of the first arm member 208A and the second arm member 208B.

Figure 23:
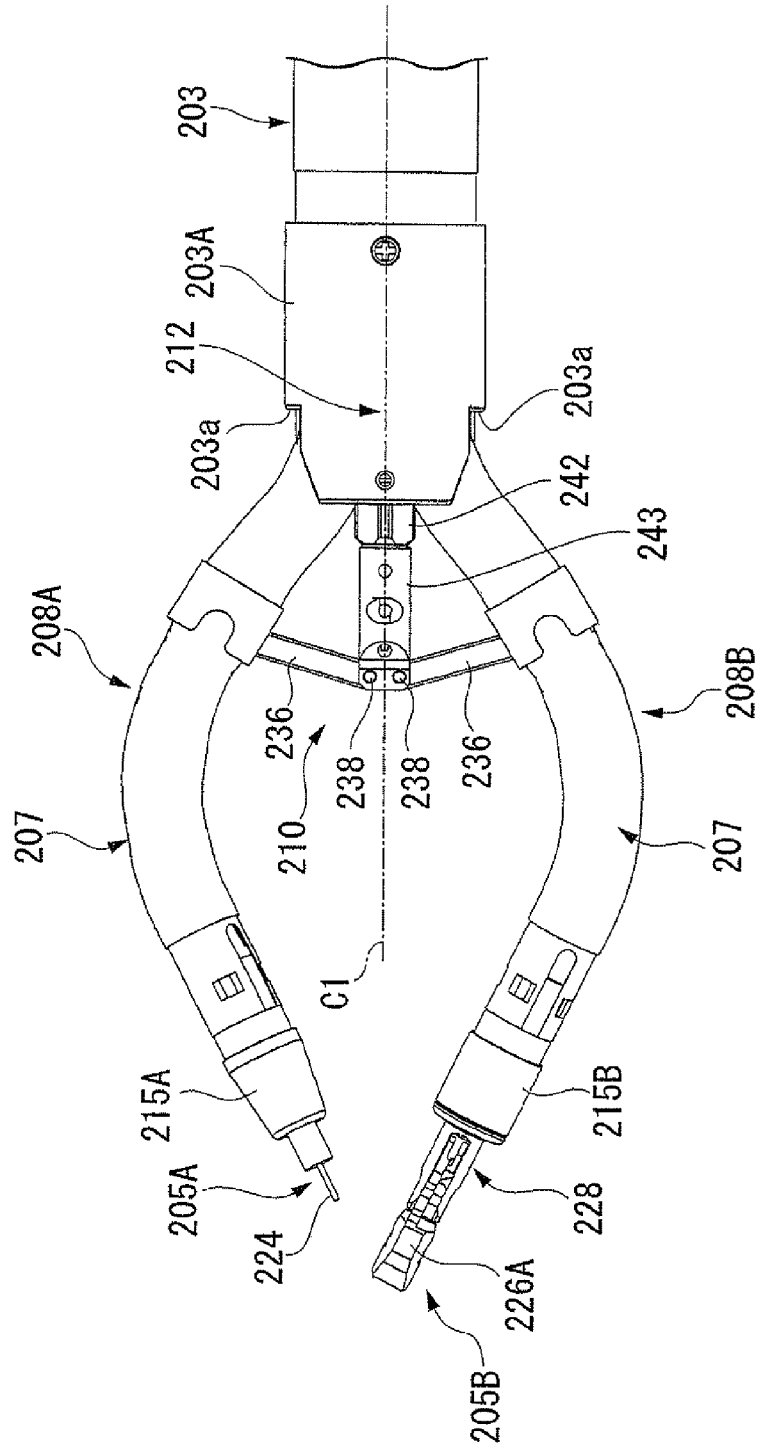
FIG. 23 is a plan view showing the structure of the front end of the medical treatment endoscope according to the third embodiment.
Figure 24A:
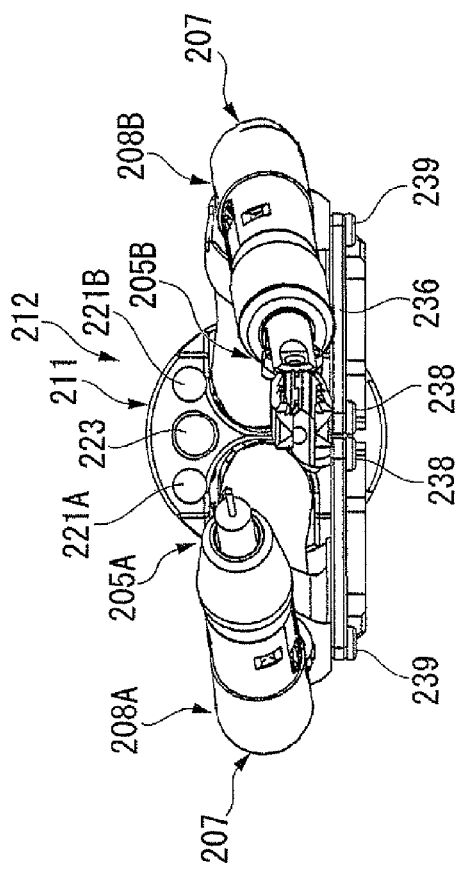
FIG. 24A is a view of the front end of the medical treatment endoscope according to the third embodiment, along the H direction.
Figure 24B:
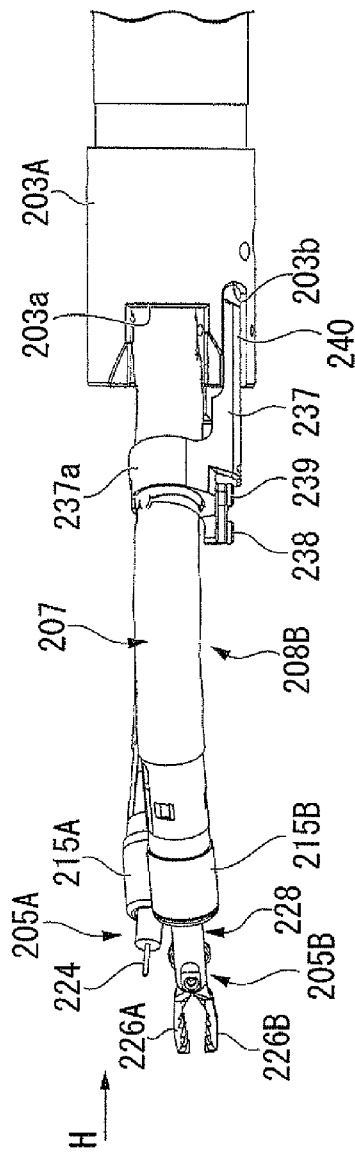
FIG. 24B is a side view of the medical treatment endoscope according to the third embodiment.
Figure 25:
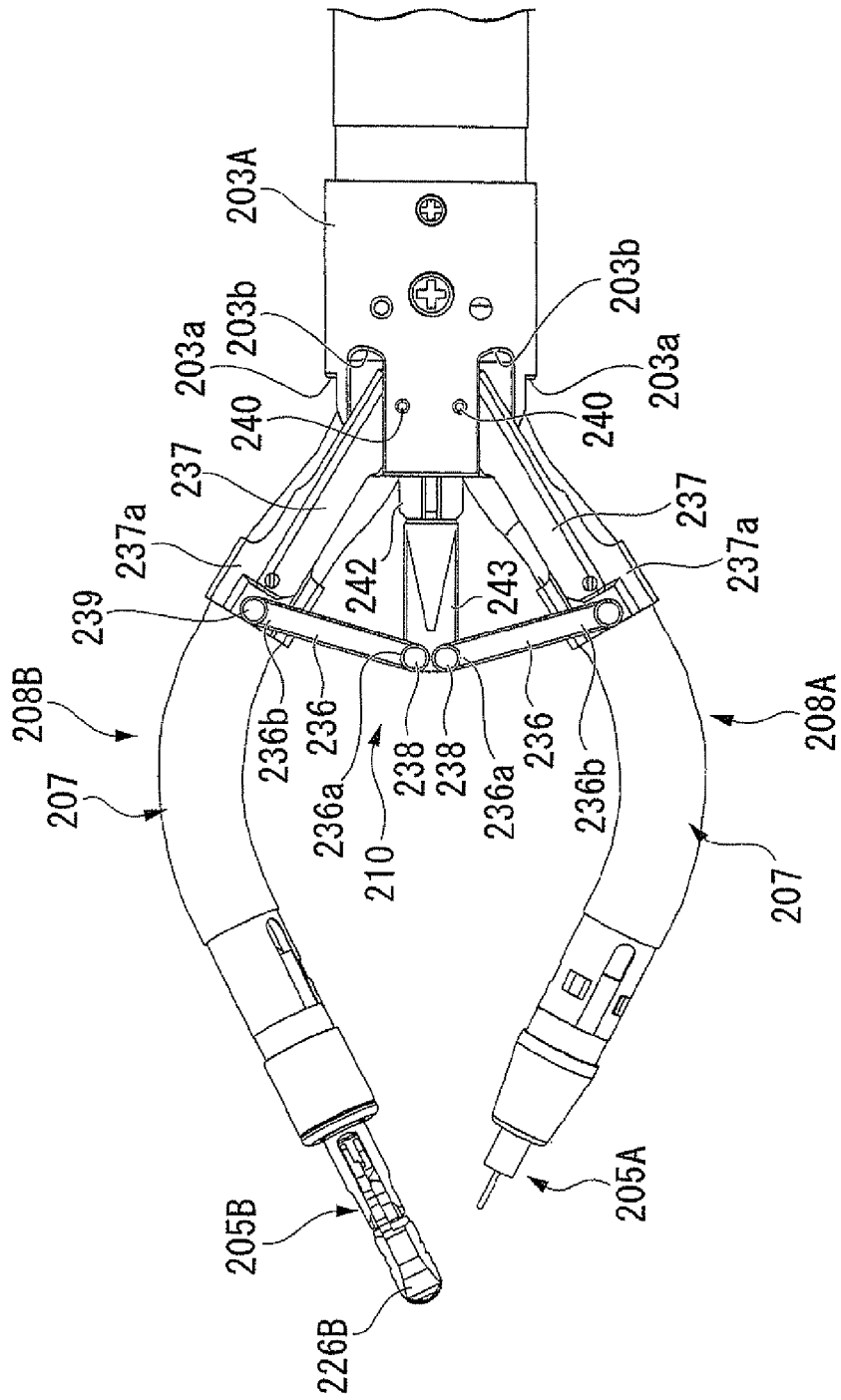
FIG. 25 is an underside view showing the structure of the front end of the medical treatment endoscope according to the third embodiment.

As shown in FIGS. 23 through 25, an open/close mechanism 210 for moving the first arm member 208A and the second arm member 208B in the directions that cause them to mutually separate or to mutually come closer together, and a viewing device 212, are provided at the sheath front end part 203A.

As shown in FIGS. 22, 23 and 25, the open/close mechanism 210 is provided with an open/close operating part 243 (a portion of which has been omitted in FIG. 22 to facilitate viewing of the figure), which is capable of advancing and retracting with respect to the first sheath 203; a sliding member 242 which supports the open/close operating part 243 and slides inside the sheath front end part 203A; two linking parts 236 to which the open/close operating part 243 is connected; and a support 237 which is connected to each of the linking parts 236 while at the same time supporting the first arm member 208A and the second arm member 208B.

The linking part 236 is formed as a plate-shaped member, the thickness and width dimensions thereof being determined so as to obtain the desired rigidity. The support 237 is constructed so that its base end side is supported to enable free rotation about a support axis 240 at the sheath front end part 203A, and to grip the first arm member 208A with link-shaped gripping members 237a that are provided at its front end side. In this way, both the first arm member 208A and the second atm member 208B are fixed in place by the gripping parts 237a of the supports 237 extending from the sheath front end part 203A, and cannot advance or retract with respect to the first sheath 203. An opening 203b is formed in the sheath front end part 203A that supports the base end side of the supports 237, for enabling advance of the supports 237 in the lateral direction.

One end 236a of the linking part 236 is supported to enable free rotation about a support axis 238 at the front end of the open/close operating part 243, and the other end is supported to enable free rotation about a support axis 239 of the gripping part 237a. A front end of the open/close operating part 243 that is connected to the one end 236a of the linking part 236 is positioned farther toward the front end of the aim members 208A and 208B than the other end 236b of the linking member 236 that is connected to support 237. In other words, the construction is provided in which the two linking parts 236 and the two supports 237 form a pantograph structure at the front end of the first sheath 203, and modification of this pantograph structure is carried out by advance and retraction of the open/close operating part 243, thereby pushing apart or pulling closed the first arm member 208A and the second arm member 208B.

As shown in FIGS. 22 and 30, the open/close operating part 243 is inserted into the sliding member 242, and is fixed in place to the portion of the bending opening/closing wire 244, which is fixed in place, that projects out from the front end of the sliding member 242. As shown in FIG. 30, the bending opening/closing wire 244 is inserted into a bending opening/closing wire coil 244A that is disposed inside the first sheath 203. As shown in FIG. 24A, the open/close operating part 243 is disposed to an opposite side from the viewing device 212, interposing the first arm member 208A and the second arm member 208B therebetween. The open/close operating part 243 is disposed closer to the central axis of the first sheath 203 than to the central axis of the first arm member 208A and the second arm member 208B.

As shown in FIGS. 24A and 30, the viewing device 212 is provided with an image pick-up unit 211 and two illuminating members 221A and 221B which are disposed on either side of the image pick-up unit 211. The image pick-up unit 211 is provided with an objective lens (optical member for viewing) 223 that is disposed at the front end surface of the sheath front end part 203A, and is connected to a video cable 220 that is inserted into the first sheath 203. The illuminating members 221A and 221B include an illuminating lens (optical member for illumination) that is disposed lateral to the objective lens 223. The objective lens 223 and the illuminating lens are disposed farther toward the front end of the bending part 207 than the position where the base end of the bending part 207 is fixed in place to the sheath front end part 203A.

Next, the operating part of the medical treatment endoscope 200 will be explained. As shown in FIGS. 32 through 36, this medical treatment endoscope 200 is provided with an operating part 151 that has a frame 145, which includes a moving frame 145A and a fixed frame 145B, and a mount 187 on which the frame 145 is mounted. The moving frame 145A and the fixed frame 145B are connected to the mount 187 via a slide mechanism 190 that is provided at their respective underbodies. The slide mechanism 190 includes slide rails 198a that are provided at a mount 187 side of base wall members 190a of the moving frame 145A and the fixed frame 145B, and a slide block 198b that is provided at the frame 45 side of the mount 187 and engages with the two slide rails 198a in a manner that enables sliding. The moving frame 145A and the fixed frame 145B are connected via a sliding mechanism 148 in which a slide rail 148a, provided at a lateral surface of the fixed frame 145B, and a slide block 148b, provided at a lateral surface of the moving frame 145A, engage in a manner to enable sliding. The slide rail 148a is disposed parallel to the slide rail 198a of the slide mechanism 190.

The moving frame 145A and the fixed frame 145B are each provided with the slide mechanism 190, and are connected via the slide mechanism 148. As a result, the moving frame 145A and the fixed frame 145B can both be made to slide with respect to the mount 187. However, in the case of this embodiment, the base wall member 190a of the fixed frame 145B is fixed to the mount 187, and only the moving frame 145A is able to slide with respect to the fixed frame 145B and the mount 187 via the slide mechanisms 148 and 198.

Figure 34:
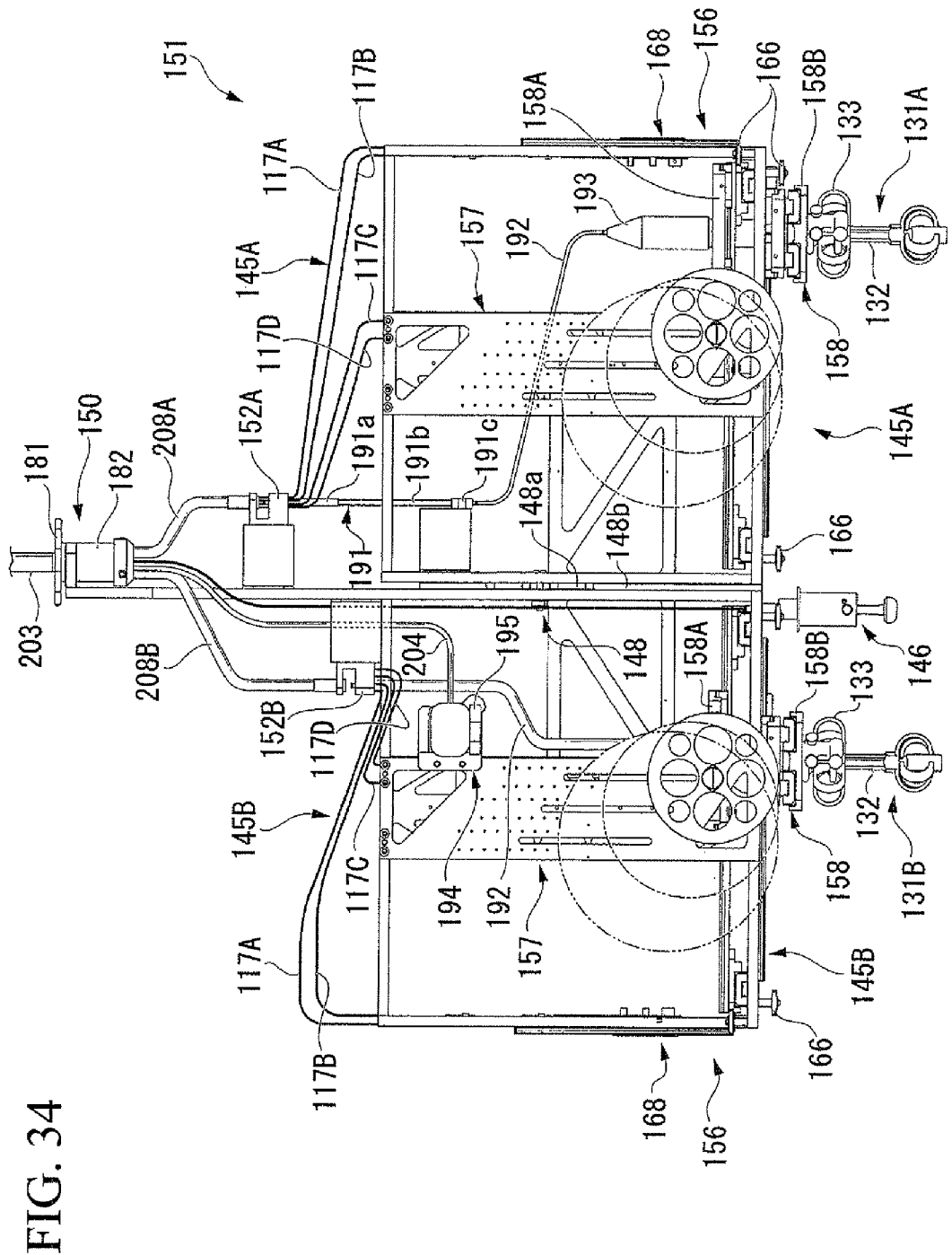
FIG. 34 is a view along direction K in FIG. 32.
Figure 35:
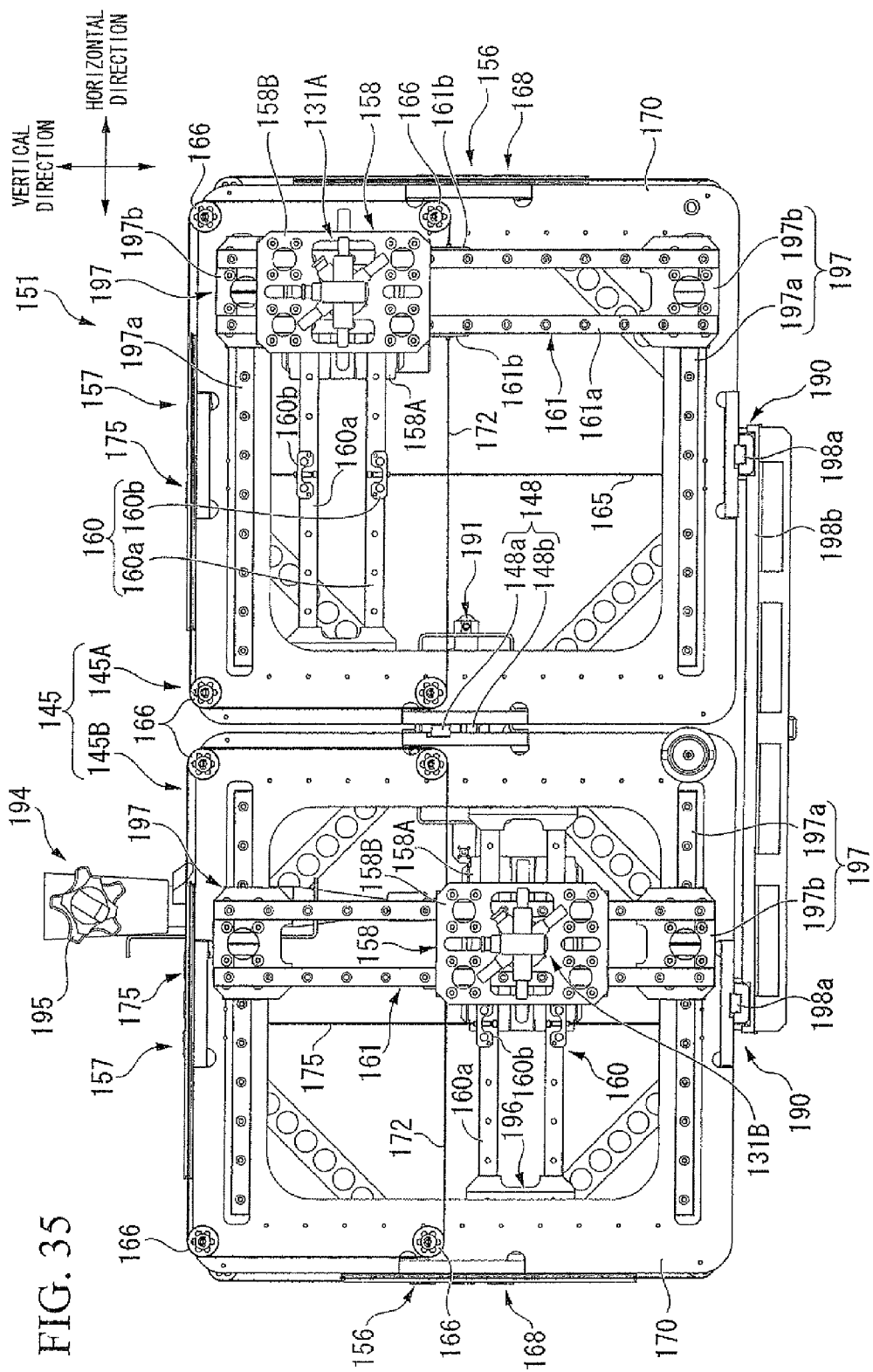
FIG. 35 is a view along direction L in FIG. 33.
Figure 36:
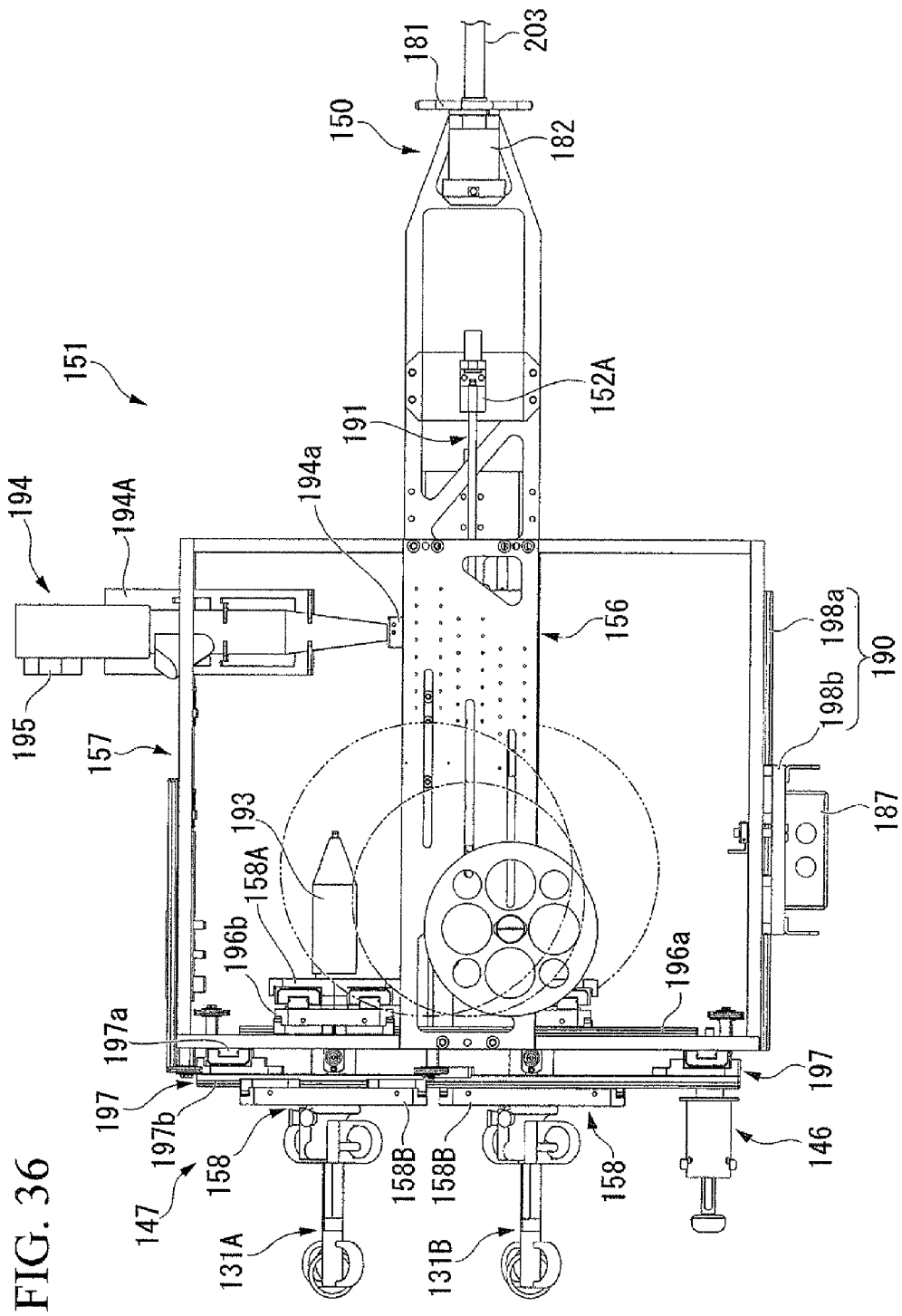
FIG. 36 is a view along direction M in FIG. 33.

The moving frame 145A is provided with a bending operating part 147 for carrying out bending operation of the first arm member 208A. The instrument operating part 131A of the high frequency scalpel 205A can be attached to and released from this bending operating part 147. On the other hand, the fixed frame 145B is provided with an open/close operating part 146 for operating the open/close mechanism 210; a bending operating part 147 for carrying out bending operation of the second arm member 208B; a sheath operating part 194 for carrying out bending operation of the bending part 203B; a rotation operating part 150 which connects the base end of the first sheath 203 to the frame 145 in a manner to enable free rotation; a first arm clamp 152A for supporting the first arm member 208A that extends out from the base end of the first sheath 203; a sheath advance/retract part 191 that is connected on the side of the first arm clamp 152A that is opposite the rotation operating part 150; and a second arm clamp 152B for supporting the second arm member 208B that extends out from the base end of the first sheath 203. Note that while a plurality of sheaths and wires are pulled around the operating part 151 of the medical treatment endoscope 200 shown in FIGS. 32 through 36, these are shown in FIG. 34, but omitted from the other figures for easier review of these drawings.

Respective bending operating parts 147 are provided corresponding to the first arm member 208A and the second arm member 208B. The bending operating part 147 is provided with a roughly rectangular frame member 170; a vertical bending operating part 156 for moving the bending part 207 in a vertical direction, for example; a horizontal bending operating part 157 for moving the bending part 207 in a direction perpendicular to the moving direction of the vertical bending operating part 156, i.e., a horizontal direction, for example; and an attachment part 158 for attaching the instrument operating parts 131A and 131B in a manner so as to enable rotation. The attachment part 158 is constructed such that the two slide blocks 158A and 158B are disposed opposite one another, and so as to be fixed in place by a tubular member 193 which passes through these slide blocks 158A and 158B. The slide block 158A is constructed to be able to slide in the horizontal direction after engaging with the two slide rails 160a that form the first movement restricting member 160 which is provided to permit relative displacement of the attachment part 158 in the horizontal direction only. The slide block 158B is constructed to be able to slide in the vertical direction after engaging with the two slide rails that form the second movement restricting member 161 which is provided to permit relative displacement of the attachment part 158 in the vertical direction only.

The instrument operating parts 131A and 131B are provided with an instrument operating part main body 132 to which the instrument insertion part 125 is connected, and an instrument handle 133 which is disposed to freely advance and retract with respect to the instrument operating part main body 132.

The vertical bending operating part 156 is provided with first bending guides 196 for causing relative displacement of the first movement restricting member 160 in the vertical direction; a first belt member 165 connected to first die parts 160b that are provided at the center along the longitudinal direction of the two slide rails 160a that form the first movement restricting member 160; four adjusting wheels 166 for adjusting the tension by winding of the first belt member 165; a first gear 168 that is connected to the first belt member 165; and a first chain belt 167 which is connected to the first gear 168.

The first bending guide 196 is provided with two slide rails 196a that are equipped at the frame body of the frame member 170, and slide blocks 196b that engage with the two slide rails 196a respectively in a manner to enable sliding, and which are connected at either end of the two slide rails 160a of the first movement restricting member 160.

Figure 42:
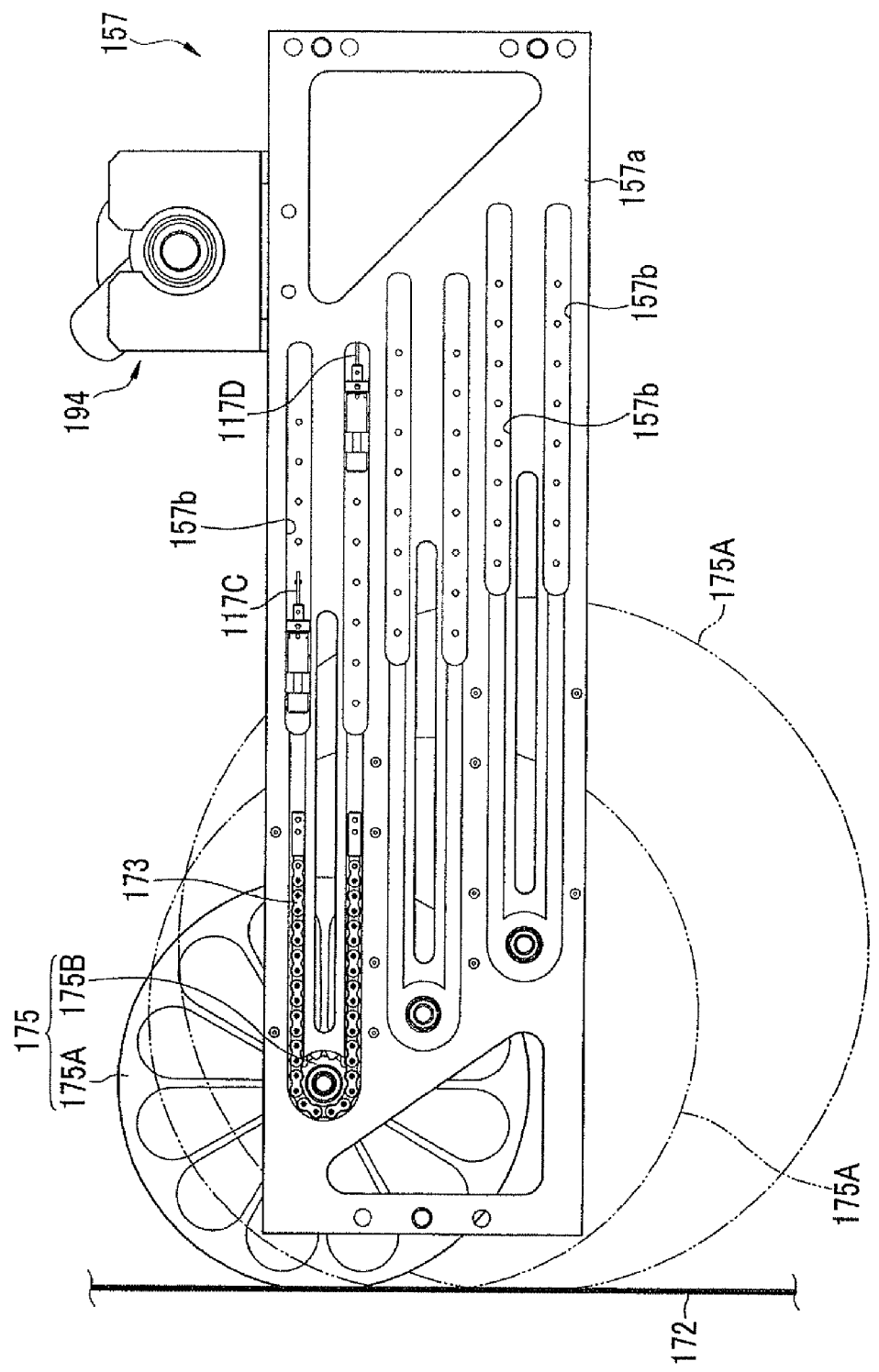
FIG. 42 is a view showing the essential part of the horizontal bending operating part.

The ends of the first belt member 165 are each connected to the first die parts 160b via four adjusting wheels 166. The first chain belt 167 and the first gear 168 are attached to a plate-shaped gear box 156a, as shown in FIG. 42. The large diameter parts 168A of the first gear 168 that are connected to the first belt member 165 are attached to one surface side of the gear box 156a, and the small diameter parts 168B, which have the same axes as the large diameter parts 168A, are disposed inside grooves 156b that are formed in the other surface side of the gear box 156a. The first belt member 165 is fixed in place at the outer peripheral surface of the large diameter parts 168A. When the first movement restricting member 160 moves due to an operational input at the bending operating part 131, the first belt member 165 is pulled in one direction accompanying this, and the large diameter parts 168A begin to rotate. The first chain belt 167 which is housed inside the groove 156b engages with the small diameter part 168B. The bending wires 117A and 117B which extend from the first sheath 203 are each connected to an end of the first chain belt 167.

In the case of this embodiment, three sets of grooves 156b for housing the first chain belt 167 and the small diameter parts 168B in the gear box 156a are prepared. By pairing these with the different diameter large diameter parts 168A, it is possible to select a reduction gear ratio at the vertical bending operating part 156. This reduction gear ratio is determined based on a force required at the bending part 207 which performs the bending operation through bending wires 117A and 117B, and a force required for an operation of the bending operating part 147, these required forces being values that can be known in advance.

The horizontal bending operating part 157 is provided with the same construction as the vertical bending operating part 156. In other words, the horizontal bending operating part 157 is provided with second bending guides 197 that are connected to two ends of a longitudinal direction of the second movement restricting member 161 for causing movement of the second movement restricting member 161 in the horizontal direction; a second belt member 172 connected to second die parts 161b that are respectively provided at the center along the longitudinal direction of the two slide rails 161a that foam the second movement restricting member 161; four adjusting wheels 166 for adjusting the tension by winding of the second belt member 172; a second gear 175 that is connected to the second belt member 172; and a second chain belt 173.

The second bending guide 197 is provided with two slide rails 197a that are provided at the frame body of the frame member 170, and slide blocks 197b that engage with the two slide rails 197a respectively in a manner to enable sliding, and which are connected at either end of the two slide rails 161a of the second movement restricting member 161.

Figure 43:
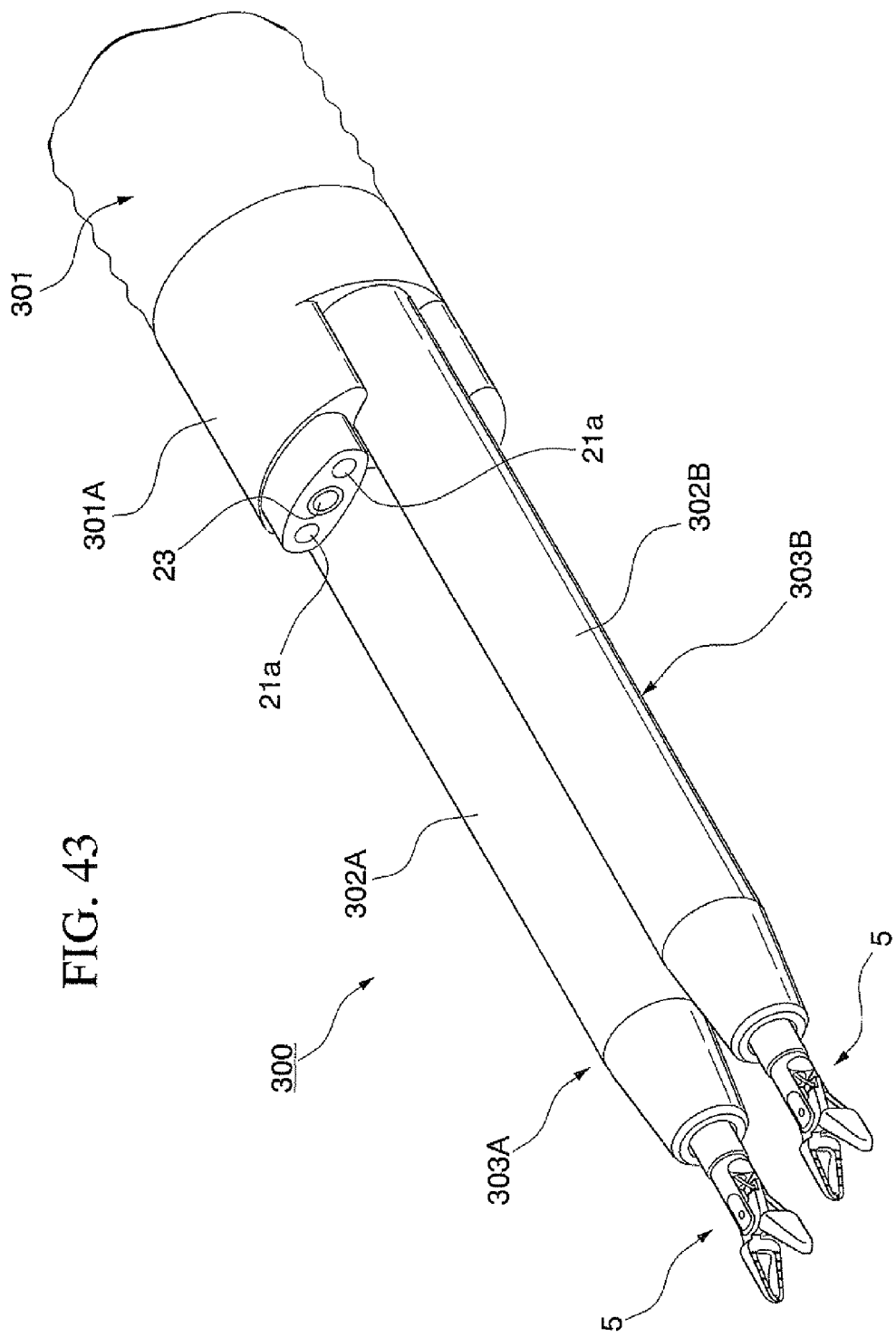
FIG. 43 is a view showing the structure of the tip of the medical treatment endoscope according to a fourth embodiment.
Figure 44:
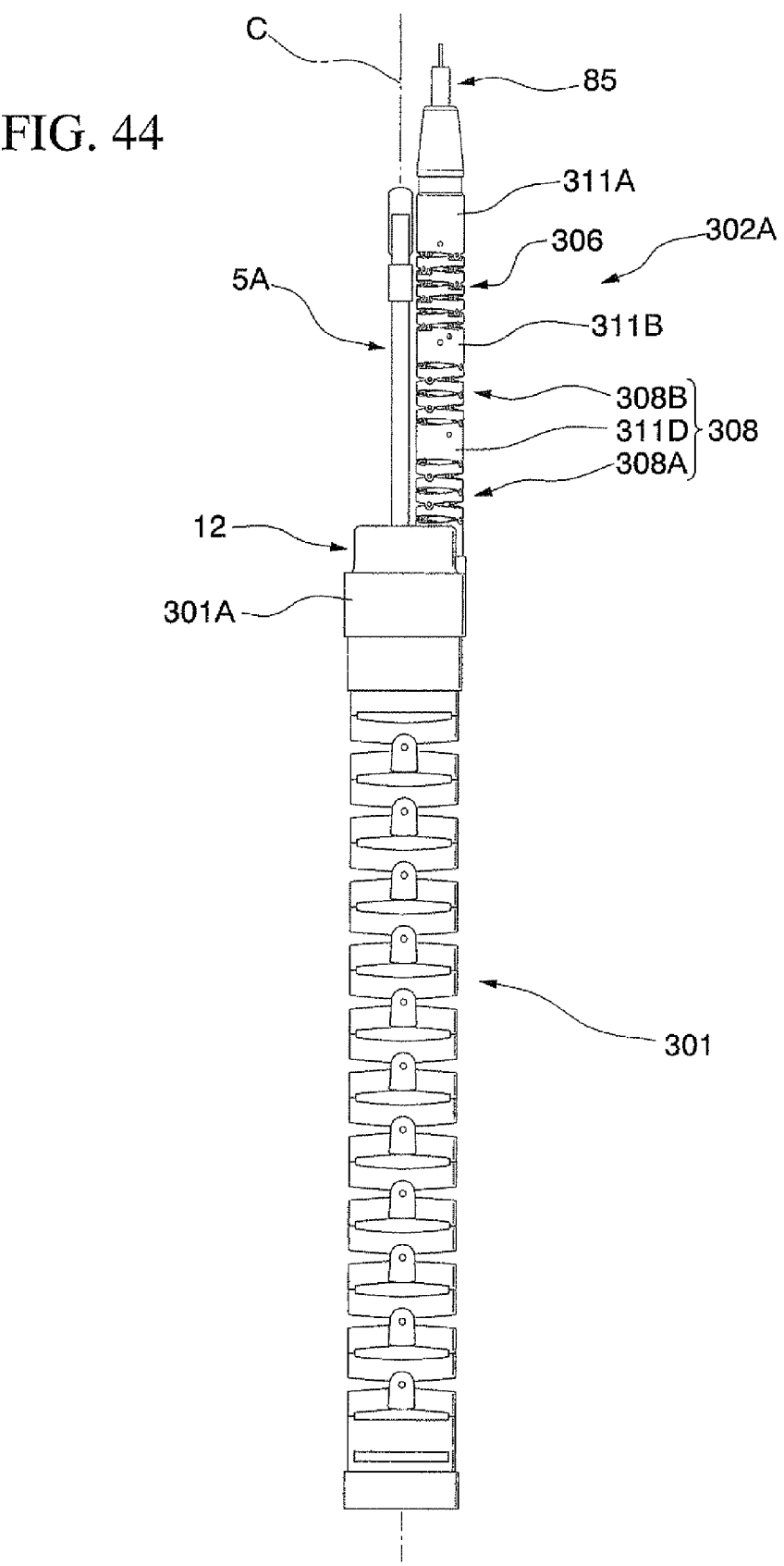
FIG. 44 shows an initial state of an arm member of the medical treatment endoscope in perspective.
Figure 45:
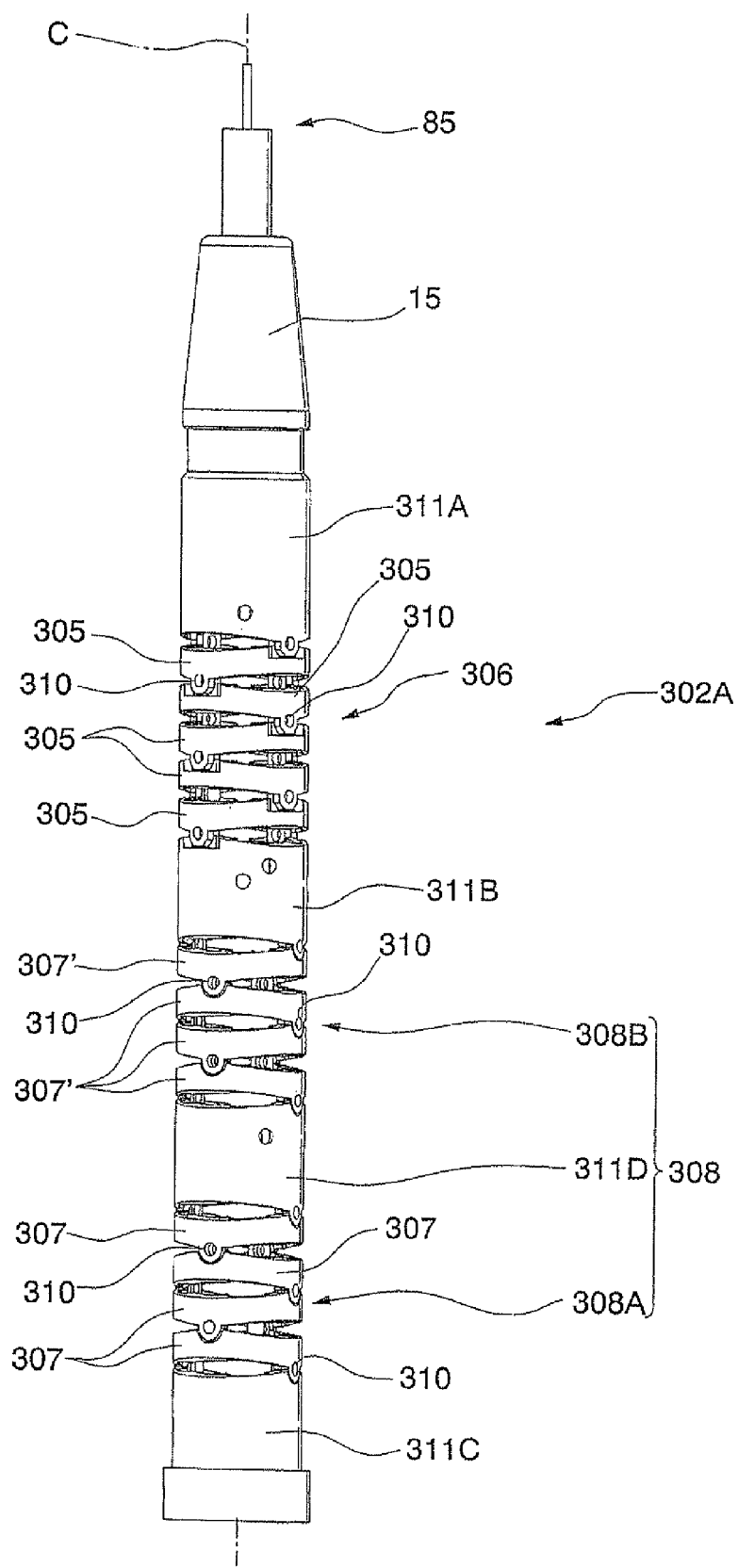
FIG. 45 shows an enlarged initial state of the arm member of the medical treatment endoscope in perspective.
Figure 46:
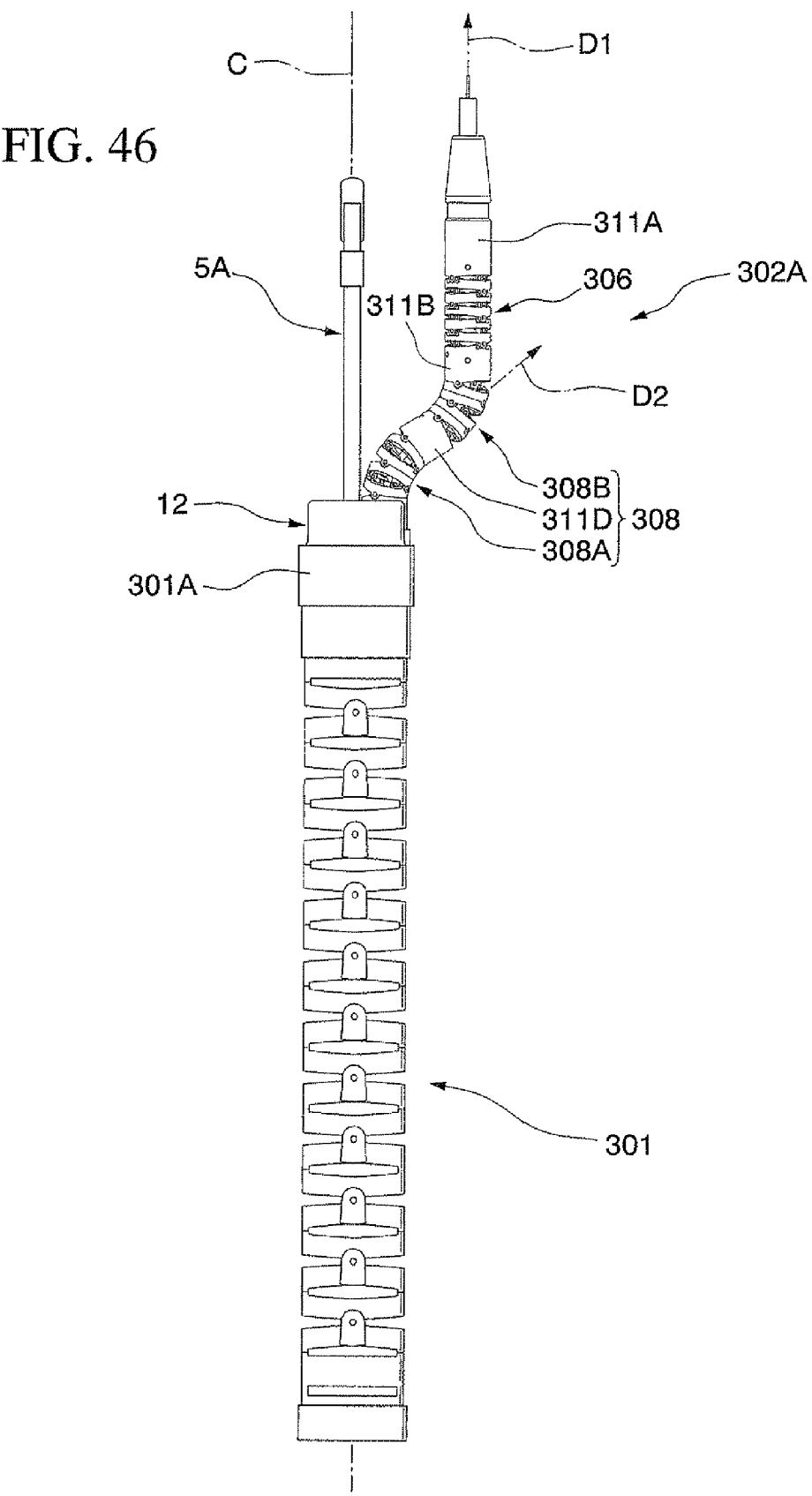
FIG. 46 shows an open state of the arm member of the medical treatment endoscope in perspective.
Figure 47:
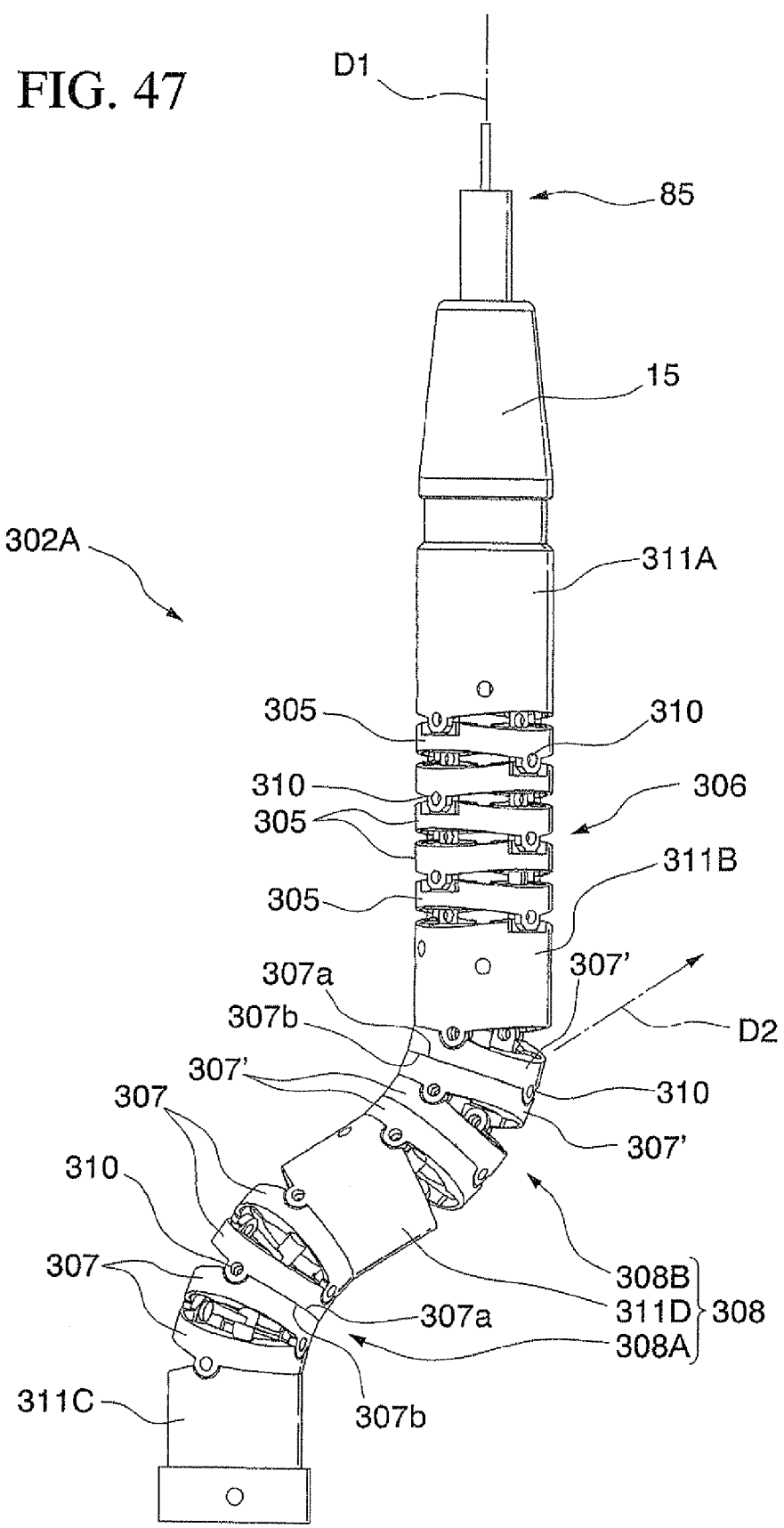
FIG. 47 shows an enlarged open state of the arm member of the medical treatment endoscope in perspective.
Figure 48:
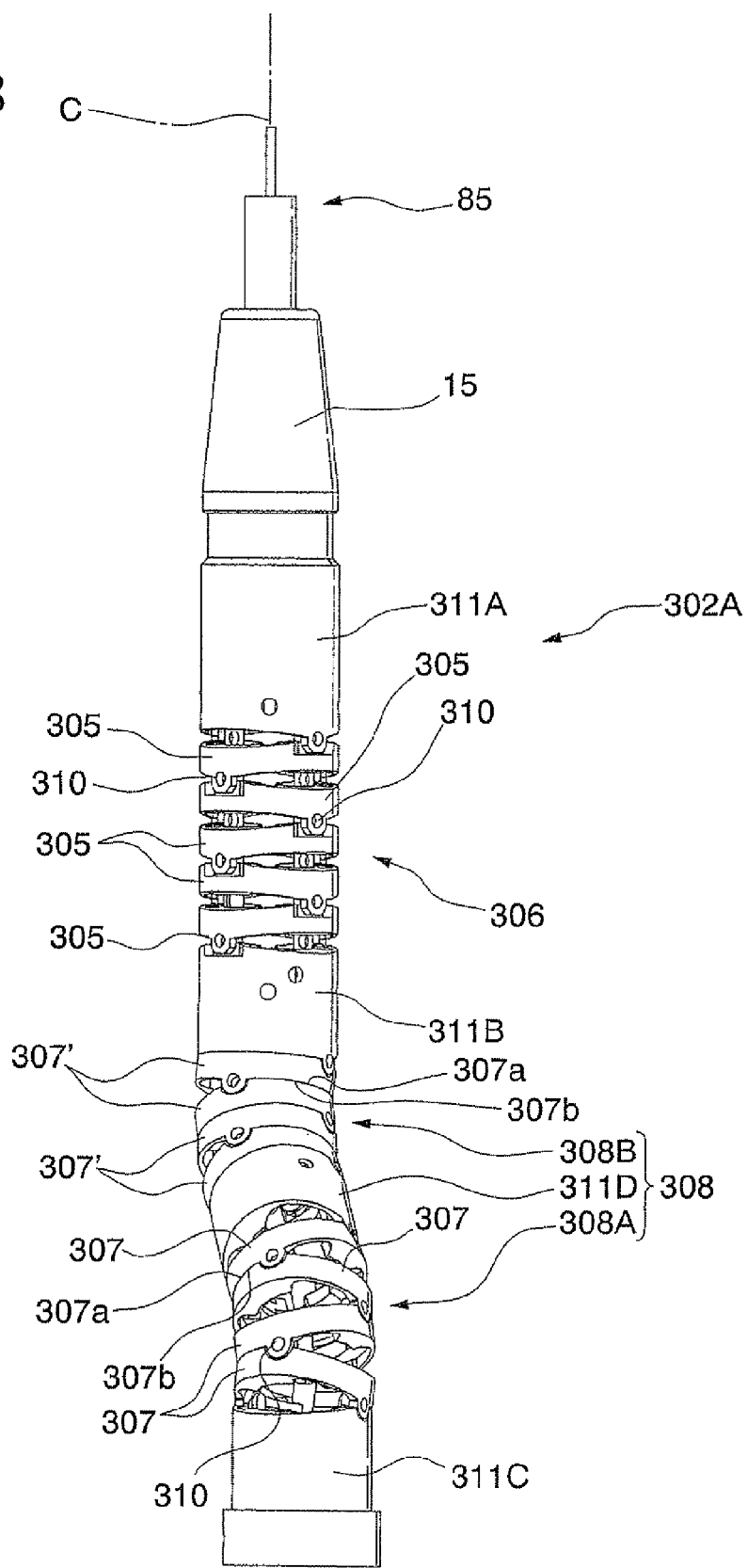
FIG. 48 shows an enlarged open state of the arm member of the medical treatment endoscope in perspective.
Figure 49:
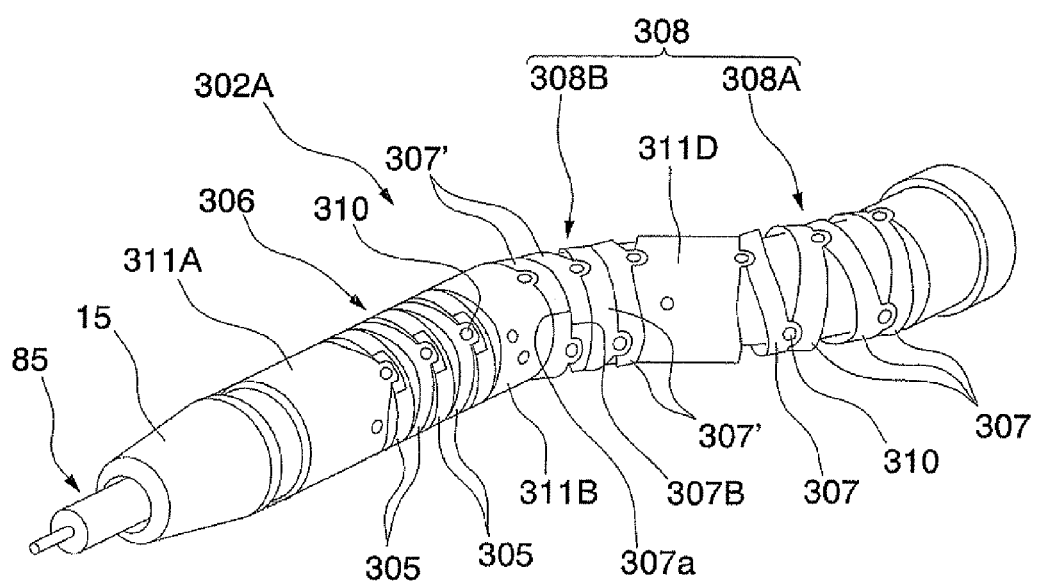
FIG. 49 shows an enlarged open state of the arm member of the medical treatment endoscope in perspective.
Figure 50:
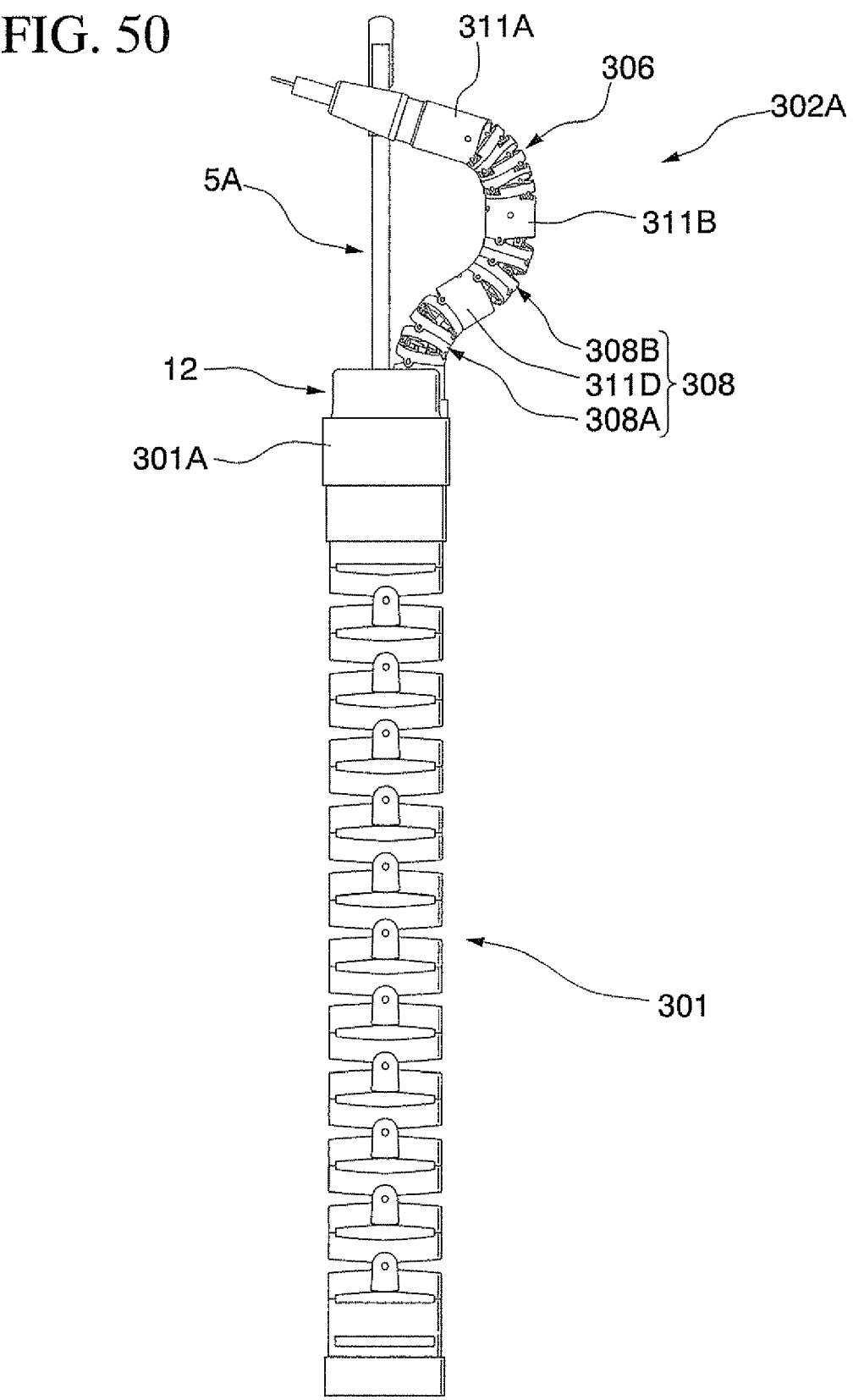
FIG. 50 shows a bending state of the arm member of the medical treatment endoscope in perspective.
Figure 51:
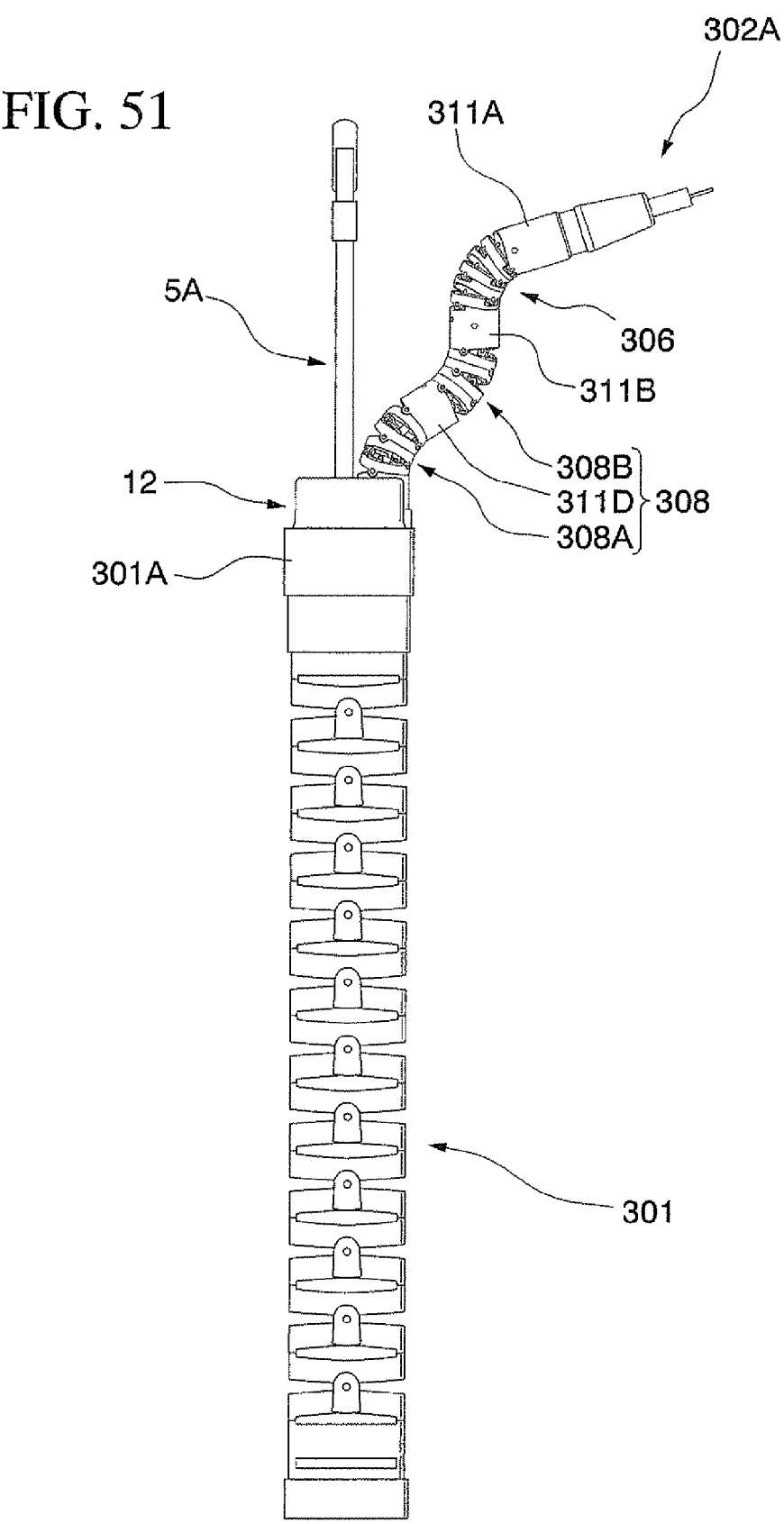
FIG. 51 shows a bending state of the arm member of the medical treatment endoscope in perspective.
Figure 52:
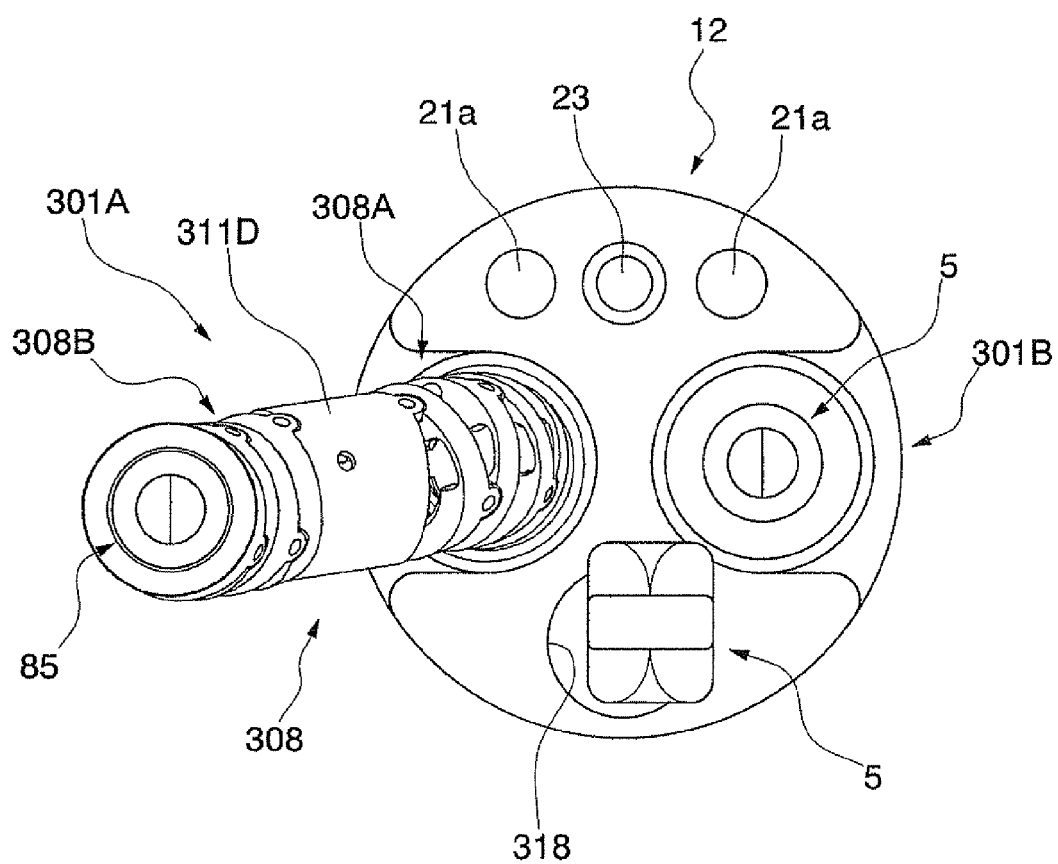
FIG. 52 is a front elevation describing a bending state of the arm member of the medical treatment endoscope in perspective diagram.
Figure 53:
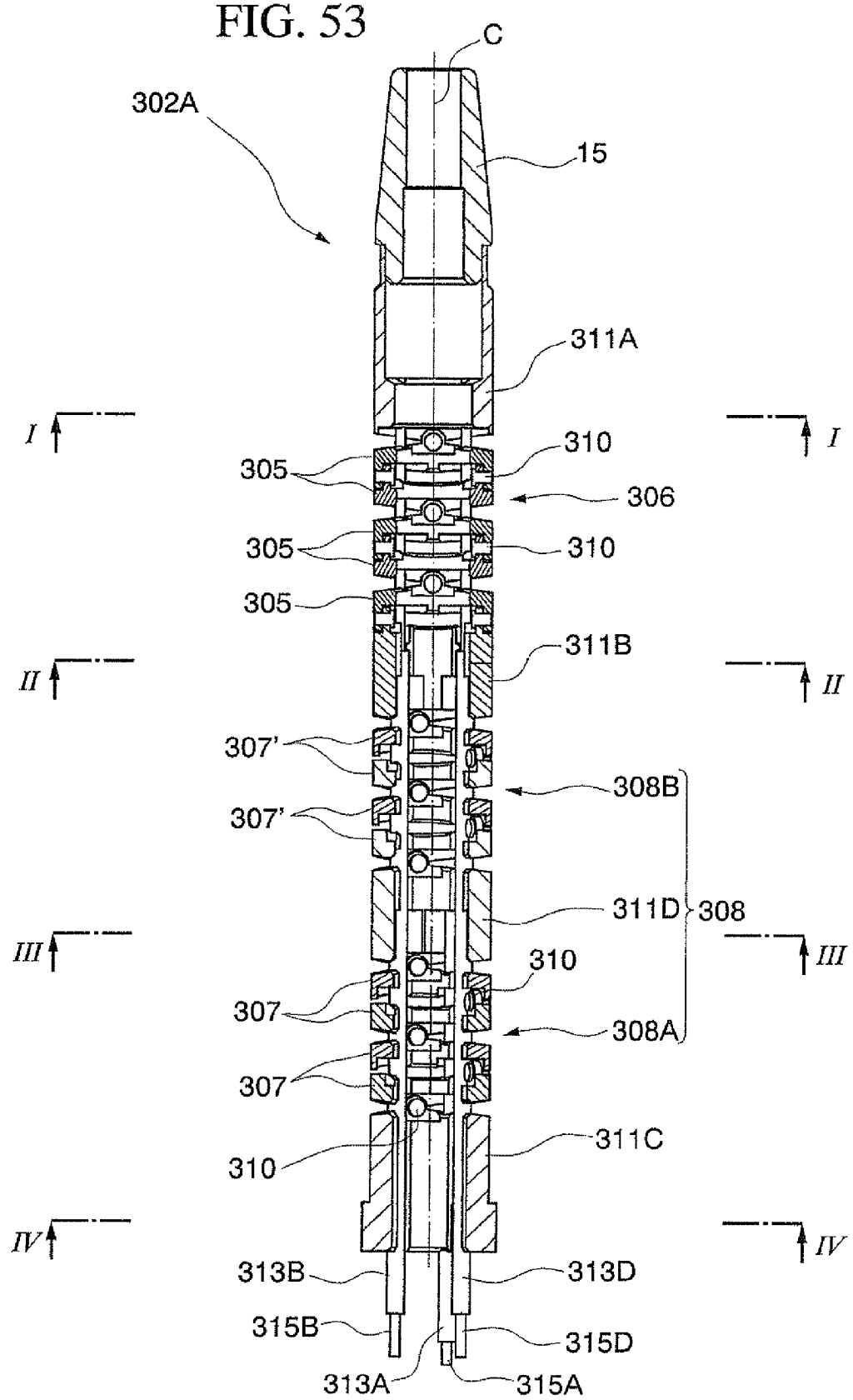
FIG. 53 shows an initial state of the arm member of the medical treatment endoscope in cross-sectional view.
Figure 54:
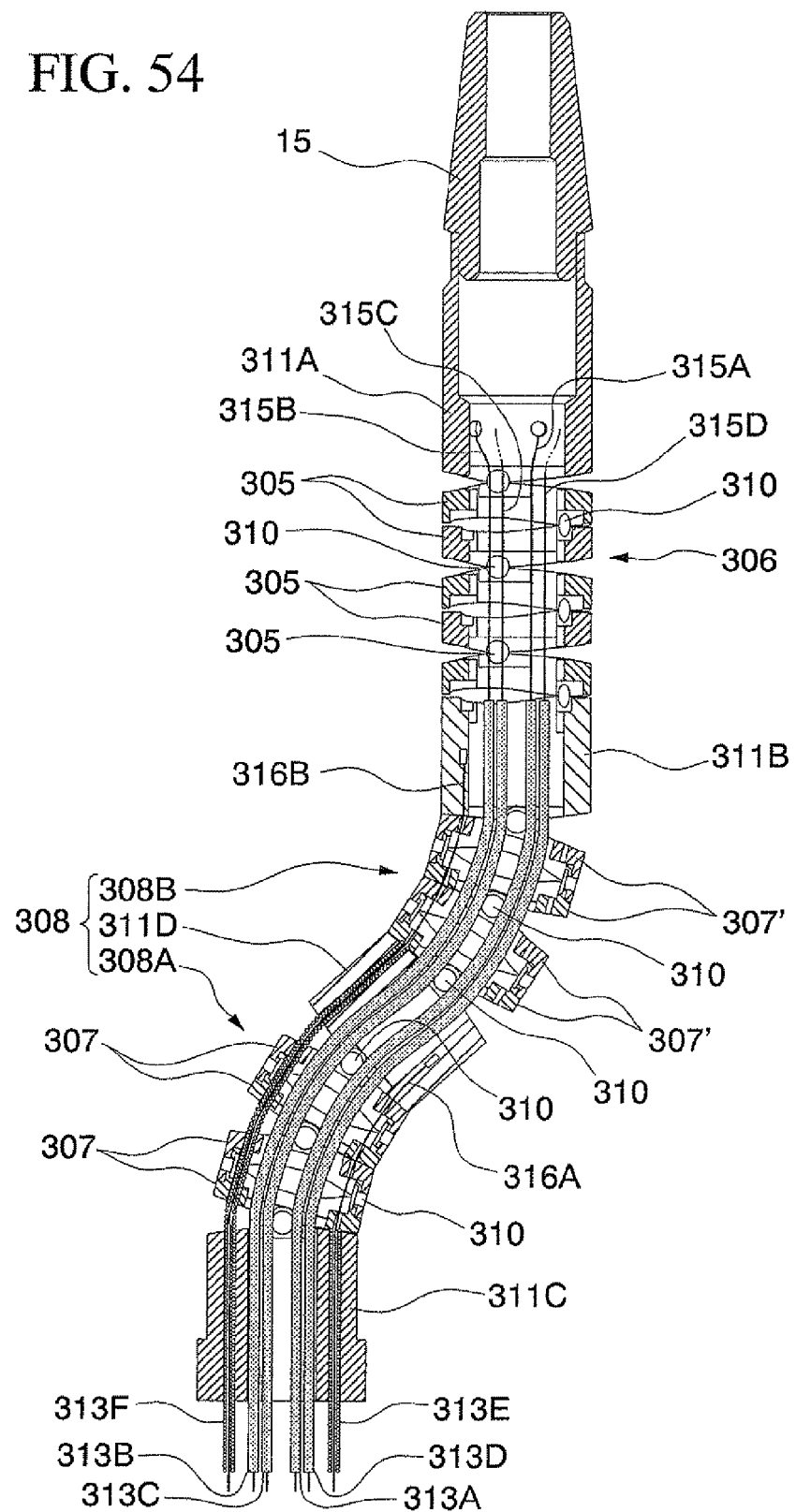
FIG. 54 shows a bending state of the arm member of the medical treatment endoscope in cross-sectional view.
Figure 55:
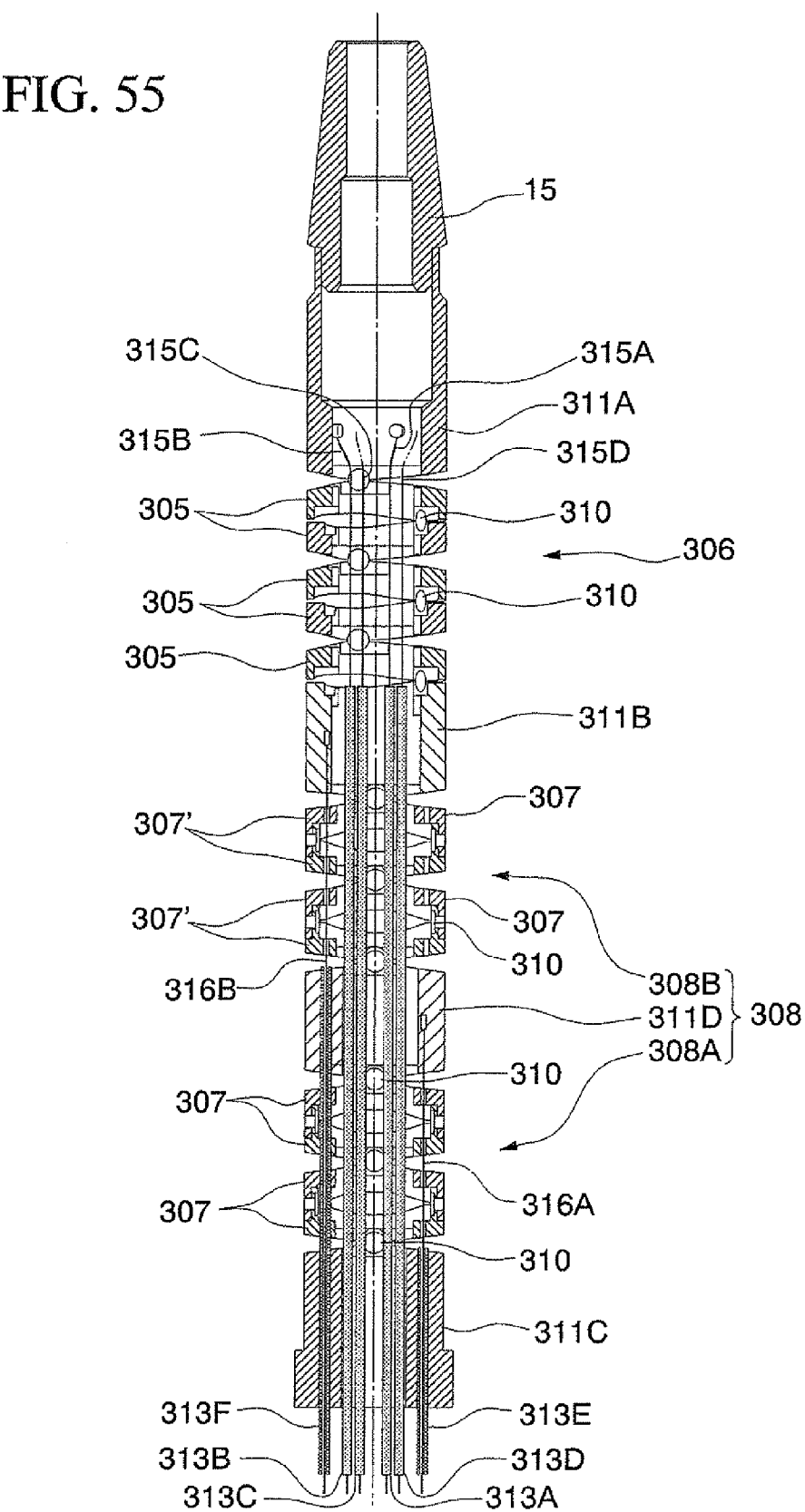
FIG. 55 shows an initial state of the arm member of the medical treatment endoscope in cross-sectional view.

Each end of the second belt member 172 is connected to the second die parts 161b via four adjusting wheels 166. The second chain belt 173 and the second gear 175 are attached to a plate-shaped gear box 157a, as shown in FIG. 43. Large diameter parts 175A of the second gear 175 which are connected to the second belt member 172 are attached on one surface side of the gear box 157a, and small diameter parts 175B, which have the same axes as the large diameter parts 175A, are disposed inside grooves 157b that are formed in the other surface side of the gear box 157a. The second belt member 172 is fixed in place at the outer peripheral surface of the large diameter parts 175A. When the second movement restricting member 161 moves due to an operational input at the instrument operating parts 131A and 131B, the second belt member 172 is pulled in one direction accompanying this, and the large diameter part 175A begins to rotate. The second chain belt 173 that is housed inside the grooves 157b engages with the small diameter parts 175B. The bending wires 117C and 117D which extend from the first sheath 203 are each connected to an end of the second chain belt 173. Furthermore, three sets of grooves 157b are prepared in the gear box 157a. By pairing these with the different diameter large diameter parts 175A, it is possible to select a reduction gear ratio at the horizontal bending operating part 157.

The rotation operating part 150 is disposed further toward the front end side than the first arm clamp 152A and the second arm clamp 152B of the fixed frame 145B, and is provided with a sheath connector 181, which has a rotation knob and to which the base end of the first sheath 203 is connected; and a rotation support 182 for supporting the sheath connector 181 in a manner to enable rotation. Through-holes 183 are disposed in the rotation support 182 through which the first arm member 208A and the second arm member 208B, which are respectively connected to the first arm clamp 152A and the second arm clamp 152B, the video cable 220, and the like, are inserted.

Figure 37:
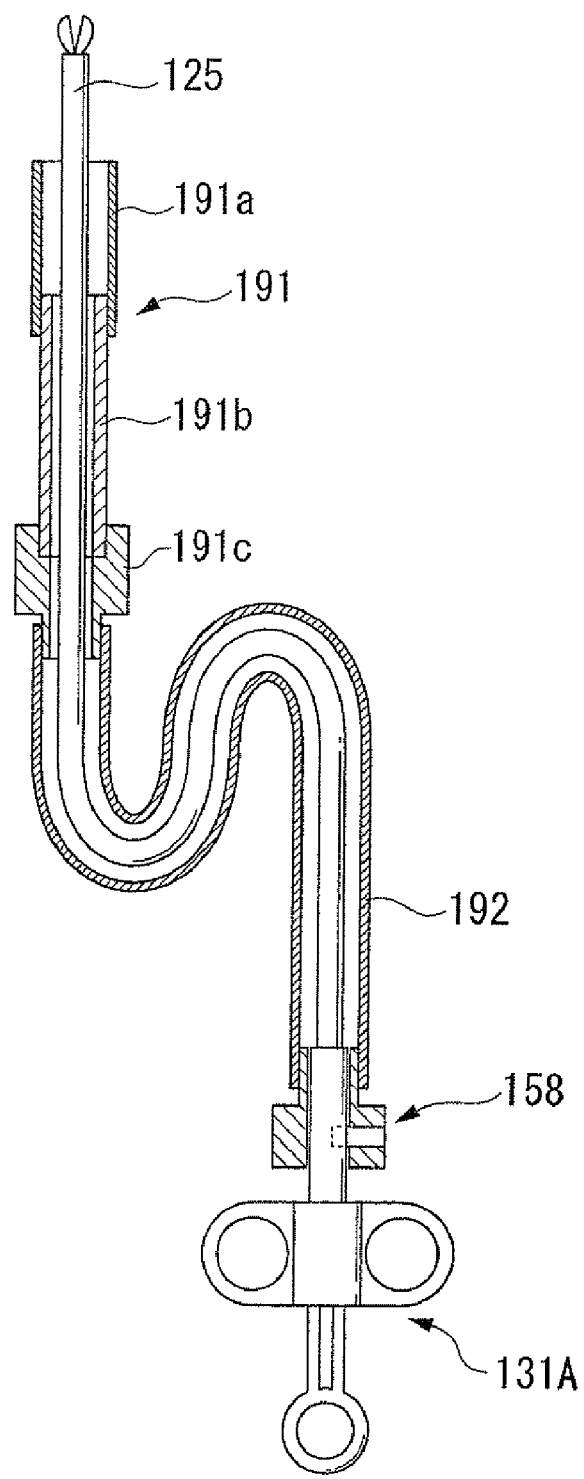
FIG. 37 is a schematic view showing the essential parts of the sheath advance/retract mechanism.

As shown in the schematic cross-sectional view in FIG. 37, the sheath advance/retract part 191, which is connected to the first arm clamp 152A, is provided with a first tubular member 191a, a second tubular member 191b which is disposed nested inside the first tubular member 191a, and a die part 191c that supports the base end of the second tubular member 191b. An instrument sheath 192 is installed between the die part 191c on the base end side and the attachment part 158, this instrument sheath 192 connecting an opening of the die part 191c and an opening of the tubular member 193 of the attachment part 158. The instrument insertion part 125 having a coil sheath that is connected to gripping forceps or the like at the front end is inserted into the sheath advance/retract part 191 and the instrument sheath 192. Of the two tubular members 191a and 191b that are disposed in nesting form, the first tubular member 191a is supported by the first arm clamp 152A and is fixed in place to the fixed frame 145B, while the second tubular member 191b is connected to the die part 191c and is fixed in place to the moving frame 145A. Accordingly by advancing and retracting the moving frame 145A with respect to the fixed frame 145B, it is possible to advance and retract the second tubular member 191b with respect to the first tubular member 191a, and thereby advance and retract the instrument insertion part 125 which is inserted inside the second tubular member 191b with respect to the first sheath 203. As a result, the high-frequency scalpel 205A that is disposed at the front end of the first arm member 208A can be made to project out from the front end of the front end part 215A, and to be retracted back from this projecting position.

Figure 38:
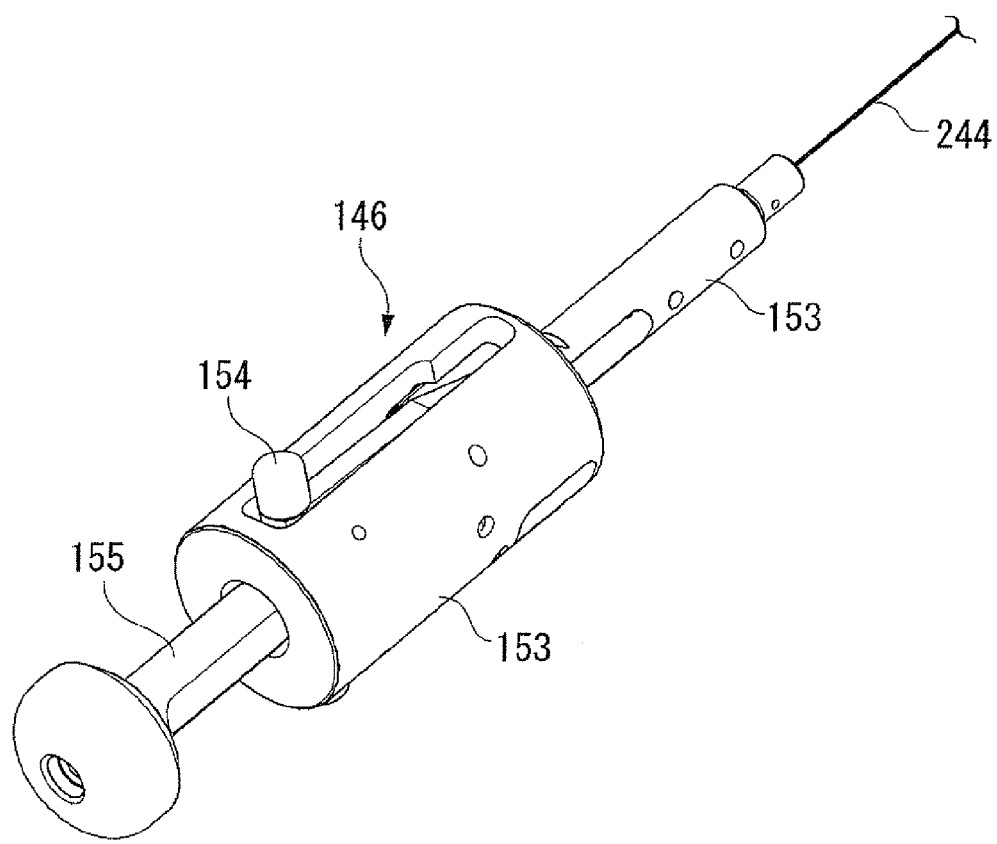
FIG. 38 is a perspective view showing the open/close operating part.
Figure 39:
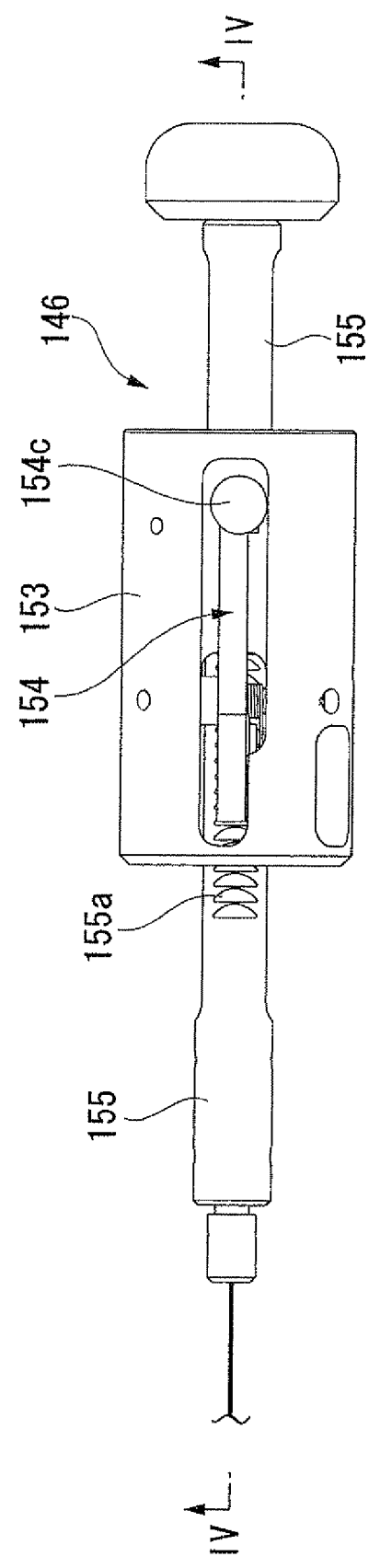
FIG. 39 is a side view showing the open/close operating part.
Figure 40:
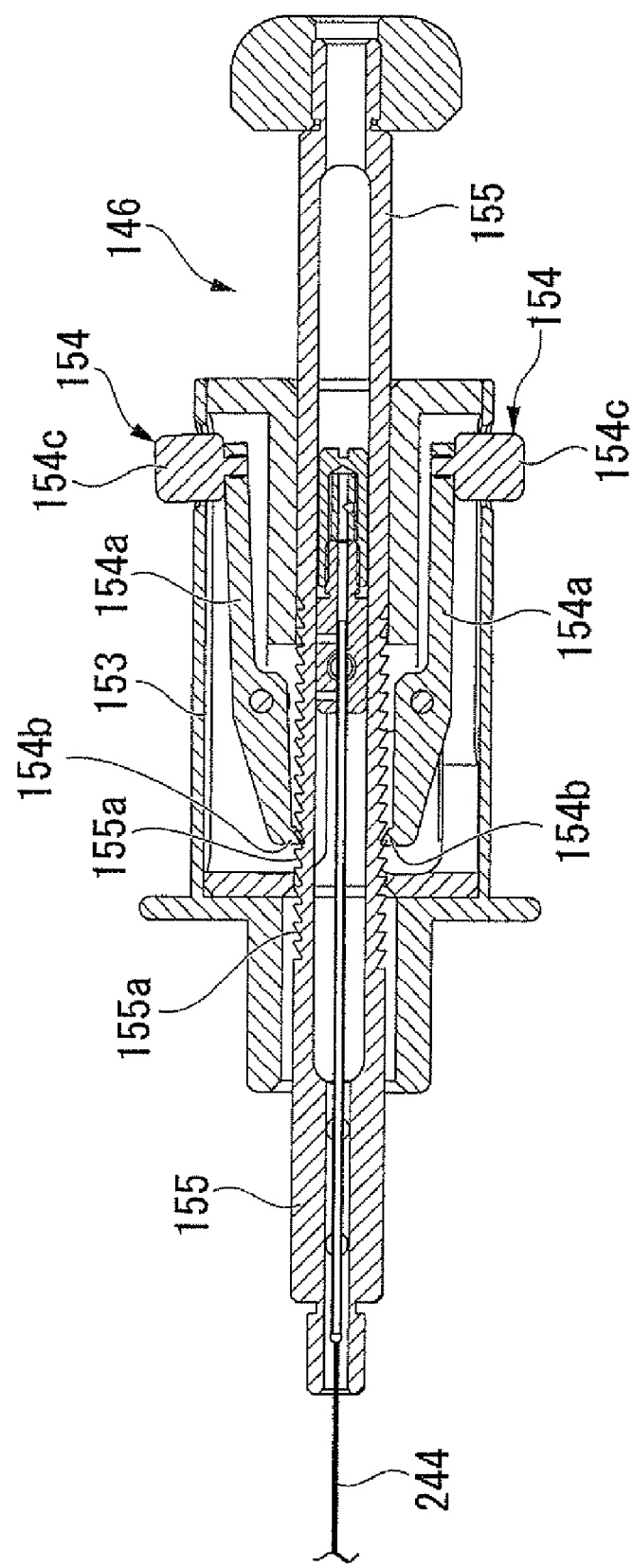
FIG. 40 is a cross-sectional view along line IV-IV in FIG. 39.
Figure 41:
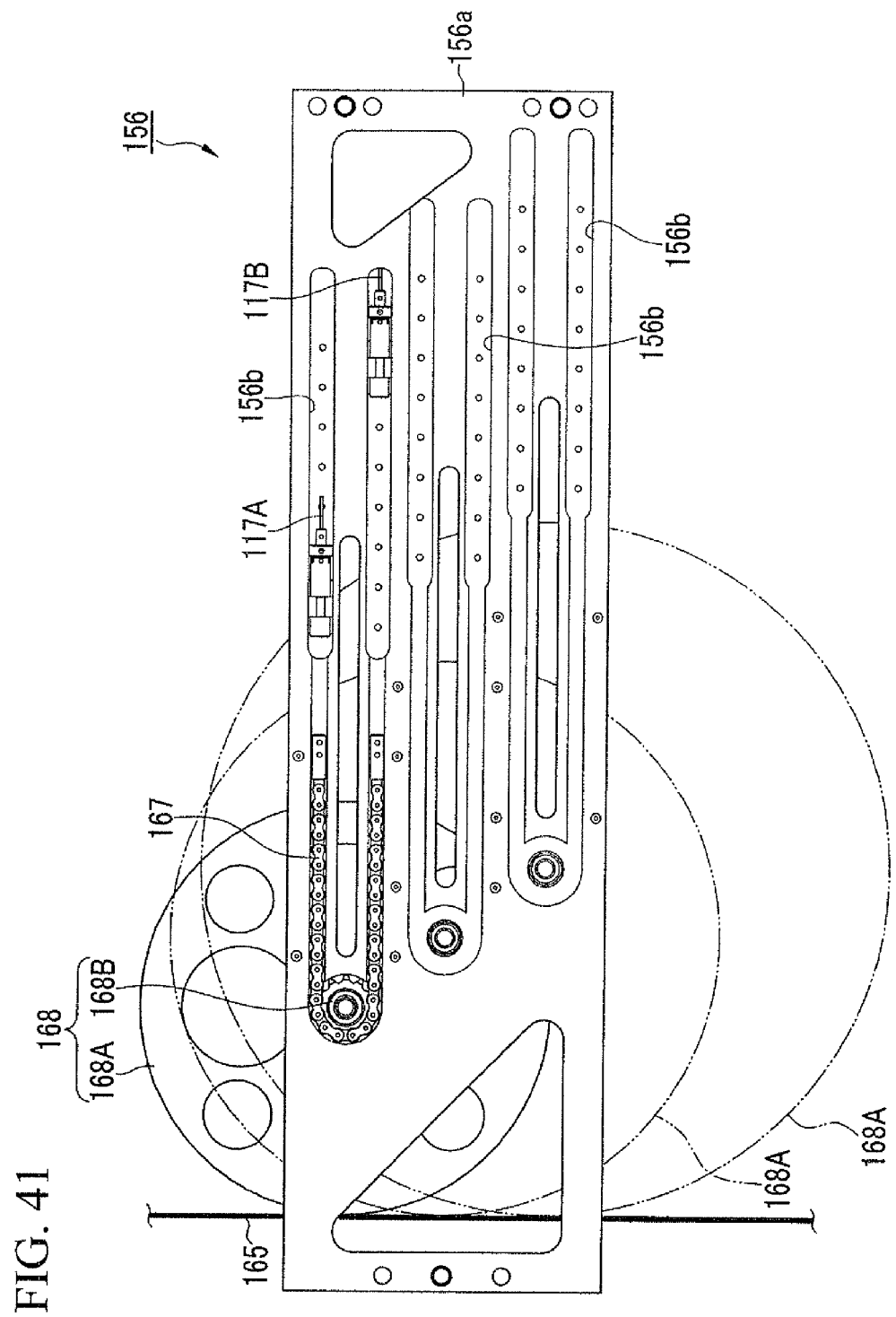
FIG. 41 is a view showing the essential part of the vertical bending operating part.

The open/close operating part 146 is attached to the frame member 170 of the fixed frame 145B. As shown in FIGS. 38 through 40, the open/close operating part 146 is provided with an open/close operating part main body 153; an open/close handle 155 to which the base end of the bending opening/closing wire 244 is connected and which can advance and retract with respect to the open/close operating part main body 153; and a gear 154 for restricting the position of the open/close handle 155 with respect to the open/close operating part main body 153. A rack 155a is formed at the open/close handle 155 for restricting movement toward the front end side when the open/close handle 155 is pulled toward the hand-held side. This rack 155a is for restricting the advance of the open/close handle 155 with respect to the open/close operating part main body 153 through engagement with a claw 154b of a gear 154 that is provided inside the open/close operating part main body 153. In this restricted state, the claw 154b of the above-mentioned gear 154 can be moved away and released from the rack 155a by pressing a release button 154c that is provided opposite the claw 154b via a gear main body 154a of the gear 154. When a starting state for the open/close mechanism 210 is defined as the state in which the first arm member 208A and the second arm member 208B are closed at a position along the direction of the central axis C1 of the first sheath 203, then, in this starting state, the open/close handle 155 is set so as to be positioned toward the front end of the open/close operating part main body 153.

The sheath operating part 194 is disposed vertically positioned to a stand part 194A that is attached to the gear box 157a of the fixed frame 145B. The sheath operating part 194 can be freely attached to or released from the stand part 194A. The sheath operating part 194 is provided with a bending knob 195 for bending operation of the bending part 203B provided at the front end side of the first sheath 203. The operating sheath 204 which extends from the first sheath 203 is connected to a front end part 194a of the sheath operating part 194. Four bending wires 201B, which are inserted into each of the joint wheels 201 of the bending part 203B are inserted into the operating sheath 204. As in the case of the typical medical treatment endoscope, the four bending wires 201B can be advanced or retracted by turning the bending knob 195 that is provided at the sheath operating part 194, enabling bending operation of the bending part 203B to be carried out by the aforementioned advance/retract operation.

Next, the operation of the embodiment of the present invention will be explained.

Figure 26:
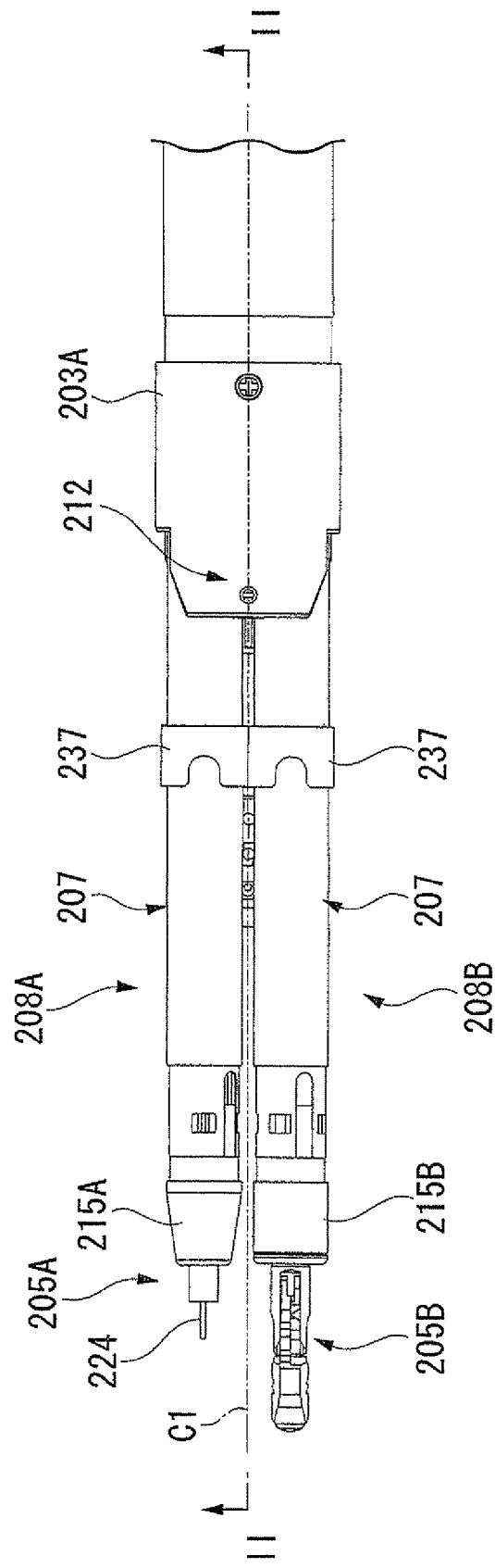
FIG. 26 is a plan view of the front end of the medical treatment endoscope showing the case where the arm member is closed.
Figure 27:
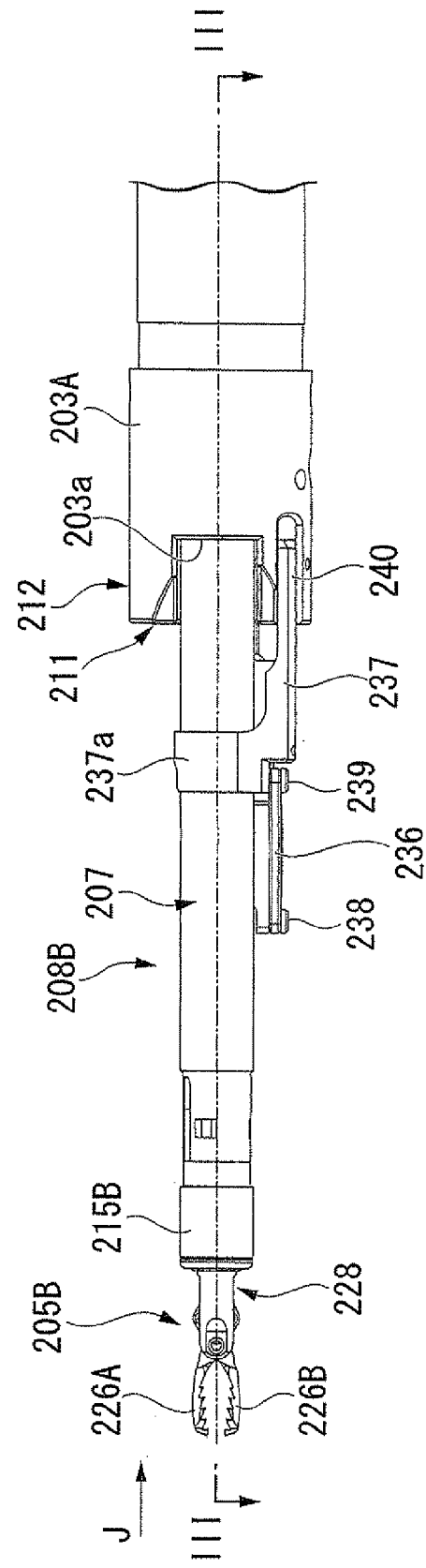
FIG. 27 is a side view of the front end of the medical treatment endoscope showing the case where the arm member is closed.
Figure 28:
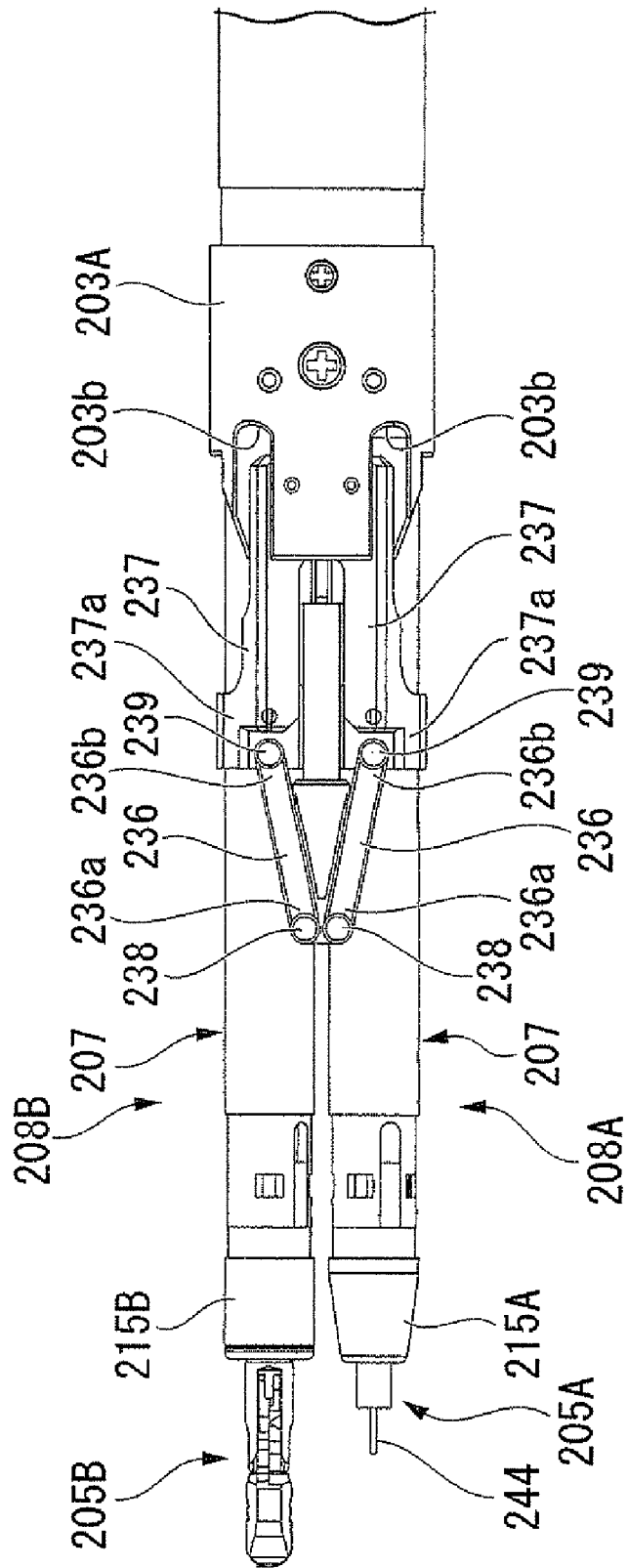
FIG. 28 is an underside view of the front end of the medical treatment endoscope showing the case where the arm member is closed.
Figure 29:
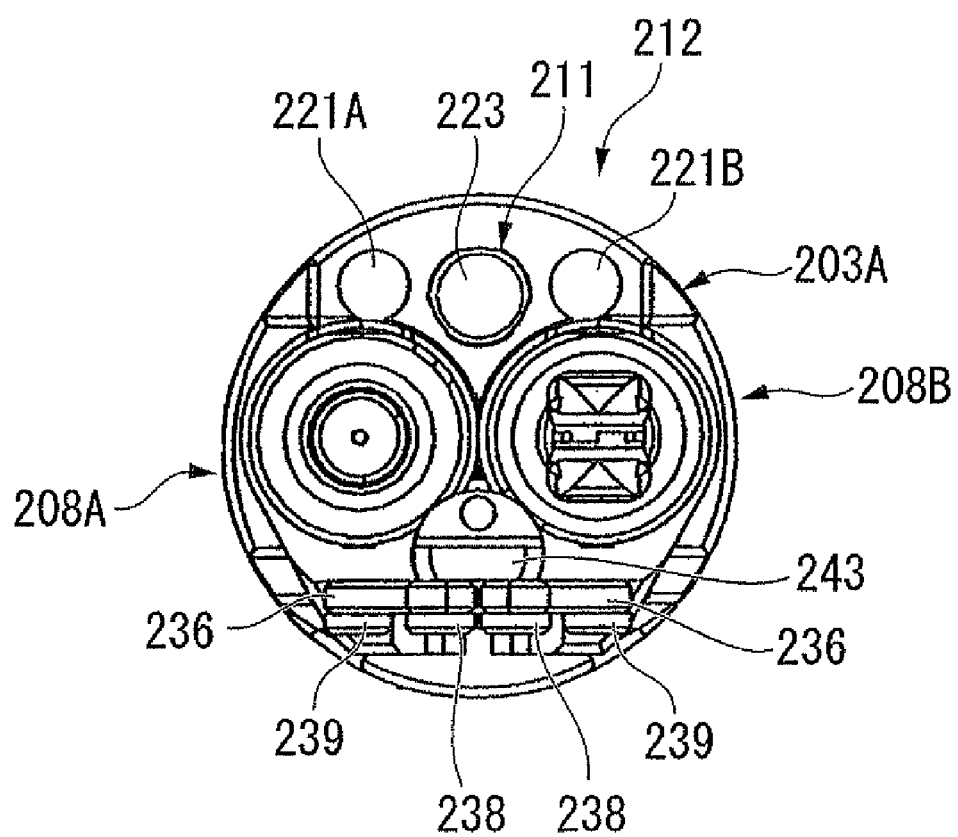
FIG. 29 is a view along direction J in FIG. 27.

When opening the first arm member 208A and the second arm member 208B with respect to the first sheath 203 from the starting state shown in FIGS. 26 and 27, the open/close handle 155 is slid with respect to the open/close operating part main body 153 a predetermined distance toward the hand-held side. At this time, the bending opening/closing wire 244 is thus retracted with respect to the sheath front end part 203A toward the hand-held side, and the open/close operating part 243 is retracted. Accompanying this, the linking part 236 receives a rotational torque directed away from the central axis of the first sheath 203, and, as a result, the other end 236b of the linking part 236 is rotated by a specific angle in the direction away from the central axis C1 of the first sheath 203, with the one end 236a of the linking part 236 serving as the rotational center. As shown in FIGS. 23 through 25, the support 237 rotates with respect to the first sheath 203, and the first arm member 208A and the second arm member 208B open. In this state, the position of the open/close handle 155 is fixed in place by the rack 155a of the open/close operating part 146, and the position of the bending opening/closing wire 244 is thus fixed in place with respect to the first sheath 203.

In contrast, when closing the first arm member 208A and the second arm member 208B with respect to the front end side of the first sheath 203, the open/close handle 155 is advanced forward with respect to the open/close operating part main body 153, while pressing on the release button 154c. At this time, the bending opening/closing wire 244 is advanced forward with respect to the front end side of the first sheath 203. Accompanying this, the rotational torque applied on the linking part 236 is released, and the other end 236b of the linking part 236 is rotated in a direction toward the central axis C1 of the first sheath 203, employing the one end 236a of the linking part 236 as the rotational center. As a result, the support 237 rotates with respect to the first sheath 203 and the first arm member 208A and the second arm member 208B close, i.e., resumes the starting state.

In the case where the high frequency scalpel 205A projecting out from the front end of the first arm member 208A is to be projected out still further from the front end of the first aim member 208A, this is accomplished by advancing the moving frame 145A of the operating part 151 with respect to the fixed frame 145B. At this time, the entirety of the moving frame 145A moves in the direction that brings it closer to the first arm clamp 152A, and the members positioned in hand-held side from the second tubular member 191b of the sheath advance/retract part 191 which is supporting the instrument insertion part 125, move in a direction that brings it closer to the first tubular member 191a, and the instrument insertion part 125 is advanced inside the first sheath 203. In this case, the first arm member 208A is fixed in place to the first arm clamp 152A, so that only the high frequency scalpel 205A is projected further out from the front end part 215A of the first arm member 208A. Furthermore, since the bending wires 117A, 117B, 117C, and 117D are separated from the instrument insertion part 125 at the first arm clamp 152A, the bending state of the bending part 207 is not altered by the operation to advance the moving frame 145A.

In contrast, when moving the high frequency scalpel 205A toward the hand-held side of the first arm member 208A, the moving frame 145A of the operating part 151 is retracted with respect to the fixed frame 145B. At this time, the members positioned at the hand-held side from the second tubular member 191b of the sheath advance/retract part 191 which is supporting the instrument insertion part 125, are retracted with respect to the first tubular member 191a. In this way, the high frequency scalpel 205A is again disposed at its starting state position.

When bending the first arm member 208A and the second arm member 208B in the vertical direction, the vertical bending operating part 156 is manipulated. In other words, the instrument operating parts 131A and 131B which are attached to the attachment parts 158 are gripped and moved in the vertical direction. In this case, the attachment part 158 moves vertically with the limits of the second movement restricting member 161, while at the same time, the first movement restricting member 160 moves together with the attachment part 158 along the first bending guides 196 in the vertical direction. Here, the first die parts 160b of the first movement restricting member 160 also move in the vertical direction, so that the first belt member 165 moves accompanying this, and the first gear 168 is rotated in either direction. At this time, the first chain belt 167 is rotated in either direction, and, accompanying this, one of the bending wires 117A and 117B is advanced with respect to the first sheath 203, while the other is retracted. In this way, the joint wheels 216 of the bending part 207 are inclined accompanying the movement of the bending wires 117A and 117B, and bend vertically.

In contrast, when bending the first arm member 208A and the second arm member 208B in the horizontal direction, the horizontal bending operating part 157 is manipulated. In other words, the instrument operating parts 131A and 131B which are attached to the attachment parts 158 are gripped and moved in the horizontal direction. In this case, the attachment part 158 moves horizontally within the limits of the first movement restricting member 160, while at the same time, the second movement restricting member 161 moves together with the attachment part 158 along the paired second bending guides 197 in the horizontal direction. Here, the second die parts 161b of the second movement restricting member 161 also move in the horizontal direction, so that the second belt member 172 moves accompanying this, and the second gear 175 is rotated in either direction. At this time, the second chain belt 173 is rotated in either direction, and, accompanying this, one of the bending wires 117C and 117D is advanced with respect to the first sheath 203, while the other is retracted. In this way, the joint wheels 216 of the bending part 207 are inclined accompanying the movement of the bending wires 117C and 117D, and bend horizontally.

When rotating the first sheath 203 with respect to the operating part 51, the rotation knob provided to the sheath connector 181 of the rotation operating part 150 is gripped and rotated in the desired direction. As a result, the sheath connector 182 rotates relative to the rotation support 181, causing the first sheath 203 to rotate in the desired direction relative to operating part 151.

In this medical treatment endoscope 200, the first arm member 208A and the second arm member 208B that are inserted into the first sheath 203 can be moved away from the central axis C1 of the first sheath 203 using the open/close mechanism 210, and can be further bent at the bending parts 207 of the first arm member 208A and the second arm member 208B. As a result, it is possible to visually confirm the distal ends of the first arm member 208A and the second arm member 208B when a sufficient visual field has been secured for the image pick-up unit 211. As a result, it is possible to reliably and safely carry out the medical procedure. In this case, the axial force generated by advancing or retracting the bending opening/closing wires 244 with respect to the first sheath 203 is converted into the opening/closing forces for the first arm member 208A and the second arm member 208B at the linking part 236 of the open/close mechanism 210. This point is equivalent to that of the first embodiment. However, in this embodiment, the opening/closing operation of the first arm member 208A and the second arm member 208B is carried out smoothly with a smaller operating force, so that the arm members can be opened even wider.

Namely, in the medical treatment endoscope 1 according to the first embodiment, the bending opening/closing wire 35 is connected to the other end 36b of the linking part 36, and the open/close mechanism 10 is operated by advancing and retracting the bending opening/closing wire 35. In this case, as shown in FIG. 8A, the bending opening/closing wire 35 that is connected to the other end 36b of the linking part 36 on the arm member 8B side has a flexed part 35a that is flexed at a position that is advanced from the sheath front end part 3A. Furthermore, as shown in FIGS. 14 and 15, a flexed part 35a is also provided on the arm member 8A side that flexes at the front end of the guide 41A that houses the bending opening/closing wire 35. For this reason, when opening or closing the arm members 8A and 8B, this flexed part 35a creates sliding resistance, increasing the operating force for bending opening/closing wires 35.

Furthermore, as shown in FIG. 8, the bending opening/closing wire 35 is supported by the flexed part 35a, and has the construction such that the front end side thereof moves along with the opening/closing operation of the arm members 8A and 8B. It is therefore difficult to open the first arm member 8A and the second arm member 8B to an angle greater than 45° with respect to the central axis C1 of the first sheath 3.

Accordingly, in the medical treatment endoscope 200 according to this embodiment, the construction is employed in which the one end 236a of the linking part 236 is connected to the open/close operating part 243 at a position that is further to the front end side of the first arm member 208A and the second arm member 208B than the support part 237, and the pantograph structure that is formed by the two linking parts 236 and the two support parts 237 is altered according to the advance or retraction of the open/close operating part 243. As a result, although a relatively larger operational force is required when initiating the opening operation, the amount of operating force required decreases as the linking part 236 and the support 237 are opened. Therefore, operation of the arm member near the lesion site can be carried out smoothly. Furthermore, since the open/close operating part 243 moves together with the slide member 242 that is disposed at the first sheath 203 side, along the direction of advance and retraction of the bending opening/closing wire 244, there is no change in the direction of operation accompanying the opening/closing operation as in the case of the bending opening/closing wire 35 according to the first embodiment, and the amount of movement of the bending opening/closing wire 242 is communicated without change to the linking part 236. As a result, a more efficient opening/closing movement can be carried out. In this embodiment, opening and closing are carried out by communication of the input on the hand-held side to the pantograph of the open/close mechanism 210 via the bending opening/closing wire 244. However, it is a characteristic of wire driving that the force from pushing the wire is less than the force from pulling the wire. For this reason, the present embodiment is constructed so that operation can be carried out by pulling the bending opening/closing wire 244 when opening the arm members 208A and 208B from a closed state, which requires a relatively large force. Conversely, the present embodiment is constructed so as to employ an arrangement in which the power factor of the pantograph is beneficial when closing arm members that are open, so that only a small force need be communicated from the bending opening/closing wire 244.

Moreover, the more that the bending opening/closing wire 244 is retracted, the further apart the first arm member 208A and the second arm member 208B are spread, such that the first arm member 208A and the second arm member 208B can be spread apart without limit within the parameters of allowable movement of the pantograph. For this reason, the first arm member 208A and the second arm member 208B can be widely spread apart to a position in which the angle exceeds 45° with respect to the central axis C1. As a result, it is possible to prevent the field of view from becoming narrower due to entrance of the first arm member 208A and the second arm member 208B into the field of view of the image pick-up unit 211. In this embodiment, the opening/closing angle of the first arm member 208A and the second arm member 208B is adjusted according to the length of the linking part 236 and the support 237 so that the front end part of the arm member 208A and the front end part of the second arm member 208B form an angle of 50° or greater at the instrument which is 50 to 70 mm distal from the objective lens 223 of the image pick-up unit 211. The angle of opening of the first arm member 208A and the second arm member 208B can be easily adjusted by suitably changing the length of the linking part 236, thereby offering superior freedom of construction.

Furthermore, in this embodiment, openings 203a are provided at the sheath front end part 203A, enabling the bending parts 207 to be advanced outward via these openings 203a. By providing this type of construction, the first arm member 208A and the second arm member 208B can open beyond the objective lens 223 at the base end side of the first sheath 203. As a result, the arm members 208A and 208B are less apt to enter into the field of view of the image pick-up unit 211, making it even easier to see the instrument.

In addition, the open/close operating part 243 and the linking part 236 are disposed to the first arm member 208A and the second arm member 208B on the side of the arm members that is opposite the image pick-up unit 211. As a result, it is possible to prevent the open/close operating part 243 from entering into the field of view of the image pick-up unit 211. Furthermore, since the open/close operating part 243 is pulled toward the hand-held side when opening the first arm member 208A and the second arm member 208B, on this point as well, the construction limits interference with the field of view. In addition, the slide member 242, which restricts the open/close operating part 243 so that it moves only in the direction of the central axis C1 of the first sheath 203, is disposed at the clearance that is formed at the center of the first sheath 203 as a result of disposing the first arm member 208A and the second arm member 208B, which are roughly round in cross-section, adjacent to one another. Accordingly, the construction provides an open/close mechanism 210, while at the same time conserving space inside the first sheath 203.

Furthermore, in the preceding first embodiment, the more that the first arm member 8A and the second aim member 813 are opened, the smaller the angle becomes at flexed part 35a of the bending opening/closing wire 35 and the greater the force required for operation becomes. Moreover, a large force is also required to hold the arms in the open state. In particular, when a force is continuously applied to hold the arms in the open state, there is a chance that the member near the flexed part 35a or the linking part 36 could break. In contrast, in this embodiment, the force required for operation when the first arm member 208A and the second arm member 208B are in the open state is small, and the force for holding the arms in the open state is little. Furthermore, when a plate-shaped member is employed for the linking part 236, the rigidity is increased. For this reason, it is possible to avoid the application of a force on the open/close mechanism 210 when the first arm member 208A and the second arm member 208B are in the open state, so that damage to the linking part 236, etc. is unlikely to occur, and reliability can be improved.

In this embodiment, the bending opening/closing wire 244 is pulled toward the hand-held side when opening the first arm member 208A and the second arm member 208B. Thus, it is possible to adjust the force that is communicated to the bending parts 207, so that the opening angle of the first sheath 203 with respect to the central axis C1 can be finely adjusted. Furthermore, by pulling the open/close handle 155 at once with respect to the open/close operating part main body 153 toward the hand-held side until it comes into contact with a contact point, so that the opening angle between the first arm member 208A and the second arm member 208B with respect to the central axis C1 is set suitable, it is possible to obtain a simplified open/close operation of the first arm member 208A and the second arm member 208B.

Furthermore, the first embodiment had the construction that did not permit changing the rotation or inclination of the front end part. Moreover, by using the medical treatment endoscope according to the first embodiment, there are unreachable points for the instrument since the bending radius of the first sheath 3 is large, resulting from a tube made of a styrene-derived elastomer being employed as the first sheath 3. In this embodiment, a bending part 203B is provided at the front end side of the first sheath 203 that connects the multiple joint wheels 201. By providing the bending part 203B, the bending radius at the front end part becomes smaller, and it is possible to freely direct the sheath front end part 203A in an optional direction. As a result, the approach of the instrument is facilitated and the procedure can be carried out smoothly.

Furthermore, the first arm member 208A and the second at in member 208B are constructed so as not to advance or retract with respect to the sheath front end part 203A due to the supports 237. Therefore, only the high frequency scalpel 205A or other such instrument projecting out from the front end part 215A of the first arm member 208A advances or retracts with respect to the first arm member 208A. In the first embodiment, the state in which the instrument is directed along the central axis of the first sheath 203 is designated as the starting state, regardless of the open/close status of the first arm member 8A and second arm member 8B. Furthermore, based on the idea of being able to move the instrument forward/backward, up/down or left/right from the starting state, the construction was provided to enable the first arm member 8A, which is provided with a bending part 7, to advance and retract with respect to the first sheath 3. However, defining the state in which the first arm member 208A and the second arm member 208B are opened by the open/close mechanism 210, and the instrument at the front end is directed inward so that the front end and the affected part come into the field of view of the image pick-up unit 211, to be the starting state of the first arm member 208A and the second arm member 208B is natural. In this starting state, the construction is employed in which only the instrument projecting out from the front end part 215A, and not the first arm member 208A, is advanced and retracted, so as to enable advance and retract of the instrument with respect to the affected part.

Next, the bending operation of the first arm member 208A and the second arm member 208B via operation of the instrument operating parts 131A and 131B can be carried out with an even smaller amount of force at the operating part 151 of the medical treatment endoscope 200 according to this embodiment.

In the preceding first embodiment, the attachment part 58 is supported in a manner to enable relatively free movement within the frames of the rectangular, plate-shaped first movement restricting member 60 and the second movement restricting member 61. The construction is provided in which the operational input to the forceps operating part 31 that is attached to the attachment part 58 is communicated via the first movement restricting member 60 and the second movement restricting member 61 to the first belt member 65, which is connected to the end part of the first movement restricting member 60, and the second belt member 72, which is connected to the end part of the second movement restricting member 61. In this construction, in the case of an operational input to grip the forceps operating part main body 32 and move it vertically or horizontally, when the forceps operating part main body 32 is inclined in the direction of input of the operation, with the attachment part 58 employed as a fulcrum, then the attachment part 58 is pressed against the first movement restricting member 60 and the second movement restricting member 61, leading to resistance. As a result, there is an undesirable increase in the force required for operation.

In addition, the first belt member 65 and the second belt member 72 are connected to the one end 60a of the first movement restricting member 60 and the one end 61a of the second movement restricting member 61, respectively. For this reason, the force for moving the first belt member 65 and the second belt member 72 becomes focused at the end part of the first movement restricting member 60 and the second movement restricting member 61. A movement is generated as a result, leading to resistance in the movement. As a result, there is an undesirable increase in the force required for operation.

Accordingly, in this embodiment, the construction is provided in which the first movement restricting member 160 and the second movement restricting member 161 are composed of the slide rails 160a and 161a, respectively, and the slide blocks 158A and 158B of the attachment part 158 engage with these respective slide rails 160a and 161a to permit sliding. According to this construction, when there is an operational input to the instrument operating parts 131A and 131B, the attachment part 158 can be smoothly displaced with a light amount of operating force, without inclining resulting from the employment of the attachment part 158 as a fulcrum. Furthermore, the first belt member 165 is connected to the first die parts 160b that are provided at the longitudinal center of the slide rails 160a. The first movement restricting member 160 is disposed on the frame member 170 via the first bending guide 196, which has the slide rail 196a and the slide block 196b that engages with the slide rail 196a in a manner to enable sliding. According to this construction, it is possible to reduce generation of a movement during the communication of the operational input from the first movement restricting member 160 to the first belt member 165 regardless of the position of the attachment part 158 on the first movement restricting member 160. This also applies to the connection between the second movement restricting member 161 and the second belt member 172. As a result, it becomes possible to realize an even greater reduction in the amount of operating force required.

Furthermore, by sliding the moving frame 45A with respect to the fixed frame 45B via the slide mechanisms 148 and 190, the instrument insertion part 125, which is inserted into the first arm member 208A, is made to advance and retract with respect to the first arm member 208A and the first sheath 203. As a result, the high frequency scalpel 205A or other such instrument can be made to project out or retract back from the front end part 215A of the first arm member 208A. Accordingly, it is possible to increase the procedure limits for the instrument for the first arm member 208A and the first sheath 203. Furthermore, the construction is provided in which the advance and retraction of the instrument is carried out by varying the length of the instrument insertion part 125 with respect to the first arm member 208A, enabling the advance and retraction of the instrument to be carried out smoothly. This type of construction provides the benefit of enabling the advance/retract mechanism for the instrument to be provided at an optional position. Furthermore, in the operating part 151 in this embodiment, the sheath advance/retract part 191 is provided at the perpendicular part that extends from the first sheath 203 to the bending operating part 147, which is essential basically. As a result, this construction succeeds in shortening the overall length of the operating part 151 while at the same time providing an instrument advance/retract mechanism. Moreover, since the sheath advance/retract part 191 is provided farther toward the first sheath 203 side than the part bending the instrument insertion part 125, the resistance between the instrument sheath 192 and the instrument insertion part 125 which is generated at the bent part of the instrument insertion part 125 is not received during operations to advance and retract the instrument. As a result, the operation of advancing and retracting the instrument can be accomplished with a light force.

Moreover, the first tubular member 191a and the second tubular member 191b that are disposed in a nesting manner are relatively long, so that it is possible to greatly adjust the length of the instrument insertion part 125. As a result, in addition to being able to increase the advance/retract width of the instrument, the sheath advance/retract part 191 can also be used to absorb differences in the length of the instrument insertion part 125 when exchanging instruments.

Furthermore, the sheath operating part 194 which is provided with a bending knob 195 for operating the bending part 203B can be freely attached to and released from the stand part 194A that is attached to the gear box 157a of the fixed frame 145B. According to this construction, when inserting the inserted part of the medical treatment endoscope 200 into a body cavity, the sheath operating part 194 can be operated after being detached from the stand part 194A, thereby improving operability during insertion. The sheath operating part 194 is constructed to attach to the stand part 194A when performing a treatment, to enable fine adjustment of the bending angle of the bending part 203B by rotational operation of the bending knob 195.

In this embodiment as well, the open/close mechanism 210 can be operated by operating the open/close operating part 146 of the operating part 151 to advance and retract the bending opening/closing wires 244 with respect to the first sheath 203. Furthermore, by performing operations in the state of the instrument operating part 131B of the gripping forceps 205B attached to the bending operating part 147, not only can open/close operation of the paired forceps pieces 226A and 226B of the gripping forceps 205B be performed, but it is also possible to carry out bending operation of the bending part 207. Thus, the procedure is facilitated. Moreover, by rotating the instrument operating part 131 with respect to the attachment part 158, the instrument can be rotated to the desired state. Moreover, since the bending part 207 is employed only for bending an instrument such as gripping forceps 205B, greater bending is possible, and a larger force can be output, as compared to conventional endoscopes in which there is a structure that is required to bend a plurality of apparatuses such as instruments, video cable (the image guide in an optical endoscope), light guides and the like.

Fourth Embodiment

A fourth embodiment will now be explained with reference to the figures. The medical treatment endoscope according to the present embodiment represents a further improvement over the medical treatment endoscope according to the first embodiment.

As illustrated in FIG. 43, a medical treatment endoscope 300 includes a first sheath 301 similarly configured to the medical treatment endoscope 1 according to the first embodiment; a second sheath 303A having a first arm member 302A and protruding from the first sheath 301; and a third sheath 303B having a second arm member 302B and protruding from the first sheath 301. Since the first arm member 302A and the second arm member 302B have approximately the same configuration, the first arm member 302A will be mainly explained hereafter.

As illustrated in FIGS. 44 to 52, the first arm member 302A includes: a first bending part 306 having a first joint ring 305 pivotally attached thereto; and a second bending part 308 where the first joint ring 305 bends in a first bending direction and in a second bending direction crossing with the first bending direction around the center of a first direction D1 that is parallel with a longitudinal direction (central axis direction) C of the first sheath 301, a second joint ring 307 which bends in the second direction D2 away from the longitudinal direction of the first sheath 301 is pivotally attached to the second base end bending part 308A, the base end of the second base end bending part 308A is joined to the sheath front end part 301A of the first sheath 301, the second joint ring 307 bending in the first direction D1 from the second direction D2 is pivotally attached to the second bending part 308, and the tip of the second tip end bending part 308B is joined to the base end of the first bending part 306.

As illustrated in FIGS. 53 to 60, the first joint ring 305 is pivotally supported at four points by support axis parts 310 which are disposed on a plane defined by a vertical direction of an image observed with a viewing device 12 (up and down direction in FIG. 56) and by a horizontal direction (right and left direction in FIG. 56) so that the vertical and horizontal direction are orthogonal (AX1 direction and AX2 direction in FIG. 56) and 45 degrees offset.

The second joint ring 307 and a second joint ring 307' are pivotally supported by four support axis parts 310 that are disposed on a plane defined by two directional lines (AX3 and AX4 illustrated in FIG. 56) rotatively offset by a predetermined angle with respect to the directions AX1 and AX2. The second bending part 308 therefore bends in the direction which passes through an object lens (objective optical system) 23 provided at the viewing device 12 and inclines relative to a plane orthogonal to the longitudinal direction C of the first sheath 301, and the tip of the second bending part 308 separates away from the perspective field of the viewing device 12.

The second joint rings 307 and 307' are pivotally attached to each other and urged in a direction so that a linear state of the second bending part 308 is maintained. A tip end surface 307a and a base end surface 307b are formed on the second joint rings 307 and 307' so that the tip end surface 307a and the base end surface 307b make contact with each other with the maximum bent state of the second bending part 308, and so that the tip end surface 307a and the base end surface 307b incline by a predetermined angle so as to be able to separate from each other according to deformation of the second bending part 308 into linear state.

A tip part 15 and the first bending part 306 are pivotally attached to each other via a solid short pipe 311A. The first bending part 306 and the second bending part 308 are pivotally attached to each other via a solid short pipe 311B. The second bending part 308 and the sheath front end part 301A are pivotally attached to each other via a solid short pipe 311C. The second base end bending part 308A and the second tip end bending part 308B are pivotally attached to each other via a solid short pipe 311D.

Notches 312 extending in the longitudinal directions of the first bending part 306 and second bending part 308 are provided to the second joint rings 307 and 307' and the short pipes 311B, 311C, 311D. Provided on the short pipe 311B are the notches 312' at four points in the up-down direction and right-left direction. Provided on the short pipe 311D is a notch 312' having an enlarged open end so that two neighboring coil tubes can be inserted. Provided on the short pipe 311C is a similar notch 312' at the position 180 degrees rotated from there.

Fitted to the notch 312 of the short pipe 311B are the tips of coil tubes 313A, 313B, 313C, 313D. The tip of the coil tube 313E is fitted to the notches 312 and 312' of the short pipe 311D, and the coil tubes 313A, 313B, 313C, 313D are inserted therethrough. The tip of the coil tube 313F is fitted to the notches 312 and 312' of the short pipe 311C, and the coil tubes 313A, 313B, 313C, 313D, and 313E are inserted therethrough.

In addition, the medical treatment endoscope 300 includes first bending wires (first operating members) 315A, 315B, 315C, and 315D, inserted through the first bending part 306 and the second bending part 308, for bending the first bending part 306; and second bending wires (second operating members) 316A and 316B, inserted through the second bending part 308, for bending the second bending part 308.

The tips of the first bending wires 315A, 315B, 315C, 315D are connected to the short pipe 311A. The first bending wires 315A, 315B, 315C, 315D are retractably inserted through the coil tubes 313A, 313B, 313C, 313D respectively between the short pipe 311B and a manipulation side of the operation part which is not shown in the drawings. That is, they are inserted in the up-down direction and in the right-left direction of FIG. 56.

The first bending wires 315A, 315C in this state are connected to a vertical bending operating part of the operation part which is not shown in the drawings. The first bending wires 315B, 315D are connected to a horizontal bending operating part of the operation part which is not shown in the drawings. Operating these operation parts extends and retracts the first bending wires 315A, 315B, 315C, 315D respectively; thereby bending the first bending part 306 in the desirable direction.

Figure 56:
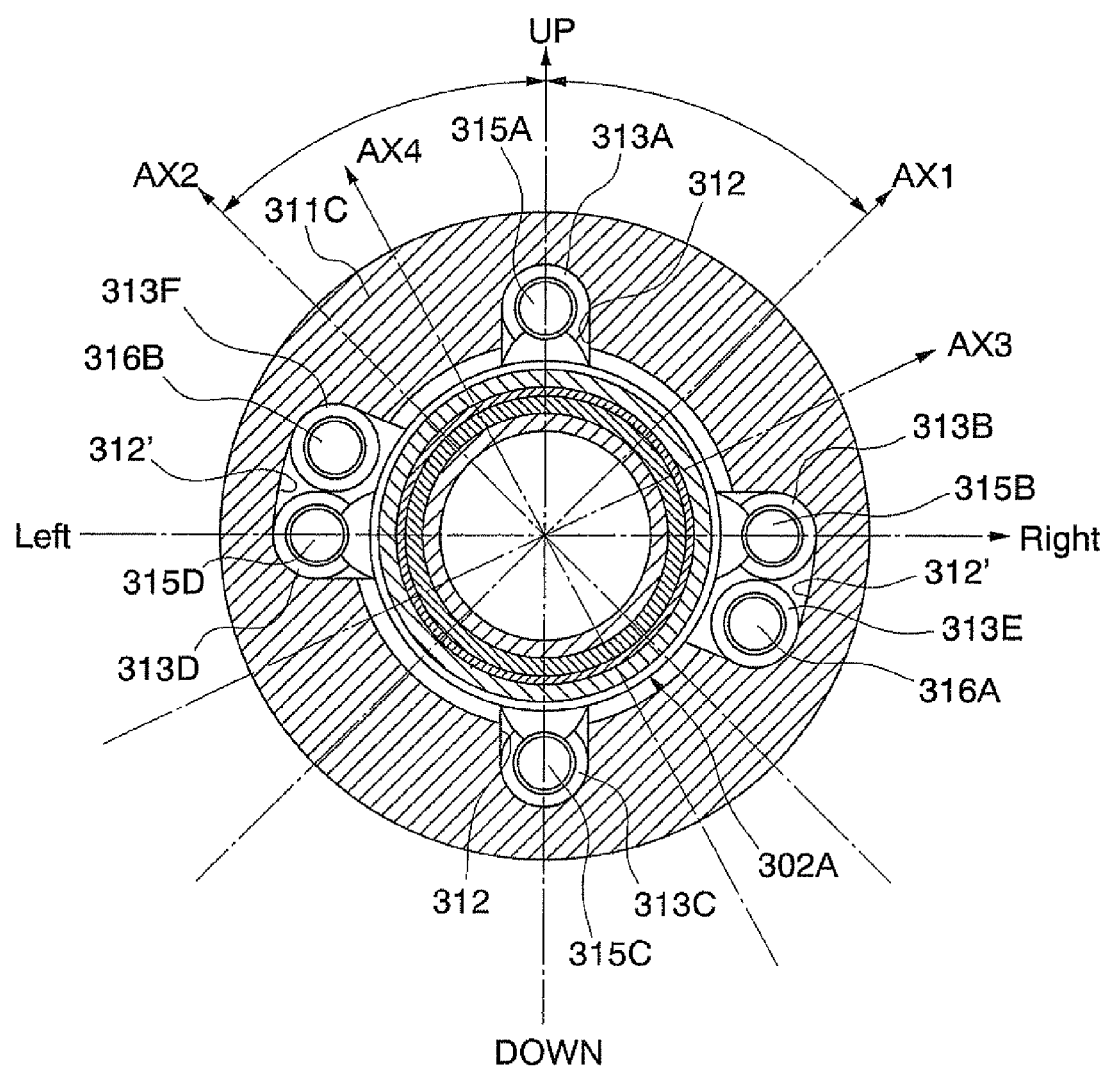
FIG. 56 shows the arm member of the medical treatment endoscope in cross-sectional view.
Figure 57:
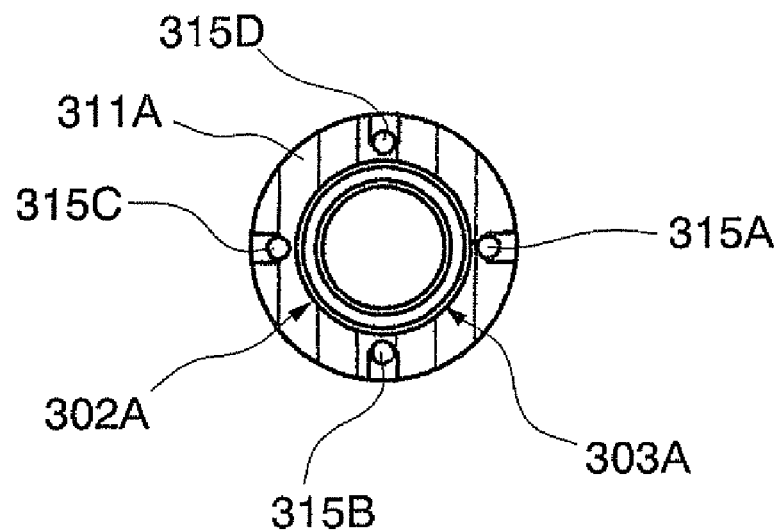
FIG. 57 is a cross-sectional view along the line I-I in FIG. 53.
Figure 58:
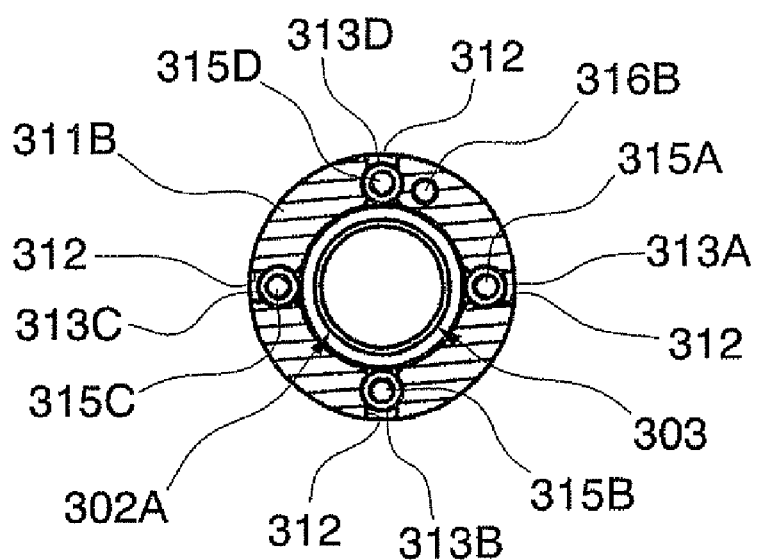
FIG. 58 is a cross-sectional view along the line II-II in FIG. 53.
Figure 59:
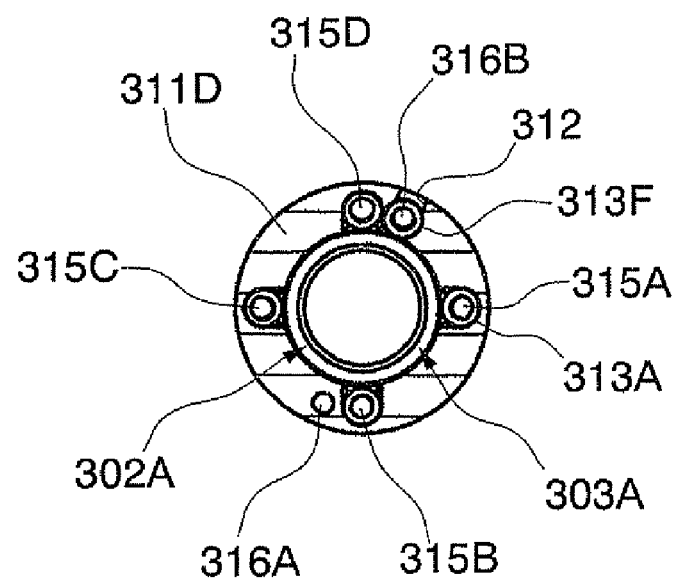
FIG. 59 is a cross-sectional view along the line in FIG. 53.
Figure 60:
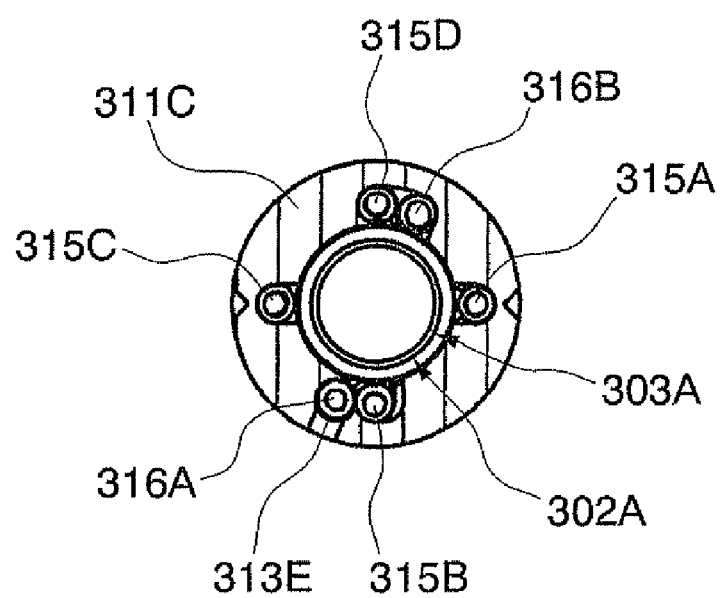
FIG. 60 is a cross-sectional view along the line IV-IV in FIG. 53.

The tip of the second bending wire 316A is connected to the short pipe 311D and retractably inserted through the coil tube 313E between the short pipe 311C and the operation part for manipulation. The tip of the coil tube 313E is connected to the short pipe 311C. That is, the coil tube 313E is inserted at a clockwise offset position by 45 degrees relative to the direction AX3 as illustrated in FIG. 56. The base end of the second bending wire 316A is connected to an open/close operating part which is not shown in the drawings. Operating the open/close operating part extends and retracts the second bending wire 316A; thereby bending the second base end bending part 308A.

The tip of the second bending wire 316B is connected to the short pipe 311B and retractably inserted through the coil tube 313F between the short pipe 311D and the operation part for manipulation. The tip of the coil tube 313F is connected to the short pipe 311D. That is, the coil tube 313F is inserted at a counter clockwise offset position by approximately 45 degrees relative to the direction AX4 as illustrated in FIG. 56. The base end of the second bending wire 316B is connected to the open/close operating part which is not shown in the drawings. Operating the open/close operating part extends and retracts the second bending wire 316B; thereby bending the second tip end bending part 308B.

The diameter of first bending wires 315A, 315B, 315C, 315D and the second bending wires 316A, 316B is 0.45 mm, which is greater than that of 0.36 mm for bending wires 17A, 17B, 17C, and 17D in the medical treatment endoscope 1 according to the first embodiment. Applied on the surfaces of the first bending wires 315A, 315B, 315C, 315D and the second bending wires 316A, 316B are a PTFE (polytetrafluoroethylene) coating for reducing friction resistance.

Figure 61:
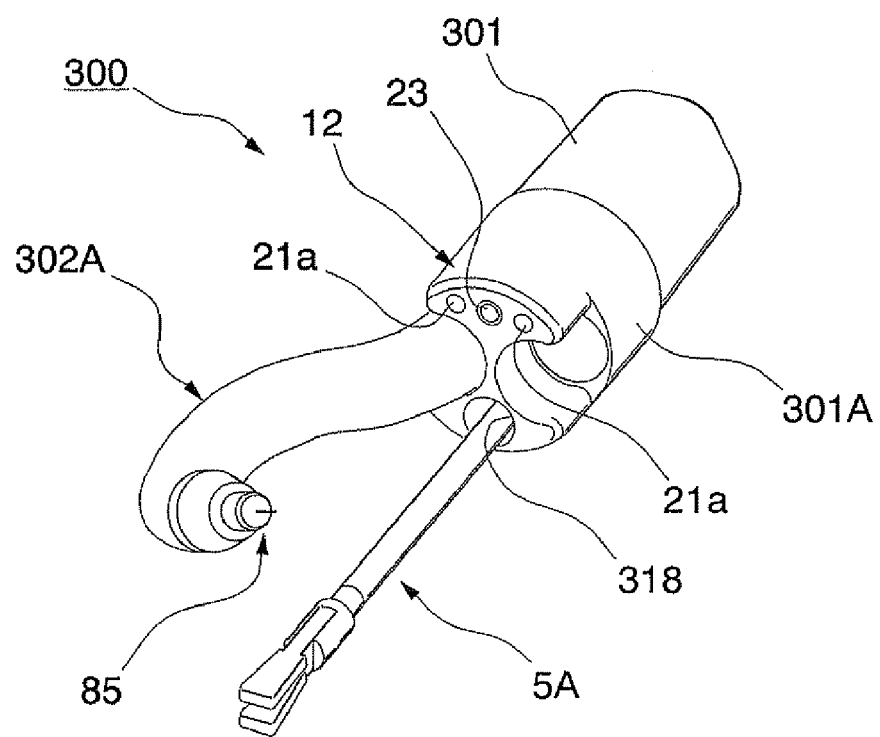
FIG. 61 is a perspective view of a tip of the medical treatment endoscope.

As shown in FIG. 61, provided through the first sheath 301 and sheath front end part 301A is a channel 318 that allows an endoscopic treatment instruments, e.g., a grasping forceps 5A to be freely inserted therethrough.

Figure 62:
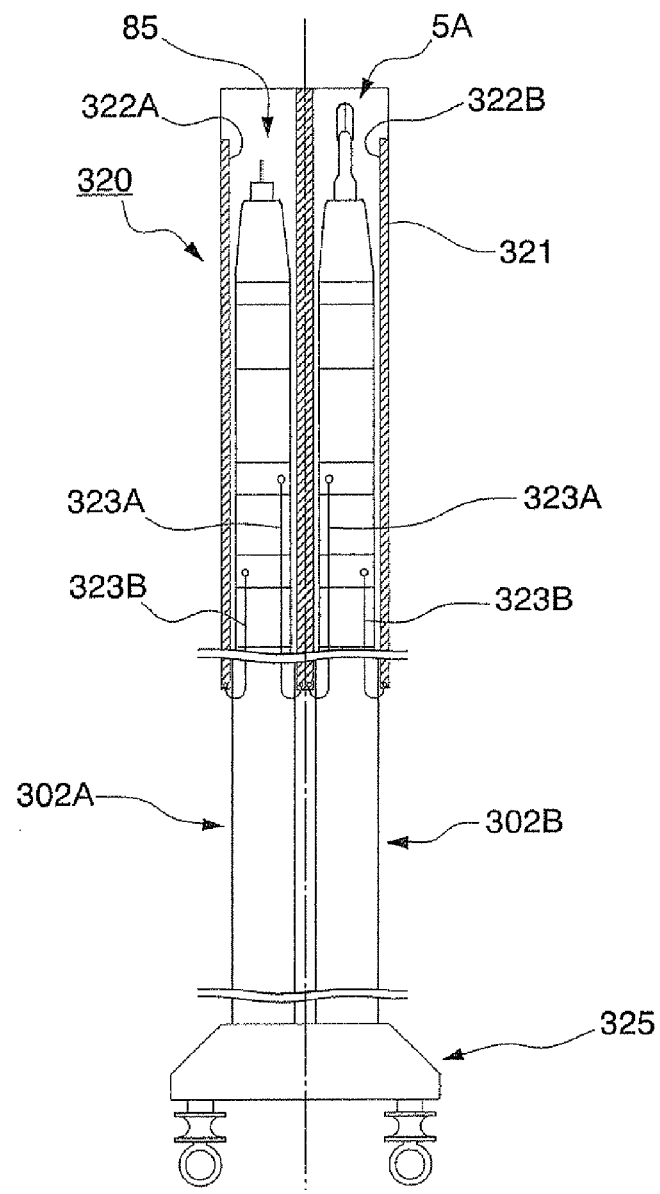
FIG. 62 is a schematic representation of a modified example of the medical treatment endoscope.
Figure 63:
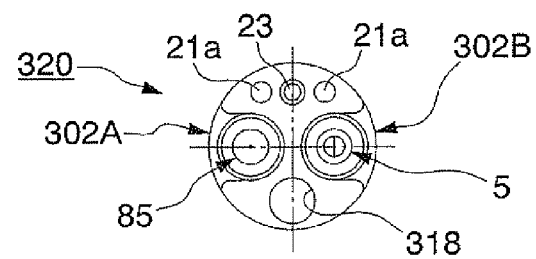
FIG. 63 shows the medical treatment endoscope of FIG. 62 viewed along the line in front view.
Figure 64:
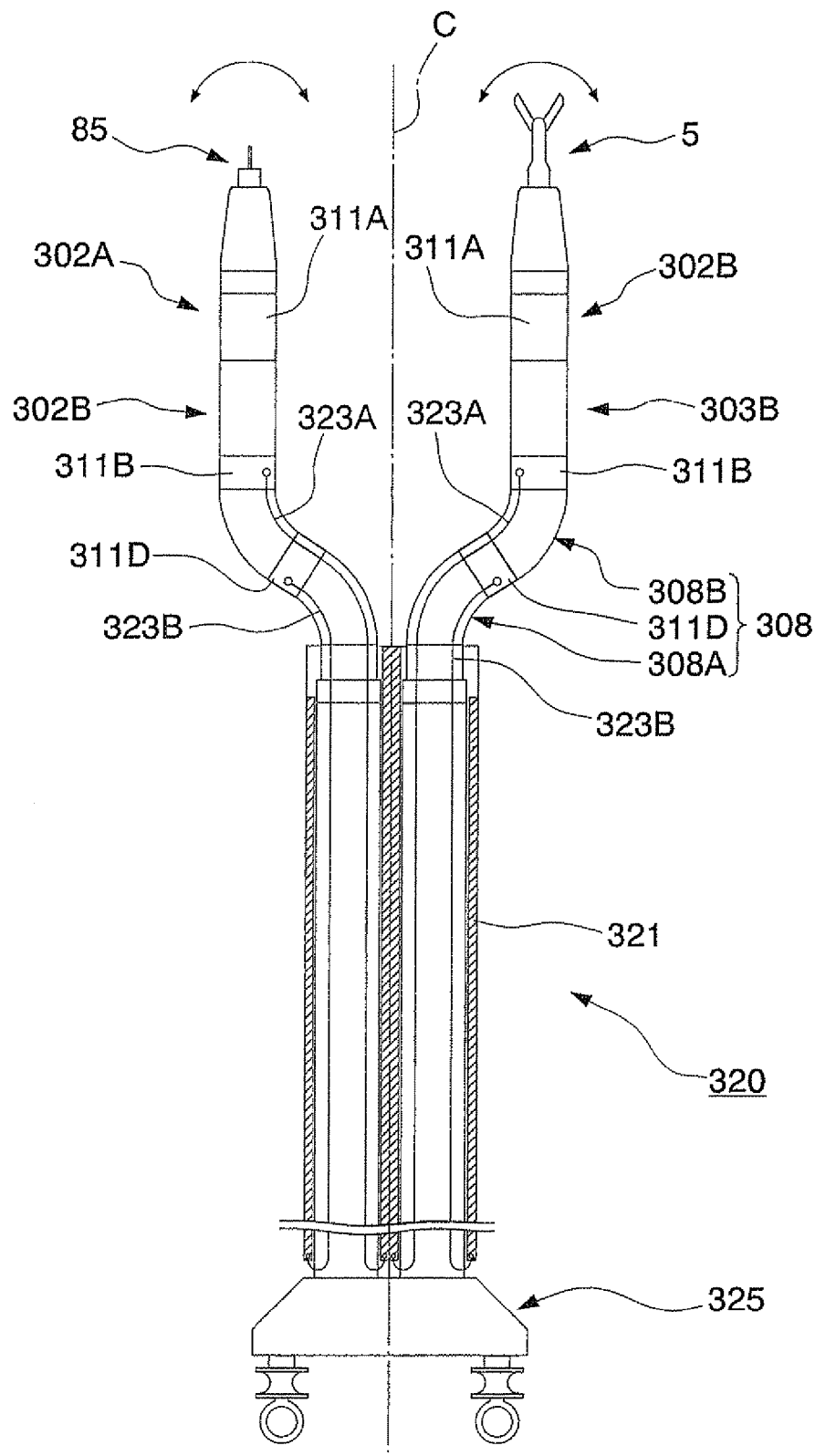
FIG. 64 shows a bending state of the medical treatment endoscope of FIG. 62.

In addition, as illustrated in FIGS. 62 to 64, the medical treatment endoscope 320 may further include a flexible storage sheath 321 for containing the tip portions of the first arm member 302A and second arm member 302B in an extended condition. Provided in the storage sheath 321 are a first arm member lumen 322A which allows the first arm member 302A to be inserted therethrough; a second arm lumen 322B which allows the second arm member 302B to be inserted therethrough; and extension/retraction operating wires 323A and 323B for bending the second bending part 308 while protruding and retracting the arm members 302A and 302B from each lumen 322A, 322B. The tip of the extension/retraction operating wire 323A connected to the short pipe 311B is inserted through the first arm member lumen 322A or the second arm lumen 322B, and is connected to the base end of the first arm member lumen 322A or the second arm lumen 322B.

The tip of the extension/retraction operating wire 323B connected to the short pipe 311D is inserted through the first arm member lumen 322A or the second arm lumen 322B, and is connected to the base end of the first arm member lumen 322A or the second arm lumen 322B.

A drawing force is applied to the extension/retraction operating wires 323A and 323B according to the protrusion of the first arm member 302A and second arm member 302B from the tip of the storage sheath 321 caused by the movement of the storage sheath 321 toward the operating part 325. This results in bending the second bending part 308 into a desirable direction since the extension/retraction operating wires 323A and 323B act similarly to the second bending wires 316A, 316B.

Next, the operation of the medical treatment endoscope 300 according to the present embodiment will be explained.

Figure 65:
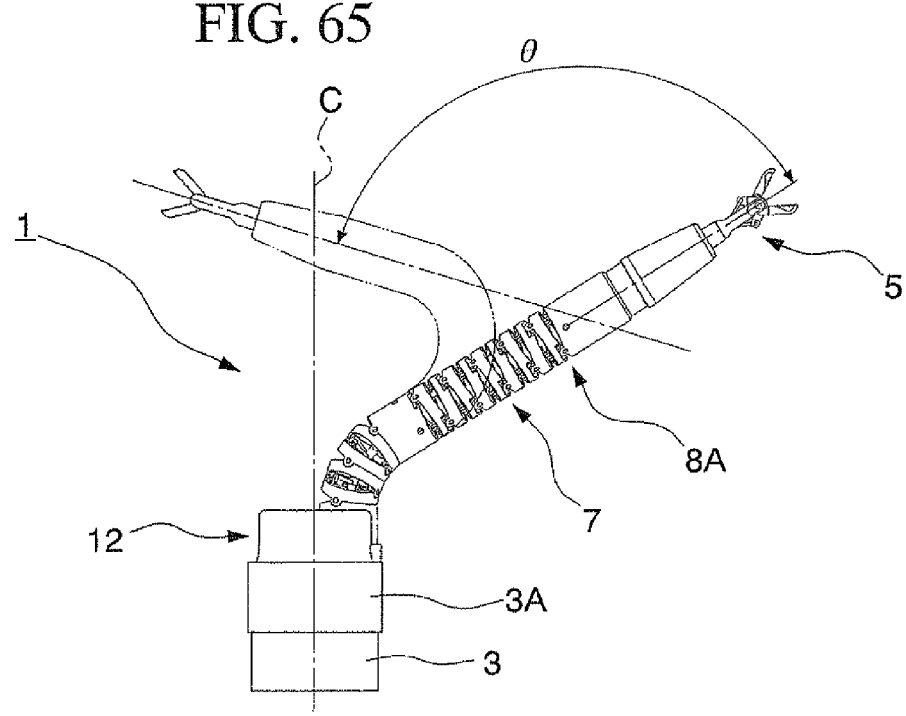
FIG. 65 is a perspective diagram illustrating a bending state of the arm member of the medical treatment endoscope according to the first embodiment.

As illustrated in FIG. 65, a bending part 7 of the medical treatment endoscope according to the first embodiment must swing in a range of angle θ for conducting a predetermined treatment by opening the first arm member 8A and the second arm member 8B relative to the first sheath 301. Some axial force caused by the extending and retracting bending wire is therefore used for bending the bending part 7. Therefore, a sufficient force may not be generated sometimes at the tip of the treatment instruments while maintaining the bending state of the bending part 7 if the first arm member 8A and the second arm member 8B are in a bending state.

Figure 66:
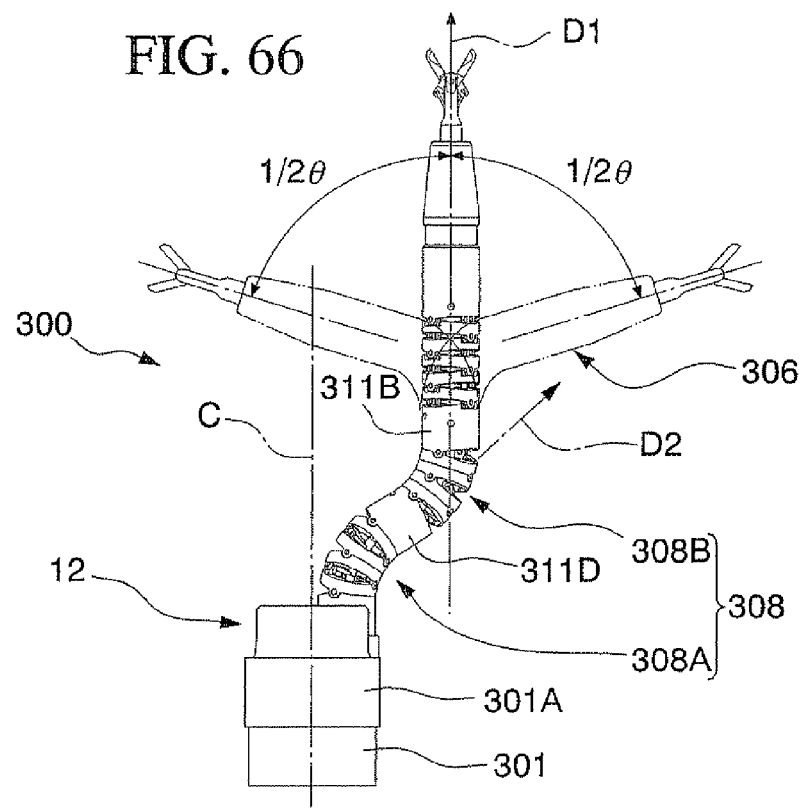
FIG. 66 is a perspective diagram illustrating a bending state of the arm member of the medical treatment endoscope according to the fourth embodiment.

In contrast, as illustrated in FIG. 66, the second base end bending part 308A of the medical treatment endoscope 300 according to the present embodiment bends in the second direction D2 which separates away from the longitudinal direction C of the first sheath 301 and bends the second tip end bending part 308B in the first direction D1. This allows the first bending part 306 in the vicinity of the tip of the short pipe 311B to bend in a range of angle θ that is the same as that of the first embodiment by a stepwise swing by approximately ½θ around the first direction D1. Therefore a smaller axial force generated in the first bending wires 315A, 315B, 315C, 315D can bend the bending part 7, thereby allowing the tip of the treatment instruments to generate a greater force.

Retracting the second bending wires 316A, 316B fixes the bending state of the second bending wires 316A, 316B at the second bending part 308 because a tip end surface 307a of the second joint ring 307 in the second bending part 308 makes contact with a base end surface 307b of the neighboring second joint ring 307 disposed separately. The continuous retraction of the second bending wires 316A, 316B thereby desirably maintains the bending state of the second bending part 308.

Instead, slacking the second bending wires 316A, 316B releases the bending state of the second bending part 308. The restoration (resilience) in this state of the second bending part 308 into the linear state increases while bending the second bending part 308 from the linear extending state. Therefore, slacking, i.e., stopping the retraction of the second bending wires 316A, 316B, releases the bending state of the second bending part 308.

Figure 67:
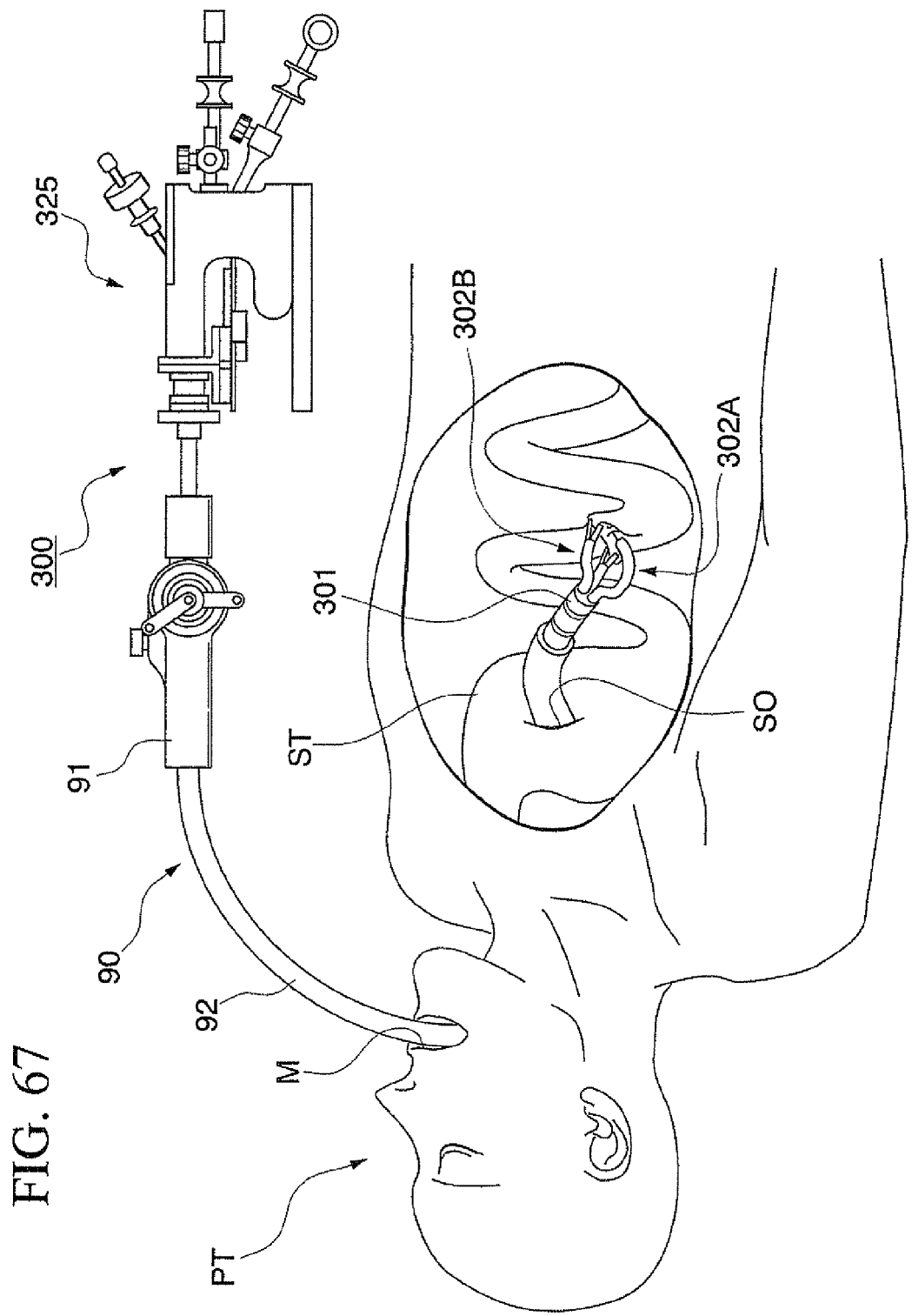
FIG. 67 is a view explaining the state where an overtube having the medical treatment endoscope according to the fourth embodiment inserted therethrough is inserted into an abdominal cavity via a stomach during medical procedure.
Figure 68:
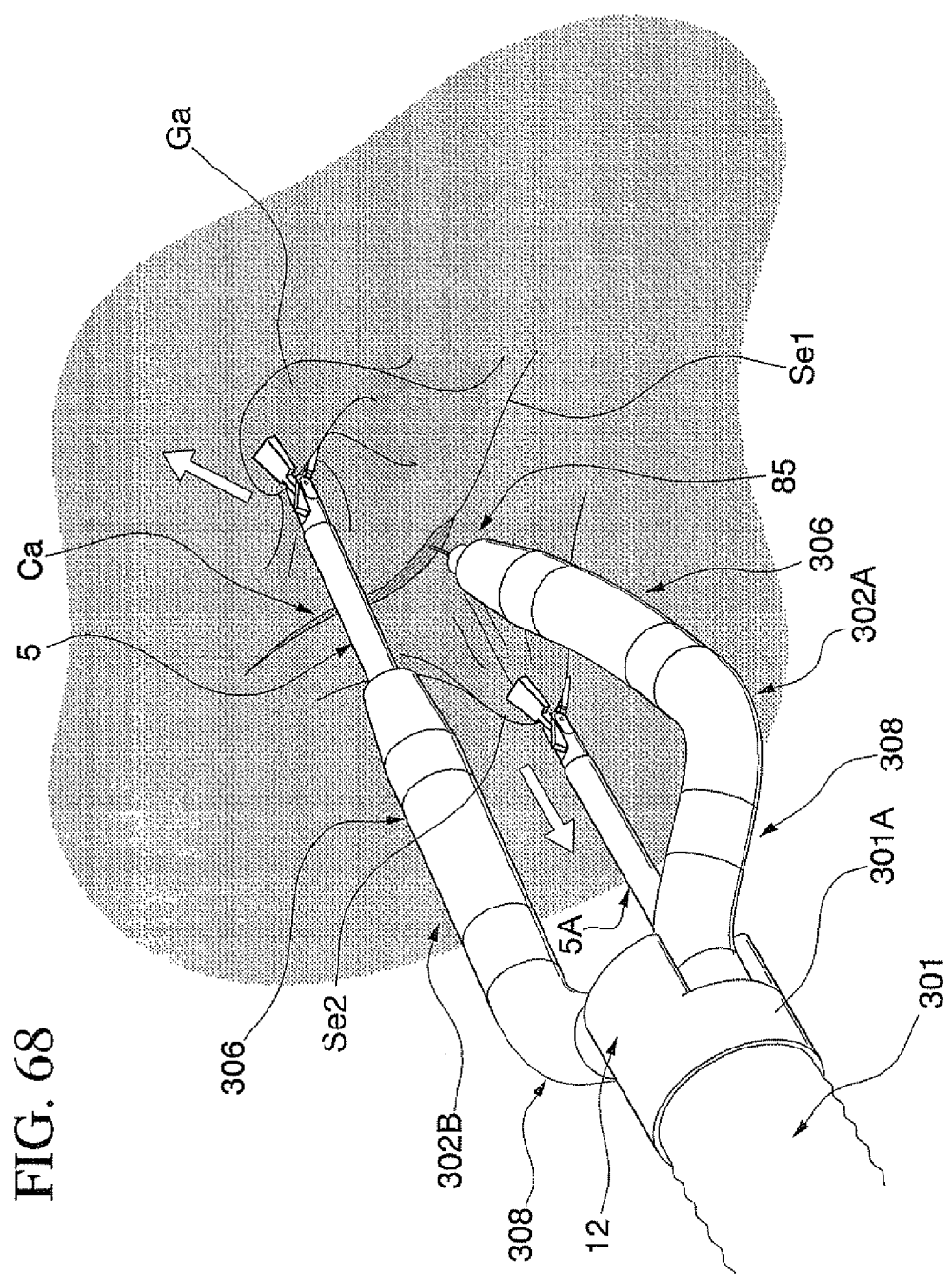
FIG. 68 illustrates a manipulation procedure using a medical treatment endoscope.

A natural orifice medical procedure using the medical treatment endoscope 300 according to the present embodiment will be explained with reference to a case as shown in FIGS. 67 and 68 where a gallbladder extraction is conducted similarly to the first embodiment by inserting the medical treatment endoscope from the mouth M of the patient PT into the stomach ST, forming an opening on the stomach wall, and inserting a first sheath 301 of the medical treatment endoscope into the abdominal cavity AC.

The medical procedure according to the present embodiment includes: a step of inserting a medical treatment endoscope 300 in the vicinity of an affected part; a step including disposing a high frequency knife (first endoscopic treatment instrument) 85 via the first arm member 302A, disposing a grasping forceps (second endoscopic treatment instrument) 5 in the vicinity of the affected part via the second arm member 302B, and disposing a grasping forceps (third endoscopic treatment instrument) 5A in the vicinity of the affected part via a channel 318 of the first sheath 301; a step of bending the first arm member 302A and the second arm member 302B into different directions respectively; and a step of conducting treatment to the affected part with the grasping forceps 5, the high frequency knife 85, and the grasping forceps 5A.

In the insertion step, an overtube 90 is introduced into an abdominal cavity AC via an opening SO formed on a stomach ST similarly to the first embodiment.

Consequently inserted through a lumen 88 of the overtube 90 are a first sheath 301, a second sheath 303A, and a third sheath 303B. The first arm member 302A and the second arm member 302B are protruded from the tip of the overtube 90.

The high frequency knife 85 is inserted into the second sheath 303A and the first arm member 302A similarly to the first embodiment, and the grasping forceps 5 is inserted into the third sheath 303B and the second arm member 302B similarly to the case of the high frequency knife 85. In addition, the grasping forceps 5A is inserted into a channel 318 provided in the first sheath 301.

The medical procedure transfers to the next step, i.e., the disposing step. The second arm member 302B is positioned to grasp the affected part with the grasping forceps 5.

Operating an open/close operating part retracts a second bending wire 316A until a tip end surface 307a of a second joint ring 307 makes contact with a base end surface 307b, thereby bending the second base end bending part 308A from a longitudinal direction C to a second direction D2. Retracting further the second bending wire 316B until the tip end surface 307a of the second joint ring 307 makes contact with the base end surface 307b bends a second tip end bending part 308B from a second direction D2 to a first direction D1. The direction of the second bending part 308 is thus fixed. Note that the second bending wires 316A, 316B may be retracted simultaneously.

The bending operating part is consequently operated to swing the first bending part 306 around the first direction D1 in order to inspect the affected part with the viewing device 12. Operating a forceps-operating part which is not shown in the drawings extends, for example, the grasping forceps 5 toward the second arm member 302B, thereby grasping and retracting a cervical part Ga of the gallbladder to expose a Calot trigone Ca.

The medical procedure in this state transfers to the treatment step.

A serosal membrane Se1 is incised a little at a time with the high frequency knife 85 inserted in the first arm member 302A by operating the bending operating part. Conducted so as to apply adequate tension to the incised part are picking the incised part with the grasping forceps 5A inserted through the channel 318 while grasping the cervical part Ga of the gallbladder with the grasping forceps 5; grasping a serosal membrane Se2 opposite the cervical part Ga of the gallbladder; drawing the grasped serosal membrane Se2 toward the endoscopist; bending the first bending part 306 of the second arm member 302B away from the grasping forceps 5A; and adjusting the drawing direction. Meanwhile, adipose tissue and fiber tissue including serous membrane are peeled with the high frequency knife 85 while bending the first bending part 306 of the first arm member 302A.

The gallbladder extraction is conducted by the operation similar to the first embodiment after identifying the gallbladder in this manner.

In addition to the previously explained gallbladder extraction, the medical treatment endoscope according to the present invention can be used for various manipulations, e.g., appendectomy, gastroduodenal bypass, liver biopsy, biopsy of the pancreas, tubal interruption, and hysterectomy.

In the medical treatment endoscope 300, provided instead of the solid open/close mechanism provided at the medical treatment endoscope according to the first embodiment are flexible second bending parts 308 disposed at root parts of the first arm member 302A and the second arm member 302B. The length of the solid portions in the first arm member 302A and the second arm member 302B shorter than that of the medical treatment endoscope provides higher flexibility, thereby improving insertability. The tip end surface 307a and the base end surface 307b formed in the second joint ring 307 incline so that the tip end surface 307a and the base end surface 307b make contact with each other in the second joint ring 307 at the second bending part 308 when the second bending wires 316A, 316B are drawn. Drawing the wires continuously to maintain the contact between the tip end surface 307a and the base end surface 307b allows the second bending part 308 to be fixed in the predetermined bending state.

The first bending part 306 in this state can be bent with respect to the first direction D1. The bending range of the first bending part 306 while using treatment instruments can be narrower than in the case of the medical treatment endoscope according to the first embodiment. In addition, it is possible to reduce a force necessary to bend the first bending part 306 and increase an operation force at the tip of the first arm member 302A and the tip of the second arm member 302B.

Also, since the first bending wires 315A, 315B, 315C, 315D are inserted at positions conforming in the vertical and horizontal directions defined on an image observed with the viewing device, intuitive operation while observing the image can be conducted. In addition, the second bending wires 316A, 316B inserted at the positions rotated by a predetermined degree relative to the positions of the first bending wires 315A, 315B, 315C, 315D allow the second base end bending part 308A to be directed outward and downward relative to the center of the first sheath 301 when the second bending part 308 is bent. The affected part, the first arm member 302A, or the second arm member 302B that is captured by the viewing device 12 can be viewed or treated from above since the central axis of the first bending part 306 is beneath the central axis of the first sheath 301.

In addition, formed at the first joint ring 305 and the second joint ring 307 are notches 312, 312' extending in the longitudinal directions of the first bending part 306 and the second bending part 308. The coil tubes 313A, 313B, 313C, 313D, 313E, and 313F are inserted through the notches 312 and 312'. The outer diameters of the first joint ring 305 and the second joint ring 307 may be desirably maintained if the thickness of the wall of these joint rings is increased.

The dispositions of the second bending wires 316A, 316B inserted through the second joint ring 307 are offset rotated by approximately 45 degrees relative to the pivotally attached second joint ring 307. Therefore, retracting the second bending wire 316A to bend the second base end bending part 308A, or retracting the second bending wire 316B to bend the second tip end bending part 308B rotates the neighboring second joint rings 307 or the joint rings 307' around the axes AX3 and Ax4, thereby abutting the neighboring second joint rings 307 or 307'. The second bending part 308 can be restored to a linear state by releasing the bending state of the second bending part 308 retracted by the second bending wires 316A, 316B since the pivotally attached second joint rings 307 and 307' are urged in a direction in which the linear state of the second bending part 308 is maintained. Therefore, a smaller outer diameter of the bending part can be maintained.

The outer diameter of each bending wire greater than the diameter of the bending wire in the medical treatment endoscope can increase the wire-breaking force, thereby allowing retraction with a greater force. The PTFE coating applied on the wire surface can reduce the friction resistance, thereby providing greater force at the tips of the wires.

Also, the channel 318 provided at the sheath front end part 301A of the first sheath 301 allows treatment instruments to be disposed in the channel 318, thereby allowing more complex procedures to be conducted. Furthermore, the number of exchanges of the treatment instruments can be reduced.

A drawing force can be applied to the extension/retraction operating wires 323A and 323B according to the protrusion of the first arm member 302A and second arm member 302B from the tip of the storage sheath 321 in use. The second bending part 308 can therefore be bent in a desired direction simply by protruding the first arm member 302A and the second arm member 302B from the tip of the storage sheath 321 since the extension/retraction operating wires 323A and 323B have similar functions as those of the second bending wires 316A, 316B.

Figure 69:
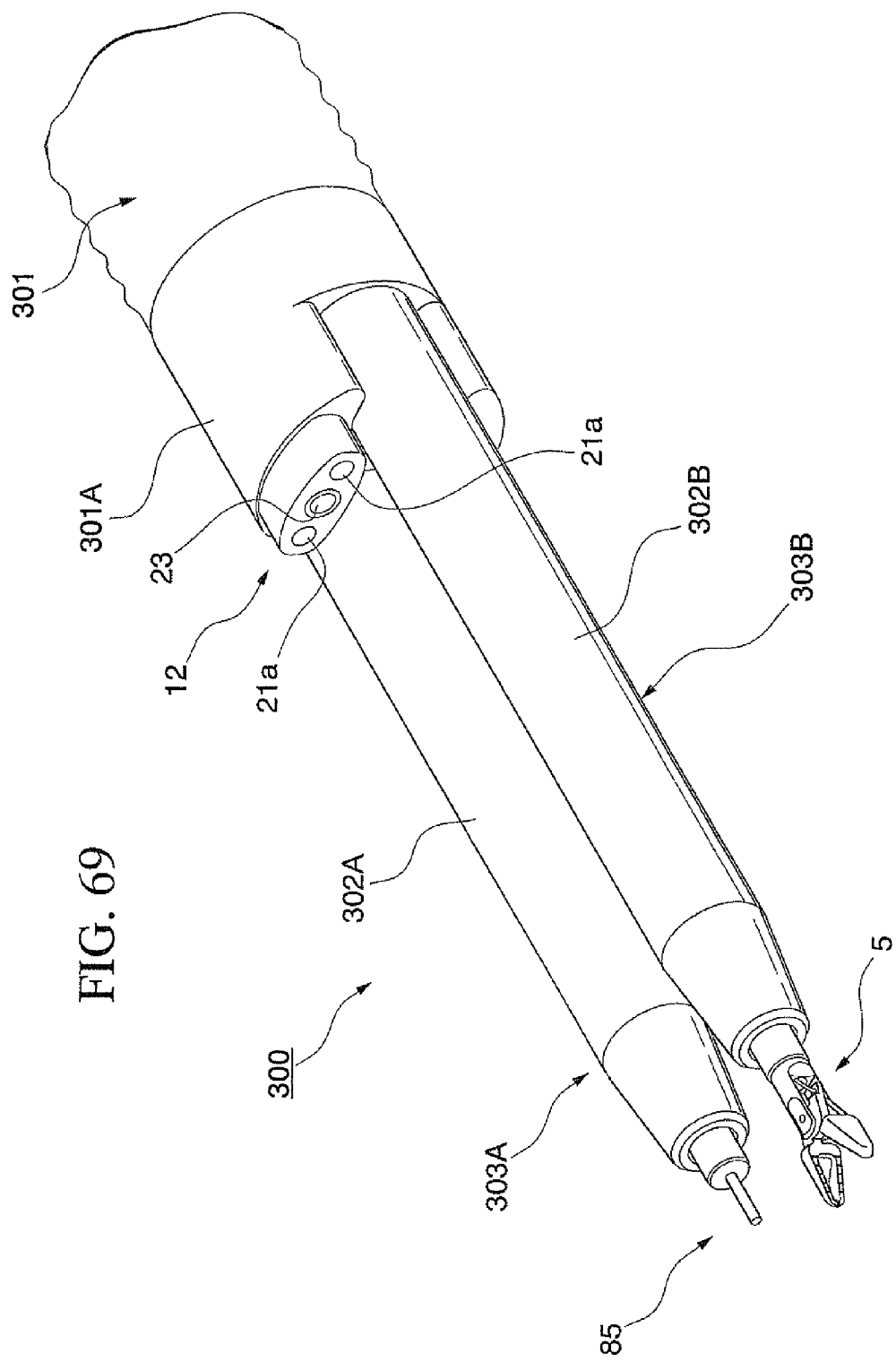
FIG. 69 is a view showing the structure of a modified example of the tip of the medical treatment endoscope according to the fourth embodiment.

Note that the second sheath 303A having the grasping forceps 5 therethrough may be used as illustrated in FIG. 69.

In addition, the high frequency knife 85 is inserted into the channel 318 provided in the first sheath 301 in this case.

Figure 70:
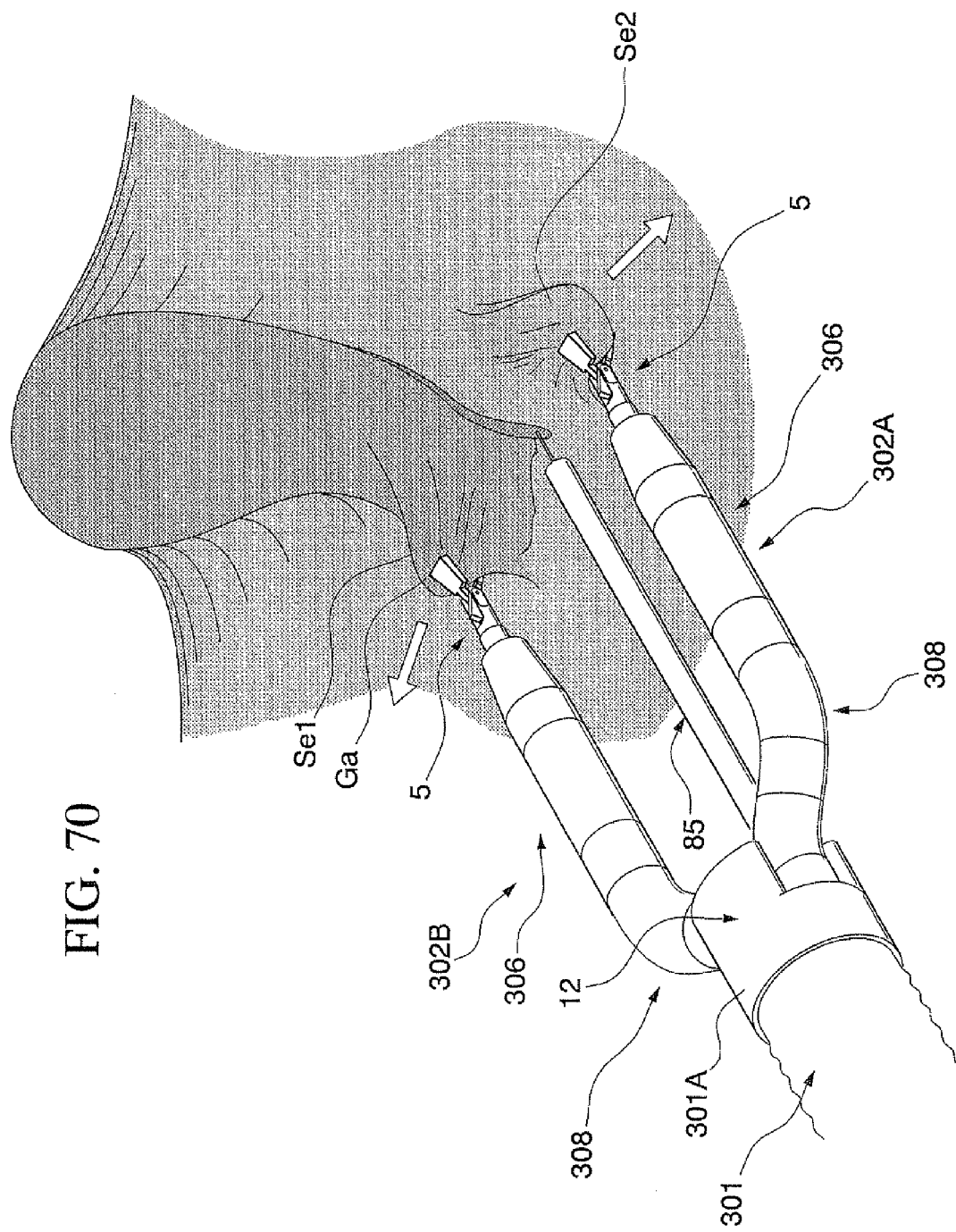
FIG. 70 illustrates a manipulation procedure using the medical treatment endoscope shown in FIG. 69.
Figure 71:
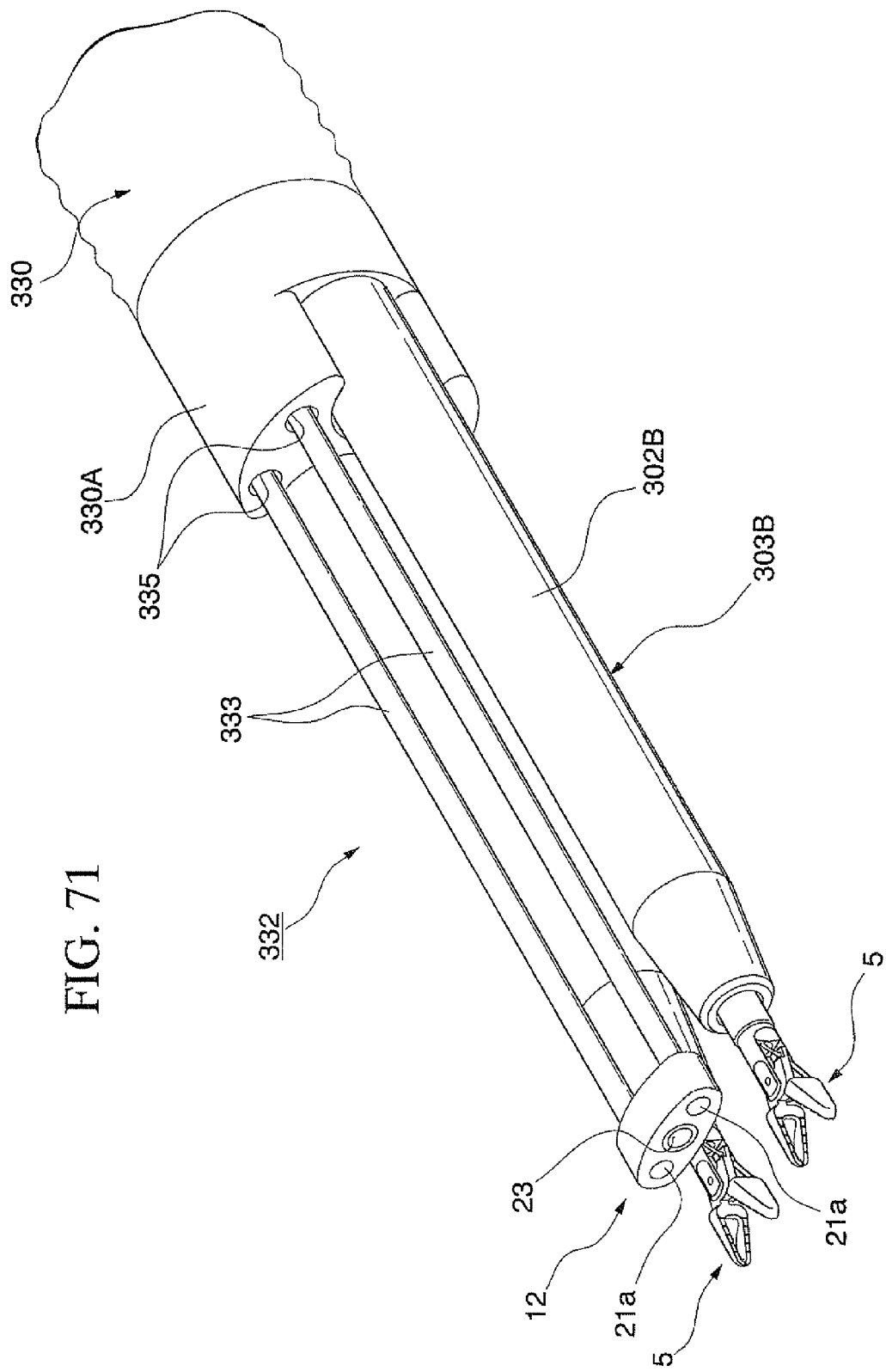
FIG. 71 is a view showing the structure of a modified example of the tip of the medical treatment endoscope according to the fourth embodiment.

The serosal membrane Set of the gallbladder is incised a little at a time with the high frequency knife 85 inserted through the channel 318 in the treatment step conducted during the medical procedure explained above. As illustrated in FIGS. 70 and 71, conducted in order to apply an appropriate tension to the incised part are grasping the cervical part Ga of the gallbladder with the grasping forceps 5 disposed at the second arm member 302B; picking up the incised part with the grasping forceps 5 disposed to the first arm member 302A; and grasping the serosal membrane Se2 opposite the cervical part Ga of the gallbladder. The first bending parts 306 of the first arm member 302A and the second arm member 302B are bent away in separate directions to adjust the retraction direction. Meanwhile, adipose tissue and fiber tissue including serous membrane can be peeled by extending and retracting the high frequency knife 85 inserted through the channel 318. Note that, in addition to the above explanation, the first arm member 302A, the second arm member 302B, and the channel 318 are variously combined regardless of the above explanation.

Also, a medical treatment endoscope 332 may include a viewing unit 331 having an illuminating lens 21a and an object lens 23 that is extendable away from a sheath front end part 330A toward the tips of the first arm member 302A and the second arm member 302B as illustrated in FIG. 71.

In this case, a flexible protection tube 333 is configured to extend from the viewing unit 331 for containing and protecting an observation optical system including the object lens 23 and the illuminating optical system for introducing a light beam into the object lens 21a. Note that these optical systems are not shown in the drawings. The protection tube 333 is configured to be extendable relative to the storage lumen 335 disposed in the first sheath 330.

The inserted state of the medical treatment endoscope 332 provides a wide perspective since the viewing unit 331 is extendable to the vicinity of the tips of the first arm member 302A and the second arm member 302B when the first arm member 302A and the second arm member 302B are inserted.

Fifth Embodiment

A medical treatment endoscope according to the present embodiment is functionally divided into an operation section for conducting necessary treatments by means of arm sections and procedure instruments; and an endoscope operation section for operating an endoscope. The present embodiment features in that the operation sections are operable in separate locations from the endoscope. An operation section built in an endoscope operation section necessitates an operator to conduct all the operations alone, i.e., inevitably complex operations. The present embodiment enables two operators to share operations, i.e., operating an endoscope and conducting a treatment; thus, facilitating the operations.

Figure 72:
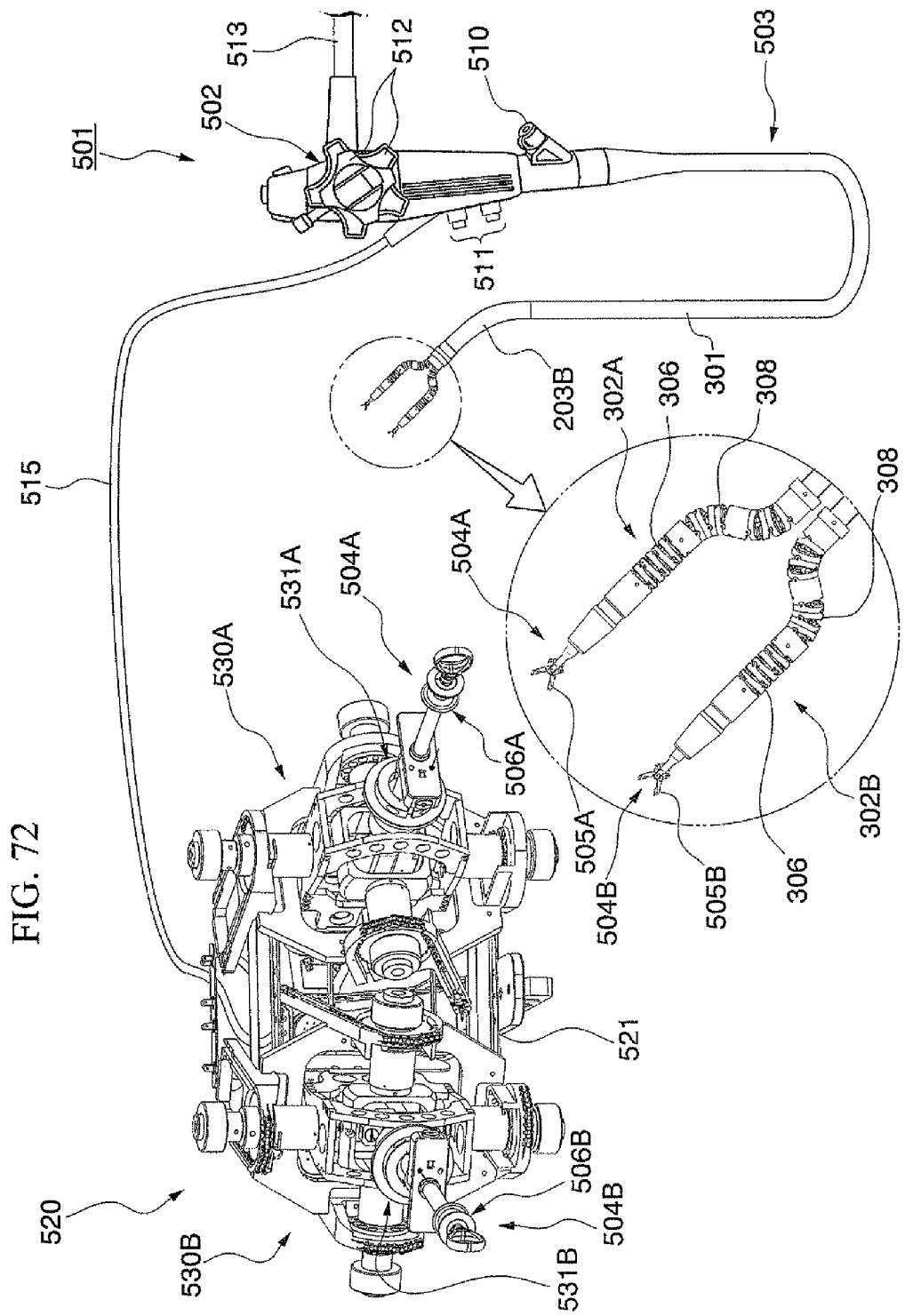
FIG. 72 is a perspective view showing a medical treatment endoscope according to a fifth embodiment.

As illustrated in FIG. 72, an endoscope insertion section 503 fully integrated with a medical treatment endoscope 501 extends from an end of an endoscope insertion section 502. The configuration of the elongated and flexible endoscope insertion section 503 is the same as that of the previous embodiments. That is, the endoscope insertion section 503 has a first sheath 301 having a first arm section 302A and a second arm section 302B on the tip of the first sheath 301. Treatment sections 505A and 505B of procedure instruments 504A and 504B each protrude from the tips of the arm sections 302A and 302B. A first bending part 306 and a second bending part 308, in this order from the tips of the tips of the arm sections 302A and 302B, are formed to each arm section 302A and 302B. Combined use with a third bending section 203B formed to the first sheath 301 enables bending operation in a human body. The first arm member 302A and second arm member 302B may be passed through a second sheath 303A and a third sheath 303B respectively. Meanwhile, the operation section 520 is enlarged in FIG. 72 to help better understanding.

A forceps cap 510 is provided to a side of the endoscope insertion section 502 near an end that continues to the endoscope insertion section 503. The forceps cap 510 communicates to an operation channel formed in the first sheath 301. Inserting another procedure instrument, which is not shown in the drawing, from here enables the procedure instrument to protrude from the tip of the endoscope insertion section 503. In addition, disposed to the endoscope insertion section 502 are a switch 511, an angle knob 512, and a universal cable 513 that is connected to a control apparatus that is not shown in the drawing. For example, operating the switch 511 provides air-supply, water-supply, and suction through a channel formed in the first sheath 301. Operating the angle knob 512 bends the third bending section 203B into four directions with respect to an axial line.

In addition, an elongated flexible connection sheath 515 extends from the other end of the endoscope insertion section 502. An operation section 520 is disposed at an end of the connection sheath 515.

The operation section 520 has a base 521 that fixes the connection sheath 515. Attached to the base 521 are a first operation unit 530A and a second operation unit 530B. The first operation unit 530A has an operation stick 531A into which an operation section 506A of the procedure instrument 504A is inserted. The procedure instrument 504A is passed through the first aim member 302A. The operation section 506A is supported by the operation stick 531A so as to be capable of extending and retracting in the axial line and bending in four directions with respect to the axial line. The second operation unit 530B has an operation stick 531B into which an operation section 506B of the procedure instrument 504B is inserted. The procedure instrument 504B is passed through the second arm member 302B. The operation section 506B is supported by the operation stick 531B so as to be capable of extending and retracting in the axial line and bending in four directions with respect to the axial line. Furthermore, the operation section 520 fixed to an operation bed enables to operate the first second operation unit 530A and the second operation unit 530B.

Figure 73:
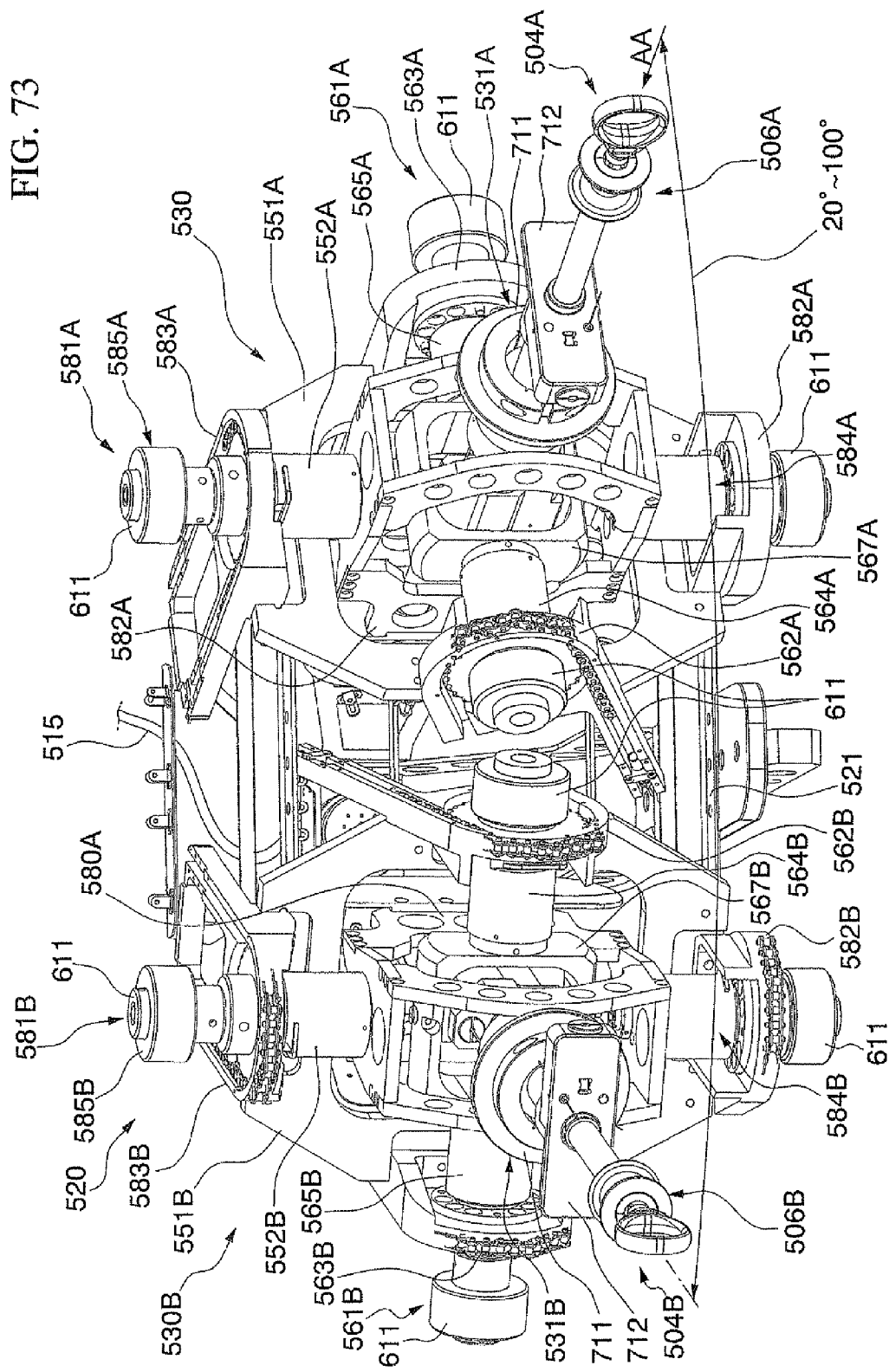
FIG. 73 is an enlarged view of an operation section.

As illustrated in FIG. 73 in enlarged view, the operation units 530A and 530B are disposed diagonally so that portions closer to the connection sheath 515 are placed closer to each other. Two operation sections 506A and 506B (or two operation sticks 531A and 531B) are disposed at angles between 20° to 100°. Disposing the operation sections 506A and 506B with the opening angle relative to an operator facilitates the operator's operation, thus improving operability. In addition, the width of the operation section 520 closer to the connection sheath 515 can be reduced. Also, as illustrated in FIG. 43, dispositions, i.e., horizontal direction, of the arm sections 302A and 302B in an image obtained through an object lens 23 of an observation device attached to the endoscope can coincide with dispositions, i.e., horizontal direction, of the operation units 530A and 530B. This improves correlation of operator's perception and actual inner-body movement, thereby facilitating manipulation. Furthermore, less force is required for an operator to operate only the operation sticks 531A and 531B and the operation sections 506A and 506B of the procedure instruments 504A and 504B. Dispositions having reverse correlation with respect to horizontal or vertical direction provide similar operational perception obtained by laparoscopic instruments.

The configuration of the first operation unit 530A is explained.

Figure 74:
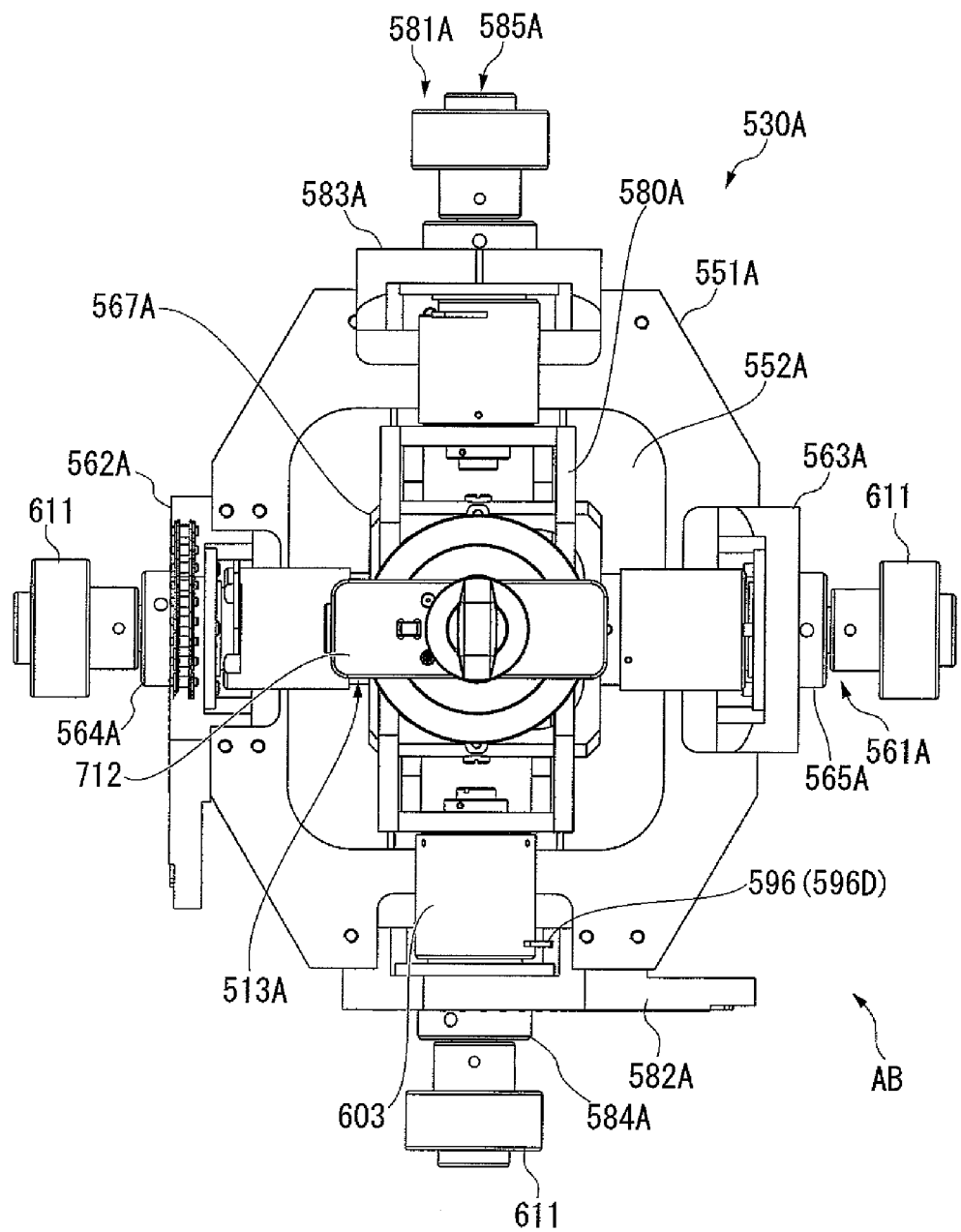
FIG. 74 is a view taken along the line A-A in FIG. 73 in parallel with an axial direction of a first operation section.
Figure 75:
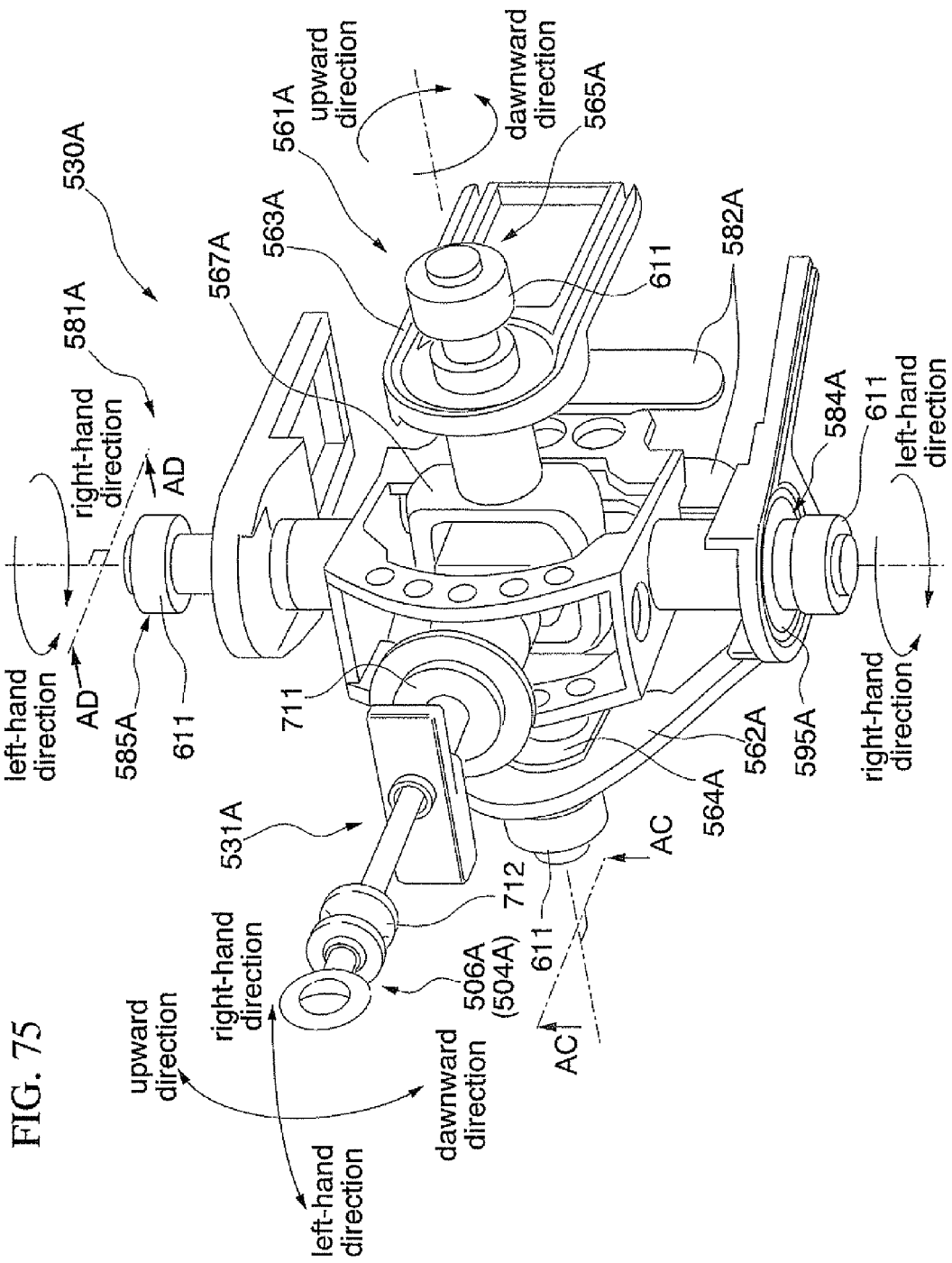
FIG. 75 is a view on arrow AB in FIG. 74.

As illustrated in FIGS. 73 to 75, the first operation unit 530A has a bracket 551A fixed to the base 521. The bracket 551A is fixed so that an opening 552A is substantially orthogonal to the center line of the first operation unit 530A. A first rotation mechanism 561A is attached to horizontal side surfaces of the bracket 551A. The first rotation mechanism 561A has a pair of support chips 562A and 563A that are fixed to place the opening 552A of the bracket 551A therebetween. A rotation shaft 564A is disposed to the support chip 562A. A rotation shaft 565A is disposed to the support chip 563A. The rotation shafts 564A and 565a are disposed coaxially. A frame 567A is supported by this pair of rotation shafts 564A and 565a so as to be freely capable of rotating with respect to the bracket 551. An opening of a rectangular frame 567A is disposed orthogonal to the center line of the first operation unit 530A. The operation stick 531A is inserted through the frame 567A. The operation stick 531A engaging with the frame 567A in rotating angles of the rotation shafts 564A and 565a is inserted so as to be independently capable of tilting in the axial lines of the rotation shafts 564A and 565A.

Figure 76:
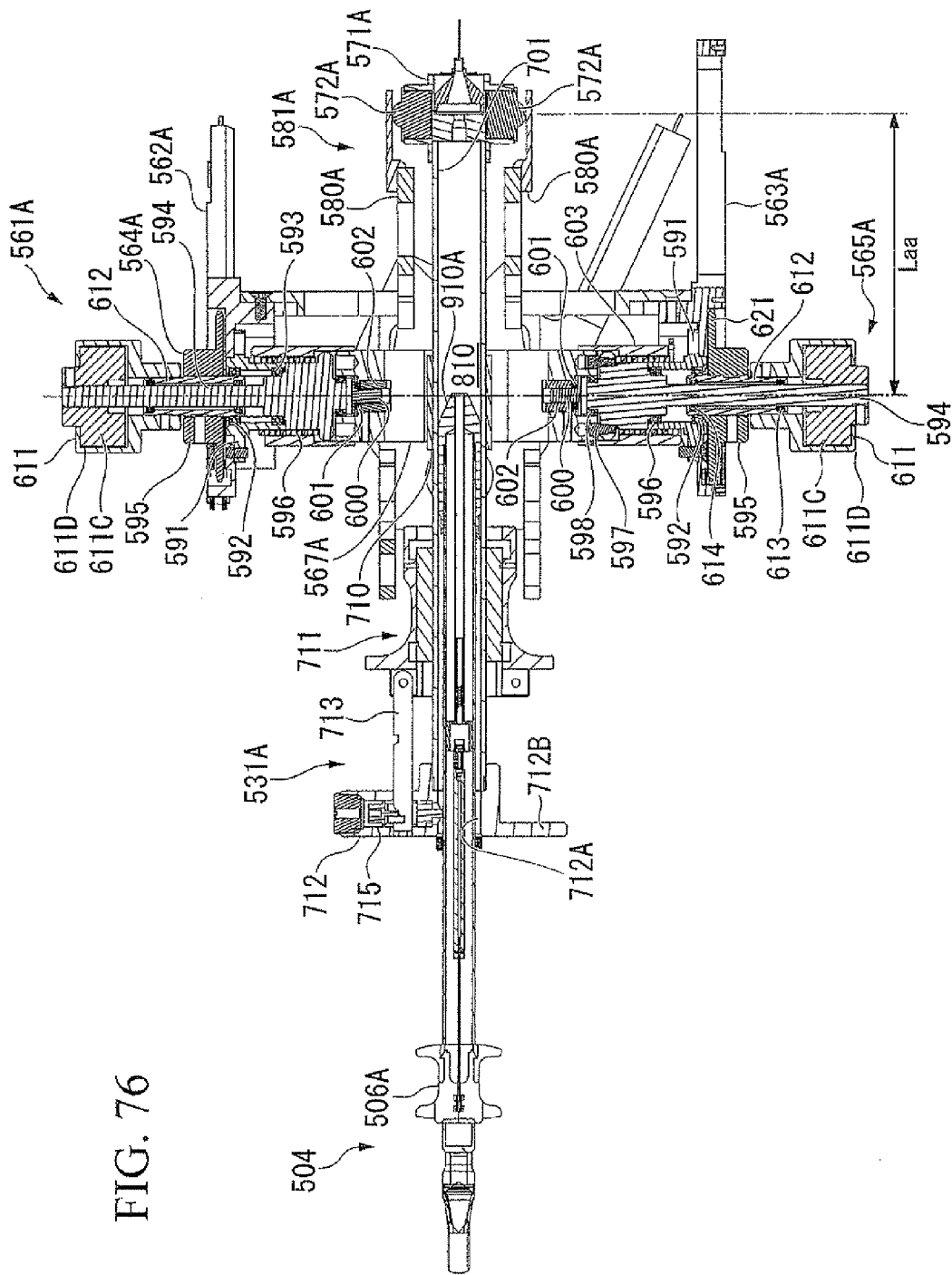
FIG. 76 is a cross-sectional view along the line AC-AC in FIG. 75.

As illustrated in FIG. 76, the tip section 571A of the operation stick 531A extends beyond the frame 567A. Ball rollers 572A are provided to the tip section 571A. The ball rollers 572A are disposed to place the center line of the operation stick 531A therebetween. The line passing through the centers of two ball rollers 572A is parallel with the axial lines of the rotation shafts 564A and 565A of the first rotation mechanism 561A as illustrated, i.e., where the operation stick 531A is not tilted. Distances Laa between the rotation shaft 564A and 565A and the ball rollers 572A are, for example, 50 to 200 mm.

Frames 580A of the second rotation mechanism 581A are further disposed so as to place the ball rollers 572A therebetween and slide on the ball rollers 572A. The frames 580A are supported rotatively by the pair of rotation shafts 584A and 585A. The pair of the rotation shafts 584A and 585A are disposed coaxially so that the axial lines are orthogonal to a pair of rotation shafts 564A and 565A and also orthogonal to the center line of the first operation unit 530A. The rotation shafts 584A and 585A are supported by support chips 582a and 583A each fixed on a vertical side surface of the bracket 551A.

The configuration of the rotation shafts 584A and 585A of the second rotation mechanism 581A will be explained here. Since the rotation shafts 584A and 585A have the same configuration, the rotation shaft 584A will be explained for reference.

Figure 77:
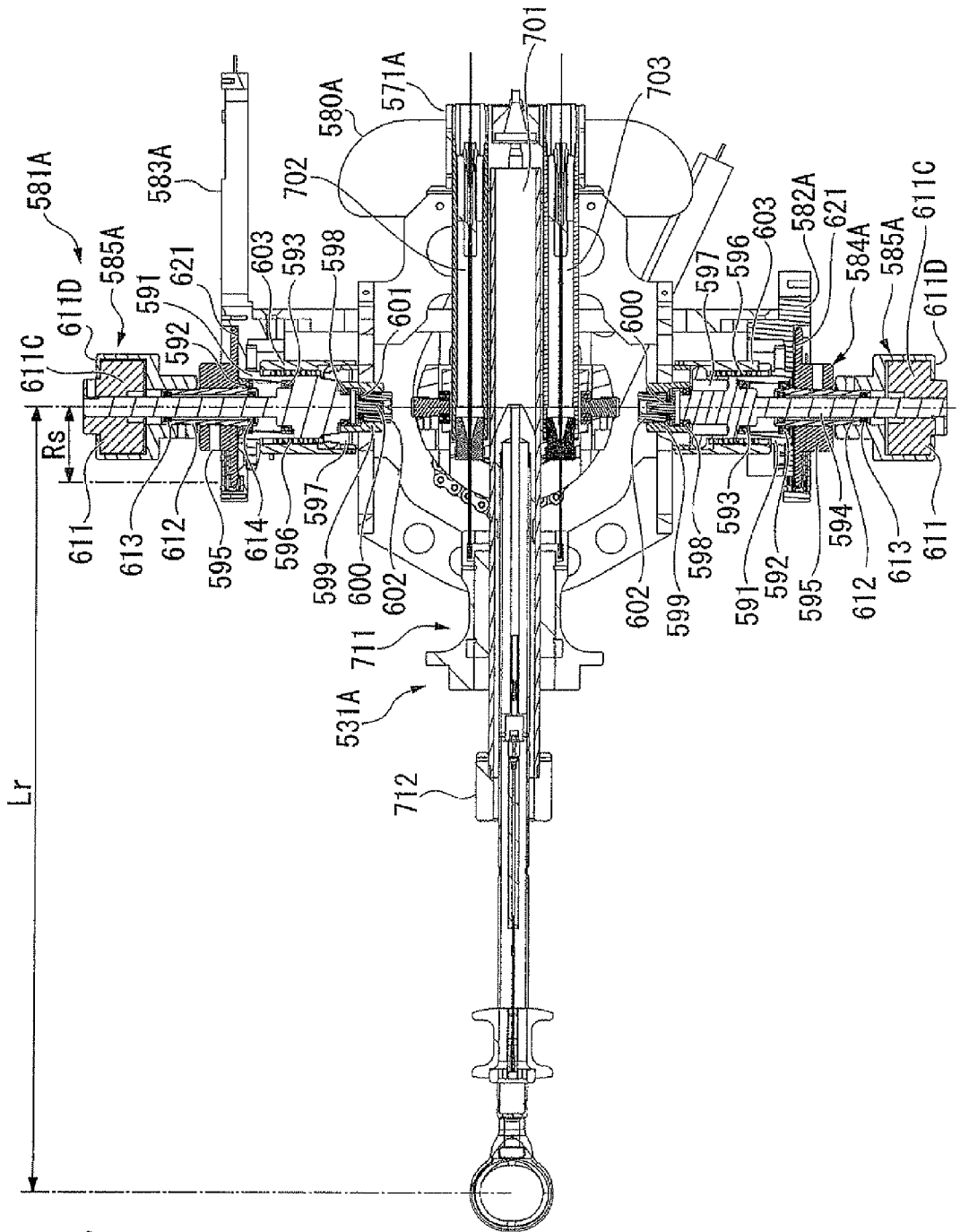
FIG. 77 is a cross-sectional view along the line AD-AD in FIG. 75.
Figure 78:
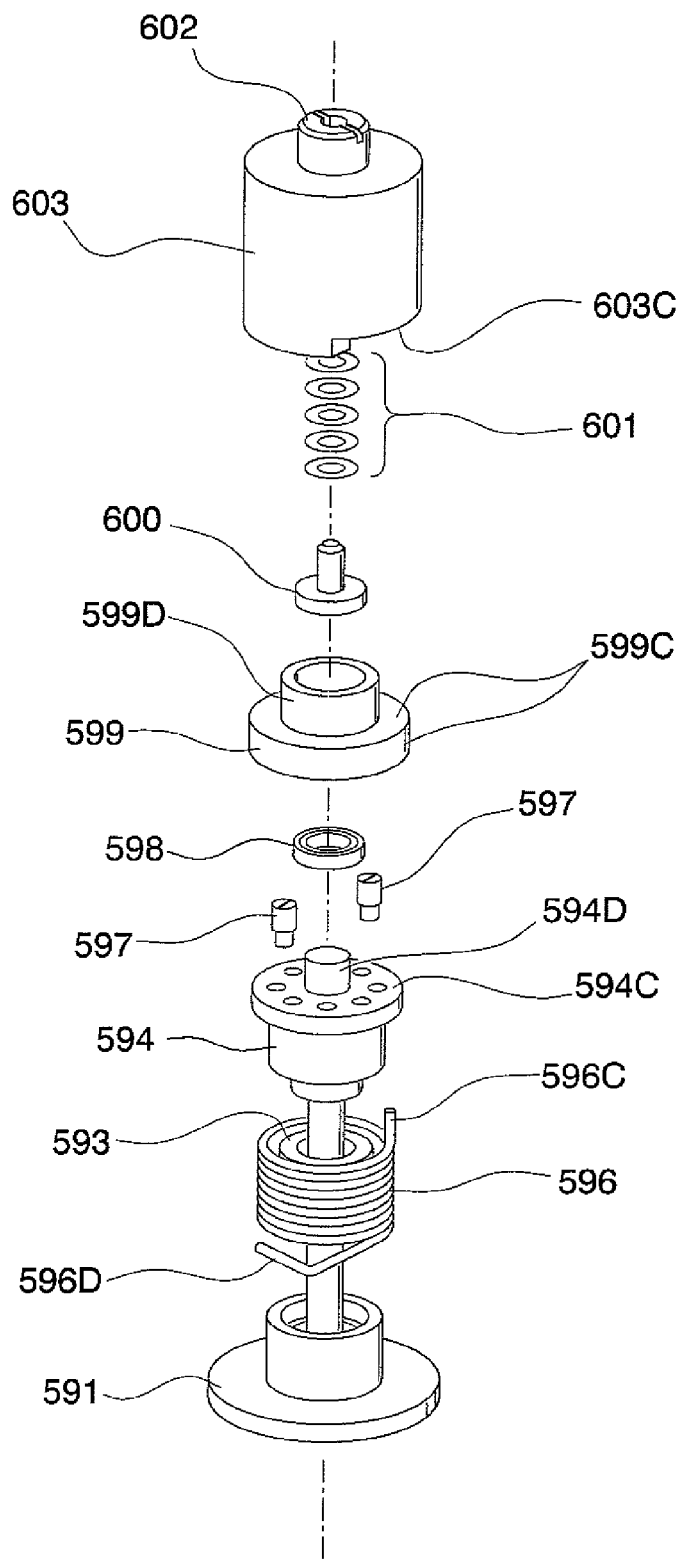
FIG. 78 is an exploded view for a rotational axis.

As illustrated in FIGS. 77 and 78, the rotation shaft 584A has a bearing 591 fixed to the support chip 582A. The bearing 591 has a flange at an end of the cylinder so that the bearing 591 is fixed to the support chip 582A by bolts passing through holes formed on the flange. Outer rings of the bearings 592 and 593 are press-fitted into the inside of the cylinder of the bearing 591 so as to be separate in the axial line. A drive shaft 594 is supported by the bearings 592 and 593 rotatively relative to the bearing 591. The reduced diameter portion of the drive shaft 594 passes through the bearing 591.

An end section of the drive shaft 594 is enlarged in diameter substantially to that of the bearing 591. A coil spring 596 is wound around between an outer periphery of the drive shaft 594 and an outer periphery of a cylindrical section of the bearing 591. Terminals 596C and 596D are bent on both sides of the coil spring 596. A terminal 596C is engaged with a groove formed on the flange 594C fowled at an end of the drive shaft 594. An elemental wire of the coil spring 596 is rectangular in cross section. The rectangular shape may be a square or a rectangle.

The drive shaft 594 is formed by a protrusion 594D and a flange 594C. A plurality of screw holes are formed around the protrusion 594D. Each rotative pin 597 is screwed into each screw hole disposed by 180 degrees offset in a circumferential direction. An inner ring of the bearing 598 is press-fitted and fixed into the protrusion 594D. A bearing 599 is attached to an outer periphery of the bearing 598. The bearing 599 has a cylindrical section 599D having a flange. Inserted in advance into the cylindrical section 599D is a ring retainer 600 that depresses the ring retainer 600 toward a drive shaft 594 with a preload screw 602 via a diaphragm spring 601. A plurality of through-holes 599C are formed on the flange of the bearing 599 at equal intervals in a circumferential direction. The through-holes 599C are disposed corresponding to the disposition of the screw holes of the drive shaft 594. The diameter of the through-hole 599C is greater than that of a head portion of the rotative pin 597. That is, the through-hole 599C has freeplay.

Provided further to cover the flange 594C of the bearing 594 and the coil spring 576 is a cylindrical cover 603. A notch 603C is formed on a base portion of the cover 603. The other terminal 596D of the coil spring 596 is hooked at the notch 603C. In addition, a cylindrical section 599D of the bearing 599 protruding from the cover 603 is fixed to the frames 580A by a pin.

Since an initial state of the coil spring 596 tightens the outer peripheries of the drive shaft 594 and the bearing 591, the drive shaft 594 is joined to the bearing 591 by the coil spring 596. Since the bearing 591 is fixed to the support chip 582A, the drive shaft 594 cannot rotate in the direction for tightening the coil spring 596. But it is rotatable in a direction for loosening the coil spring 596. In contrast, tilting movement provided by an operator of the operation stick 531A into the direction for tightening the coil spring 596 tilts the frames 580A that makes contact with the operation stick 531A. Tilting the frames 580A rotates the bearing 594 of the rotation shaft 584A and the cover 603. Rotating the cover 603 loosens the coil spring 596, thereby releasing the drive shaft 594 locked to the bearing 591. This results in allowing the drive shaft 594 to rotate, thereby transferring the rotation to the sprocket 595. The present symmetric disposition of the rotation shaft 585A with respect to the operation stick 531A transfers the rotational movement of the operation stick 531A but not the rotational movement for tightening the coil spring 596 from the sprocket 595. The operator's operation is transferred but a reaction force by the sprocket 595 is maintained when the operator stops the operation. Thus, the position is maintained, and the operation can be facilitated.

The coil spring 596 for use in such a spring clutch must be made from a high-hardness material. Use of a high-gravity material, e.g., iron, may cause an increase in the weight of the operation section 520. Therefore, a high-hardness and low-gravity material, e.g., duralumin (#2000) or extra super duralumin (#7000), may be used.

Meanwhile, loosening the coil spring 596 to release the locked state and transferring the rotation via the coil spring 596 inevitably provide an excessive force acting on the coil spring 596. In order to avoid such a state, a play is provided so that the head portion of the rotative pin 597 of the drive shaft 594 makes contact to a periphery wall of the through-hole 599C of the bearing 594 after releasing the locked state. Rupture of the coil spring 596 is prevented by transferring the rotation by means of the rotative pin 597. The spring clutch having such a configuration is not limited to the present embodiment and can be used for a rotative structure for the procedure instrument or for the overtube.

In addition, the drive shaft 584 protruding from the flange of the bearing 591 is supported by bearings 613 and 614 so as to be rotative with respect to the hollow shaft 612. A sprocket 595 is fixed to a hollow shaft 611. It should be noted that a rotative member for pushing and drawing a wire, e.g., a wire pulley, may be used in place of the sprocket 595.

The hollow shaft 612 is rotatively supported by the bearing 592 with respect to the bearing 591. The drive shaft 594 and the hollow shaft 612 both protruding over the sprocket 595 are inserted in a torque limiter 611. The torque limiter 611 includes an outer 611C fixed to the hollow shaft 612 and an inner 611D fixed to the drive shaft 594. The inner 611D and the outer 611C unitarily rotate until a predetermined torque is applied. When excessive torque is applied, the outer 611C slides on the inner 611D; and thus, the rotation is not transferred.

Figure 79:
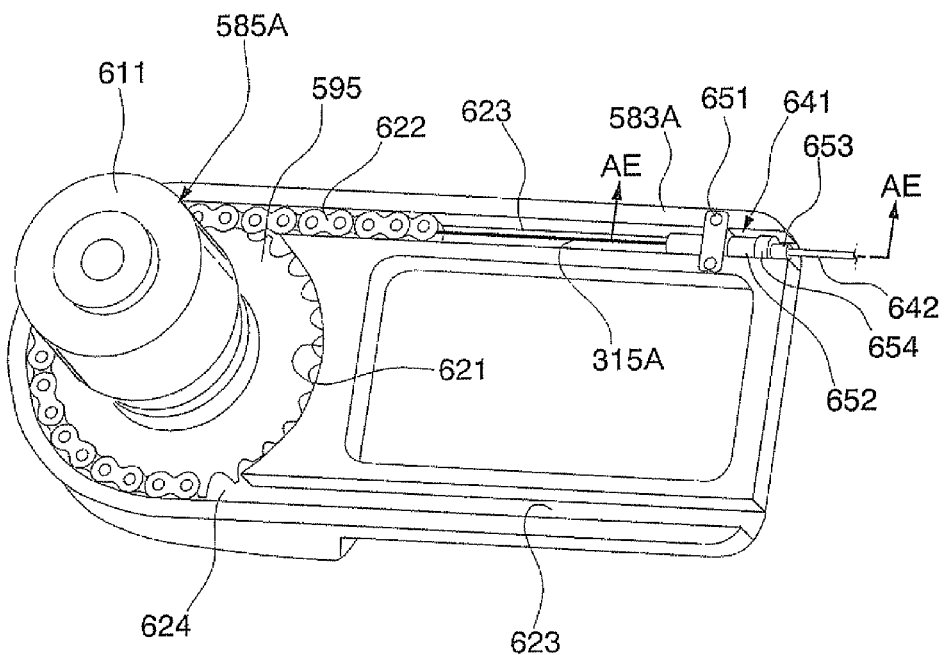
FIG. 79 is a perspective view for the other rotational axis, a support chip, and a bending wire.

As illustrated in FIG. 79 showing a configuration of the rotation shaft 585A, the sprocket 595 is rotatively housed in a circular recessing section 621 formed in the support chip 583A. A chain 622 is wound on teeth of the sprocket 595. A groove 623 is formed to the support chip 583A. An end part of the chain 622 can be drawn into the groove 623 that continues to the recessing section 621. The groove 623 is formed deeper than the recessing section 621. Providing a gap 624 between the groove 623 and the recessing section 621 prevents the chain 622 from being entangled between the sprocket 595 and the recessing section 621, thus guiding the chain 622 into the groove 623.

A first bending wire 315A is fixed to an end part of the chain 622. The first bending wire 315A bends the first bending parts 306 of the first arm members 302A illustrated in FIG. 72 in a right-hand direction.

Figure 80:
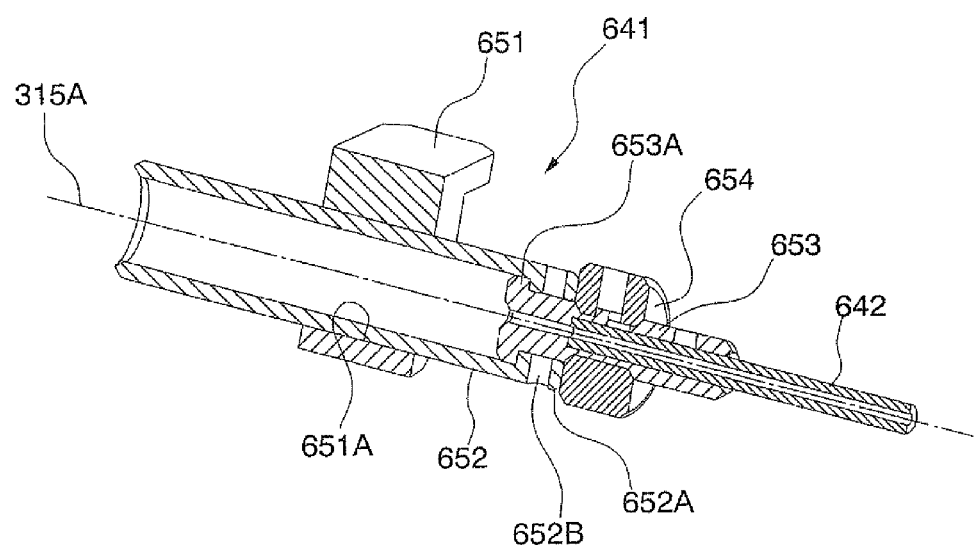
FIG. 80 is a cross-sectional view along the line AE-AE in FIG. 79.

As illustrated in FIG. 79, the first bending wire 315A is drawn into an adjuster 641 disposed at an end part of the groove 623 of the support chip 583A and introduced into a connection sheath 515 together with the coil sheath passing through the coil sheath 642 connected to the adjuster 641. The first bending wire 315A is finally reached to the first arm member 302A. As illustrated in FIGS. 79 and 80, the adjuster 641 has a coil base 651 fixed to the support chip 583A. A screw hole 651A is formed to the coil base 651. An adjustment shaft 652 having a thread on its outer periphery is screwed into the screw hole 651A. The adjustment shaft 652 is a cylinder having a bottom. An end section 652A corresponds to the bottom part into which a coil stopper 653 is inserted. The removal of the coil stopper 653 is prevented by engaging a flange-shaped protrusion 653D with an inner surface of the end section 652A. The removal prevention in the reverse direction is provided by attaching a lock-screw 654 to the outer periphery. An end part of the coil sheath is fixed to the coil stopper 653. The first bending wire 315A passes through the adjustment shaft 652, followed by the coil stopper 653 and the coil sheath 642. The first bending wire 315A sometimes loosely extends during the step using the medical treatment endoscope 501. In this case, inserting a fixture into the hole 652B of the adjustment shaft 652 and rotating them cause the coil sheath 642 together with the adjustment shaft 652 to move in the axial direction. Forwarding the coil sheath 642 draws the first bending wire 315A from the coil sheath 642, thereby adjusting the loose state. Since the loose state can be adjusted by means of a screw, it is not necessary to dissemble the apparatus. Since the adjustment shaft 652 is rotatively engaged with the coil stopper 653, rotating the adjustment shaft 652 will never rotate the coil sheath 642.

Also, a sprocket 595 of the rotation shaft 584A is housed in the support chip 582A, and the chain 622 is wound around the sprocket 595. The first bending wire 315B (see FIG. 54) is attached to the chain 622. The first bending wire 315B bends the first bending parts 306 of the first arm members 302A illustrated in FIG. 72 in a right-hand direction. An adjuster 641, also provided to the support chip 582A, can adjust the loose state by forwarding or drawing the coil sheath 642 having the first bending wire 315B therethrough. The first bending wire 315B inserted through the coil sheath 642 is introduced into the connection sheath 515 together with the coil sheath 642 and reached to the first arm member 302A.

As explained previously, the torque limiters 611 provided to the rotation shafts 584A and 585A prevent the rotation of the rotation shaft 585A from being transferred to the sprocket 595 when an excessive input is provided from the operation stick 531A. This results in preventing an excessive force from being applied to the first bending wire 315A. Considering a case assumed to use no torque limiter 611 may lead the possibility where an excessive force is applied to the first bending wire 315A. The torque limiter 611 for controlling the maximum torque can prevent the first bending wire 315A from being fractured. In addition, disposing the torque limiter 611, the sprocket 595, and the rotation shafts 564A and 565A in this order from the outside shorten the distance between the support chips 582a and 583A, thereby downsizing the bracket 551A. This increases freedom in layout and contributes to a downsized and light-weight configuration.

The first rotation mechanism 561A will be explained next principally with reference to FIG. 76.

A rotation shaft 564A has a similar configuration to the rotation shaft 584A of the second rotation mechanism 581A except for the drive shaft 594 attachably engaged with the frame 567A via the rotative pin 597 in the rotative direction. Similarly, the other rotation shaft 565A has a similar configuration to the rotation shaft 585A of the second rotation mechanism 581A except for the drive shaft 594 attachably engaged with the frame 567A via the rotative pin 597 in the rotative direction.

Furthermore, a first bending wire 315D is joined to the sprocket 595 of one of the rotation shafts 564A via the chain 622. A first bending wire 315C is joined to the sprocket 595 of the other rotation shaft 565A via the chain 622. The first bending wire 315C and the bending wire 315D bend two first bending parts 306 of the first arm members 302A illustrated in FIG. 72 in vertical opening directions. The adjuster 641, also provided to the support chip 562A and 563A, can adjust the loose state by forwarding or drawing the coil sheath 642 having the first bending wires 315C and 315D therethrough.

Next, the operation stick 531A will be described.

Figure 81:
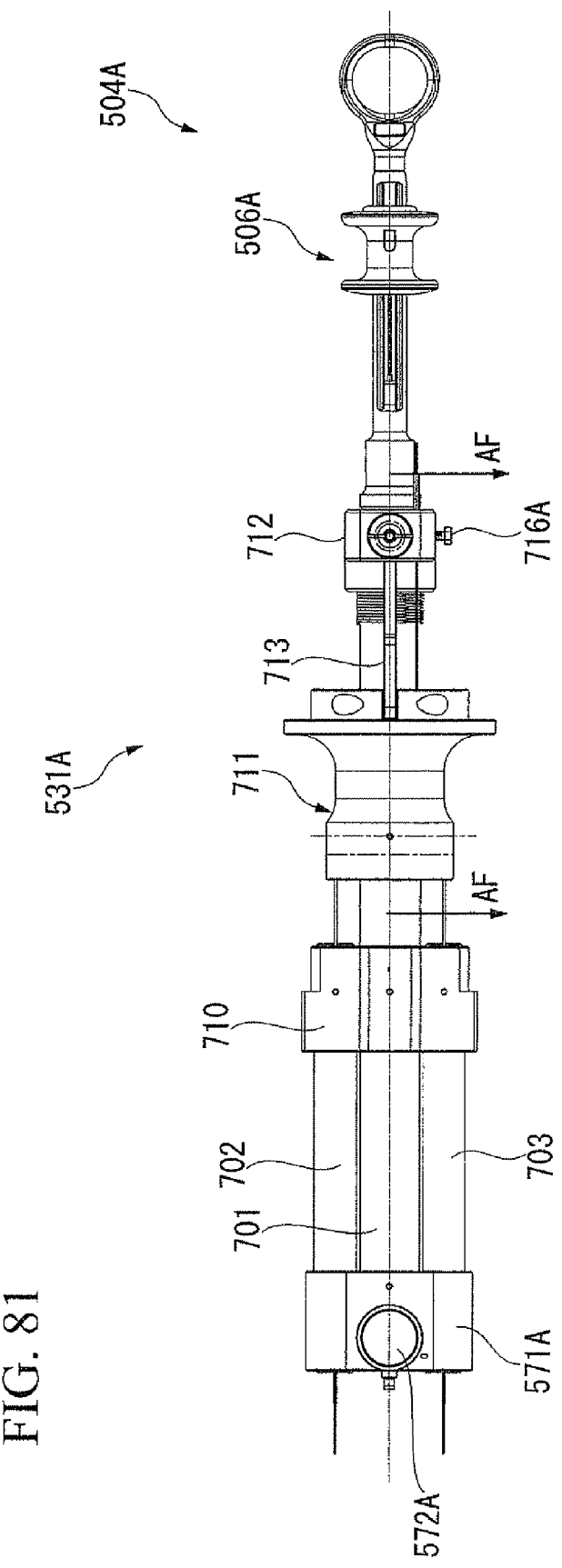
FIG. 81 is a plan view illustrating a first operation stick and a procedure instrument.

In the operation stick 531A as illustrated in FIGS. 76, 77, and 81, three cylindrical shafts 701, 702, and 703 bundled together are fixed to a tip portion to which a ball roller 572A is attached. The central shaft 701 is longer than two shafts, i.e., shafts 702 and 703. The other two shafts 702 and 703 barely reach to an abutment section 710 that serves as a rotative fulcrum making contact with the frame 567A of the first rotation mechanism 561A. In contrast, the central shaft 701 extends beyond the abutment section 710.

A second bending slider 711 capable of freely forwarding or retracting in the axial direction is attached to the central shaft 701. Furthermore, a ratchet base 712 is fixed to a base end of the shaft 701. In the initial state, the second bending slider 711 cannot be forward or retracted because the second bending slider 711 is joined to the ratchet base 712 by a connection plate 713 connected to the second bending slider 711.

Figure 82:
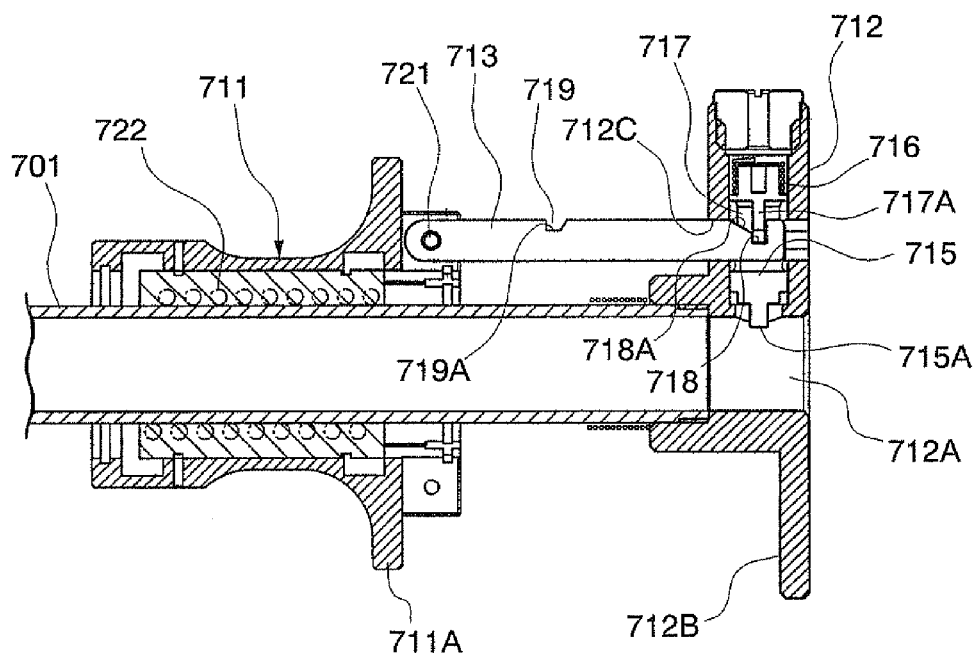
FIG. 82 is a cross-sectional view along the line AF-AF in FIG. 81 illustrating a pre-insertion state of the procedure instrument.
Figure 83:
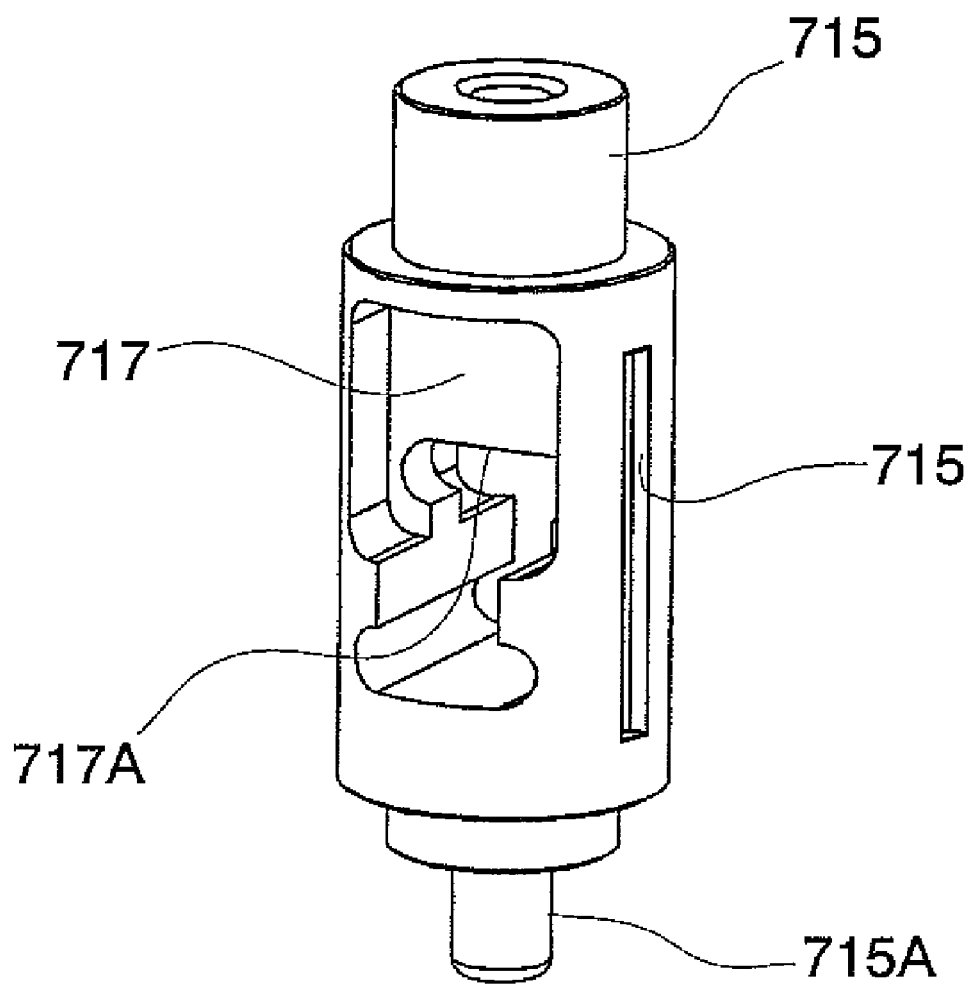
FIG. 83 is a perspective view for a piston.

As illustrated in FIG. 82, a through-hole 712A is formed to the center of the ratchet base 712. The through-hole 712A serves as an entrance from which the operation section 506A of the procedure instrument 504A is inserted. Furthermore, a part 712B of an outer periphery of the ratchet base 712 extends in a direction orthogonal to the axial line direction. Putting a thumb here allows the second bending slider 711 to be smoothly forwarded or retracted. A piston 715 slidable in a radial direction is housed in the ratchet base 712. The piston 715 is urged by a coil spring 716 in a radial direction orthogonal to the axial line direction. The protrusion 715A at the tip protrudes into a through-hole 712A that is an insertion path for the procedure instrument 504A. A slit 717 is formed on the piston 715. An engagement chip 717A is formed in the slit 717. A first groove 718 of the connection plate 713 is engaged with the engagement chip 717A. The first groove 718 is inserted through the slit 712C penetrating the ratchet base 712. Meanwhile, a vertical groove 717C that is parallel in a radial direction may be formed on the piston 715 as illustrated in FIG. 83. Inserting the tip portion of a clamping-bolt 716A (see FIG. 81) into the vertical groove 717C of an outer periphery of the ratchet base 712 can prevent the rotation of the piston 715. This prevents the piston 715 from galling the connection plate 713, thereby providing smooth movements of the piston 715 and the connection plate 713 as explained later.

Figure 94:
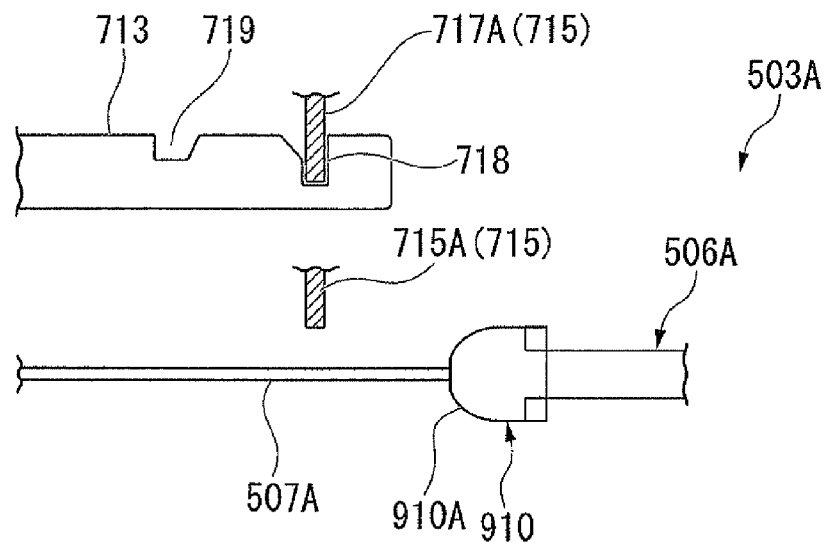
FIG. 94 illustrates motions provided by a cam, a piston, and a connection plate when the procedure instrument is inserted into the first operation stick.
Figure 96:
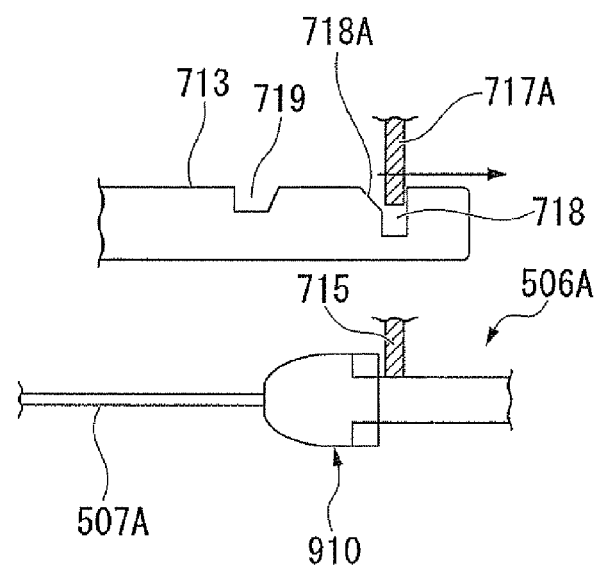
FIG. 96 illustrates a retractable state of the connection plate.
Figure 98:
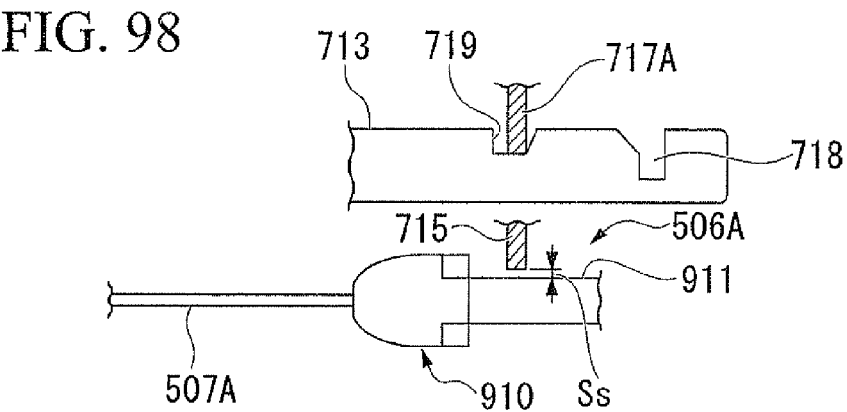
FIG. 98 illustrates an engaged state of the cam to a second groove.
Figure 99:
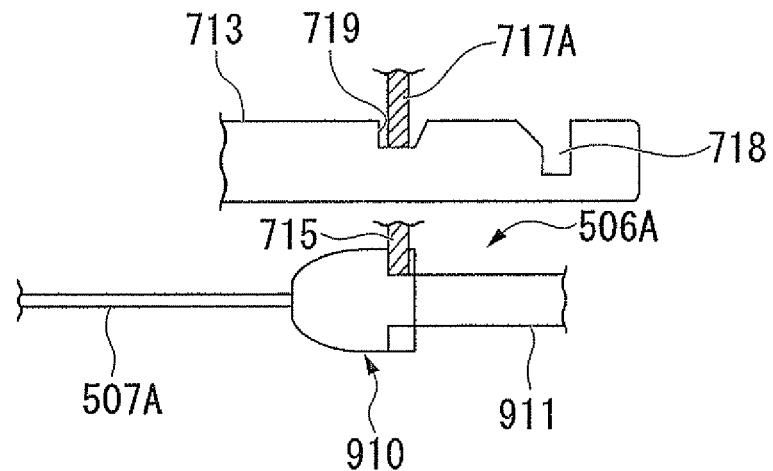
FIG. 99 illustrates the cam pushing up the piston when removing the procedure instrument.
Figure 100:
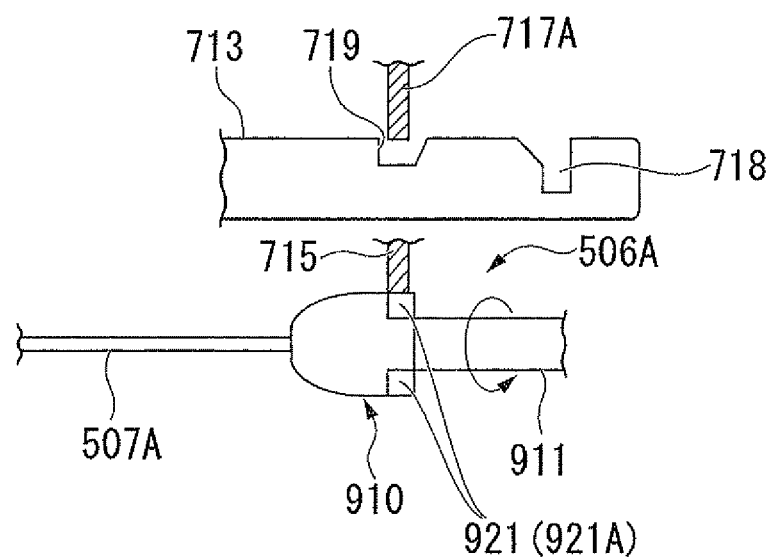
FIG. 100 illustrates the piston pushed up by rotating the cam.

The tip of the connection plate 713 is joined to the second bending slider 711 by a fulcrum pin 721 and extends substantially parallel in the axial line from here toward the ratchet base 712. The recessing shape of the first groove 718 allows the engagement chip 717A of the piston 715 to enter there, and a midpoint of the wall surface of the tip portion of the first groove 718 forms an inclination surface 718A. The inclination surface 718A gradually widens the first groove 718 from the midpoint to the tip portion. A second groove 719 is formed at a further tip portion than the first groove 718 is formed. The recessing shape of the second groove 719 allows the engagement chip 717A of the piston 715 to enter there. The second groove 719 is deeper than the first groove 718. The base end wall surface of the second groove 719 forms an inclination surface 719A. The inclination surface 719A gradually widens the second groove 719 toward the tip portion. The first groove 718 is positioned so that the second bending part 308 of the first arm member 302A as illustrated in FIG. 72 becomes straightened. The second groove 719 is positioned so that the second bending parts 308 bend to open the first arm member 302A. This allows the arm section 302A to close by engaging the first groove 718 with the piston 715, and allows the second arm member 303A to open by engaging the second groove 719 with the piston 715. As previously described, the engagement of the piston 715 with the grooves 718 and 719 can be released with a small force since the inclination surfaces 718A and 719A are formed to the grooves 718 and 719. This facilitates smooth switching of the engagement position of the piston 715 with the grooves 718 and 719. As illustrated in FIG. 94, the spring 791 forces the second bending slider 711 and the connection plate 713 to be positioned toward the tip portion by the spring force when the procedure instrument 504A is not inserted and thus, the first groove 718 engages with the piston 715. As illustrated in FIG. 96, the piston 715 is pushed by the operation section 506A of the procedure instrument 504A when the procedure instrument 504A is inserted. Since this state of the engagement chip 717A can move up the inclination surface 718A, the second bending slider 711 can be drawn, and the second bending part 308 can be opened. In this configuration, the procedure instrument 504A must be inserted to draw the second bending slider 711 because the tip of the procedure instrument 504A can hardly be passed through the opening state of the second bending part 308. As illustrated in FIG. 98, the engagement chip 717A makes contact with the inclination surface 719A as long as the second bending slider 711 is drawn toward the base end. The tension applied by the second bending wires 316A and 316B urges the slider 711 toward the tip. As illustrated in FIGS. 99 and 100, raising the piston 715 necessitates a significant force if the disposition angle of the inclination surface 719 is significantly 90°. If the disposition angle is substantially horizontal, the piston 715 is spontaneously raised by the tension applied by the second bending wires 316A and 316B and therefore, the second bending slider 711 moves toward the tip, and the second bending part 308 is closes. The suitable angle α of the inclination surface 719 is $60° \leq \alpha \leq 90°$.

The second bending slider 711 is disposed coaxially with the axial line of the operation stick 531A. Therefore, the compact first operation unit 530A can be obtained. Formed at the base end thereof is an edge section 711A for putting a thumb. A linear stroke 722 is built in a portion making contact with the shaft 701 to provide smooth sliding movement on the shaft 701.

Figure 84:
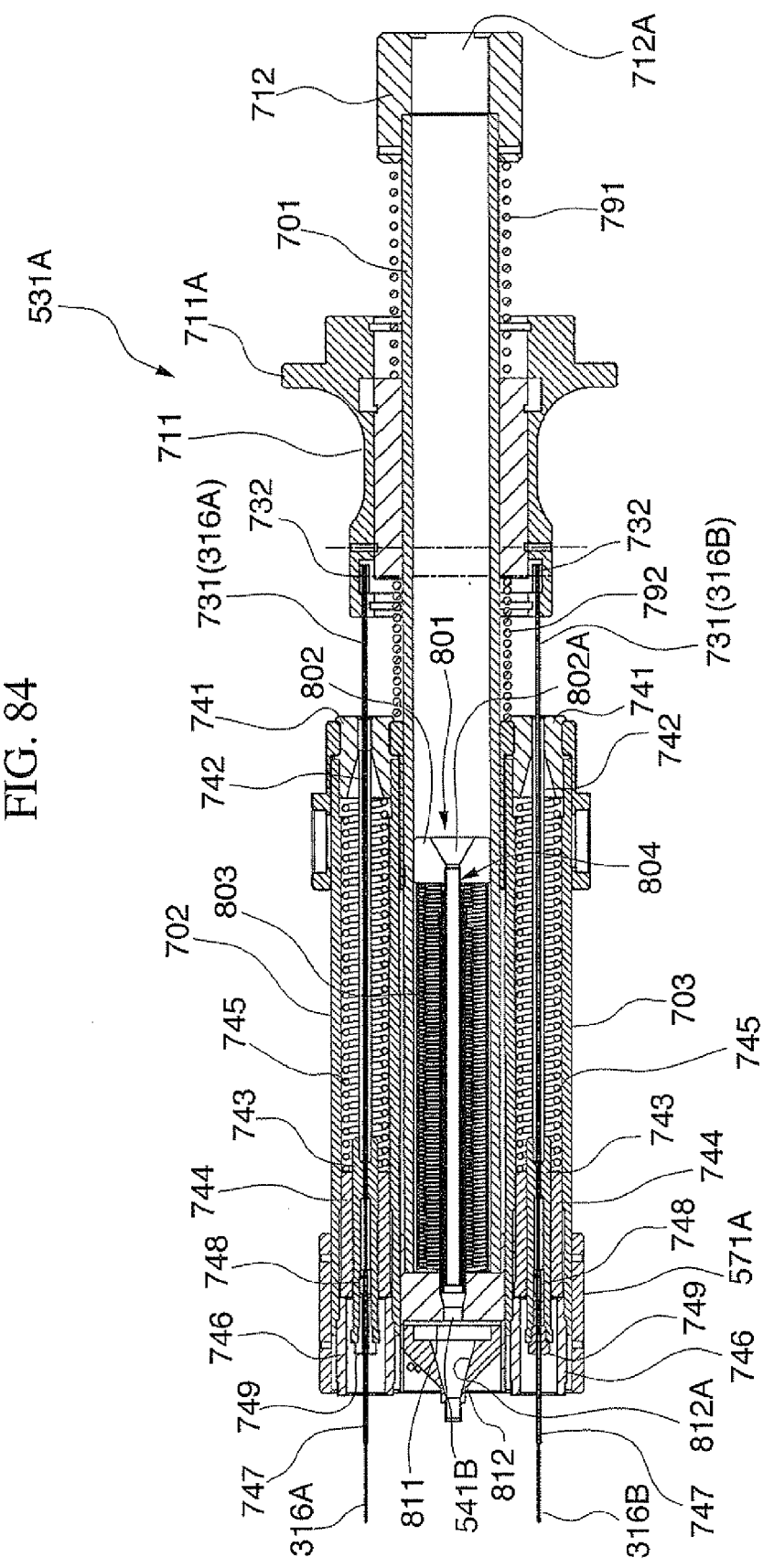
FIG. 84 is a cross-sectional view showing an enlarged state of a first operation stick illustrated in FIG. 77.

As illustrated in FIG. 84, two pipes 731 are attached to the tip of the second bending slider 711 so as to place the axial line between the pipes 731. Second bending wires 316A and 316B are passed respectively through these pipes 731. The second bending wires 316A and 316B are fixed in the second bending slider 711 so that the second bending wires 316A and 316B cannot be removed from the second bending slider 711. Disposing the second bending wires 316A and 316B symmetrically with respect to the second bending slider 711 equalizes the force applied to the second bending slider 711 and thus providing smooth movement thereof.

Two shafts 702 and 703, disposed further toward the tip, each have the pipe 731 inserted therethrough. The pipe 731 and the second bending wires 316A and 316B are inserted through the shafts 702 and 703 disposed side by side. The shafts 702 and 703 each have a retainer member 741 at the base end. Another pipe 742 is inserted from the tip through the retainer member 741. The tip of the pipe 742 is supported by a coil-receiving casing 743. The coil-receiving casing 743 is screwed in the hole of the cylindrical pusher 744 and fixed there. An end portion of the coil spring 745 makes contact with the base end of the pusher 744. The other end portion of the coil spring 745 is butted against the retainer member 741. The pusher 744 is urged by the coil spring 745 toward the tip. In response to excessive force that draws the second bending wires 316A and 316B, a force that relatively moves the coil sheath 747 to an operator's hand is applied and thus, the coil spring 745 is compressed via the pusher 744. The coil spring 745 that is preset to a length exerting a predetermined force begins to contract if the preset force is overreached. Since the second bending wires 316A and 316B can further be drawn in accordance with the contraction of the coil spring 745, an excessive force is not applied to the second bending wires 316A and 316B. A force applied to the second bending wires 316A and 316B will never increase rapidly as long as the coil spring 745 can be contracted if an excessive force is applied and therefore, the second bending wires 316A and 316B will never be cut since overload mass is curbed. Meanwhile, the coil spring 745 is compressed by a pusher retainer 746 screwed from the tips of the shafts 702 and 703. Since the initial position of the pusher 744 can be adjusted in accordance with the compression mass of the pusher retainer 746, differences in rigidity and bending force based on the coil springs 745 can be adjusted.

Furthermore, only the second bending wires 316A and 316B are extracted from the pipe 74. The second bending wires 316A and 316B are inserted through the pusher retainer 746 in the coil-receiving casing 743 and introduced through the connection sheath 515 together with the coil sheath 747 to reach to the second bending part 308. The base end of the coil sheath 747 is brazed to a tubular coil receiver 748 and fixed there in the coil-receiving casing 743. A coil-receiver-retainer 749 is screwed from the tip through the coil-receiving casing 743. The coil-receiver-retainer 749 rotatively locking the coil receiver 748 prevents the coil sheath 747 from being removed from the coil-receiving casing 748, thereby preventing the pusher retainer 746 from being twisted. The lengths of the second bending wires 316A and 316B corresponding to the coil sheath 747 may sometimes have assembly error, and such error may sometimes be caused by the stretching of the second bending wires 316A and 316B. Adjusting the screwing amount of the coil-receiving casing 743 relative to the pusher 744 can adjust the error.

Figure 85:
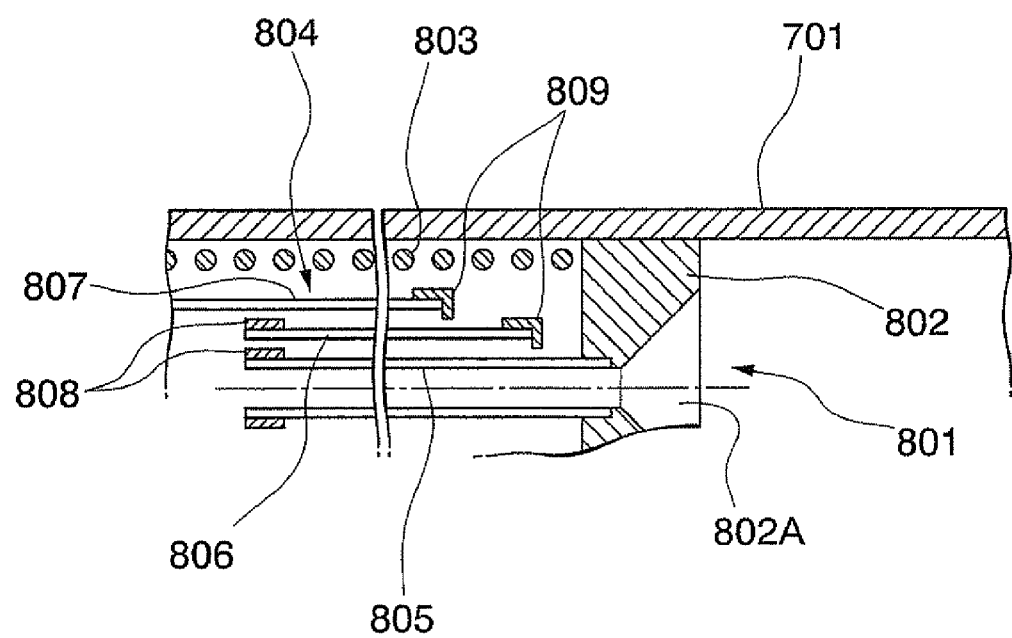
FIG. 85 shows an enlarged state of a channel illustrated in FIG. 84.

As illustrated in FIGS. 84 and 85, a channel 801 for passing a procedure instrument 504A therethrough is built in the central shaft 701. The channel 801 has, in order from the base end, a retainer 802 that accommodates the procedure instrument 504A, a coil spring 803 inserted between the retainer 802 and the tip section 571A, and an extendable pipe 804 disposed in the coil spring 803. A hole 802A is formed in the center of the retainer 802. The hole 802A serves as an entrance for inserting the procedure instrument 504A therefrom. The hole 802A is a tapered hole where the opening diameter increases toward the base end. The hole 802A having a funnel shape facilitates the insertion of a distal end of the insertion section 507A of the procedure instrument 504A. The extendable pipe 804 has three pipes 805, 806, and 807 each of which are different in diameter. These pipes are disposed coaxially. A removal stop 808 is attached to the pipes 805 and 806. A stopper 809 locked to the removal stop 808 is attached to each pipe 806 and 807. That is, the extendable pipe 804 becomes the shortest when three pipes 805, 806, and 807 substantially overlap. Extending each pipe 805, 806, and 807 until locking the stopper 809 to the removal stop 808 allows the extendable pipe 804 to be the longest. While the drawings illustrate the compressed state of the coil spring 803, it restores under the no-load condition. The retainer 802 moves to the vicinity of a shaft 701 and to the vicinity of the distal end of the piston 715. Since the retainer 802 is disposed at the base end of the shaft 701 unless the procedure instrument 504A is not inserted, the insertion section 507A of the procedure instrument 504A can be inserted easily. The retainer 802 is pushed by the tip portion of the operation section 506A of the procedure instrument 504A to be forwarded to the position illustrated in FIG. 84 when the procedure instrument 504A is inserted. It should be noted that the extendable pipe 807 is not limited to a triple-pipe structure.

A space for passing the procedure instrument 504A therethrough is provided in a tip section 571A that joins three shafts 701, 702, and 703. An airtight valve 811 is provided on a path into which the procedure instrument 504A is inserted and thus, the airtight condition inside of the body subjected to a medical operation can be maintained even if the procedure instrument 504A is removed during the medical operation. The airtight valve 811 is made of, for example, a rubber sheet disposed to seal a hole 571B that communicates with the shaft 701. Formed to the rubber sheet is a notch into which an insertion portion of the procedure instrument 504A can be inserted. Passing the procedure instrument 504A therethrough necessitates opening the notch. Removing the procedure instrument 504A closes the notch, thereby maintaining the airtight condition. A retainer 812 is used to fix the airtight valve 811. Fixing the retainer 812 onto the tip section 571A by screws facilitates exchanging the airtight valve 811 made of a rubber sheet. Meanwhile, the procedure instrument 504A is introduced into the body through a hole 812A formed in the retainer 812. Forming the hole 812A so as to be tapered toward the tip facilitates the insertion of the procedure instrument 504A.

The configuration of the second operation unit 530B is explained.

The second operation unit 530B has a symmetric configuration to the first operation unit 530A with respect to the horizontal center line of the operation section 520. A symbol "B" is added to some components included in the operation unit 530B to distinguish them from those of the first operation unit 530A.

A procedure instrument 504A inserted through the operation section 520 will be explained next. Although only the procedure instrument 504A will be explained here, it should be noted that the procedure instrument 504B has the same configuration. An end of each procedure instrument 504A and 504B may be a high-frequency knife, a puncture needle, a snare, a clip, or other forceps.

Figure 86:
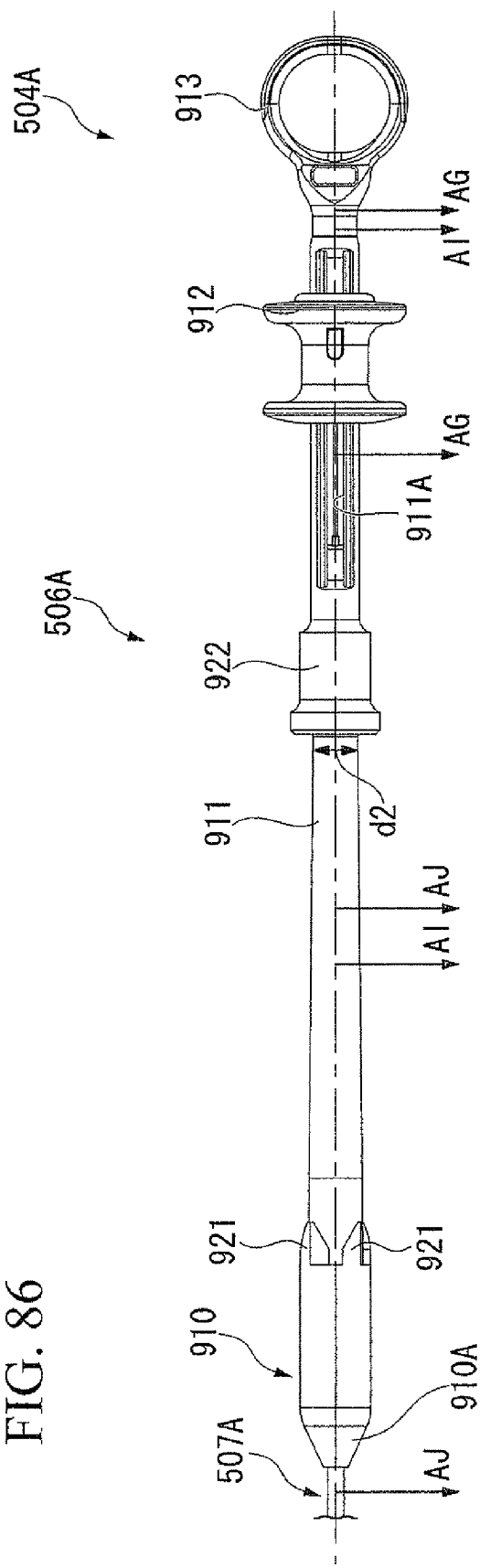
FIG. 86 is a plan view illustrating a procedure instrument.

As illustrated in FIG. 86, a treatment section 505A (see FIG. 72) and an operation section 506A both provided to the tip of the procedure instrument 504A are joined by an elongated flexible insertion section 507A. The operation section 506A has a main body section 911 having a cam 910 at the tip thereof. A slider 912 that drives the treatment section 505A is attached at the base end of the main body section 911 rotatively in the axial line direction. In addition, a finger-hook ring 913 is attached to the base end of the main body section 911.

Figure 87:
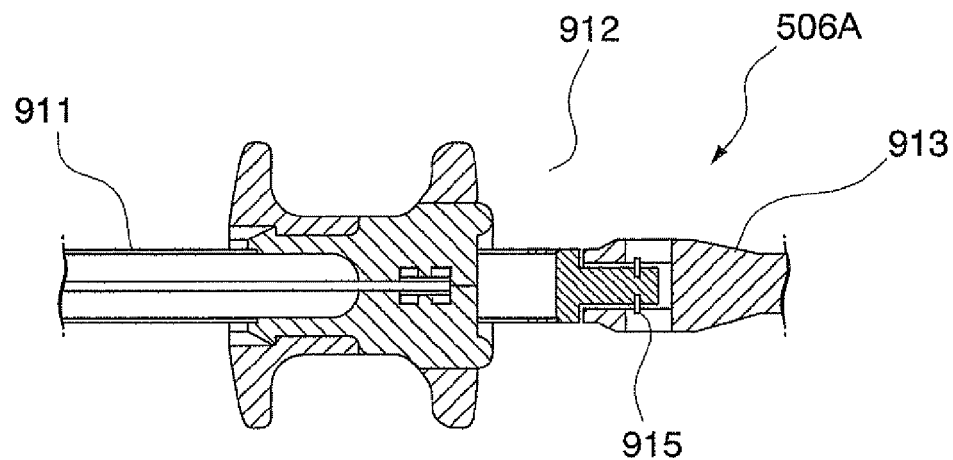
FIG. 87 is a cross-sectional view along the line AG-AG in FIG. 86.
Figure 88:
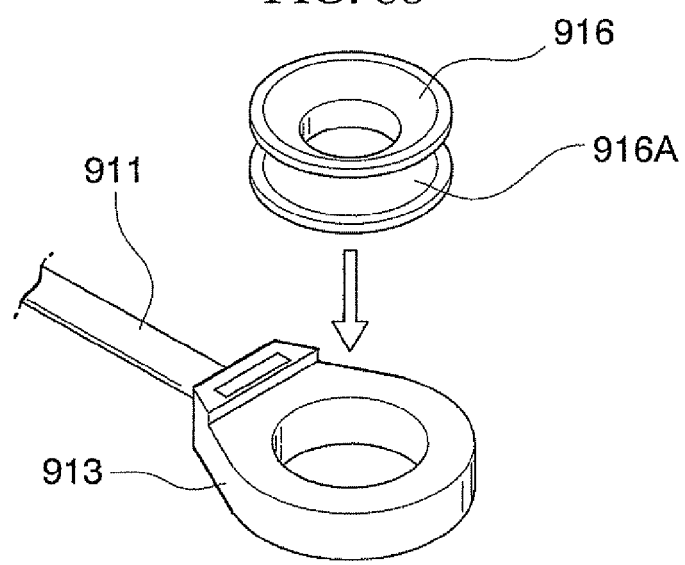
FIG. 88 describes how to attach a protection member to a ring.
Figure 89:
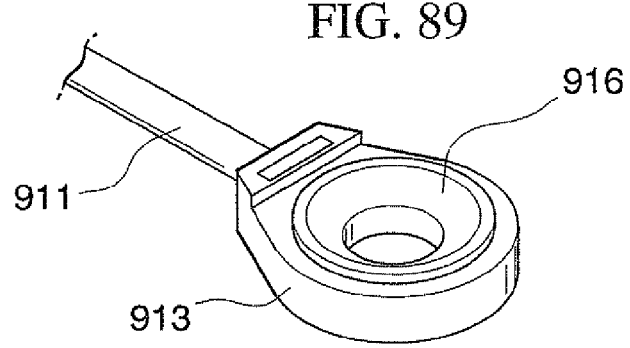
FIG. 89 describes a post-attached protection member disposed to the ring.

As illustrated in FIG. 87, a ring 913 is joined to the main body section 911 via an E ring 915. Operability is desirable since the ring 913 can be rotated by the E ring 915 around the axial line. It should be noted that a rubber-made protection member 916 may be used to be fitted to the inside of the ring 913 as illustrated in FIGS. 88 and 89. A groove 916A detachable from the ring 913 is formed on an outer periphery of the protection member 916. The use of rubber eases pain on fingers during operation. In addition, a detachable configuration is superior in maintaining cleanliness and sterilization. Making the protection member 916 of, for example, a silicone rubber, imparts chemical resistance and sterilization.

Figure 90A:
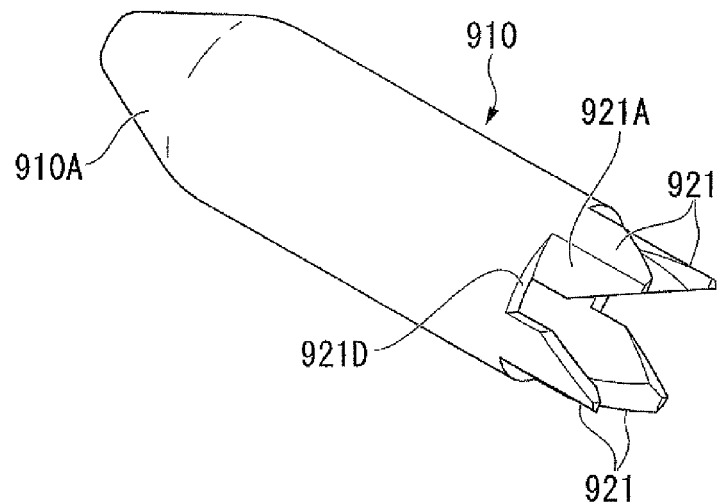
FIGS. 90A and 90B illustrate a cam in a perspective view.

As illustrated in FIGS. 76 and 86, the tip portion of the cam 910 is a taper where an opening diameter decreases. When the taper surface 910A is inserted through the operation stick 531A, the taper surface 910A serves for pushing up the piston 715 and pressing the channel 801. The outer diameter of the cam 910 is substantially the same as the inner diameter of the shaft 701 so that the cam 910 is slidable on the shaft 701. Four blade sections 921 extending in the axial line direction are provided to the base end of the cam 910. As illustrated in FIG. 90A, each blade section 921 is provided only on the outer periphery of the cam 910. A side surface 921A in the circumferential direction forms a tilted and curved surface from the center toward radially outward.

Figure 90B:
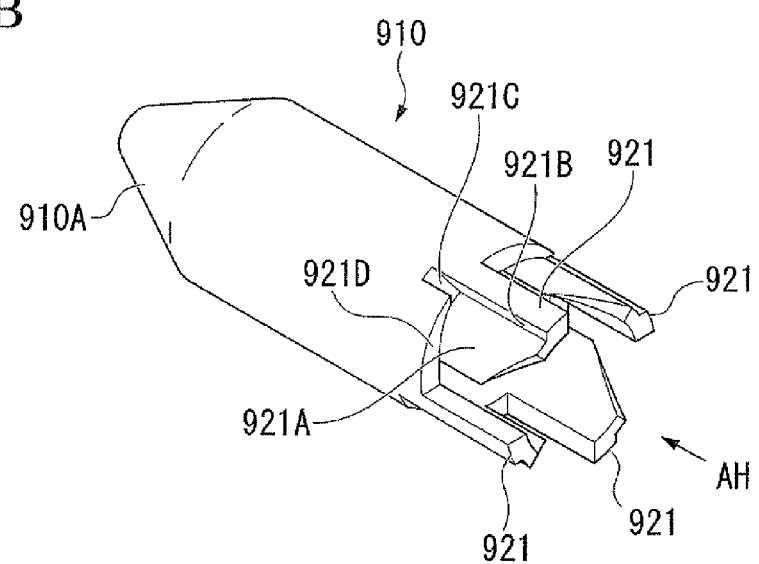
Figure 91:
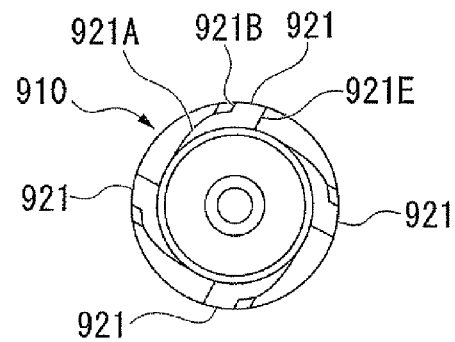
FIG. 91 is a view on arrow AH in FIG. 90.

In addition, as illustrated in FIGS. 90b and 91, a slope 921C directed to the tip together with a gap surface 921B standing in a radial direction may be formed on the outer periphery of the tilted side surface 921A of the cam 910. A gap 921D between the tilted side surface 921A and the outer periphery of the cam 910 is smoothly resolved by the slope 921C. A side surface 921E disposed opposite to the side surface 921A in the blade section 921 has a space greater than the diameter of the piston 715 between the side surface 921A of another blade section 921 adjacent in the circumferential direction and the side surface 921E. The side surface 921E is tilted in the direction the same as the tilting direction of the side surface 921A. The tilting direction of the side surface 921E is significant, i.e., forms a steep surface.

A main body section 911 is screwed into an inner hole of the cam 910 and fixed there. The outer diameter of the main body section 911 including a part inserted into the cam 910 and a stopper 922 having an increased diameter may be reduced gradually toward the base end. That is, FIG. 86 shows an example in which a diameter d2 at the base end is smaller than a diameter d1 at the tip. An operation section 506A of the hole 571B has a play relative to the operation stick 531A to prevent the main body section 911 from pushing up the piston 715 even if the operation section 506A is tilted or bent. Also, the tip of the piston 715 protruding into the shaft 701 is configured to have a correlation with the second groove 719 so that a space is formed between the piston 715 and the second groove 719. Thus, the piston 715 is prevented from interfering with the main body section 911 and therefore, the forward movement or retracting movement of the procedure instrument 504A can be smooth. In addition, the stopper 922 makes contact with a ratchet base 712 when the procedure instrument 504A is inserted through the operation stick 531A and regulates so that the procedure instrument 504A is prevented from being further pushed.

Figure 92:
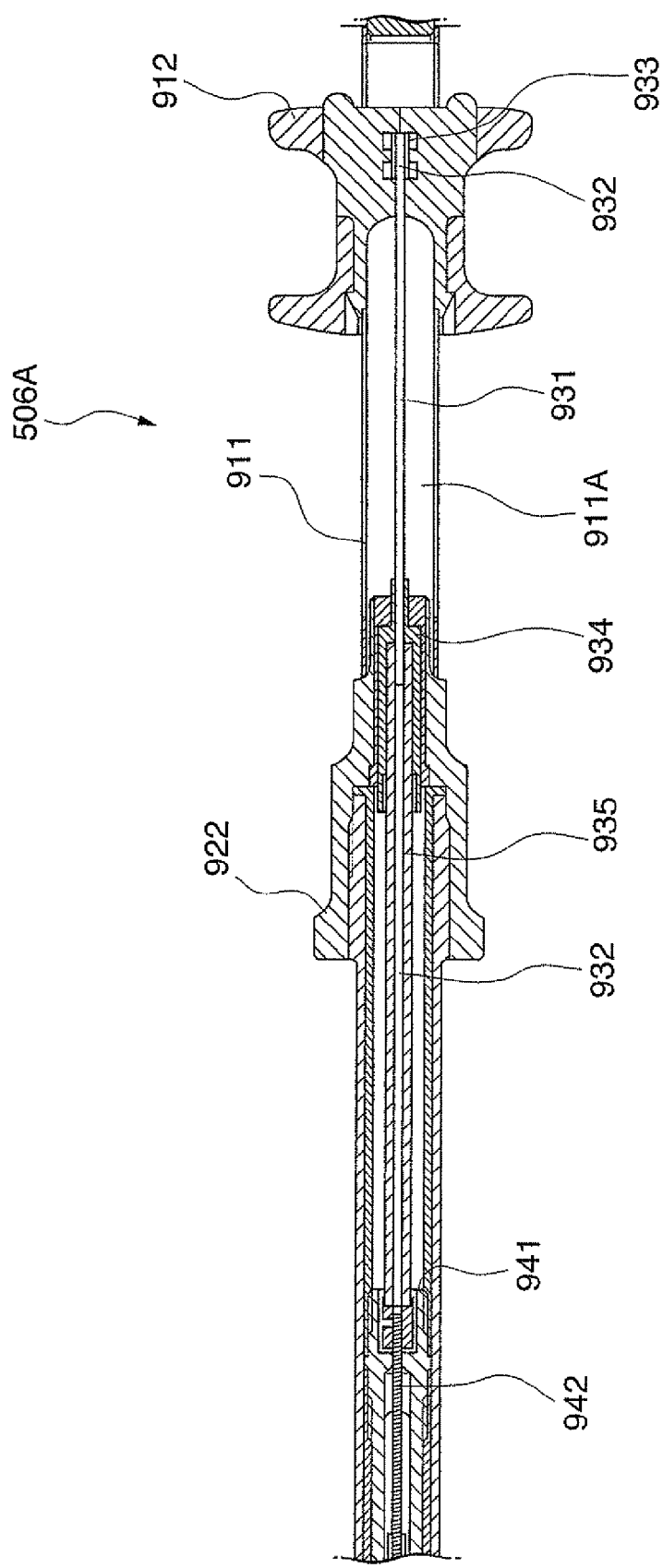
FIG. 92 is a cross-sectional view along the line AI-AI in FIG. 86.

As illustrated in FIG. 92, a pipe 931 is fixed to a slider 912. An operation wire 932 for driving the treatment section 505A is passed through the pipe 931. The base end of the operation wire 932 and the base end of the pipe 931 are locked to the slider 912 by an engagement member 933. The pipe 931 passing through a slit 911A of the main body section 911 is extendably supported by a resin-made pipe retainer 934. An operation wire 932 passing through another pipe 935 fixed to the pipe retainer 934 is extracted and enters an intermediate coupling 941 together with the pipe 935, and is inserted into a metal-made single-layered coil 942 therein. Isolation is imparted to the pipe 935 by coating it with a thermally-contracting tube.

Figure 93:
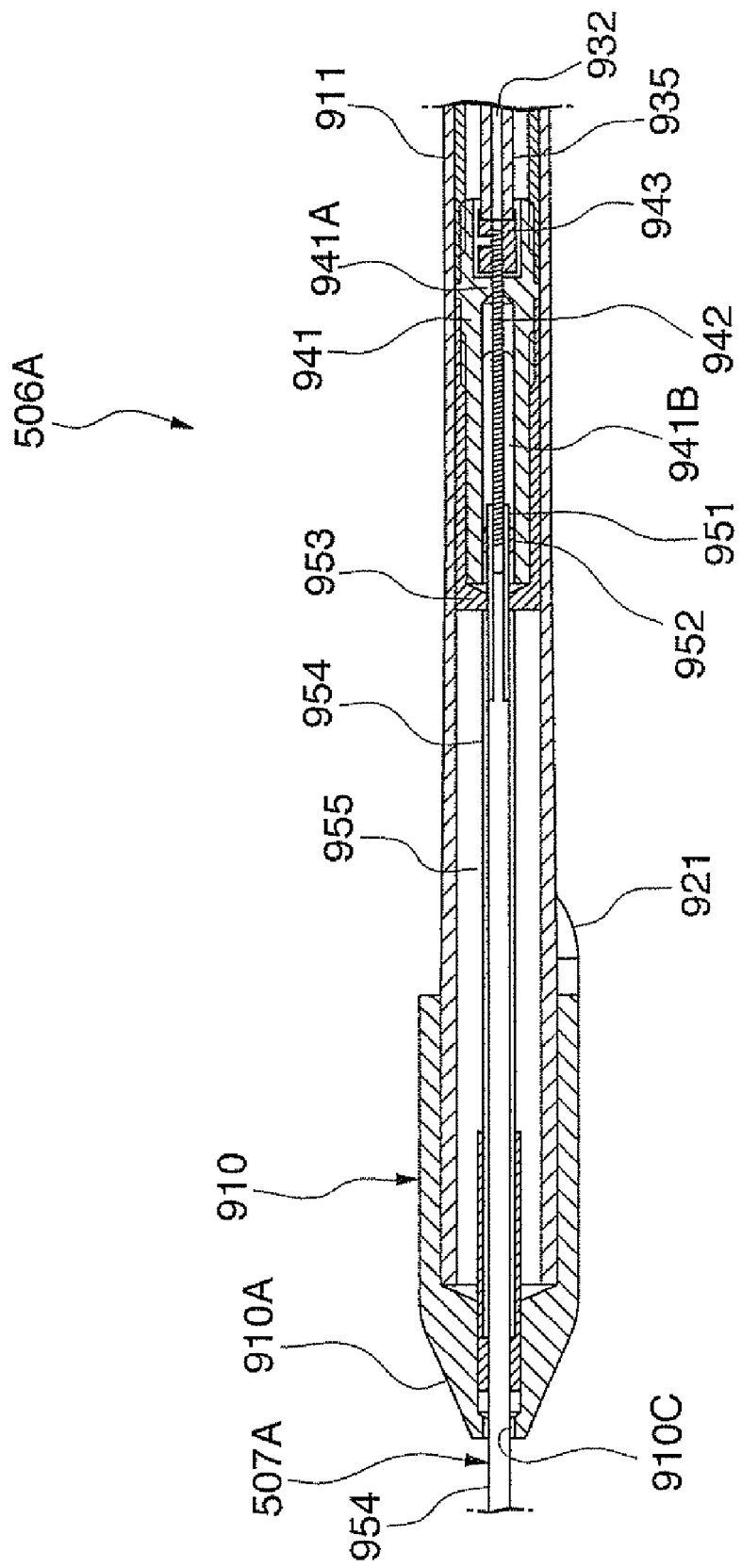
FIG. 93 is a cross-sectional view along the line AJ-AJ in FIG. 86.

As illustrated in FIG. 93, a coil receiver 943, to which the base end of the single-layered coil 942 is fixed, is housed in the base end of the intermediate coupling 941. The tip of the previously described pipe 935 is inserted into the coil receiver 943. A diameter-contracting section 941A is provided to the intermediate coupling 941 to prevent the coil receiver 943 from being removed toward the tip. The single-layered coil 942 is inserted into the multi-layered coil 951 at farther toward the tip than the diameter-contracting section 941A. The multi-layered coil 951 is configured to have more than three coils disposed coaxially. For example, an innermost layer coil and an outermost layer coil are wound in the same direction, and an intermediate-layer coil is wound in the opposite direction in the ease of three layer structure. This results in that rotating of the innermost layer coil and the outermost layer coil in the coil-loosening direction tightens the intermediate-layer coil, thereby causing the intermediate layer coil to interfere with the innermost layer coil. Thus, the rotation torque is transferred to the treatment section 505A at the tip. Rotating in the opposite direction causes the loosening intermediate layer coil to interfere with the outermost layer coil, thereby transferring the rotation torque to the treatment section 505A. In addition, using a metal-made multi-layered coil 951 improves the transferred rotation torque. A resin-made coil may be used for obtaining insulation.

A coil receiver 952 is brazed to the multi-layered coil 951. The coil receiver 952 is slidably inserted through a longitudinal groove 941B formed on the insulative intermediate coupling 941. Accordingly the multi-layered coil 951 can engage with the intermediate coupling 941 in the rotative direction, but not in the forward direction or the retracting direction. Meanwhile, a resin-made removal stop 953 is attached to the tip of the intermediate coupling 941. Since the removal stop 953 regulates the protrusion of the coil receiver 952, the multi-layered coil 951 will never be removed from the intermediate coupling 941. Also, the coil receiver 952 will never make contact with the main body section 911. This configuration will not affect the length of the multi-layered coil 951 even if the single-layered coil 942 contracts or extends during a medical operation.

Also, the single-layered coil 942 can be brazed to the coil receiver 943 that is slid toward the base end and extracted from the intermediate coupling 941 after brazing the multi-layered coil 951 to the coil receiver 952. Meanwhile, the intermediate coupling 941 should preferably be made of high heat-resistance resin, e.g., PEEK (polyetheretherketone) taking the high temperature applied during the brazing operation into account.

The outer periphery of the multi-layered coil 951 extracted from the intermediate coupling 941 is coated by an insulative tube 954. A fluoro resin-made insulative tube 954 has lower sliding friction, thus providing desirable rotation. The isolated and coated multi-layered coil 951 passing through a winding-protection pipe 955 is extracted from a hole 910C formed at the tip of the cam 910.

The main body section 911 should preferably be made of a metal material taking durability into account. In this case, providing insulation to the operation section 506A realizes a procedure instrument 504A for use in a medical operation with a high-frequency apparatus. Therefore, the use of a resin in the removal stop 953, intermediate coupling 941, thermally-contracting tube of the pipe 935, pipe retainer 934, and slider 912 reliably isolates the main body section 911 from the operation wire 932 and coils 942 and 951. This results in using high-frequency waves with the procedure instrument 504A such as an incision knife or a high-frequency forceps. Apparatuses of this type can be used compatibly. Insulation coating onto the multi-layered coil 951 may not be necessary unless the procedure instrument is of a high frequency application-type apparatus. In this case, increasing the thickness of the multi-layered coil 951 corresponding to the thickness of the thermally contracting tube for use as a coating will provide a more rotative procedure instrument. The thickness of the thermally contracting tube utilized for the single-layered coil 942 will provide a more significant resistance against compression or expansion.

Consequently, steps for carrying out operations using the medical treatment endoscope 501 will be explained. Meanwhile, a case will be explained as follows where an endoscope is introduced from a mouth as a natural orifice of a patient, a procedure instrument is introduced from an opening formed in a stomach into an abdominal cavity to grasp tissue. It should be noted that operations can be carried out through another organ or another path. Although we concentrate on the procedure instrument 504A and the first operation unit 530A in the explanation, the procedure instrument 504B and the operation unit 530B can be used independently because they are mere symmetric components.

Figure 95:
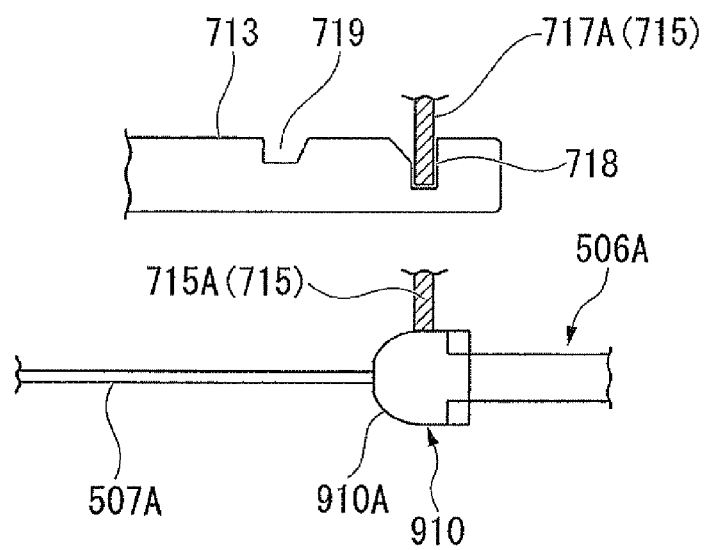
FIG. 95 illustrates the piston pushed up by the cam.

Two procedure instruments 504A and 503B are inserted into the medical treatment endoscope 501. The procedure instrument 504A is inserted into the first operation unit 530A. As schematically illustrated in FIG. 94, when the procedure instrument 504A is not inserted yet, the piston 715 provided to the ratchet base 712 at the tip of the first operation stick 531A engages with the first groove 718 of the connection plate 713 and locks the connection plate 713. Locking the connection plate 713 prevents the second bending slider 711 from moving since the ratchet base 712 is unmovable. This corresponds to a position where the second bending part 308 becomes straightened. That is, the second bending part 308 is always straightened in the medical treatment endoscope 501 when the procedure instrument 504A is inserted. As illustrated in FIG. 95, forwarding the operation section 506A into the first operation stick 531A pushes up the piston 715 with the taper surface 910A of the cam 910 at the tip of the operation section 506A. As illustrated in FIG. 96, the piston 715 being capable of moving up the inclination surface 718A of the first groove 718 of the connection plate 713 allows the second bending slider 711 to be controlled in the direction indicated by an arrow shown in the drawing.

As illustrated in FIG. 76, the insertion section 507A of the procedure instrument 504A passing through the channel 801 is introduced into a channel in the connection sheath 515. The insertion section 507A further passing through the endoscope insertion section 503 is introduced to the tip of the first arm member 302A. Similarly, the procedure instrument 504B inserted into the operation stick 531B of the operation unit 530B is introduced to the tip of the second arm member 303A.

After closing the arm sections 302A and 303A having the procedure instruments 504A and 504B previously passing therethrough, the endoscope insertion section 503 is introduced into a body cavity from an opening previously formed in a stomach wall. In addition, the endoscope insertion section 503 may be passed through an overtube previously inserted into a body.

A section to be treated is confirmed while observing with a monitor an image obtained by an endoscopic image-pickup device provided to the tip of the endoscope insertion section 503. At this time, a first operator manipulates an angle knob 512 of the endoscope insertion section 502 and bends a third bending part 203B. Furthermore, a second operator bends the second bending part 308 and the first bending part 306 if necessary.

Figure 97:
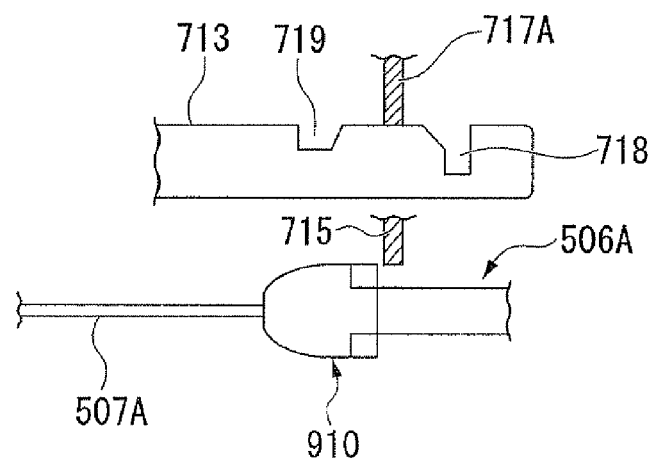
FIG. 97 illustrates the cam disposed between two grooves of the connection plate.

Bending the second bending part 308 necessitates retracting the second bending slider 711 provided to the operation sticks 531A and 531B. As illustrated in FIG. 96, retracting the second bending slider while the piston 715 is elevated causes the engagement chip 717A of the piston 715 to go up the inclination surface 718A, thereby causing the connection plate 713 to slide on the piston 715 as illustrated in FIG. 97. The second bending slider 711 cannot be farther retracted after the piston 715 is housed in the second groove 719 as illustrated in FIG. 98. The second bending part 308 as illustrated in FIG. 72 bends at this position, causing the first arm member 302A to open. In addition, since the second groove 719 is shallower than the first groove 718, a space Ss is formed between the cam 910 and the main body section 911 of the operation section 506A when the piston 715 engages with the second groove 719. Absence of slide between the main body section 911 and the piston 715 allows smooth extension and retraction of the main body section 911.

Furthermore, bending the first bending part 306 necessitates tilting the operation sections 506A and 506B of the procedure instruments 504A and 504B while observing the endoscopic image.

As illustrated in FIG. 75, tilting the operation section 506A upwardly relative to the operator causes the rotation shafts 564A and 565A of the first rotation mechanism 561A to rotate in accordance with the tilting angle. The rotation of the sprocket 595 attached to the rotation shafts 546A and 565a causes extension and retraction of the first bending wires 315A and 315B attached to the chain 622, thereby bending the first bending part 306 upwardly. In contrast, tilting the operation section 506A downwardly relative to the operator causes the rotation shafts 564A and 565A of the first rotation mechanism 561A to rotate in the direction reverse to the upward tilting direction in accordance with the tilting angle. The reverse rotation of the sprocket 595 attached to the rotation shafts 546A and 565a causes extension and retraction of the first bending wires 315A and 315B attached to the chain 622, thereby bending the first bending part 306 downwardly.

Tilting the operation section 506A in a right-hand direction relative to the operator causes the rotation shafts 584A and 585A of the second rotation mechanism 581A to rotate in accordance with the tilting angle. The rotation of the sprocket 595 attached to the rotation shafts 584A and 585A causes extension and retraction of the first bending wires 315C and 315D attached to the chain 622, thereby bending the first bending part 306 in the right-hand direction. In contrast, tilting the operation section 506A in a left-hand direction relative to the operator causes the rotation shafts 584A and 585A of the second rotation mechanism 581A to rotate in the reverse direction in accordance with the tilting angle. The reverse rotation of the sprocket 595 attached to the rotation shafts 584A and 585A causes extension and retraction of the first bending wires 315C and 315D attached to the chain 622, thereby bending the first bending part 306 in the left-hand direction.

Since the second rotation mechanism 581A is not driven when the first rotation mechanism 561A is driven, and the first rotation mechanism 561A is not driven when the second rotation mechanism 581A is driven, each bending can be obtained without being affected by these rotation mechanisms. Meanwhile, tilting the operation section 506A drives the first and second rotation mechanisms 561A and 581A in accordance with the tilting ratio with respect to the vertical and horizontal directions, thereby bending the first bending part 306 diagonally in the direction the same as the tilting direction of the operation section 506A. Since the center or barycenter of the operation stick 531A in the longitudinal direction is configured to substantially coincide with the positions of the rotation shafts 546A, 565A, 584A, and 585A, the operation stick 531A and the operation section 506A of the procedure instrument 504A during hands-free operation by the operator will not descend with gravity; therefore, erroneous operation can be prevented.

A necessary force is optimized to operate the first bending part 306 by means of a non-electric wire-assisted operation. To be more specific, a portion of the operation stick 531A operated by the operator who inputs a force is decelerated by separating and offsetting the portion from the rotation shafts 546A, 565A, 584A, and 585A. As illustrated in FIG. 77, since a deceleration ratio is obtained corresponding to a ratio between a distance Lr an a radius Rs of the sprocket 595, the bending operation can be carried out with a small force while downsizing the operation section 520. In this case the distance Lr indicates a length between the base end section of the operation section 506A of the procedure instrument 504A. In addition, the deceleration enhances resolution, thereby enabling accurate bending operation.

As illustrated in FIGS. 76 and 77, since the point of the second rotation mechanism 581A to which a force is transmitted from the first operation stick 531A is offset toward the tip relative to the rotation shafts 564A and 565A such as a roller bearing 572A as illustrated in FIG. 77, the force necessary at the transfer position is decreased, and friction among components can be reduced. This decreases the rigidity required for components used there and obtains a small and light-weight operation section 520. Also, the use of the ball roller 572A at the point of the second rotation mechanism 581A to which the force is transferred from the first operation stick 531A reduces the friction due to the second rotation mechanism 581A when rotating the first operation stick 531A vertically, thereby reducing the necessary force for the vertical operation.

Grasping tissue necessitates adjusting the position of a forceps member that is opened or closed by the operation section 506A of the procedure instrument 504A. For example, pushing the operation section 506A into the first operation stick 531A causes the treatment section 505A to protrude further from the first arm member 302A. Also, retracting the operation section 506A from the first operation stick 531A causes the treatment section 505A to be retracted into the first arm member 302A. As illustrated in FIG. 99, since this state of the cam 910 is hooked on the piston 715, the procedure instrument 504A will not be removed from the first operation stick 531A undesirably.

Adjusting the direction of the procedure instrument 504A around the axial line necessitates the main body section 911 of the operation section 506A to rotate around the axial line. Thus, rotational torque is input into the multi-layered coil 951 that is engaged to the intermediate coupling 941 in the rotational direction as illustrated in FIGS. 92 and 93. In the multi-layered coil 951, two coils adjacent to each other in a radial direction interfere with each other while they are tightened or loosened based on their combination of the winding direction and the rotational direction of the operation section 506A and thus, rotational torque is transferred. Since the treatment section 505A is fixed to the tip of the multi-layered coil 951, the transferred rotational torque rotates the treatment section 505A around the axial line. The rotation in the vicinity of the operator's hand is stopped after confirming that a desirable direction is obtained by means of an endoscopic image.

The slider 912 is forwarded after adjusting the direction and position of the treatment section 505A. The operation wire 932 moves an opening-and-closing mechanism of the treatment section 505A to open a pair of forceps members. The single-layered coil 942 receives an extension force generated by pushing the operation wire 932. The extension force is not applied to the multi-layered coil 951 because the multi-layered coil 951 is not engaged with the operation section 506A in the extension and retraction directions. This allows the treatment section 505A to be adjusted even if the forceps members are opened. Consequently, retracting the slider 912 causes the forceps members to close and grasp tissue. The compression force generated temporarily is received by the single-layered coil 942.

The procedure instruments 504A and 504B are retracted from the medical treatment endoscope 501 after completing necessary treatments. The procedure instruments 504A and 505B are also retracted from the medical treatment endoscope 501 in order to exchange procedure instruments necessary for a treatment. As illustrated in FIG. 99, the operation section 506A is rotated around the axial line after the cam 910 abuts the piston 715. The piston 715 is pushed up along the tilted side surface 921A of the blade section 921 of the cam 910. As illustrated in FIG. 100, providing the tilted side surface 921A enables to push up the piston 715 with a small force. Meantime, as illustrated in FIGS. 90 and 91, the procedure instrument 504A will never be rotated excessively if the gap surface 921B is provided. Furthermore, providing the slope 921C facilitates offsetting the piston 715 from the cam 910 in an axial line direction (thrust direction), thereby removal is easy. Meantime, it is preferable that the entire cam 910 should be made of a metal in view of breakage protection. In addition, the cam 910 may be made of POM (polyoxymethylene) that has desirable slidability in view of facilitating operation in an extension and retraction operations in the first operation stick 531A.

However, the treatment sections 505A and 505B cannot be removed if the second bending part 308 of the arm sections 302A and 303A is opened, and the engagement of the piston 715 and the cam 910 can be released. The piston 715 pushed up by the cam 910 in the operation section 520 is configured to automatically restore the second bending part 308 to a straightened state. That is, pushing up the piston 715 and releasing the engagement with the second groove 719 retract the second bending slider 711 with tension applied by the second bending wires 316A and 316B and a resilience of the coil spring 745. This results in causing the second bending part 308 to restore into the straightened state. In addition, a resilient part like the spring 792 as illustrated in FIG. 84 may be added to prevent energetic restoration of the second bending slider 711. Consequently, the medical treatment endoscope 501 is removed from the body after removing the procedure instrument 504A.

Next, a modified example of the present embodiment will be described as follows.

Figure 101:
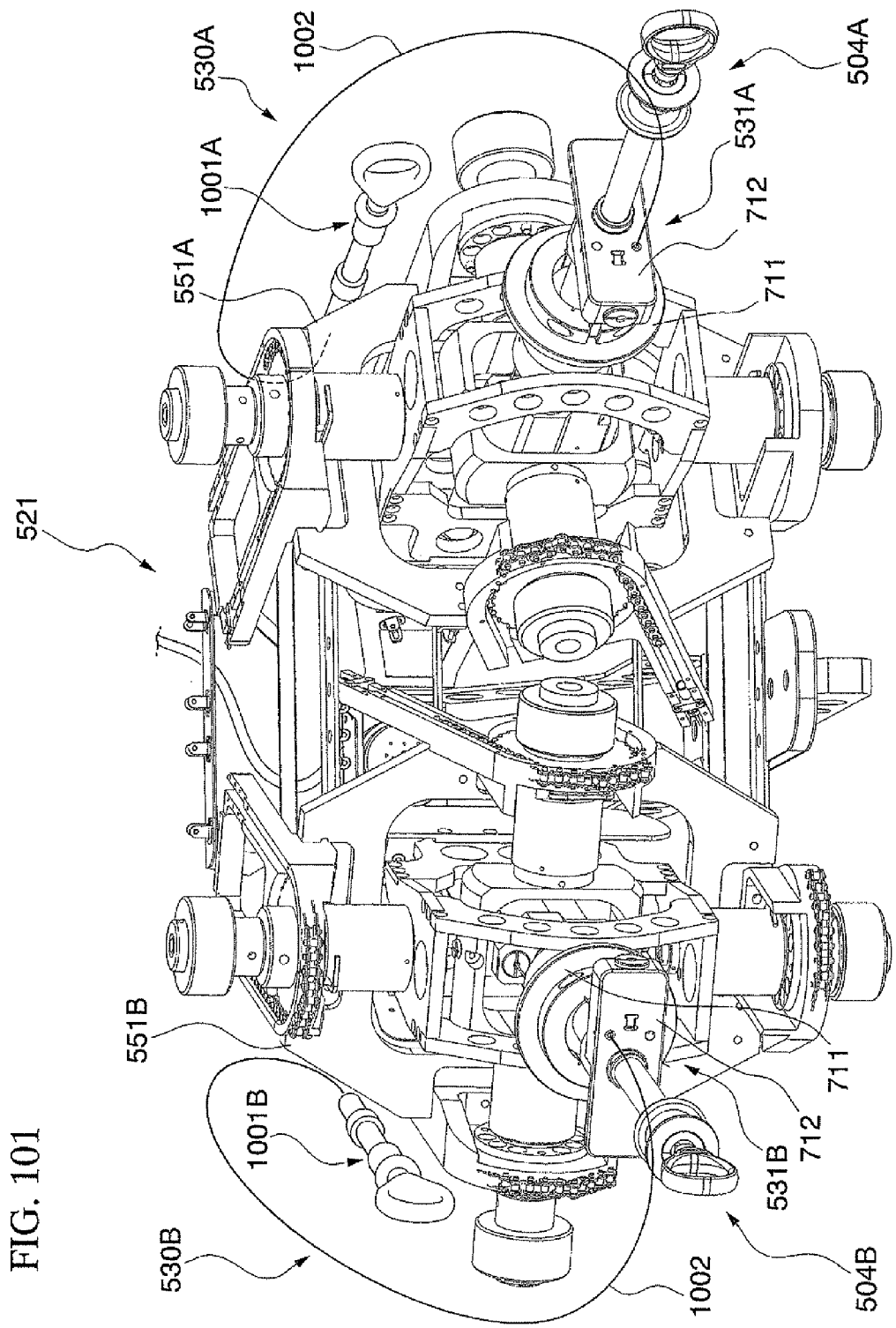
FIG. 101 illustrates a base having an operation section joined to a second bending slider disposed on a side of a base.
Figure 102:
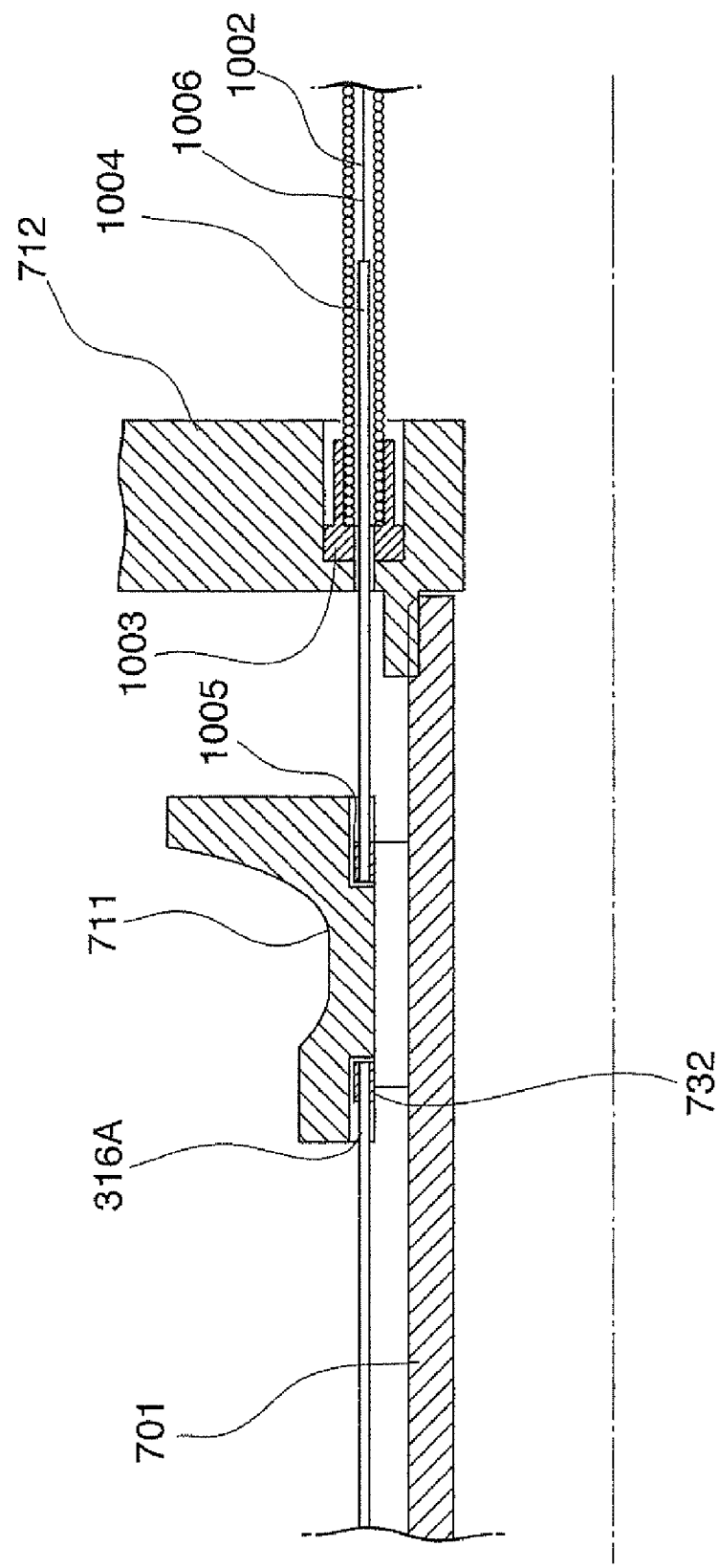
FIG. 102 is a cross-sectional view illustrating a mechanism for joining the second bending slider to the operation section in the configuration shown in FIG. 101.

As illustrated in FIG. 101, the operation sections 1001A and 1001B each for operating the second bending slider 711 may be fixed to the brackets 551A and 551B in parallel with each axial line of the operation sticks 531A and 531B. The operation sections 1001A and 1001B each have an extendable and retractable slider. Moving the slider causes the wire in the coil sheath 1002 to be extended or retracted. As illustrated in FIG. 102, the coil sheath 1002 is fixed to the coil receiver 1003 attached to the ratchet base 712. A pipe 1004 is passed through the coil receiver 1003. The pipe 1003 passing through the coil sheath 1002 is rotatively engaged with the second bending slider 711 via the wire receiver 1005 together with the second bending wires 316A, 316B. A wire 1006 joined to the sliders of the operation sections 1001A and 1001B is passed through the pipe 1004. Retracting the sliders of the operation sections 1001A and 1001B moves the wire 1006, thereby drawing the second bending slider 711 and opening the second bending part 308. In this configuration, the operation section 520 can be downsized and thus, operation of the second bending part 308 can be facilitated. Also, this configuration prevents the movement of the operation sticks 531A and 531B during the operation of the second bending part 308. Thus, grasped tissue will never be moved unexpectedly.

Figure 103:
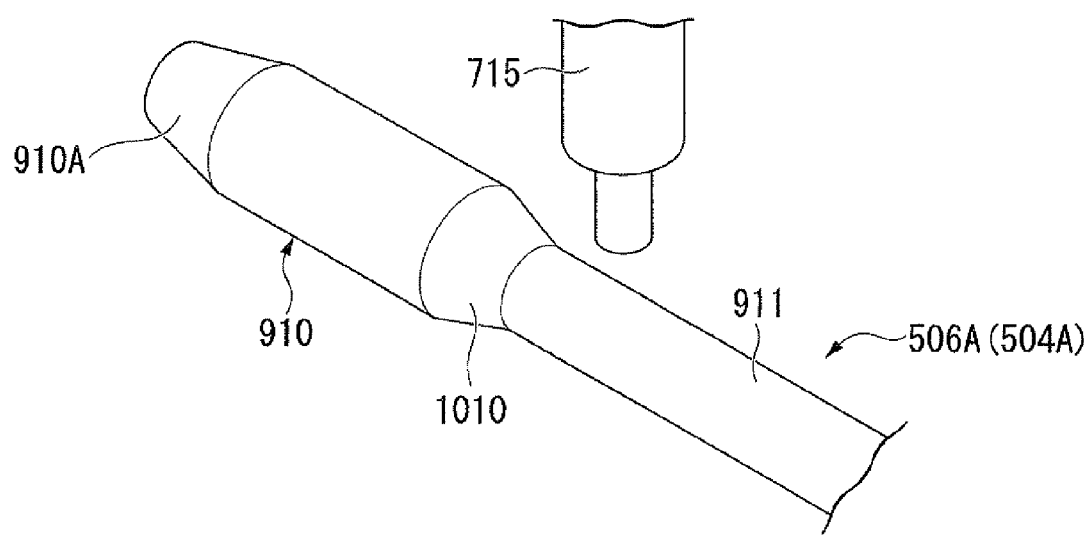
FIG. 103 is a view showing a modified example of the cam.

As illustrated in FIG. 103, the base end of the cam 910 may be the inclination surface 1010. Drawing the procedure instrument 504A from the first operation stick 531A causes the piston 715 to move up the inclination surface 1010, thereby removing the procedure instrument 504A. The procedure instrument 504A cannot be removed with a force based on the retraction of the procedure instrument 504A toward the operator during a treatment. Further additional force will provide retraction. In this configuration, the procedure instrument 504A can be removed without rotating the operation section 506A.

Figure 104:
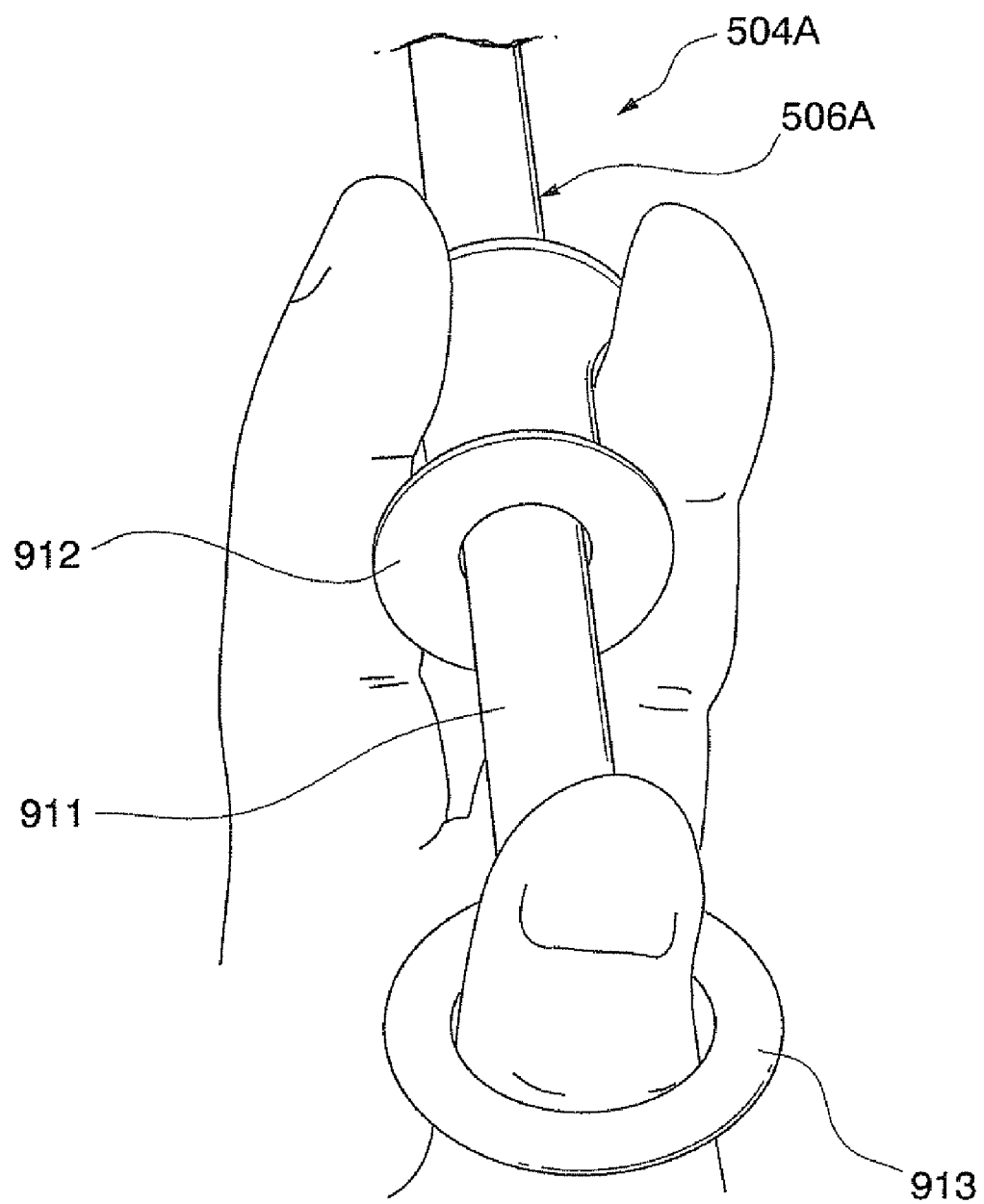
FIG. 104 illustrates a feed operation for the procedure instrument.
Figure 105:
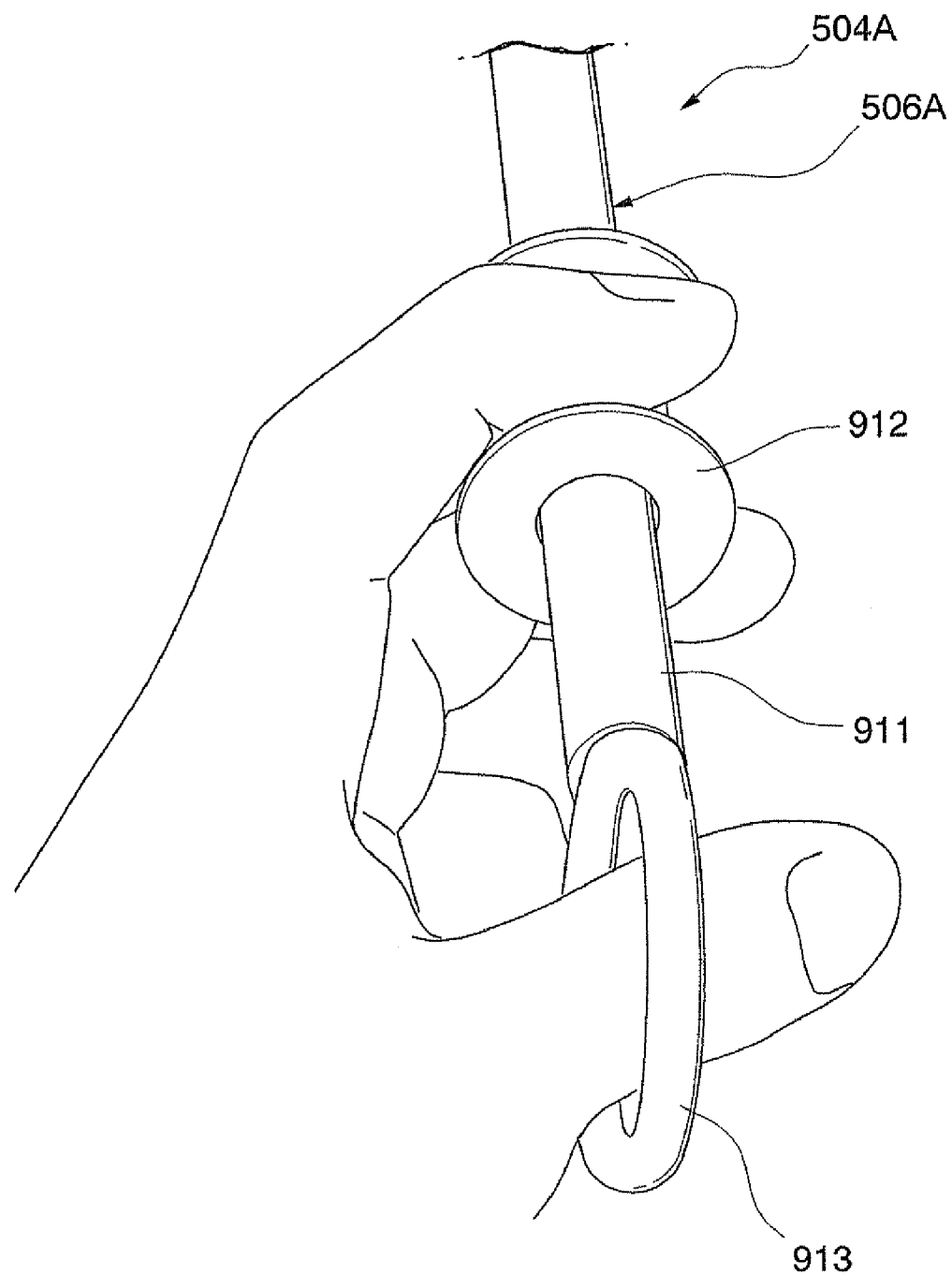
FIG. 105 illustrates a feed operation for the procedure instrument.

In addition, operations for significant rotations of the procedure instruments 504A and 504B will be explained with reference to FIGS. 104 and 105. This includes cases where we intend to adjust the treatment section 505A in the optimum direction to grasp tissue. As illustrated in FIG. 104, the slider 912 is held with an index finger and a middle finger. The hand-held state of the slider 912 is rotated in a clockwise direction by 90°. The index finger and the middle finger are withdrawn from the slider 912 after rotating the slider 912 and the main body section 911 to the positions illustrated in FIG. 105. The hand not holding the slider 912 is rotated in a counterclockwise direction by 90° to the position illustrated in FIG. 104. This state of the insertion section 507A of the procedure instrument 504A has friction relative to channels in a first operation stick 531A and the second arm member 302A. To be more specific, the channels are a channel 801, a channel in the connection sheath 515, and a channel in the endoscope insertion section 503. Therefore, the insertion section 507A will not rotate in the counterclockwise direction with a mere touch with the slider 912 and thus, its disposition is maintained. Repeating the above steps enables 90° feed operation of the procedure instrument 504A.

Figure 106:
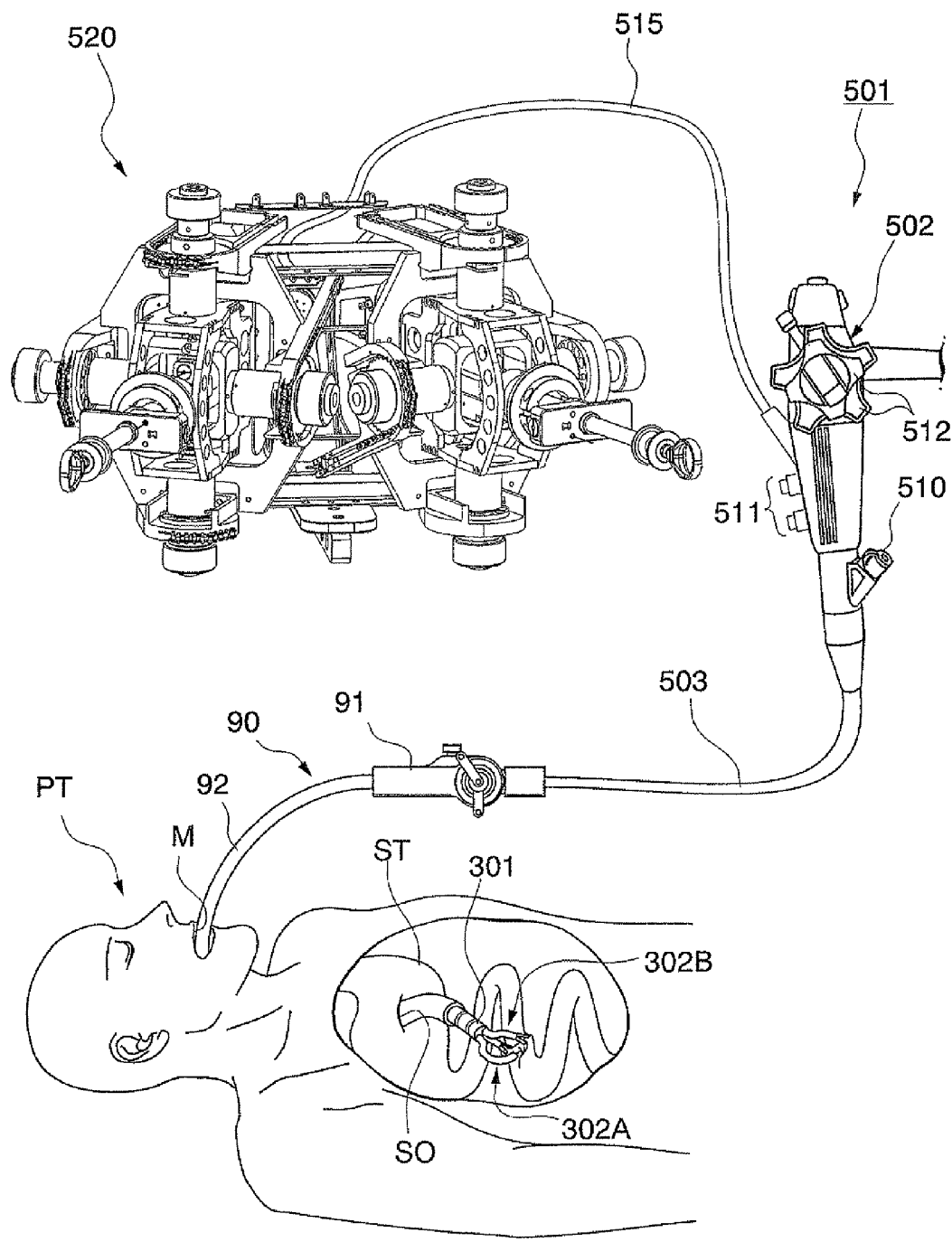
FIG. 106 illustrates a combined use of the medical treatment endoscope and an overtube.

As illustrated in FIG. 106, the medical treatment endoscope 501 may be passed through the overtube 90. The first operator handling the endoscope insertion section 502 conducts ordinary endoscopic operation with his/her left hand while operating the endoscope insertion section 503 and overtube 90 with his/her right hand. The intention to bend the overtube 90 improves the approachability to the object position in the abdominal cavity.

Sixth Embodiment

Figure 107:
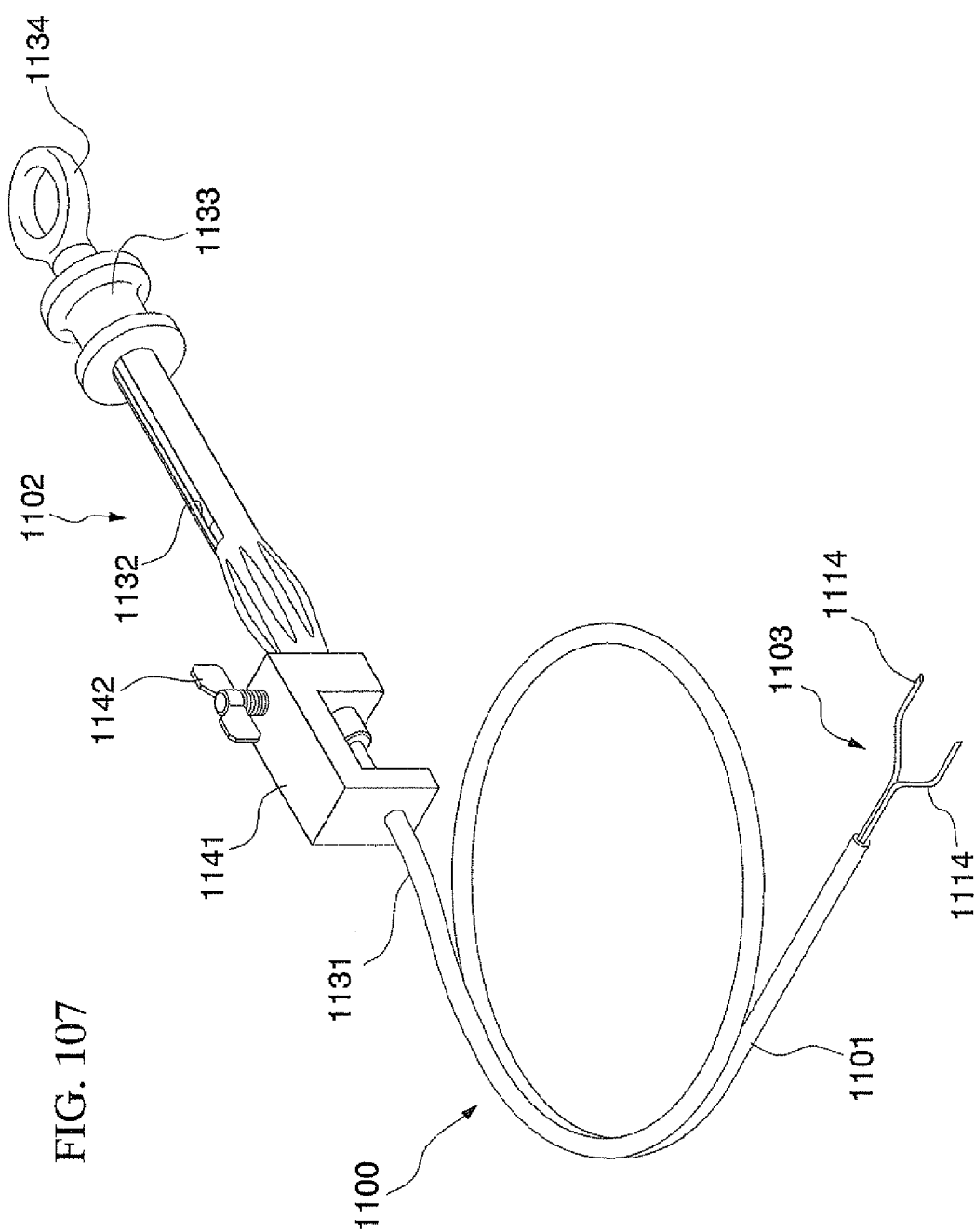
FIG. 107 is an external view for the procedure instrument.
Figure 108:
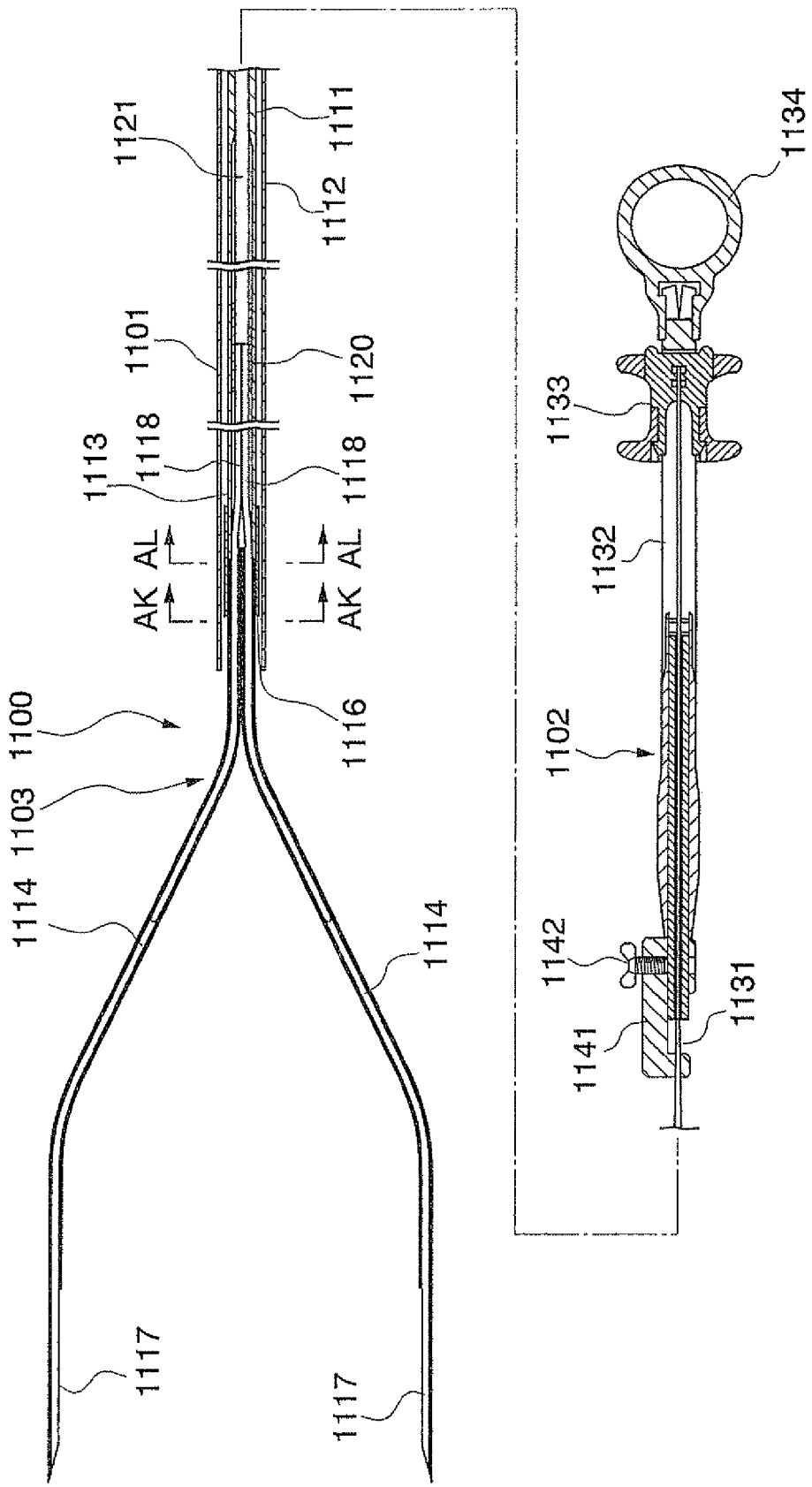
FIG. 108 is a cross-sectional view for the procedure instrument.

A procedure instrument usable with an endoscope is illustrated in FIGS. 107 and 108.

A procedure instrument 1100 has a overcoat tube 1101 constituting a flexible and elongated insertion section. An operation section 1102 is provided on the base end of the overcoat tube 1101. A needle section 1103 serving as a treatment section is passed through the overcoat tube 1101 extendably and retractably. The tip portion of the needle section 1103 protrudes from the opening of the tip of the overcoat tube 1101 as illustrated in FIG. 107.

Figure 109:
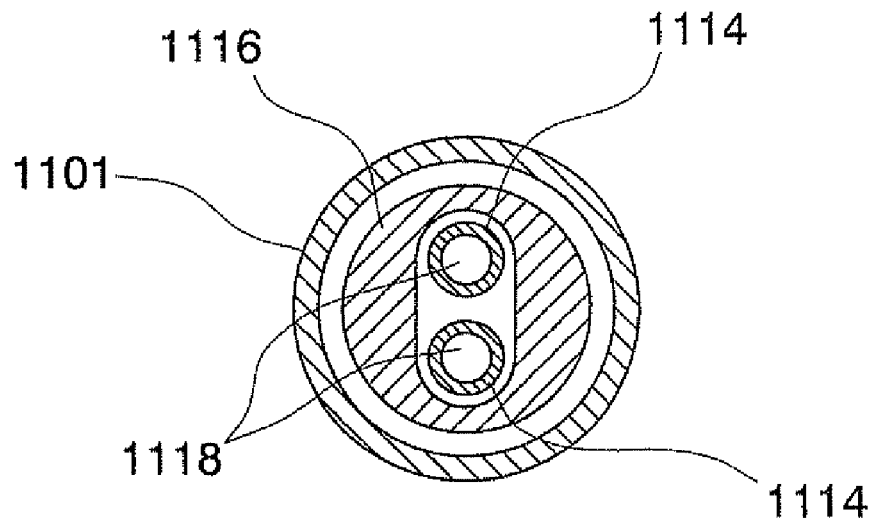
FIG. 109 is a cross-sectional view along the line AK-AK in FIG. 108.
Figure 110:
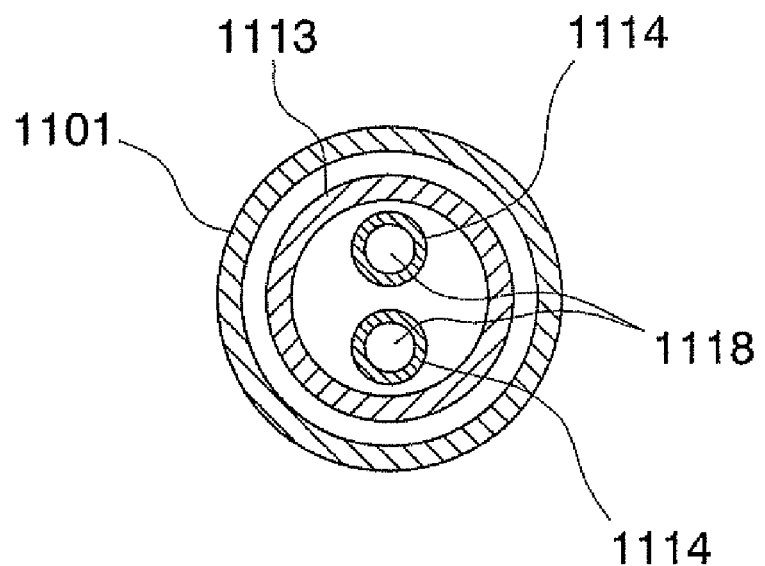
FIG. 110 is a cross-sectional view along the line AL-AL in FIG. 108.

The needle section 1103 has a second coil 1111 passed through the overcoat tube 1101. The connecting part 1112 joins the tip of the second coil 1111 to the base end of the first coil 1113. The first coil 1113 is substantially the same as the second coil 1111 in outer diameter. The inner diameter of the first coil 1113 is greater than that of the second coil 1111. A supporting section 1116 for supporting a pair of needles 1114 is attached to the tip of the first coil 1113. As illustrated in FIGS. 109 and 110, a supporting section 1116 has two parallel through holes each having a hollow needle 1114 passing therethrough extendably and retractably. The pair of the needles 1114 are bending at the base end supported by the supporting section 1116 to spread with respect to an axial line. The acute tips are disposed substantially parallel at a predetermined distance. A slit 1117 is formed at the acute tip along the axial line. A pusher wire 1118 is passed through each needle 1114. The pusher wire 1118 extracted from the base end of the needle 1114 is joined to the operation wire 1121 in the first coil 1113 via the connecting part 1020. The operation wire 1121 passing through the second coil 1111 extendably and retractably is introduced to the operation section 1102. Meantime, the outer diameter of the connecting part 1020 is greater than that of the operation wire 1121. However, since the inner diameter of the first coil 1111 is significant, extendable and retractable movement can be obtained in the first coil 1113.

Figure 111:
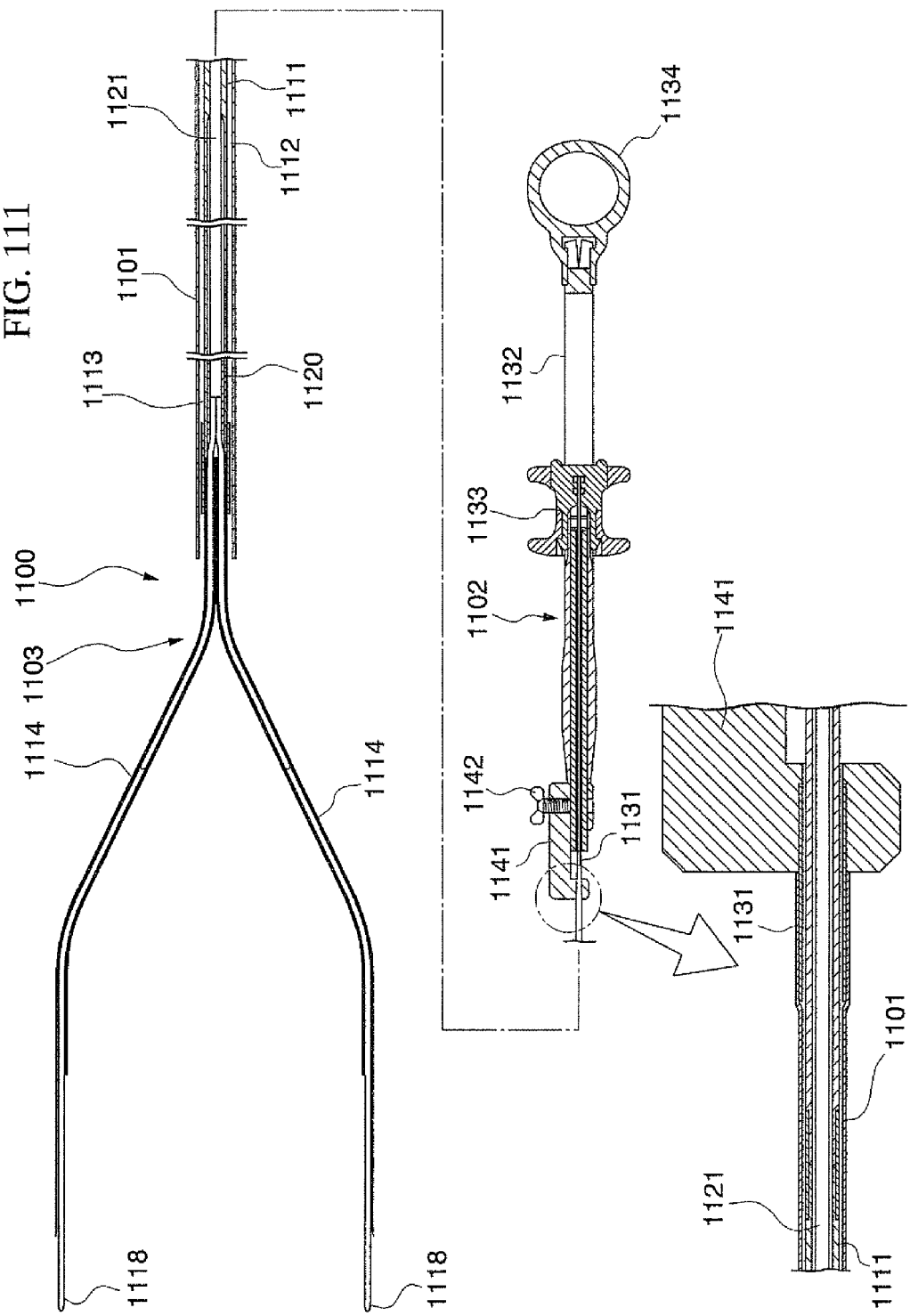
FIG. 111 illustrates a pusher wire protruding from a needle.

The base end of the second coil 1111 is a hard section 1131 that is fixed to the operation section main unit 1132 of the operation section 1102. The operation wire 1121 passing through the operation section main unit 1132 is joined to the slider 1133 attached to the operation section main unit 1132 extendably and retractably. A finger-hook ring 1134 is attached to an end of the operation section main unit 1132 rotatively around the axial line. Sliding back and forth the slider 1133 relative to the operation section main unit 1132 while inserting a thumb into the finger-hook ring 1134 and supporting the slider 1133 with an index finger and a middle finger provide extending or retracting movement to the pusher wire 1118 relative to the overcoat tube 1101. As illustrated in FIG. 111, the pusher wire 1118 can be extended until protruding from the tip of the needle 1114. Meantime, a coating may be applied to the pusher wire 1118 for smooth extension and retraction of the pusher wire 1118 in the needle 1114.

The base end of the overcoat tube 1101 is fixed to the overcoat tube end member 1141. The overcoat tube end member 1141 can move along the hard section 1131 of the second coil 1111. Tightening the fixing screw 1142 allows the overcoat tube 1101 to be fixed to a front end section 1132A of the operation section main unit 1132.

Figure 112:
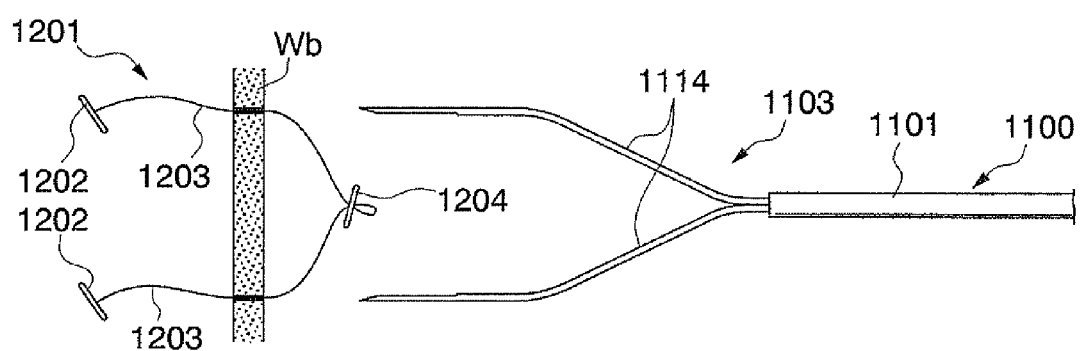
FIG. 112 illustrates a retainer embedded in tissue of an inner wall of a body cavity.

FIG. 112 illustrates a retainer 1201 loaded in the needle 114. The retainer 1201 has two anchors 1202 each housed in the needle 1114, a thread 1203 joining two anchors 1202, and a fastener plate 1204 having the thread 1203 passing therethrough.

Manipulation using the procedure instrument 1100 will be explained.

Figure 113:
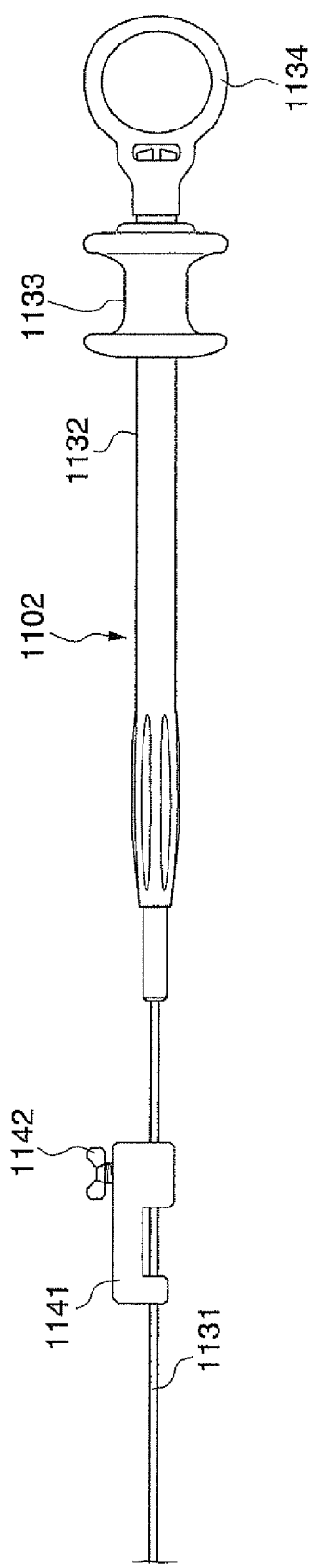
FIG. 113 illustrates a disposition of the operation section having an overcoat tube enclosing a needle.
Figure 114:
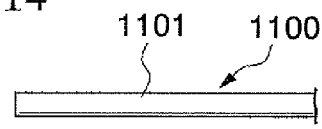

The retainer 1201 is loaded first in the procedure instrument 1100. To be more specific, each anchor 1202 is housed in the inside of the acute end of each needle 1114, and the thread 1203 is extracted from the slit 1117. A fixing screw 1142 is loosened after loading the retainer 1201. As illustrated in FIG. 113, a overcoat tube end member 1141 is extended relative to the operation section main unit 1132. As illustrated in FIG. 114, the pair of the needles 114 are drawn into the overcoat tube 1101 and housed there.

Figure 115:
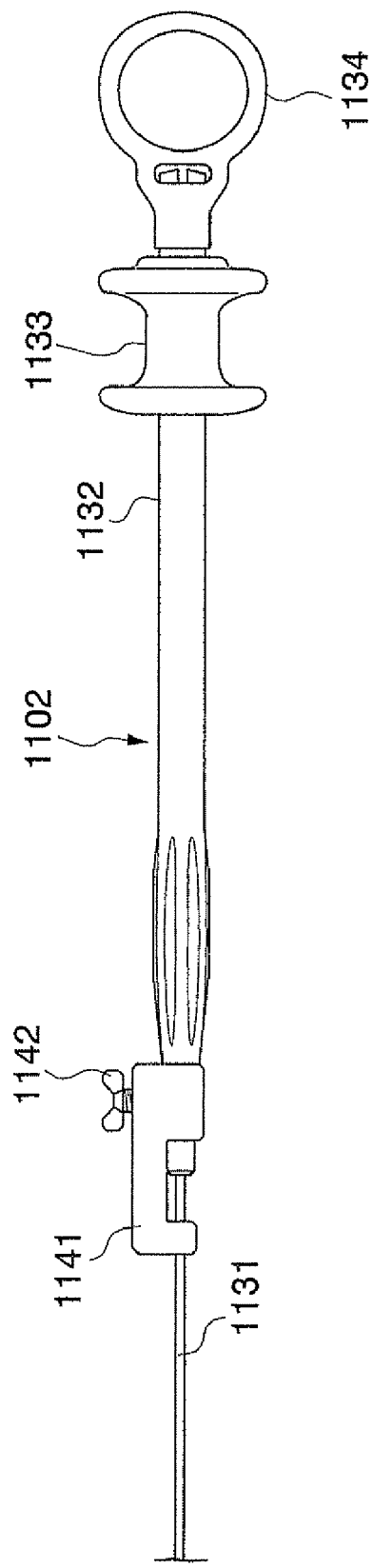

The overcoat tube 1101 is next inserted into a body cavity through a channel of the endoscope, and the overcoat tube 1101 is protruded from the tip of the endoscope. As illustrated in FIG. 115, an operation section main unit 1132 is pushed into the overcoat tube end member 1141 after loosening the fixing screw 1142. As illustrated in FIG. 115, the needle 1114 protrudes from the overcoat tube 1101. The acute ends of the needle 1114 opens by releasing the urging force applied by the overcoat tube 1101. Tightening this state of fixing screw 1142 of the overcoat tube end member 1141 causes the needle section 1103 of the overcoat tube 1101 to be fixed.

Figure 116:
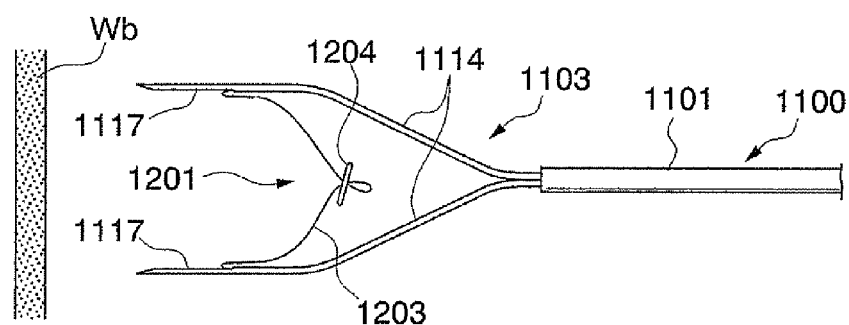

As illustrated in FIG. 116, forwarding the procedure instrument 1100 relative to the endoscope provides protrusion of the needle 1114 into the inner wall Wb of a body cavity. The acute ends and the slits 1117 penetrate the inner wall Wb of a body cavity and protrude into the exterior of the body cavity. The thread 1203 extracted from the slit 1117 is reached to the endoscope through tissue. The fastener plate 1204 exists in the endoscope.

Figure 117:
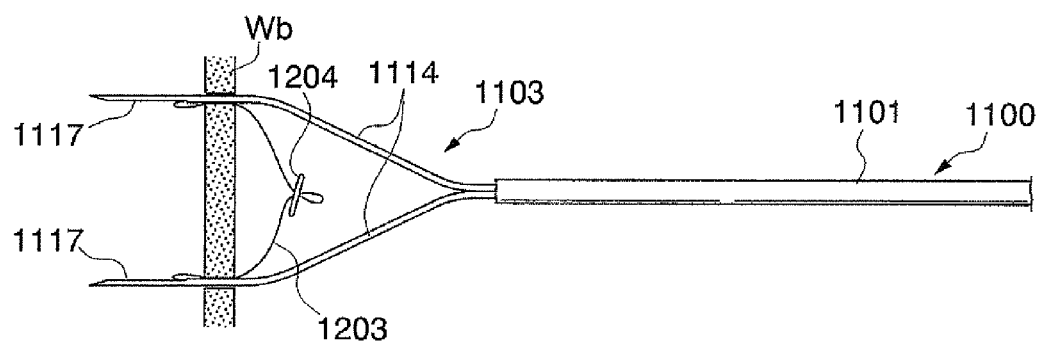
Figure 118:
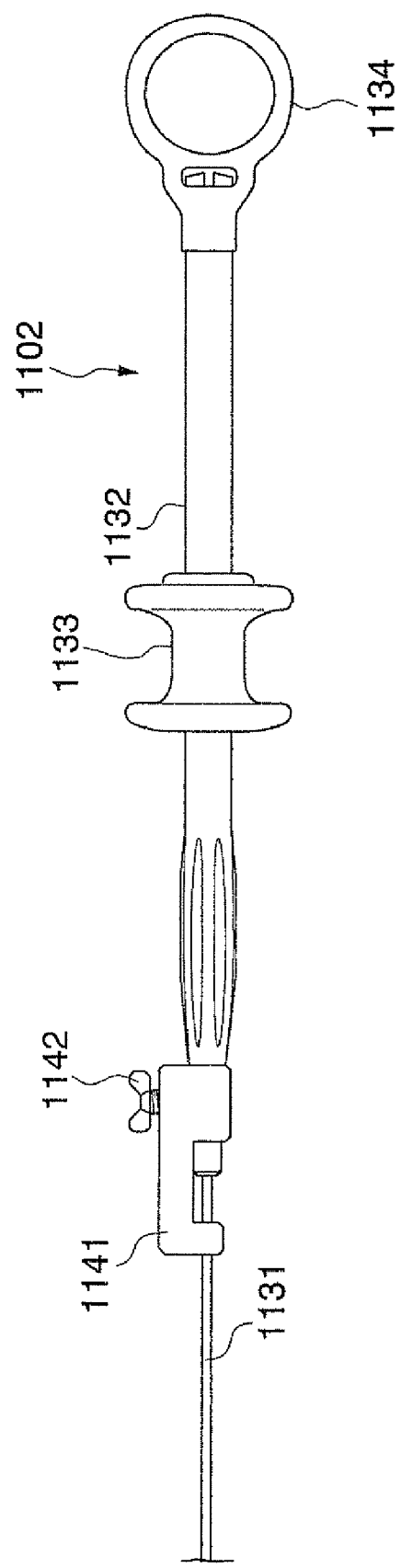
Figure 119:
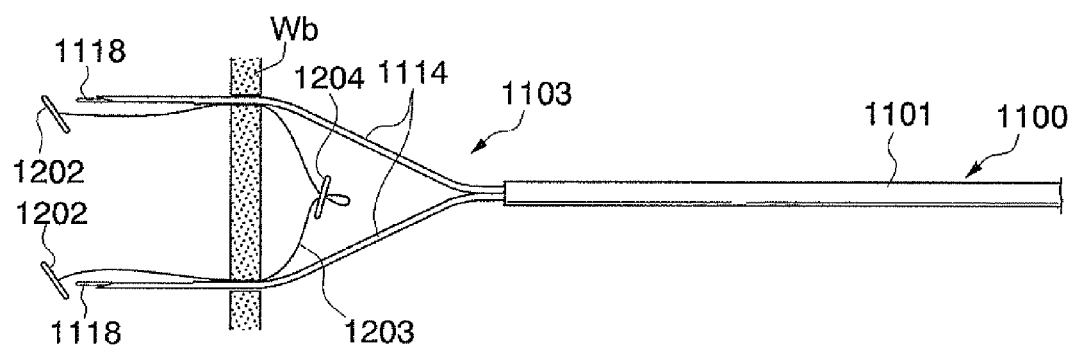

As illustrated in FIG. 117, forwarding the slider 1133 causes the pusher wire 1118 to be forwarded. As illustrated in FIG. 118, the pusher wire 1118 pushes the anchor 1202 from the opening at the tip of the needle 1114. The procedure instrument 1100 is subsequently retracted relative to the endoscope. As illustrated in FIG. 112, the pair of needles 1114 are removed from the inner wall Wb of a body cavity. The anchor 1202 previously discharged from the needles 1114 remains in the exterior of the body cavity. Accordingly, the thread 1203 penetrates the inner wall Wb of a body cavity. Drawing the thread 1203 extracted in loop with forceps, which is not shown in the drawing, from the fastener plate 1204 causes the anchor 1202 to be attracted to the fastener plate 1204. Since the anchor 1202 closely contacting the outer surface of the inner wall Wb of a body cavity is unremovable, the fastener plate 1204 is relatively compressed to the inner surface of the inner wall Wb of a body cavity, and the inner wall Wb of a body cavity is tightened by the thread 1203.

Since the needles 1114 and the pusher wire 1118 are provided to only the tip of the procedure instrument 1100, the operation wire 1121 can be significant in size. The significant size of the operation wire 112 improves power transmission and enhances the operability of the pusher wire 1118. Although the connection part of the pusher wire 1118 and the operation wire 1121 may be significant in diameter, providing the first coil 1113 having a greater inner diameter enables extension and retraction of the pusher wire 1118 and power transmission. This results in enabling smooth releasing of the retainer 1201 in a case where the overcoat tube 1101 bends complexly.

Although the present invention has been described with respect to its preferred embodiments, the present invention is not limited to the embodiments described above. The configuration of the present invention allows for addition, omission, substitution and further replacement without departing from the spirit and scope of the present invention. The present invention is not limited to the above descriptions but is limited only by the appended claims.

What is claimed is:

1. A medical treatment endoscope comprising:
   a flexible sheath having a tip at a distal end thereof, the flexible sheath being capable of a bending operation;
   a viewing unit for observing the tip farther than the sheath;
   an arm section protruding from the tip of the sheath, the arm section being capable of bending movement; and
   an operation stick provided with a slider allowing an operator to carry out an extending and retracting operation for bending the arm section, the operation stick configured to pass a procedure instrument therethrough, wherein
   the operation stick has a piston capable of protruding into an insertion path of the procedure instrument, and
   the piston engages with a connection plate attached to the slider along an axis thereof outside the sheath when the procedure instrument is not inserted, the piston fixing the slider at a position where the arm section becomes straightened, and the piston is pushed up by the procedure instrument and allows the slider to advance and retract when the procedure instrument is inserted.

2. The medical treatment endoscope according to claim 1, wherein an operation section including the operation stick is distant from an operation section for carrying out the bending operation of the sheath.

3. The medical treatment endoscope according to claim 1, wherein when the piston is moved to draw the procedure instrument inserted in the operation stick, the slider is urged so that the slider moves to a position where the arm section becomes straightened.

4. The medical treatment endoscope according to claim 1, wherein
   the connection plate is disposed to correspond to the position where a first groove engaging with the piston bends the arm section or the position where a second groove engaging with the piston straightens the arm section, and
   a tilting surface is formed to the first and second grooves in a direction which releases the engagement with the piston.

5. The medical treatment endoscope according to claim 4, further comprising:
   a ratchet base provided at a proximal end of the operation stick,
   wherein the connection plate connects to the slider at a distal end thereof and to the ratchet base at a proximal end thereof, and the ratchet base includes the piston and the grooves.

6. The medical treatment endoscope according to claim 1, wherein the procedure instrument is provided with a cam for pushing up the piston when the procedure instrument is rotated around an axis of the main body section.

7. The medical treatment endoscope according to claim 6, wherein the cam has a gap for regulating a rotation amount necessary to push up the piston.

8. The medical treatment endoscope according to claim 1, wherein the operation stick has a built-in channel through which a flexible elongated insertion section provided to the procedure instrument is passed, and
   an entrance to the channel into which the insertion section is passed has a funnel shape having an opening enlarged in diameter toward the procedure instrument.

9. The medical treatment endoscope according to claim 1, wherein
   the operation stick has a built-in channel through which a flexible elongated insertion section provided to the procedure instrument is passed, and
   the channel is capable of extending and contracting in the axial line direction of the operation stick according to relative displacement of a plurality of coaxial tube parts, and
   the channel is urged to a position where an entrance into which the insertion section is inserted substantially coincides with the entrance of the operation stick.

10. The medical treatment endoscope according to claim 1, further comprising a wire for joining the slider and a bending mechanism of the arm section, wherein
    an end of the slider of the sheath through which the wire is passed is joined to the operation stick via a spring.

11. The medical treatment endoscope according to claim 1, wherein
    the procedure instrument has a main body section and a slider for driving a drive unit provided to the tip of the procedure instrument, and
    a base end of the main body section inserted into the operation stick is reduced in diameter relative to the tip thereof.

12. The medical treatment endoscope according to claim 11, wherein a space is provided between the main body section of the procedure instrument and the piston when the procedure instrument is inserted through the operation stick and the slider is positioned where the arm section is bent.

13. The medical treatment endoscope according to claim 1, wherein
    a channel for passing a flexible elongated insertion section of the procedure instrument is provided from the operation stick to the arm section,
    the procedure instrument is provided with a main body section; a slider for driving a drive unit provided to the tip of the procedure instrument; and a finger-hook ring provided to the tip of the main body section,
    the channel supports the procedure instrument with a friction force for restricting the rotation of a no-load state of the procedure instrument, and
    the ring is attached to the main body section rotatively around the axis of the main body section.

\* \* \* \* \*